US009896702B2

(12) United States Patent
Conradie et al.

(10) Patent No.: US 9,896,702 B2
(45) Date of Patent: *Feb. 20, 2018

(54) METHODS, REAGENTS AND CELLS FOR BIOSYNTHESIZING COMPOUNDS

(71) Applicant: INVISTA North America S.á r.l., Wilmington, DE (US)

(72) Inventors: Alex Van Eck Conradie, Eaglescliffe (GB); Adriana Leonora Botes, Rosedale East (GB)

(73) Assignee: INVISTA NORTH AMERICA S.A.R.L., Wilmington, DE (US)

( * ) Notice: Subject to any disclaimer, the term of this patent is extended or adjusted under 35 U.S.C. 154(b) by 41 days.

This patent is subject to a terminal disclaimer.

(21) Appl. No.: 14/740,554

(22) Filed: Jun. 16, 2015

(65) Prior Publication Data

US 2015/0361458 A1 Dec. 17, 2015

Related U.S. Application Data

(60) Provisional application No. 62/012,735, filed on Jun. 16, 2014, provisional application No. 62/012,674, filed on Jun. 16, 2014.

(51) Int. Cl.

| | |
|---|---|
| *C12P 7/62* | (2006.01) |
| *C12P 13/00* | (2006.01) |
| *C12P 7/42* | (2006.01) |
| *C12N 9/18* | (2006.01) |
| *C12P 7/44* | (2006.01) |
| *C12P 7/18* | (2006.01) |
| *C12P 11/00* | (2006.01) |
| *C12N 9/16* | (2006.01) |
| *C12N 9/10* | (2006.01) |
| *C12N 9/02* | (2006.01) |
| *C07C 69/533* | (2006.01) |
| *C12P 7/24* | (2006.01) |
| *C12P 7/40* | (2006.01) |
| *C12P 17/10* | (2006.01) |

(52) U.S. Cl.
CPC .............. *C12P 7/62* (2013.01); *C07C 69/533* (2013.01); *C12N 9/0008* (2013.01); *C12N 9/1029* (2013.01); *C12N 9/1096* (2013.01); *C12N 9/16* (2013.01); *C12N 9/18* (2013.01); *C12P 7/18* (2013.01); *C12P 7/24* (2013.01); *C12P 7/40* (2013.01); *C12P 7/42* (2013.01); *C12P 7/44* (2013.01); *C12P 11/00* (2013.01); *C12P 13/001* (2013.01); *C12P 13/005* (2013.01); *C12P 17/10* (2013.01); *C12Y 102/99006* (2013.01); *C12Y 203/01016* (2013.01); *C12Y 206/01018* (2013.01); *C12Y 206/01019* (2013.01); *C12Y 206/01029* (2013.01); *C12Y 206/01048* (2013.01); *C12Y 206/01082* (2013.01); *C12Y 301/01085* (2013.01); *C12Y 301/02* (2013.01)

(58) Field of Classification Search
None
See application file for complete search history.

(56) References Cited

U.S. PATENT DOCUMENTS

| | | | |
|---|---|---|---|
| 2,439,513 | A | 4/1948 | Hamblet et al. |
| 2,557,282 | A | 6/1951 | Hamblet et al. |
| 2,791,566 | A | 5/1957 | Jeffers |
| 2,840,607 | A | 6/1958 | Attane, Jr. et al. |
| 2,971,010 | A | 2/1961 | Gilby, Jr. et al. |
| 3,023,238 | A | 2/1962 | Chapman et al. |
| 3,338,959 | A | 8/1967 | Sciance et al. |
| 3,365,490 | A | 1/1968 | Arthur et al. |
| 3,515,751 | A | 6/1970 | Oberster |
| 3,719,561 | A | 3/1973 | Tanaka et al. |
| 4,058,555 | A | 11/1977 | Mims |
| 6,255,451 | B1 | 7/2001 | Koch et al. |
| 6,372,939 | B1 | 4/2002 | Bunnel et al. |
| 8,088,607 | B2 | 1/2012 | Buggard et al. |
| 8,361,769 | B1 | 1/2013 | Koch et al. |
| 2004/0054235 | A1 | 3/2004 | Fodor et al. |
| 2010/0035309 | A1 | 2/2010 | Havemen et al. |
| 2010/0151536 | A1 | 6/2010 | Baynes et al. |
| 2010/0203600 | A1 | 8/2010 | Dubois |

(Continued)

FOREIGN PATENT DOCUMENTS

| | | |
|---|---|---|
| EP | 2647718 | 10/2013 |
| WO | WO 2008/006037 | 1/2008 |

(Continued)

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Kizer et al. Appl Environ Microbiol. May 2008;74(10):3229-41.*
Prather et al. Curr Opin Biotechnol. Oct. 2008;19(5):468-74.*
Hsu et al., "Addition of Autotrophic Carbon Fixation Pathways to Increase the Theoretical Heterotrophic Yield of Acetate", The Fourth International Conference on Computational Systems Biology (ISB2010), Suzhou, China, Sep. 9-11, 2010, pp. 314-322.*
Zhang et al. Electronic Journal of Biotechnology (2011), 14(6), 1.*
Accession B2HHT4. Jun. 10, 2008.*
Accession M5AD45. May 29, 2013.*
Accession C4ZUR7. Sep. 22, 2009.*
Accession Q59111. Jul. 15, 1998.*
Accession P69452. Mar. 1, 2005.*

(Continued)

*Primary Examiner* — Christian Fronda
(74) *Attorney, Agent, or Firm* — William J. Simmons; Carla A. Mouta-Bellum

(57) ABSTRACT

This document describes biochemical pathways for producing 2(E)-heptenedioyl-CoA methyl ester from precursors such as 2-oxo-glutarate, acetyl-CoA, or succinyl-CoA using one or more of a fatty acid O-methyltransferase, a thioesterase, a CoA-transferase, a CoA ligase, as well as recombinant hosts expressing one or more of such enzymes. 2(E)-heptenedioyl-CoA methyl ester can be enzymatically converted to pimeloyl-CoA using a trans-2-enoyl-CoA reductase, and a methylesterase. Pimeloyl-CoA can be enzymatically converted to pimelic acid, 7-aminoheptanoate, 7-hydroxyheptanoate, heptamethylenediamine, or 1,7-heptanediol.

30 Claims, 39 Drawing Sheets

(56) References Cited

U.S. PATENT DOCUMENTS

| | | |
|---|---|---|
| 2010/0298612 A1 | 11/2010 | Behrouzian et al. |
| 2010/0317069 A1 | 12/2010 | Burk et al. |
| 2011/0171699 A1 | 7/2011 | Raemakers-Franken et al. |
| 2011/0256599 A1 | 10/2011 | Hu et al. |
| 2012/0064252 A1 | 3/2012 | Beatty |
| 2012/0101009 A1 | 4/2012 | Beatty |
| 2013/0065279 A1 | 3/2013 | Burk et al. |
| 2013/0183728 A1 | 7/2013 | Botes |
| 2013/0210090 A1 | 8/2013 | Pearlman et al. |
| 2013/0217081 A1 | 8/2013 | Pearlman et al. |
| 2013/0224807 A1 | 8/2013 | Pearlman et al. |
| 2013/0267012 A1 | 10/2013 | Steen et al. |
| 2014/0186902 A1 | 7/2014 | Botes et al. |
| 2014/0186904 A1 | 7/2014 | Botes et al. |
| 2014/0193861 A1 | 7/2014 | Botes et al. |
| 2014/0193862 A1 | 7/2014 | Botes et al. |
| 2014/0193863 A1 | 7/2014 | Botes et al. |
| 2014/0193864 A1 | 7/2014 | Botes et al. |
| 2014/0193865 A1 | 7/2014 | Botes et al. |
| 2014/0196904 A1 | 7/2014 | Fontenelle et al. |
| 2014/0199737 A1 | 7/2014 | Botes et al. |
| 2014/0248673 A1 | 9/2014 | Botes et al. |
| 2015/0111262 A1 | 4/2015 | Botes et al. |
| 2015/0267211 A1 | 9/2015 | Botes et al. |

FOREIGN PATENT DOCUMENTS

| | | |
|---|---|---|
| WO | WO 2008/145737 | 12/2008 |
| WO | WO 2009/121066 | 1/2009 |
| WO | WO 2009/113853 | 9/2009 |
| WO | WO 2009/113855 | 9/2009 |
| WO | WO 2009/140159 | 11/2009 |
| WO | WO 2009/140695 | 11/2009 |
| WO | WO 2009/140696 | 11/2009 |
| WO | WO 2009/151728 | 12/2009 |
| WO | WO 2010/068944 | 6/2010 |
| WO | WO 2010/068953 | 6/2010 |
| WO | WO 2010/071759 | 6/2010 |
| WO | WO 2010/104390 | 9/2010 |
| WO | WO 2010/104391 | 9/2010 |
| WO | WO 2010/129936 | 11/2010 |
| WO | WO 2010/132845 | 11/2010 |
| WO | WO 2011/003034 | 1/2011 |
| WO | WO 2011/031146 | 3/2011 |
| WO | WO 2011/031147 | 3/2011 |
| WO | WO 2012/031910 | 3/2012 |
| WO | WO 2012/071439 | 5/2012 |
| WO | WO 2012/094425 | 7/2012 |
| WO | WO 2012/174430 | 12/2012 |
| WO | WO 2012/177721 | 12/2012 |
| WO | WO 2013/003744 | 1/2013 |
| WO | WO2013003744 * | 1/2013 |
| WO | WO 2013/028519 | 2/2013 |
| WO | WO 2013/082542 | 6/2013 |
| WO | WO 2013/090837 | 6/2013 |
| WO | WO 2013/096898 | 6/2013 |
| WO | WO 2014/031724 | 2/2014 |
| WO | WO 2014/093865 | 6/2014 |
| WO | WO 2014/105788 | 7/2014 |
| WO | WO 2014/105793 | 7/2014 |
| WO | WO 2014/105794 A2 | 7/2014 |

OTHER PUBLICATIONS

Accession Q73Q47. Mar. 29, 2005.*
Accession B2HN69. Jun. 10, 2008.*
Accession Q7NWG4. Dec. 15, 2003.*
Accession P0AGG3. Dec. 20, 2005.*
Accession Accession D2I940. Feb. 9, 2010.*
International Search Report and Written Opinion in International Application No. PCT/US2015/036074, dated Sep. 9, 2015, 14 pages.
Invitation to Pay Fees in International Application No. PCT/US2015/036086, dated Sep. 16, 2015, 7 pages.

"Enterococcus faecalis V583 bifuntional acetaldehyde-CoA/Alcohol Dehydrogenase," biocyc.org, retrieved on Jun. 19, 2014, http://biocyc.org/EFAE226185/N_EW-IMAGE?type=ENZYME&object=GH11-877-MONOMER, 9 pages.
"Information on EC 1.2.1.57—butanal dehydrogenase," brenda-enzymes.org, retrieved on Jun. 19, 2014, http://www.brenda-enzymes.org/php/result_flat.php4?ecno=1.2.1.57, 6 pages.
"Brenda—The comprehensive Enzyme Information System," Jul. 2011, retrieved on Sep. 19, 2014, http://web.archive.org/web/20111009205602/http://www.brenda-enzymes.org/, 1 page.
Aimin et al., "Nocardia sp. carboxylic acid reductase: cloning, expression, and characterization of a new aldehyde oxidoreductase family," Appl. Environ. Microbiol., 2004, 70:1874-1881.
Akita et al., "Highly stable meso-diaminopimelate dehydrogenase from an Ureibacillus thermosphaericus strain A1 isolated from a Japanese compost: purification, characterization and sequencing," AMB Express, 2011, 1:43, 8 pages.
Alber et al., "Malonyl-coenzyme A reductase in the modified 3-hydroxypropionate cycle for autotrophic carbon fixation in archaeal Metallosphaera and Sulfolobus spp," J. Bacteriology, 2006, 188:8551-8559.
Aloulou et al., "Purification and biochemical characterization of the LIP2 lipase from Yarrowia lipolytica," Biochim. Biophys. Acta, 2007, 1771:228-237.
Anton et al., Polyamides, Fibers, Encyclopedia of Polymer Science and Engineering, 2001, 11:409-445.
Atsumi et al., "Acetolactate synthase from Bacillus subtilis serves as a 2-ketoisovalerate decarboxylase from isobutanol synthesis in Escherichi coli," Applied and Environ. Microbiol., 2009, 75(19):6306-6311.
Aursnes et al., "Total Synthesis of the Lipid Mediator PD1(n-3 DPA): Configurational Assignments and Anti-Inflammatory and Pro-resolving Actions," Journal of Natural Products, Feb. 2014, 77:910-916.
Azuma et al., "Naphthalene—a constituent of Magnolia flowers," Phytochemistry, 1996, 42:999-1004.
Barker et al., "Enzymatic reactions in the degradation of 5-aminovalerate by Clostridium aminovalercum," J Biol Chem., 1987, 262(19):8994-9003.
Becker et al., "Metabolic flux engineering of L-lysine production in Corynebacterium glutamicum—over expression and modification of G6P dehydrogenase," J Biotechnol. 2007, 132(2):99-109.
Bellmann et al., "Expression control and specificity of the basic amino acid exporter LysE of Corynebacterium glutamicum," Microbiology 2001, 147:1765-1774.
Bennett et al., "Purification and properties of ε-caprolactone hydrolases from Acinetobacter NCIB 9871 and Nocardia globevula CL1," Journal of General Microbiology, 1988 134: 161-168.
Bergler et al., "Protein EnvM is the NADH-dependent enoyl-ACP reductase (FabI) of Escherichia coli," J. Bio Chem, 1993, 269(8):5493-5496.
Bernstein et al., "Transfer of the high-GC cyclohexane carboxylate degradation pathway from Rhodopseudomonas palustris to Escherichia coli for production of biotin," Metabolic Engineering, May 2008, 10(3-4):131-140.
Berthold et al., "Structure of the branched-chain keto acid decarboxylase (KdcA) from Lactococcus lactis provides insights into the structural basis for the chemoselective and enantioselective carboligation reaction," Acta Crystallographica Sec. D, 2007, D63:1217-1224.
Binieda et al., "Purification, characterization, DNA Sequence and cloning of a pimeloyl-CoA synthetase from Pseudomonas medocin 35," Biochem J., 1999, 340:793-801.
Bond-Watts et al., "Biochemical and Structural Characterization of the trans-Enoly-CoA Reductase from Treponema denticola," Biochemistry, 2012, 51:6827-6837.
Bordeaux et al., "Catalytic, Mild, and Selective Oxyfunctionalization of Linear Alkanes: Current challenges," Angew. Chem. Int. Ed., 2012, 51:10712-10723.
Bordes et al., "Isolation of a thermostable variant of Lip2 lipase from Yarrowia lipolytica by directed evolution and deeper insight into the denaturation mechanisms," Journal of Biotechnology, 2011, 156: 117-124.

(56) References Cited

OTHER PUBLICATIONS

Botting, "Substrate Specificity of the 3-Methylaspartate Ammonia-Lyase Reaction: Observation of Differential Relative Reaction Rates for Substrate-Product Pairs," Biochemistry, 1988, 27:2953-2955.
Boylan et al., "Functional identification of the fatty acid reductase components encoded in the luminescence operon of Vibrio fischeri," Journal of Bacteriology, 1985, 163(3):1186-1190.
Boylan et al., "Lux C, D and E genes of the Vibrio fischeri luminescence operon code for the reductase, transferase, and synthetase enzymes involved in aldehyde biosynthesis," Photochemistry and photobiology, 1989, 49:681-688.
Bramer et al., "The methylcitric acid pathway in Ralstonia eutropha: new genes identified involved in propionate metabolism," Microbiology 2001, 147:2203-2214.
Breithaupt et al., "Crystal structure of 12-oxophytodienoate reductase 3 from tomato: self-inhibition by dimerization," Proc Natl. Acad Sci. USA, 2006, 103:14337-14342.
Brigham et al., "Engineering Ralstonia eutropha for Production of Isobutanol from CO2, H2, and O2," Advanced Biofuels and Bioproducts 2013, Chapter 39, pp. 1065-1090.
Brzostowicz et al., "mRNA differential display in a microbial enrichment culture: simultaneous identification of three cyclohexanonemonooxygenases from three species," Applied and Environmental Microbiology, 2003, 69: 334-342.
Brzostowicz et al., "Identification of two gene clusters involved in cyclohexanone oxidation in Brevibacterium epidermidis strain HCU," Applied and Microbiological Biotechnology, 2002, 58:781-789.
Buckel et al., "Glutaconate CoA-transferase from Acidaminococcus fermentans," Eur J. Biochem, 1981, 118:315-321.
Budde et al., "Roles of Multiple Acetoacetyl Coenzyme A Reductases in Polyhydroxybutyrate Biosynthesis in Ralstonis eutropha H16," J Bacteriol. 2010, 192(20):5319-5328.
Bugg et al., "The emerging role for bacteria in lignin degradation and bio-product formation," Curr Opin Biotechnol 2011, 22(3):394-400.
Buhler et al., "Occurrence and the possible physiological role of 2-enoate reductases," FEBS Letters, 1980, 109:244-246.
Bult et al., "Complete genome sequence of the methanogenicarchaeon, Methanococcus jannaschii," Science, 1996, 273: 1058-1073.
Bunik et al., "Kinetic properties of the 2-oxoglutarate dehydrogenase complex from Azotobacter vinelandii evidence for the formation of a precatalytic complex with 2-oxoglutarate," Eur J Biochem., 267(12):3583-3591, Jun. 2000.
Cantu et al., "Thioesterases: A new perspective based on their primary and tertiary structures," Protein Science 2010, 19:1281-1295.
Chayabutra and Ju, "Degradation of n-hexadecane and its metabolites by Pseudomonas aeruginosa under microaerobic and anaerobic denitrifying conditions," Appl Environ Microbiol., 66(2):493-498, Feb. 2000.
Cheesbrough and Kolattukudy, "Alkane biosynthesis by decarbonylation of aldehydes catalyzed by a particulate preparation from Pisum sativum," PNAS USA, 1984, 81(21):6613-7.
Chen et al., "Termites fumigate their nests with naphthalene," Nature, 1998, 392:558-559.
Cheng et al., "Genetic Analysis of a Gene Cluster for Cyclohexanol Oxidation in Acinetobacter sp. Strain SE19 by In Vitro Transposition," Journal of Bacteriology, 2000, 182(17):4744-4751.
Clomburg et al., "Integrated engineering of Beta-oxidation reversal and omega-oxidation pathways for the synthesis of medium chain omega-functionalized carboxylic acids," Metabolic Engineering, Jan. 2015, 28:202-212.
Coon, "Omega oxygenases: nonheme-iron enzymes and P450 cytochromes," Biochemical & Biophysical Research Communications, 2005,338:378-385.
Cronan and Lin, "Synthesis of the α,ω-dicarboxylic acid precursor of biotin by the canonical fatty acid biosynthetic pathway," Current Opinion in Chem Biol., 2011, 15:407-413.
Cryle and Schlichting, "Structural insights from a P450 Carrier Protein complex reveal how specificity is achieved in the P450BioI ACP complex," Proceedings of the National Academy of Sciences, Oct. 2008, 105(41):15696-15701.
Cryle et al., "Carbon-carbon bond cleavage by cytochrome P450BioI (CYP107H1) E1," Chemical Communications, Jan. 2004, 86-87.
Cryle, "Selectivity in a barren landscape: the P450BioI-ACP complex," Biochemical Society Transactions, Aug. 2010, 38(4):934-939.
Da Silva et al., "Glycerol: A promising and abundant carbon source for industrial microbiology," Biotechnology Advances, 2009, 27:30-39.
Daisy et al., "Naphthalene, an insect repellent, is produced by Muscodor vitigenus, a novel endophytic fungus," Microbiology, 2002, 148:3737-3741.
Dalby, "Optimizing enzyme function by directed evolution," Current Opinion in Structural Biology, 2003, 13, 500-505.
Davis et al., "Overproduction of acetyl-CoA carboxylase activity increases the rate of fatty acid biosynthesis in Escherichia coli," J. Biol. Chem., 2000, 275(37): 28593-28598.
Day et al., "Partial purification and properties of acyl-CoA reductase from Clostridum butyricum," Archives of Biochemistry and Biophysics, 1978, 190(1):322-331.
Deana et al., "Substrate specificity of a dicarboxyl-CoA: Dicarboxylic acid coenzyme. A transferase from rat liver mitochondria," Biochem Int., 1992, 26:767-773.
Dekishima et al., "Extending Carbon Chain Length of 1-Butanol Pathway for 1-Hexanol Synthesis from Glucose by Engineered Escherichia coli," J. Am. Chem. Soc., Aug. 2011, 133(30):11399-11401.
Dellomonaco et al., "Engineered reversal of the [beta]-oxidation cycle for the synthesis of fuels and chemicals," Nature, Jan. 2011, 476(7360):355-359.
Deshmukh and Mungre, "Purification and properties of 2-aminoadipate: 2-oxoglutarate aminotransferase from bovine kidney," Biochem J, 1989, 261(3):761-768.
Doan et al., "Functional expression of five Arabidopsis fatty acyl-CoA reductase genes in Escherichia coli," J. Plant Physiology, 2009, 166:787-796.
Dobritzsch et al., "High resolution crystal structure of pyruvate decarboxylase from Zymomonas mobilis. Implications for substrate activation in pyruvate decarboxylases," J. Biol. Chem., 1998, 273:20196-20204.
Donoghue and Trudgill, "The Metabolism of Cyclohexanol by Acinetobacter NCIB9871," Eur J Bochem., 1975, 60:1-7.
Drevland et al., "Enzymology and Evolution of the Pyruvate Pathway to 2-Oxobutyrate in Methanocaldococcus jannaschii," J. Bacteriol., Apr. 2007, 189(12):4391-4400.
Drevland et al., "Methanogen homoaconitase catalyzes both hydrolyase reactions in coenzyme B biosynthesis," J Biol Chem., Oct. 2008, 283: 28888-28896.
Egmond et al., "Fusarium solani pisi cutinase," Biochimie, Nov. 2000, 82(11):1015-1021.
Eikmanns and Buckel, "Properties of 5-hydroxyvalerate CoA-transferase from Clostridium aminovalericum," Biol. Chem, 1990, 371:1077-1082.
Elkins et al., "Substrate Specificity of the RND-Type Multidrug Efflux Pumps AcrB and AcrD of Esherichia coli Is Determined Predominately by Two Large Periplasmic Looops," J Bacteriol. 2002, 184(23):6490-6499.
Elshahed et al., "Benzoate Fermentation by the Anaerobic bacterium Syntrophus aciditrophicus in the Absence of Hydrogen-Using Microorganisms," Applied and Environ Microbiology, 2001, 67(12):5520-5525.
Elshahed et al., "Metabolism of Benzoate, Cyclohex-1-ene Carboxylate, and Cyclohexane Carboxylate by Syntrophus aciditrophicus Strain SB in Syntrophic Association with H2-Using Microorganisms," Applied and Environ. Microbiol., Apr. 2001, 67(4):1728-1738.
Eurich et al., "Cloning and characterization of three fatty alcohol oxidase genes from Candida tropicalis strain ATCC 20336," Applied & Environmental Microbiology, 2004, 70(8): 4872-4879.

(56) References Cited

OTHER PUBLICATIONS

Ferreira et al. "A member of the sugar transporter family, Stl1p is the glycerol/H= symporter in *Saccharomyces cerevisiae*," Molecular Biology of the Cell, American Society for Cell Biology, Apr. 1, 2005, 16(4):2068-2076.
Fickers et al., "Carbon and nitrogen sources modulate lipase production in the yeast *Yarrowia lipolytica*," Journal of Applied Microbiology , 2004, 96:742-9.
Fickers et al., "The lipases from Yarrowia lipolytica: Genetics, production, regulation, biochemical characterization and biotechnological applications," Biotechnology Advances, 2011, 29: 632-644.
Fonknechten et al., "Clostridium sticklandii, a specialist in amino acid degradation: revisiting its metabolism through its genome sequence," BMC Genomics, 2010, 11:1-12.
Fuchs et al., "Microbial degradation of aromatic compounds—from one strategy to four," Nat Rev Microbiol., Oct. 3, 2011;9(11):803-816, Oct. 2011.
Fukui et al., "Expression and Characterization of ®-Specific Enoly Coenzyme A Hydratase Involved in Polyhydroxyalkanoate Biosynthesis by Aeromonas caviae," J Bacteriol. 1998, 180(3):667-673.
Funhoff et al., "CYP153A6, a Soluble P450 Oxygenase Catalyzing Terminal-Alkane Hydroxylation," J Bacteriol. 2006, 188(14):5220-5227.
Funhoff et al., "Expression and Characterization of (R)-Specific Enoyl Coenzyme A Hydratase Involved in Polyhydroxyalkanoate Biosynthesis by Aeromonas caviae," J. Bacteriol., 2006, 188(14):5220-5227.
Gallus and Schink, "Anaerobic degradation of pimelate by newly isolated denitrifying bacteria," Microbiology, 1994, 140:409-416.
Gao et al: "A novel meso-diaminopimelate dehydrogenase from Symbiobacterium thermophilum: overexpression, characterization, and potential for D-amino acid synthesis," Applied and Environmental Microbiology, 2012, 78:8595-8600.
Gasmi et al., "A molecular approach to optimize hIFN α2b expression and secretion in Yarrowia lipolytica," Appl Microbiol Biotechnol, 2011, 89:109-119.
GenBank Accession No. AAA23536, Apr. 26, 1993, 1 page.
GenBank Accession No. AAA24664.1, Mar. 25, 1993, 1 page.
GenBank Accession No. AAA24665.1, Apr. 26, 1993, 1 page.
GenBank Accession No. AAA57874.1, Nov. 21, 2011, 2 pages.
GenBank Accession No. AAA69178.1, Jul. 1, 1995, 1 page.
GenBank Accession No. AAA92347.1, Mar. 15, 1996, 1 page.
GenBank Accession No. AAB35106, Nov. 1995, 1 page.
GenBank Accession No. AAB60068.1, dated Jul. 1995, 1 page.
GenBank Accession No. AAB98494.1, Oct. 23, 2009, 2 pages.
GenBank Accession No. AAB99007.1, Oct. 23, 2009, 2 pages.
GenBank Accession No. AAB99100, Aug. 27, 1996, 2 pages.
GenBank Accession No. AAB99277.1, Oct. 23, 2009.
GenBank Accession No. AAC23921, Apr. 23, 2003, 2 pages.
GenBank Accession No. AAC76437.1, dated Oct. 2010, 2 pages.
GenBank Accession No. AAF02538.1, Oct. 20, 1999, 2 pages.
GenBank Accession No. AAG08191.1, Jan. 31, 2014, 2 pages.
GenBank Accession No. AAK73167.2, retrieved May 19, 2014, 1 page.
GenBank Accession No. AAN37290.1, retrieved May 19, 2014, 1 page.
GenBank Accession No. AAO77182, Mar. 28, 2003, 1 page.
GenBank Accession No. AAQ59697.1, Jan. 31, 2014, 2 pages.
GenBank Accession No. AAS11092.1, Mar. 5, 2010, 1 page.
GenBank Accession No. AAS43086.1, dated Nov. 2011, 1 page.
GenBank Accession No. AAT43726, retrieved May 19, 2014, 1 page.
GenBank Accession No. AAW66853.1, Feb. 12, 2005, 1 page.
GenBank Accession No. AAY39893.1, Jan. 31, 2014, 2 pages.
GenBank Accession No. AB005294, Feb. 2000, 2 pages.
GenBank Accession No. ABA81135.1, Jan. 28, 2014, 2 pages.
GenBank Accession No. ABC76100.1, Mar. 11, 2010, 1 page.
GenBank Accession No. ABC76101.1, Mar. 11, 2010, 1 page.
GenBank Accession No. ABC76114.1, Mar. 11, 2010, 1 page.
GenBank Accession No. ABC76260.1, Mar. 11, 2010, 1 page.
GenBank Accession No. ABC76948.1, Mar. 11, 2010, 1 page.
GenBank Accession No. ABC76949.1, Mar. 11, 2010, 1 page.
GenBank Accession No. ABC77793.1, Mar. 11, 2010, 1 page.
GenBank Accession No. ABC77794.1, Mar. 11, 2010, 1 page.
GenBank Accession No. ABC77898.1, Mar. 11, 2010, 1 page.
GenBank Accession No. ABC77899.1, Mar. 11, 2010, 1 page.
GenBank Accession No. ABC77900.1, Mar. 11, 2010, 1 page.
GenBank Accession No. ABC78517.1, Mar. 11, 2010, 1 page.
GenBank Accession No. ABC78756.1, Mar. 11, 2010, 1 page.
GenBank Accession No. ABC78863.1, Mar. 11, 2010, 1 page.
GenBank Accession No. ABC78881.1, Mar. 11, 2010, 1 page.
GenBank Accession No. ABC78950.1, Mar. 11, 2010, 1 page.
GenBank Accession No. ABE47158.1, Jan. 26, 2014, 1 page.
GenBank Accession No. ABE47159.1, Jan. 28, 2014, 2 pages.
GenBank Accession No. ABE47160.1, Jan. 28, 2014, 1 page.
GenBank Accession No. ABI83656.1, Jan. 3, 2007, 1 page.
GenBank Accession No. ABJ63754.1, dated Mar. 2010, 1 page.
GenBank Accession No. ABK71854.1, Jan. 31, 2014, 2 pages.
GenBank Accession No. ABK75684.1, Jan. 31, 2014, 2 pages.
GenBank Accession No. ACC40567.1, Jan. 31, 2014, 2 pages.
GenBank Accession No. ACJ06772.1, Dec. 4, 2009, 1 page.
GenBank Accession No. ADG98140.1, Jan. 28, 2014, 2 pages.
GenBank Accession No. ADK19581.1, Sep. 20, 2010, 2 pages.
GenBank Accession No. AE000666.1, Jan. 5, 2006, 309 pages.
GenBank Accession No. AEA39183.1, Apr. 4, 2011, 1 page.
GenBank Accession No. AJ012480.1, Apr. 2005, 2 pages.
GenBank Accession No. AY143338, Apr. 2003, 5 pages.
GenBank Accession No. AY495697, Mar. 2004, 3 pages.
GenBank Accession No. BAB91331.1, retrieved May 19, 2014, 1 page.
GenBank Accession No. BAC06606, Aug. 1, 2002, 1 page.
GenBank Accession No. BAD69624, Sep. 2005, 1 page.
GenBank Accession No. BAF92773, Nov. 27, 2007, 1 page.
GenBank Accession No. BAF94304.1, retrieved May 19, 2014, 1 page.
GenBank Accession No. CAA44858.1, Apr. 28, 1992, 1 page.
GenBank Accession No. CAA81612.1, Apr. 18, 2005, 2 pages.
GenBank Accession No. CAA90836.1, Apr. 18, 2005, 2 pages.
GenBank Accession No. CAB13029.2, Nov. 20, 1997, 2 pages.
GenBank Accession No. CAC48239.1, Apr. 15, 2005, 2 page.
GenBank Accession No. CAE26094.1, Apr. 17, 2005, 2 pages.
GenBank Accession No. CAE26097.1, Apr. 17, 2005, 2 pages.
GenBank Accession No. CAH04396.1, Apr. 7, 2005, 1 page.
GenBank Accession No. CAH04397.1, Apr. 7, 2005, 2 pages.
GenBank Accession No. CAH04398.1, Apr. 7, 2005, 1 page.
GenBank Accession No. CCC78182.1, dated Jul. 2011, 1 page.
GenBank Accession No. D84432, replaced by Q9SKC9.1, Feb. 2005, 2 pages.
GenBank Accession No. D87518, Jul. 31, 1997, 2 pages.
GenBank Accession No. EFV11917.1, Sep. 9, 2013, 2 pages.
GenBank Accession No. EIV11143.1, Jun. 19, 2012, 2 pages.
GenBank Accession No. HQ418483.1, Apr. 4, 2011, 2 pages.
GenBank Accession No. JA114119.1, Apr. 19, 2011, 1 page.
GenBank Accession No. JA114148, Apr. 2011, 1 page.
GenBank Accession No. JA114151, Apr. 2011, 1 page.
GenBank Accession No. JA114154, Apr. 2011, 1 page.
GenBank Accession No. JA114157, Apr. 2011, 1 page.
GenBank Accession No. L42023, Oct. 2009, 285 pages.
GenBank Accession No. MJ0663, Oct. 1, 2014, 4 pages.
GenBank Accession No. NC_013156.1, Jun. 10, 2013, 2 pages.
GenBank Accession No. NC_014122.1, Jun. 10, 2013, 2 pages.
GenBank Accession No. NC_015562.1, Jun. 10, 2013, 2 Pages.
GenBank Accession No. NM_001246944, Dec. 2011, 2 pages.
GenBank Accession No. NM_001247852, Dec. 2011, 2 pages.
GenBank Accession No. NM_133240, Feb. 25, 2002, 2 pages.
GenBank Accession No. NP_247129, Jun. 10, 2013, 2 pages.
GenBank Accession No. NP_247250, Jun. 10, 2013, 2 pages.
GenBank Accession No. NP_247647, Jun. 10, 2013, 2 pages.
GenBank Accession No. P22822, Mar. 1, 1992, 1 page.
GenBank Accession No. P94129 (replaced by Q6F7B8), Mar. 1, 2004, 1 page.
GenBank Accession No. S48141, May 1993, 2 pages.

(56) References Cited

OTHER PUBLICATIONS

GenBank Accession No. XM_001827609, Mar. 2011, 2 pages.
GenBank Accession No. YP_001394144.1, Jul. 26, 2007, 1 page.
GenBank Accession No. YP_003127480, Jun. 10, 2013, 2 pages.
GenBank Accession No. YP_003128272, Jun. 10, 2013, 2 pages.
GenBank Accession No. YP_003615747, Jun. 10, 2013, 1 page.
GenBank Accession No. YP_003615922, Jun. 10, 2013, 2 pages.
GenBank Accession No. YP_004483786, Jul. 6, 2013, 2 pages.
GenBank Accession No. YP_400611, Nov. 10, 2005, 2 pages.
GenBank Accession No. YP_959486, Jan. 3, 2007, 2 pages.
GenBank Accession No. YP_959769, Jan. 3, 2007, 2 pages.
Gerbling et al., "A new acyl-CoA synthetase, located in higher plant cytosol," J Plant Physiol, 1994, 143:561-564.
Gloeckler et al., "Cloning and characterization of the *Bacillus sphaericus* genes controlling the bioconversion of pimlate into dethiobiotin," Gene, 1990, 87:63-70.
Gloerich et al., "Peroxisomal trans-2-enoyl-CoA reductase is involved in phytol degradation," FEBS Letters 2006, 580:2092-2096.
Gocke et al., "Comparative characterization of ThPP-dependent decarboxylases," J. Mol. Cat. B: Enzymatic, 2009, 61:30-35.
Gonzalez-Lopez, "Genetic control of extracellular protease synthesis in the yeast *Yarrowia lipolytica*," Genetics, 2002, 160: 417-427.
Graupner et al., "Identification of the gene encoding sulfopyruvate decarboxylase, an enzyme involved in biosynthesis of coenzyme M," J Bacterial., 2000, 182: 4862-4867.
Guerrillot et al., "Purification and Characterization of Two Aldehyde Dehydrogenases from Pseudomonas aeruginosa," Eur. J. Biochem. 1977, 81:185-192.
Hall, "The Contribution of Horizontal Gene Transfer to the Evolution of Fungi," Duke University Libraries, May 10, 2007, 163 pages.
Hall, "Asymmetric bioreduction of activated alkenes using cloned 12-oxophytodienoate reductase isoenzymes OPR-1 and OPR-3 from *Lycopersicon esculentum* (tomato): a striking change of stereoselectivity," Agnew Chem Int. Ed., 2007, 46:3934-3937.
Han et al., "Oxaloacetate hydrolase, the C—C bond lyase of oxalate secreting fungi," J. Biol. Chem. 2007, 282:9581-9590.
Harrison and Harwood, "The pimFABCDE operon from Phodopseudomonas palustris mediates dicarboxylic acid degradation and participates in anaerobic benzoate degradation," Microbiology, 2005, 151:727-736.
Harwood and Parales, "The beta-ketoadipate pathway and the biology of self-identity," Ann. Rev. Microbiol., 1996, 50:553-590.
Harwood et al., "Anaerobic metabolism of aromatic compounds via the benzoyl-CoA pathway," FEMS Microbiology Reviews, 1999, 22:439-458.
Hasson et al., "The crystal structure of benzoylformate decarboxylase at 1.6A resolution—Diversity of catalytic residues in ThDP-dependent enzymes," Biochemistry, 1998, 37:9918-9930.
Hayaishi et al., "Enzymatic Studies on the Metabolism of β-Alanine," J. Biol. Chem., 1961, 236, p. 781-790.
Haywood et al., "Characterization of two 3-ketothiolases possessing differing substrate specificities in the polyhydroxyalkanoate synthesizing organism Alcaligenes eutrophus," FEMS Microbiology Letters 1988, 52(1-2):91-96.
He et al., "*Nocardia* sp. carboxylic acid reductase: cloning, expression, and characterization of a new aldehyde oxidoreductase family," Applied and Environmental Microbiology, 2004, 70:1874-1881.
Heath et al., "The enoyl-[acyl-carrier-protein] reductases FabI and FabL from Bacillus subtilis," J Biol Chem., 275(51):40128-40133, Dec. 22, 2000.
Hermann et al, "Industrial production of amino acids by coryneform bacteria," J Biotechnol. 2003, 104(1-3):155-172.
Hess et al., "Extremely thermostable esterases from the thermoacidophilic euryarchaeon Picrophilus torridus," Extremophiles, 2008, 12:351-364.
Ho and Weiner, "Isolation and characterization of an aldehyde dehydrogenase encoded by the aldB gene of *Escherichia coli*," J. Bacteriol., 2005, 187(3):1067-1073.
Hoffmeister et al., "Mitochondrial trans-2-enoyl-CoA reductase of wax ester fermentation from Euglena gracilis defines a new family of enzymes involved in lipid synthesis," J Biol Chem., 280(6):4329-4338. Epub Nov. 29, 2004.
Hofvander et al., "A prokaryotic acyl-CoA reductase performing reduction of fatty acyl-CoA to fatty alcohol," FEBS Letters, 2001, 585:3538-3543.
Holden et al., "Chorismate lyase: kinetics and engineering for stability," Biochim Biophys Acta., Jan. 31, 2002, 1594(1):160-167.
Hooks et al., "Long-chain acyl-CoA oxidases of *Arabidopsis*," Plant J., 1999, 20:1-13.
Horning et al., "α-Ketoglutaric Acid," Organic Syntheses, 1955, 3: 510-512.
Hotta et al., "Extremely Stable and Versatile Carboxylesterase from a Hyperthermophilic Archaeon," Applied and Environmental Microbiology, 2002, 68(8):3925-3931.
Howell et al., "Alpha-keto acid chain elongation reactions involved in the biosynthesis of coenzyme B (7-mercaptoheptanoyl threonine phosphate) in methanogenicArchaea," Biochemistry, 1989, 37: 10108-10117.
Howell et al., "Identification of enzymes homologous to isocitrate dehydrogenase that are involved in coenzyme Band leucine biosynthesis in methanoarchaea," J Bacteriol., Sep. 2000, 182: 5013-5016.
Hugler et al., "Malonyl-coenzyme A reductase from Chloroflexus aurantiacus, a key enzyme of the 3-hydroxypropionate cycle for autotrophic CO(2) fixation," J. Bacteriology, 2002, 184:2404-2410.
Huhn et al., "Identification of the membrane protein SucE and its role in succinate transport in Corynebacterium glutamicum," Appl Microbiol Biotechnol. 2011, 89(2):327-335.
Hunt et al., "Characterization of an acyl-CoA thioesterase that functions as a major regulator of peroxisomal lipid metabolism," J. Biol Chem, 2002, 277:1128-1138.
International Preliminary Report on Patentability for International Application No. PCT/US2012/069934, dated Jun. 17, 2014, 15 pages.
International Preliminary Report on Patentability in International Application No. PCT/US 2012/042777, dated Jan. 10, 2013, 22 pages.
International Preliminary Report on Patentability in International Application No. PCT/US 2012/044984, dated Jan. 28, 2014, 11 pages.
International Preliminary Report on Patentability for International Application No. PCT/US2013/075058, dated Jun. 25, 2015, 11 pages.
International Preliminary Report on Patentability for International Application No. PCT/US2013/075087, dated Jun. 25, 2015, 11 pages.
International Preliminary Report on Patentability for International Application No. PCT/US2013/077445, dated Jul. 9, 2015, 11 pages.
International Preliminary Report on Patentability for International Application No. PCT/US2013/077420, dated Jul. 9, 2015, 14 pages.
International Preliminary Report on Patentability for International Application No. PCT/US2013/077419, dated Jul. 9, 2015, 13 pages.
International Preliminary Report on Patentability for International Application No. PCT/US2013/077430, dated Jul. 9, 2015, 18 pages.
International Preliminary Report on Patentability for International Application No. PCT/US2013/077413, dated Jul. 9, 2015, 13 pages.
International Preliminary Report on Patentability for International Application No. PCT/US2013/077411, dated Jul. 9, 2015, 12 pages.
International Preliminary Report on Patentability for International Application No. PCT/US2013/077423, dated Jul. 9, 2015, 14 pages.
International Search Report and Written Opinion in International Application No. PCT/US2014/052950, dated Dec. 3, 2014, 15 pages.
International Search Report and Written Opinion for International Application No. PCT/US2012/069934, dated Jan. 17, 2014, 21 pages.

(56) References Cited

OTHER PUBLICATIONS

International Search Report and Written Opinion in International Application No. PCT/US2012/042747, dated Jan. 14, 2013, 19 pages.
International Search Report and Written Opinion in International Application No. PCT/US 2012/042777, dated Sep. 11, 2012, 9 pages.
International Search Report and Written Opinion in International Application No. PCT/US 2012/044984, dated Dec. 17, 2013, 17 pages.
International Search Report and Written Opinion in International Application No. PCT/US 2012/071472, dated Dec. 17, 2013, 17 pages.
International Search Report and Written Opinion in International Application No. PCT/US2013/075058, dated Sep. 15, 2014, 17 pages.
International Search Report and Written Opinion in International Application No. PCT/US2013/075087, dated Aug. 4, 2014, 18 pages.
International Search Report and Written Opinion in International Application No. PCT/US2013/077411, dated Sep. 24, 2014, 18 pages.
International Search Report and Written Opinion in International Application No. PCT/US2013/077413, dated Jul. 22, 2014, 20 pages.
International Search Report and Written Opinion in International Application No. PCT/US2013/077419, dated Jun. 16, 2014, 19 pages.
International Search Report and Written Opinion in International Application No. PCT/US2013/077420, dated Jul. 21, 2014, 21 pages.
International Search Report and Written Opinion in International Application No. PCT/US2013/077423, dated Jul. 21, 2014, 22 pages.
International Search Report and Written Opinion in International Application No. PCT/US2013/077430, dated Nov. 10, 2014, 23 pages.
International Search Report and Written Opinion in International Application No. PCT/US2013/077445, dated Sep. 15, 2014, 17 pages.
International Search Report and Written Opinion in International Application No. PCT/US2014/053222, dated Mar. 4, 2015, 18 pages.
International Search Report and Written Opinion in International Application No. PCT/US2015/031227, dated Jul. 31, 2015, 40 pages.
International Search Report and Written Opinion in International Application No. PCT/US2015/036050, dated Aug. 14, 2015, 38 pages.
International Search Report and Written Opinion in International Application No. PCT/US2015/036057, dated Aug. 14, 2015, 74 pages.
Invitation to Pay Additional Fees in International Application No. PCT/US2013/075058, dated Jul. 7, 2014, 7 pages.
Invitation to Pay Additional Fees in International Application No. PCT/US2013/07745, dated Jul. 7, 2014, 9 pages.
Invitation to Pay Additional Fees in International Application No. PCT/US2014/053222, dated Dec. 15, 2014, 8 pages.
Invitation to Pay Fees in International Application No. PCT/US2013/075087, dated May 16, 2014, 9 pages.
Invitation to Pay Fees in International Application No. PCT/US2013/077411, dated Jul. 16, 2014, 9 pages.
Invitation to Pay Fees in International Application No. PCT/US2013/077413, dated May 12, 2014, 9 pages.
Invitation to Pay Fees in International Application No. PCT/US2013/077419, dated Apr. 16, 2014, 9 pages.
Invitation to Pay Fees in International Application No. PCT/US2013/077420, dated May 13, 2014, 9 pages.
Invitation to Pay Fees in International Application No. PCT/US2013/077423, dated May 13, 2014, 10 pages.
Invitation to Pay Fees in International Application No. PCT/US2013/077430, dated Aug. 25, 2014, 9 pages.
Ishige et al., "Wax Ester Production from n-Alkanes by *Acinetobacter* sp. Strain M-1: Ultrastructure of Cellular Inclusions and Role of Acyl Coenzyme A Reductase," Appl. Envtl. Microbilogy, 2002, 68:1192-1195.
Ishikawa et al., "The pathway via D-galacturonate/L-galactonate is significant for ascorbate biosynthesis in Euglena gracilis: identification and functional characterization of aldonolactonase," Journal of Biologiocal Chemistry, 2008, 283:31133-31141.
Iwaki et al., "Cloning and Characterization of a Gene Cluster Involved in Cyclopentanol Metabolism in *Comamonas* sp. Strain NCIMB 9872 and Biotransformations Effected by *Escherichia coli*-Expressed Cyclopentanone 1,2-Monooxygenase," Appl Environ Microbiol., 2002, 68(11):5671-5684, 14 pages.
Iwaki et al., "Identification of a Transcriptional Activator (ChnR) and a 6-Oxohexanoate Dehydrogenase (ChnE) in the Cyclohexanol Catabolic Pathway in *Acinetobacter* sp. Strain NCIMB 9871 and Localization of the Genes That Encode Them," Appl. Environ. Microbiol., 1999, 65(11):5158-5162.
Izumi et al., "Structure and Mechanism of HpcG, a Hydratase in the Homoprotocatechuate Degradation Pathway of *Escherichia coli*," J. Mol. Biol., 2007, 370:899-911.
Izumi et al., "The pimeloyl-CoA synthetase responsible for the first step in biotin biosynthesis by microorganisms," Agr. Biol. Chem., 1974, 38:2257-2262.
Jacob et al., "Glutaconate CoA-transferase from *Acidamiococcus fermentans*: the crystal structure reveals homology with other CoA-transferases," Structure, 1997, 5:415-426.
Jang et al., "Bio-based production of C2-C6 platform chemicals," Biotechnol. & Bioengineering, 2012, 109(10):2437-2459.
Jarboe, "YqhD: a broad-substrate range aldehyde reductase with various applications in production of biorenewable fuels and chemicals," Appl Microbiol Biotechnol., 2011, 89(2):249-257.
Jaremko et al., "The initial metabolic conversion of levulinic acid in Cupriavidus nectar," J. Biotechnol., 2011, 155(3):293-298.
Jeyakanthan et al., "Substrate specificity determinants of the methanogen homoaconitase enzyme: structure and function of the small subunit," Biochemistry, 2010, 49:2687-2696.
Jing et al., "Phylogenetic and experimental characterization of an acyl-ACP thioesterase family reveals significant diversity in enzymatic specificity and activity," BMC Biochemistry, 2011, 12:44, 16 pages.
Joon-Young et al., "Production of 1,2-Propanediol from Glycerol in *Saccharomyces cerevisiae*," J. Microbiology and Biotechnology, May 19, 2011, 21(8):846-853.
Kakugawa et al., "Purification and Characterization of a Lipase from the Glycolipid-Producing Yeast *Kurtzmanomyces* sp I-11," Bioscience Biotechnology Biochemistry, 2002, 66(5): 978-985.
Kato and Asano, "Cloning, nucleotide sequencing, and expression of the 2-methylasparatate ammonia-lyase gene from *Citrobacter amalonaticus* strain YG-1002," Appl. Microbiol Biotechnol, 1998, 50:468-474.
Kaulmann et al., "Substrate spectrum of omega-transaminase from Chromobacterium violaceum DSM30191 and its potential for biocatalysis," Enzyme Microb Technol. 2007, 41:628-637.
KEGG Enzyme 1.2.99.6 (last viewed on Aug. 17, 2015).
KEGG Enzyme 3.1.2.14 (last viewed on Aug. 17, 2015).
Kikuchi et al., "Characterization of a second lysine decarboxylase isolated from *Escherichia coli*," J Bacteriol, 1997, 179(14): 4486-4489.
Kim et al., "Cloning and characterization of a cyclohexanone monooxygenase gene from *Arthrobacter* sp. L661," Biotechnology Bioprocess Engineering, 2008, 13:40-47.
Kim, "Purification and properties of a diamine alpha-ketoglutarate transaminase from *Escherichia coli*," J Biol Chem 1964, 239(3):783-786.
Kitzing et al., "The 1.3 A crystal structure of the flavoprotein YqjM reveals a novel class of Old Yellow Enzymes," J. Biol. Chem., 2005, 280:27904-27913.
Kizer, "Application of Functional Genomics to Pathway Optimization for Increased Isoprenoid Production," Applied and Environmental Microbiology, 2008, 74(10)3229-3241.

(56) References Cited

OTHER PUBLICATIONS

Klatte et al., "Redox self-sufficient whole cell biotransformation for amination of alcohols," Bioorg & Medicinal Chem, May 2014, 22: 5578-5585.
Koch et al., "Products of Enzymatic Reduction of Benzoyl-CoA, A Key Reaction in Anaerobic Aromatic Metabolism," Eur. J. Biochemistry, Jan. 1993, 211(3):649-661.
Koch et al., "In Vivo Evolution of Butane Oxidation by Terminal Alkane Hydroxylases AlkB and CYP153A6," Appl. Environ. Microbiol., 2009, 75(2):337-344.
Kockelkorn and Fuchs, "Malonic semialdehyde reductase, succinic semialdehyde reductase, and succinyl-coenzyme A reductase from Metallosphaera sedula: enzymes of the autotrophic 3-hydroxypropionate/4-hydroxybutyrate cycle in Sulfolobales," J. Bacteriology, 2009, 191:6352-6362.
Kolattukudy, "Enzymatic synthesis of fatty alcohols in *Brassica oleracea*," Archives of Biochemistry and Biophysics, 1971, 142(2):701-709.
Köpke et al., "2,3-Butanediol Production by Acetogenic Bacteria, an Alternative Route to Chemical Synthesis, Using Industrial Waste Gas," Appl Environ Microbiol., 2011, 77(15):5467-5475.
Kulkarni and Kanekar, "Bioremediation of epsilon-caprolactam from nylon-6 waste water by use of Pseudomonas aeruginosa MCM B-407," Curr. Microbiol., 1998, 37:191-194.
Kung et al., "Cyclohexane carboxyl-coenzyme A (CoA) and cyclohex-1-ene-1-carboxyl-CoA dehydrogenases, two enzymes involved in the fermentation of benzoate and crotonate in Syntrophus aciditrophicus," J Bacteriol., 195(14):3193-3200, Epub May 10, 2013.
Lan et al., "Oxygen-tolerant coenzyme A-acylating aldehyde dehydrogenase facilitates efficient photosynthetic n-butanol biosynthesis in cyanobacteria," Energy Environ Sci, 2013, 6:2672-2681.
Larroy et al., "Characterization of the *Saccharomyces cerevisiae* YMR318C (ADH6) gene product as a broad specificity NADPH-dependent alcohol dehydrogenase: relevance in aldehyde reduction," Biochem J., 2002, 361(Pt 1):163-172.
Le Dall et al., "Multiple-copy integration in the yeast *Yarrowia lipolytica*," Current Genetics, 1994 26:38-44.
Lea et al., "Long-chain acyl-CoA dehydrogenase is a key enzyme in the mitochondrial B-oxidation of unsaturated fatty acids," Biochmica et Biophysica Acta, 2000, 1485: 121-128.
Lee and Meighen, "Cysteine-286 as the site of acylation of the LUX-specific fatty acyl-CoA reductase," Biochim Biophys Acta, 1997, 1338:215-222.
Lee et al., "Metabolic Engineering of Pentose Phosphate Pathway in Ralstonia eutropha for Enhanced Biosynthesis of Poly-β-hydroxybutyrate," Biotechnology Progress, 2003, 19(5):1444-1449.
Lee et al., "Synthesis of pure meso-2,3-butanediol from crude glycerol using an engineered metabolic pathway in *Escherichia coli*," Appl Biochem Biotechnol., 2012, 166(7):1801-1813.
Li et al., "Cupriavidus necator JMP 134 rapidly reduces furfural through a Zn-dependent alcohol dehydrogenase," Biodegradation, 2011, 22:1215-1225.
Lim et al., "Amplification of the NADPH-related genes zwf and gnd for the oddball biosynthesis of PHB in an *E. coli* transformant harboring a cloned phbCAB operon," J Bioscience and Bioengineering, 2002, 93(6):543-549.
Lin and Cronan, "Closing in on complete pathways of biotin biosynthesis," Molecular Biosystems, 2011, 7:1811-1821.
Lin et al., "Biotin Sythesis Begins by Hijacking the Fatty Acid Synthetic Pathway," Nature Chem Biol., Sep. 2010, 6:682-688.
Lin et al., "The BioC O-Methyltransferase Catalyzed Methyl Esterification of Malonyl-Acyl Carrier Protein, an Essential Step in Biotin Synthesis," Journal of Biological Chemistry, Sep. 2012, 287(44):37010-37020.
Lin, "Biotin Synthesis in *Escherichia coli*," PhD Dissertation, University of Illinois at Urbana-Champaign, 2012, 140 pages.
Liu and Chen, "Production and characterization of medium-chain-length polyhydroxyalkanoate with high 3-hydroxytetradecanoate monomer content by fadB and fadA knockout mutant of Pseudomonas putida KT2442," Appl. Microbiol. Biotechnol., 2007, 76(5):1153-1159.
Liu et al., "Two novel metal-independent long-chain alkyl alcohol dehydrogenases from Geobacillus thermodenitrificans NG80-2," Microbiology, 2009, 155:2078-2085.
Lopez-Sanchez et al., "Tetralin-Induced and ThnR-Regulated Aldehyde Dehydrogenase and β-Oxidation Genes in Sphingomonas macrogolitabida Strain TFA," Appl. Environ. Microbiol., 2010, 76(1):110-118.
Luo et al., "Production of 3-hydroxypropionic acid through propionaldehyde dehydrogenase PduP mediated biosynthetic pathway in Klebsiella pneumoniae," Bioresource Technology, 2012, 103:1-6.
Lütke-Eversloh & Steinbüchel, "Biochemical and molecular characterization of a succinate semialdehyde dehydrogenase involved in the catabolism of 4-hydroxybutyric acid in Ralstonia eutropha," FEMS Microbiology Letters, 1999, 181(1):63-71.
Mack and Buckel, "Conversion of glutaconate CoA-transferase from Acidaminococcus fermentans into an acyl-CoA hydrolase by site-directed mutagenesis," FEBS Letters, 1997, 405:209-212.
Maeda et al., "Purification and characterization of a biodegradable plastic-degrading enzyme from Aspergillus oryzae," Applied and Environmental Biotechnology, 2005, 67: 778-788.
Mahadik et al., "Production of acidic lipase by Aspergillus niger in solid state fermentation," Process Biochemistry, 2002, 38: 715-721.
Martin and Prather, "High-titer production of monomeric hydroxyvalerates from levulinic acide Pseudomonas putida," J. Biotechnol., 2009, 139: 61-67.
Martinez et al., "Fusarium solani cutinase is a lipolytic enzyme with a catalytic serine accessible to solvent," Nature, 1992, 356:615-618.
Matsumoto et al., "A new pathway for poly(3-hydroxybutyrate) production in *Escherichia coli* and Corynebacterium glutamicum by functional expression of a new acetoacetyl-coenzyme A synthase," Biosci. Biotechnol. Biochem., 2011, 75(2):364-366.
Mawal and Deshmukh, "Alpha-aminoadipate and kynurenine aminotransferase activities from rat kidney. Evidence for separate identity," J. Biol Chem, 1991, 266(4):2573-2575.
McAndrew et al., "Structural basis for substrate fatty acyl chain specificity: crystal structure of human very-long-chain acyl-CoA dehydrogenase," J. Biol. Chem., 2008, 283:9435-9443.
Meijnen et al., "Improved p-hydroxybenzoate production by engineered Pseudomonas putida S12 by using a mixed-substrate feeding strategy," Appl. Microbiol. Biotechnol., 2011, 90:885-893.
Mhetras et al., "Purification and characterization of acidic lipase from Aspergillus niger NCIM 1207," Bioresource Technology, 2009, 100: 1486-1490.
Millar et al., "CUT1, an *Arabidopsis* Gene Required for Cuticular Wax Biosynthesis and Pollen Fertility, Encodes a Very-Long-Chain Fatty Acid Condensing Enzyme," The Plant Cell, May 1999, 11(5):825-838, retrieved on Sep. 30, 2014, http://www.plantcell.org/content/11/5/825.full.
Miyazaki et al., "Alpha-Aminoadipate aminotransferase from an extremely thermophilic bacterium, Thermus thermophilus," Microbiology, 2004, 150(7): 2327-2334.
Mo et al., "Connecting extracellular metabolomic measurements to intracellular flux states in yeast," BMC Systems Biology, 2009, 3(37):1-17.
Mouttaki et al., "Cyclohexane Carboxylate and Benzoate Formation from Crotonate in Sytrophus aciditrophicus," Applied and Environ Microbiology, Feb. 2007, 73(3):930-938.
Murphy et al., "Fusarium polycaprolactone depolymerase is cutinase," Appl. Environm. Microbiol., 1996, 62:456-460.
Mutti et al., "Amination of ketones by employing two new (S)-selective w-transaminases and the His-tagged w-TA from Vibrio fluvialis," Eur. J. Org. Chem, 2012, 1003-1007 (Abstract).
Naggert et al., "Cloning, sequencing, and characterization of *Escherichia coli* thioesterase II," J. Biol. Chem., 1991, 266(17):11044-11050.
Neyfakh, "The Multidrug Efflux Transporter of Bacillus subtilis is a Structural and Functional Homolog of the *Staphylococcus* NorA Protein," Antimicrob Agents Chemother, 1992, 36(2):484-485.

(56) References Cited

OTHER PUBLICATIONS

Ng et al., "Quinolone Resistance Mediated by norA: Physiologic Characterization and Relationship to flqB, a Quinolone Resistance Locus on the *Staphylococcus aureus* Chromosome," Antimicrob Agents Chemother, 1994, 38(6):1345-1355.

Nicol et al., "Bioconversion of crude glycerol by fungi," Applied Microbiology and Biotechnology, Feb. 10, 2012, 93(5):1865-1875.

Nieder and Shapiro, "Physiological function of the Pseudomonas putida PpG6 (Pseudomonas oleovorans) alkane hydroxylase: monoterminal oxidation of alkanes and fatty acids," J. Bacteriol., 1975, 122(1):93-98.

Nishimaki et al., "Studies on the Metabolism of Unsaturated Fatty Acids. XIV.1 Purification and Properties of NADPH-Dependent trans-2-Enoyl-CoA Reductase of *Escherichia coli* K-12," J. Biochem., 1984, 95:1315-1321.

Nomura et al., "Expression of 3-Ketoacyl-Acyl Carrier Protein Reductase (fabG) Genes Enhances Production of Polyhydroxyalkanoate Copolymer from Glucose in Recombinant *Escherichia coli* JM109," Appl. Environ. Microbiol., 2005, 71(8):4297-4306.

Ohashi et al., "Continuous production of lactic acid from molasses by perfusion culture of Lactococcus lactis using a stirred ceramic membrane reactor," J. Bioscience and Bioengineering, 1999, 87(5):647-654.

Okuhara et al., "Formation of Glutaric and Adipic Acids from n-Alkanes with Odd and Even Numbers of Carbons by Candida tropicalis OH23," Agr. Biol. Chem., 1971, 35(9):1376-1380.

Onakunle et al., "The formation and substrate specificity of bacterial lactonases capable of enantioselective resolution of racemic lactones," Enzyme and Microbial Technology, 1997, 21: 245-251.

Oppenheim and Dickerson, "Adipic Acid," Kirk-Othmer Encyclopedia of Chemical Technology, 2003.

Ouchi et al., "Dual roles of a conserved pair, Arg23 and Ser20, in recognition of multiple substrates in alpha-aminoadipate aminotransferase from Thermus thermophilus," Biochem Biophys Res Commun, 2009, 388(1):21-27.

Palosaari and Rogers, "Purification and properties of the inducible coenzyme A-linked butyraldehyde dehydrogenase from Clostridium acetobutylicum," J. Bacteriol., 1988, 170(7):2971-2976.

Papanikolaou et al., "Citric acid production by Yarrowia lipolytica cultivated on olive-mill wastewater-based media," Bioresource Technol., 2008, 99(7):2419-2428.

Parthasarthy et al., "Substrate specificity of 2-hydroxyglutaryl-CoA dehydratase from *Clostiridium symbiosum*: Toward a bio-based production of adipic acid," Biochemistry, 2011, 50:3540-3550.

Pelletier and Harwood et al., "2-Hydroxycyclohexanecarboxyl coenzyme A dehydrogenase, an enzyme characteristic of the anaerobic benzoate degradation pathway used by Rhodopseudomonas palustris," J Bacteriol., 182(10):2753-2760, May 2000.

Pérez-Pantoja et al., "Metabolic reconstruction of aromatic compounds degradation from the genome of the amazing pollutant-degrading bacterium *Cupriavidus necator* JMP134," FEMS Microbiol. Rev., 2008, 32:736-794.

Peterson et al., "The Thermal Stability of the Fusarium solani pisi Cutinase as a Function of pH," BioMed Research International, 2001, 1.2:62-69.

Pignede et al., "Autocloning and Amplification of LIP2 in Yarrowia lipolytica," Appl. Environ. Microbiol, 2000 66:3283-3289.

Pignede et al., "Characterization of an extracellular lipase encoded by LIP2 in Yarrowia lipolytica," Journal of Bacteriology, 2000, 182:2802-2810.

Ploux et al., "Investigation of the first step of biotin biosynthesis in Bacillus sphaericus: Purification and characterization of the pimloyl-CoA synthase, and uptake of pimelate," Biochem J., 1992, 287:685-690.

Prabhu et al., "Lactate and Acrylate Metabolism by Megasphaera elsdenii under Batch and Steady-State Conditions," Applied and Environ. Microbiology, Sep. 2012, 78(24): 8564-8570.

Prather et al., "De novo biosynthetic pathways: rational design of microbial chemical factories," Current Opinion in Biotechnology, 2008, 19:468-474.

Prybylski et al., "Third-generation feed stocks for the clean and sustainable biotechnological production of bulk chemicals: synthesis of 2-hydroxyisobutyric acid," Energy, Sustainability and Society, 2012, 2:11.

Qian et al., "Metabolic engineering of *Escherichia coli* for the production of cadaverine: a five carbon diamine," Biotechnol Bioeng, 2011, 108(1):93-103.

Qiu et al., "Crystal structure and substrate specificity of the β-ketoacyl-acyl carrier protein synthase III (FabH) from *Staphylococcus aureus*," Protein Sci, 2005, 14(8):2087-2094.

Rajashekhara et al., "Propionyl-coenzyme A synthetases of Ralstonia solanacearum and *Salmonella choleraesuis* display atypical kenetics," FEBS Letters, 2004, 556:143-147.

Ramsay et al., "Use of a Nylon Manufacturing Waste as an Industrial Fermentation Substrate," Applied and Environmental Microbiology, 1986, 52(1):152-156.

Ray et al., "Cocrystal structures of diaminopimelate decarboxylase: mechanism, evolution, and inhibition of an antibiotic resistance accessory factor," Structure, 2002, 10(11):1499-1508.

Rea et al., "Structure and Mechanism of HpcH: A Metal Ion Dependent Class II Aldolase from the Homoprotocatechuate Degradation Pathway of *Escherichia coli*," J. Mol. Biol., 2007, 373:866-876.

Reiser and Somerville, "Isolation of mutants of *Acinetobacter calcoaceticus* deficient in wax ester synthesis and complementation of on mutation with gene encoding a fatty acyl coenzyme A reductase," J. Bacteriol., 1997, 179:2969-2975.

Rizzarelli et al., "Evidence for Selective Hydrolysis of Aliphatic Copolyesters Induced by Lipase Catalysis," Biomacromolecules, 2004, 5:433-444.

Rohdich et al., "Enoate reductases of Clostridia. Cloning, sequencing, and expression," J. Biol. Chem., 2001, 276:5779-5787.

Roje, "Vitamin B biosynthesis in plants," Phytochemistry, 2007, 68:1904-1921.

Roujeinikova et al., "Structural studies of fatty acyl-(acyl carrier protein) thioesters reveal a hydrophobic binding cavity that can expand to fit longer substrates," J Mol Biol., 365(1):135-145, Epub Sep. 23, 2006.

Ryu et al., "A novel synthesis of .beta.-trichlorostannyl ketones from siloxycyclopropanes and their facile dehydrostannation affording 2-methylene ketones," JOC, 1986, 51:2389-2391.

Salcher and Lingens, "Regulation of phospho-2-keto-3-deoxyheptonate aldolase (DAHP synthase) and anthranilate synthase of Pseudomonas aureofaciens," J Gen Microbiol., 121(2):473-476, Dec. 1980.

Sambrook et al., Molecular Cloning—a Laboratory Manual, Cold Spring Harbor Laboratory Press, 2001.

Samsonova et al., "Molecular cloning and characterization of *Escherichia coli* K12 ygjG gene," BMC Microbiology, 2003, 3:2.

Sanders et al., "Characterization of the human ω-oxidation pathway for ω-hydroxy-very-long-chain fatty acids," FASEB Journal, 2008, 22(6):2064-2071.

Sanders et al., "Evidence for two enzymatic pathways for ω-oxidation of docosanoic acid in rat liver microsomes," J. Lipid Research, 2005, 46(5):1001-1008.

Satoh et al., "Enzyme-catalyzed poly(3-hydroxybutyrate) synthesis from acetate with CoA recycling and NADPH regeneration in vitro," J Bioscience and Bioengineering, 2003, 95(4):335-341.

Scheller et al., "Generation of the Soluble and Functional Cytosolic Domain of Microsomal Cytochrome P450 52A3," J Biol Chem., 1994, 269(17):12779-12783.

Scheps et al., "Synthesis of omega-hydroxy dodecanoic acid based on an engineered CYP153A fusion construct," Microbial Biotechnology, 2013, 6:694-707.

Schirmer et al., "Microbial Biosynthesis of Alkanes," Science, 2010, 329:559-562.

Schwartz et al., "A proteomic view of the facultatively chemolithoautotrophic lifestyle of Ralstonia eutropha H16," Proteomics, 2009, 9:5132-5142.

(56) References Cited

OTHER PUBLICATIONS

Seedorf et al., "The genome of Clostridium kluyveri, a strict anaerobe with unique metabolic features," Proc. Natl. Acad. Sci. USA, 2008, 105(6):2128-2133.
Shapiro et al., "Remarkable Diversity in the Enzymes Catalyzing the Last Step in Synthesis of the Pimelate Moiety of Biotin," PLoSOne, Nov. 2012, 7(11):e49440, 11 pages.
Shen et al., "Driving Forces Enable High-Titer Anaerobic 1-Butanol Synthesis in *Escherichia coli*," Appl. Environ. Microbiol., 2011, 77(9):2905-2915.
Shikata et al., "A novel ADP-forming succinyl-CoA synthetase in Thermococcus kodakaraensis structurally related to the archaeal nucleoside diphosphate-forming acetyl-CoA synthetases," J. Biol. Chem, 2007, 282(37):26963-26970.
Siegert et al., "Exchanging the substrate specificities of pyruvate decarboxylase from Zymomonas mobilis and benzoylformate decarboxylase from Pseudomonas putida," Port. Eng. Des. Sel., 2005, 18:345-357.
Simon et al., "Chiral Compounds Synthesized by Biocatalytic Reductions [New Synthetic Methods (51)]," Angew Chem Ed Engl., 1985, 24:539-553.
Simon, "Properties and mechanistic aspects of newly found redox enzymes from anaerobes suitable for bioconversions on preparatory scale," Pure and Appl. Chem, 1992, 64:1181-1186.
Slater et al., "Multiple β-Ketothiolases Mediate Poly(β-Hydroxyalkanoate) Copolymer Synthesis in Ralstonia eutropha," J Bacteriol., 1998, 180(8):1979-1987.
Smith et al., "Complete genome sequence of Methanobacterium thermoautotrophicum deltaH: functional analysis and comparative genomics," J Bacteriol., 1997, 179: 7135-7155.
Smith et al., "Structural analysis of ligand binding and catalysis in chorismate lyase," Archives of Biochemistry and Biophysics, Jan. 2006, 445(1):72-80.
Stok et al., "Expression, Purification, and Characterization of BioI: A Carbon-Carbon Bond Cleaving Cytochrome P450 Involved in Biotin Biosynthesis in Bacillus Subtilis," Archives of Biochemistry and Biophysics, Dec. 2000, 384(2):351-360.
Strassner et al., "A homolog of old yellow enzyme in tomato. Spectral properties and substrate specificity of the recombinant protein," J. Biol. Chem. 1999, 274:35067-35073.
Stueckler, "Stereocomplementary bioreduction of alpha,beta-unsaturated dicarboxylic acids and dimethyl esters using enoate reductases: enzyme- and substrate-based stereocontrol," Org. Lett., 2007, 9:5409-5411.
Suzuki et al., "Acetylputrescine deacetylase from Micrococcus luteus K-11," BBA—General Subjects, 1986, 882(1):140-142.
Kobayashi et al., "Antimicrobial Activity of Meropenem Against Main Bacterial Species Isolated from Patient Blood in 2006," Jpn J. Antibiot., 2007, 60(6):378-86 (with English abstract).
Suzuki et al., "GriC and GriD Constitute a Carboxylic Acid Reductase Involved in Grixazone Biosynthesis in Streptomyces griseus," J. Antibiot., 2007, 60(6):380-387.
Tomita et al., "Mechanism for multiple-substrates recognition of alpha-aminoadipate aminotransferase from Thermus thermophilus," Proteins, 2009, 75(2):348-359.
Tseng et al., "Biosynthesis of chiral 3-hydroxyvalerate from single propionate-unrelated carbon sources in metabolically engineered *E. coli*," Microbial Cell Factories, 2010, 9:96.
Uniprot Accession No. I5YEB8, Sep. 5, 2012, 1 page.
U.S. Non-Final Office Action in U.S. Appl. No. 13/524,883, dated Nov. 29, 2013, 13 pages.
U.S. Non-Final Office Action in U.S. Appl. No. 13/715,981, dated Jun. 27, 2014, 23 pages.
U.S. Notice of Allowance in U.S. Appl. No. 13/524,883, dated May 29, 2014, 7 pages.
U.S. Notice of Allowance in U.S. Appl. No. 13/715,981, dated Dec. 16, 2014, 23 pages.
U.S. Notice of Allowance in U.S. Appl. No. 13/715,981, dated Apr. 6, 2015, 10 pages.
U.S. Non-Final Office Action in U.S. Appl. No. 13/715,826, dated Jan. 30, 2015, 24 pages.
U.S. Non-Final Office Action in U.S. Appl. No. 14/106,033, dated Apr. 6, 2015, 37 pages.
U.S. Non-Final Office Action in U.S. Appl. No. 14/138,827, dated Apr. 24, 2015, 35 pages.
U.S. Non-Final Office Action in U.S. Appl. No. 14/138,971, dated Jun. 9, 2015, 44 pages.
U.S. Non-Final Office Action in U.S. Appl. No. 14/138,904, dated Jun. 9, 2015, 50 pages.
U.S. Non-Final Office Action in U.S. Appl. No. 14/490,270, dated Jul. 17, 2015, 49 pages.
U.S. Non-Final Office Action in U.S. Appl. No. 14/130,117, dated Aug. 21, 2015, 49 pages.
U.S. Notice of Allowance in U.S. Appl. No. 14/106,124, dated Dec. 24, 2014, 31 pages.
Vamecq et al., "The microsomal dicarboxylyl-CoA synthetase," Biochem J., 1985, 230:683-693.
Van Beilen and Funhoff, "Expanding the alkane oxygenase toolbox: new enzymes and Applications," Curr. Opin. Biotechnol., 2005, 16:308-314.
Venkitasubramanian et al., "Aldehyde oxidoreductase as a biocatalyst: Reductions of vanillic acid," Enzyme and Microbial Technology, 2008, 42:130-137.
Vioque et al., Resolution and purification of an aldehyde-generating and an alcohol-generating fatty-acyl-CoA reductase from Pea leaves (*Pisum sativum* L), Archives of Biochemistry and Biophysics, 1997, 340(1):64-72.
Vyazmensky et al., "Isolation and Characterization of Subunits of Acetohydroxy Acid Synthase Isozyme III and Reconstruction of the Holoenzyme," Biochemistry, 1996, 35:10339-10346.
Wahlen et al., "Purification, characterization and potential bacterial wax production role of an NADPH-dependent fatty aldehyde reductase from Marinobacter aquaeolei VT8," Appl. Environ Microbiol, 2009, 75:2758-2764.
Wang and Kolattukudy, "Solubilization and purification of aldehyde-generation fatty acyl-CoA reductase from green alga *Botryococcus braunii*," FEBS Letters, 1995, 370:15-18.
Wee et al., "Biotechnological Production of Lactic Acid and Its Recent Applications," Food Technol. Biotechnol., 2006, 44(2):163-172.
Westin et al., "Molecular cloning and characterization of two mouse peroxisome proliferator-activated receptor alpha (PPARalpha)-regulated peroxisomal acyl-CoA thioesterases," J. Biol Chem, 2004, 279:21841-21848.
Westin et al., "The identification of a succinyl-CoA thioesterase suggests a novel pathway for succinate production in peroxisomes," J. Biol Chem, 2005, 280:38125-38132.
White and Kelly, "Purification and Properties of Diaminopimelate Decarboxylase From *Escherichia coli*," Biochem J., 1965, 96:75-84.
White, "A novel biosynthesis of medium chain length alpha-ketodicarboxylic acids in methanogenic archaebacteria," Archivers of Biochemistry and Biophysics, 1989, 270: 691-697.
White, "Biosynthesis of the 7-mercaptoheptanoic acid subunit of component B [(7-mercaptoheptanoyl)threonine phosphate] of methanogenic bacteria," Biochemistry, 1989, 28: 860-865.
White et al., "Carboxylic acid reductase: a new tungsten enzyme catalyses the reduction of non-activated carboxylic acids to aldehydes," Eur. J. Biochem., 1989, 184(1):89-96.
White, "Steps in the conversion of a-ketosuberate to 7-mercaptoheptanoic acid in methanogenic bacteria," Biochemistry, 1989, 28: 9417-9423.
Widmann et al., "Structural classification by the Lipase Engineering Database: a case study of Candida antarctica lipase A," BMC Genomics, 2010, 11:123-130.
Willis et al., "Characterization of a fatty acyl-CoA reductase from *Marinobacter aquaeolei* VT8: a bacterial enzyme catalyzing the reduction of fatty acyl-CoA to fatty alcohol," Biochemistry, 2011, 50:10550-10558.
Wilson and Bouwer, "Biodegradation of aromatic compounds under mixed oxygen/denitrifying conditions: a review," J Ind Microbiol Biotechnol., 18(2-3):116-130, Feb.-Mar. 1997.

(56) References Cited

OTHER PUBLICATIONS

Wischgoll et al., "Structural basis for promoting and preventing decarboxylation in glutaryl-coenzyme, A dehydrogenases," Biochemistry, 2010, 49:5350-5357.
Woolridge et al., "Efflux of the natural polyamine spermidine facilitated by the Bacillus subtilis multidrug transporter Blt," J Biol Chem., 1997, 272(14):8864-8866.
Xiong et al., "A bio-catalytic approach to aliphatic ketones," Sci Rep., 2:311, Epub Mar. 13, 2012.
Yang et al., "Value-added uses for crude glycerol—a byproduct of biodiesel production," Biotechnology for Biofuels, 2012, 5:13.
Yonaha et al., "4-Aminobutyrate : 2-oxoglutarate aminotransferase of *Streptomyces griseus*: Purification and properties," Eur. J. Biochem., 1985, 146:101-106.
Zhang et al., "Expanding metabolism for biosynthesis of non-natural alcohols," Proc Natl Acad Sci U S A., 105(52):20653-20658 Epub Dec. 8, 2008.
Zhao et al., "Prediction and characterization of enzymatic activities guided by sequence similarity and genome neighborhood networks," E-Life, Jun. 2014, 3: 1-32.
Zhuang et al., "Divergence of function in the hot dog fold enzyme superfamily: the bacterial thioesterase YciA," Biochemistry, 2008, 47(9):2789-2796.
Zomorrodi et al., "Improving the iMM904 S. Cerevisiae metabolic model using essentiality and synthetic lethality data," BMC Systems Biology, Dec. 2010, 4(1):1-15.
"Metabolic engineering," Wikipedia, Jun. 8, 2014 (Jun. 8, 2014), XP002744570, Retrieved from the Internet: URL:https://en.wikipedia.org/w/index.php?title=Metabolicengineering&oldid=612026466 [retrieved on Sep. 15, 2015] last paragraph.
Akatsuka et al., "The Serratia marcescens bioH gene encodes an esterase," Gene, Jan. 2003, 302:185-192.
Eriksen et al., "Protein Design for Pathway Engineering," Journal of Structural Biology, Apr. 2013, 185(2):234-242.
Invitation to Pay Fees in International Application No. PCT/US2015/036015, dated Oct. 2, 2015, 9 pages.
Invitation to Pay Fees in International Application No. PCT/US2015/036092, dated Sep. 21, 2015, 8 pages.
Invitation to Pay Fees in International Application No. PCT/US2015/036067, dated Sep. 18, 2015, 12 pages.
Klapa and Stephanopoulos, "Bioreaction Engineering: Modeling and Control," 2000, Springer Verlag, Heidelberg, pp. 106-124.
Moreno-Sanchez et al., "Experimental validation of metabolic pathway modeling—An illustration with glycolytic segments from Entamoeba histolytica," FEBS Journal, Jul. 2008, 275(13):3454-3469.
Palsson, "The challenges of in silico biology," Nature Biotechnology, Nature Publishing Group, US, Nov. 2000, 18(1):1147-1150.
Price et al., "Genome-scale models of microbial cells: evaluating the consequences of constraints," Nature Reviews. Microbiology, Nature Publishing Group, GB, Nov. 2004, 2(11):886-897.
Uniprot Accession No. O32472, Jun. 11, 2014, 2 pages.
Uniprot Accession No. P69909, Jan. 4, 2005, 1 page.
Uniprot Accession No. P0A6RO, May 14, 2014, 5 pages.
Uniprot Accession No. P0A8Z0, Jun. 11, 2014, 3 pages.
Uniprot Accession No. P0AGG2, Jun. 11, 2014, 3 pages.
Uniprot Accession No. P0AEK4, Jun. 11, 2014, 6 pages.
Uniprot Accession No. P0A953, Jun. 11, 2014, 4 pages.
Uniprot Accession No. P0A6Q6, Jun. 11, 2014, 3 pages.
Uniprot Accession No. P0AEK2, May 14, 2014, 4 pages.
Uniprot Accession No. P13001, Jun. 11, 2014, 4 pages.
Uniprot Accession No. Q5EU90, Feb. 19, 2014, 2 pages.
Uniprot Accession No. Q73Q47, May 14, 2014, 2 pages.
Uniprot Accession No. Q818X2, Jun. 11, 2014, 2 pages.
Yadav et al., "The future of metabolic engineering and synthetic biology: Towards a systematic practice," Metabolic Engineering, Feb. 2012, 14(3):233-241.
Adkins, J. et al., "Engineering microbial chemical factories to produce renewable 'biomonomers'," *Front Microbiol.*, 2012, 3:313.
Blombach, B. et al., "Current knowledge on isobutanol production with *Escherichia coli*, Bacillus subtilis and Corynebacterium glutamicum," Bioeng Bugs., 2011, 2(6):346-50.
Bornke, F. et al., "Tailoring plant metabolism for the production of novel polymers and platform chemicals," *Curr Opin Plant Biol.*, 2010, 13(3):354-62.
Chan, S. et al., "Production of succinic acid from sucrose and sugarcane molasses by metabolically engineered *Escherichia coli*," *Bioresour Technol.*, 2012, 103(1):329-36.
Choi, Y.J. et al., "Metabolic engineering of *Escherichia coli* for the production of 1-propanol," *Metab Eng.*, 2012, 14(5):477-86.
Davids, T., et al., "Strategies for the discovery and engineering of enzymes for biocatalysis," *Curr. Opin. Chem. Biol.* 17(2):215-220 (2013.
Jang, YS et al., "Engineering of microorganisms for the production of biofuels and perspectives based on systems metabolic engineering approaches," *Biotechnol Adv.* Sep.-Oct. 2012; 30(5):989-1000. doi: 10.1016/j.biotechadv.2011.08.015. Epub Aug. 25, 2011. Review. PubMed PMID: 21889585.
Kim J. et al, "OptORF: Optimal metabolic and regulatory perturbations for metabolic engineering of microbial strains," *BMC Syst Biol.* Apr. 28, 2010: 4:53. doi: 10.1186/1752-0509-4-53. PubMed PMID: 20426856; PubMed Central PMCID: PMC2887412.
Lee, S. et al., "Heterologous co-expression of accA, fabD, and thioesterase genes for improving long-chain fatty acid production in Pseudomonas aeruginosa and *Escherichia coli*," *Appl Biochem Biotechnol.*, 2012, 167(1):24-38.
Liang, J. et al., "Coordinated induction of multi-gene pathways in *Saccharomyces cerevisiae*," *Nucleic Acids Res.*, 2013;41(4):e54, Epub Dec. 22, 2012.
Marchler-Bauer, A. et al., "CDD: specific functional annotation with the Conserved Domain Database," *Nucleic Acids Res.* 37.suppl 1: D205-D210 (2009).
Nawabi, P. et al., "Engineering *Escherichia coli* for Biodiesel Production Utilizing a Bacterial Fatty Acid Methyltransferase," Applied and Environmental Microbiology. vol. 77. No. 22., Sep. 16, 2011 (Sep. 16, 2011). 10 pages, 8052-8061. XP055111317, ISSN: 0099-2240. DOI: 10.1128/AEM.05046-11.
PCT International Search Report and Written Opinion dated Mar. 7, 2016, issued in International Application No. PCT/US2015/035947 (23 pages).
PCT International Search Report and Written Opinion dated Dec. 12, 2015, issued in International Application No. PCT/US2015/036015 (23 pages).
Rathnasingh, C. et al., "Development and evaluation of efficient recombinant *Escherichia coil* strains for the production of 3-hydroxypropionic acid from glycerol," *Biotechnol Bioeng.*, 2009, 104(4):729-39.
Ranganathan S. et al., "OptForce: an optimization procedure for identifying all genetic manipulations leading to targeted overproductions," *PLoS Comput Biol.* Apr. 15, 2010; 6(4):e1000744. doi: 10.1371/journal.pcbi.1000744. PubMed PMID: 20419153; PubMed Central PMCID: PMC2855329.
Rocha, I. et al., "OptFlux: an open-source software platform for in silico metabolic engineering," *BMC Syst Biol.* Apr. 19, 2010; 4:45. doi: 10.1186/1752-0509-4-45. PubMed PMID: 20403172; PubMed Central PMCID: PMC2864236.
Weeks, A.M. et al., "Constructing de novo biosynthetic pathways for chemical synthesis inside living cells," *Biochemistry.* Jun. 21, 2011; 50(24):5404-18. doi: 10.1021/bi200416g. Epub May 26, 2011. Review. PubMed PMID: 21591680: PubMed Central PMCID: PMC3768262.
Xu, P. et al., "ePathBrick: a synthetic biology platform for engineering metabolic pathways in *E. coli*," *ACS Synth Biol.*, 2012, 1(7):256-66.

\* cited by examiner

FIG. 9A

| SEQ ID NO | Organism | GENBANK reference | Amino acid sequence |
|---|---|---|---|
| 1 | Mycobacterium marinum | ACC41782.1 | MPREIRLPESSVVVRPAPMESATYSQSSRLQAAGLSPAITLFEKAAQTVPLPDAPQPVVI ADYGVATGHNSLKPMMAAINALRRIREDRAIMVAHTDVPDNDFTALFRTLADDPDSYLH HDSASFASAVGRSFYTQILPSNTVSLGWSSWAIQWLSRIPAGAPELTDHVQAYSKDERA RAAYAHQAATDWQDFLAFRGRELCPGGRLVVLTMALDEHGHFGYRPMNDALVAALNDQVR DGLLRPEELRRMAIPVVARAEKDLRAPFAPRGWFEGLTIEQLDVFNAEDRFWAAFQSDGD AESFGAQWAGFARAALFPTLAAALDCGTGDPRATAFIEQLEASVADRLASQPEPMRIPLA SILVLAKRA |
| 2 | Mycobacterium smegmatis | ABK73223.1 | MPKFRVAVDPEPDDPTPKMRAPRPHAAGLNSAIALLEEAARTVPLPEAPYPIVIADYGVG TGRNSMRPIAAAIAALRGRTRPEHSVLVTHTDNADNDFTAVFRGLADNPDSYLRRDTSTY PSAVGRSFYTQILPSKSVHVGWSAWAIVRVGRMPMPVPDHVAASFSGDPQVVAAYARQAA FDWHEFVAFRGRELASGAQLVVLTAALGDDGDFGYRPLFAAVMDTLRELTADGVLRQDEL HRMSLPIVGRRANDFMAPFAPSGRFERLSISHLEVYDAEDVIYSSYQKDRDTDVFGLRWA DFCRFTFFSDLCTALDDDAARCTQFQDRLHAGIAARLSAQPEQMRIPLAQLVLERRRSG |
| 3 | Pseudomonas putida | CAA39234.1 | MLAQLPPALQSLHPLRLKLWDGNQOFDLGPSPQVTILVKEPQLIGQLTHPSMEQLGTAFV EGKLELEGDIGEARVCDELSEALFTDEDEQPPERRSHDKRTDAEAISYHYDVSNAFYQL WLDQDMAYSCAYFREPDNTLDQAQQDKFDHLCRKLRLNAGDYLLDVGCGWGGLARFAARE YDAKVFGITLSKEQLKLGRQRVKAEGLTDKVDLQILDYRDLPQDGRFDKVVSVGMFEHVG HANLALYCQKLFGAVREGGLVMNHGITAKHVDGRPVGRGAGEFIDRYVFPHGELPHL5MI SASICEAGLEVVDVESILRLHYAKTLHHWSENLENQLHKAAALVPEKTLRIWRLYLAGCAY AFEKGWINLHQILAVKPYADGHHDLPWTREDMAYR |
| 4 | Lactobacillus brevis | ABJ63754.1 | MAANEFSETHRVVYEADDTGQLTLAMLINLFVLVSEDQNDALGLSTAFVQSHGVGWVVT QYHLHIDELPRTGAQVTIKTRATAYNRFYAYREVWLLDDAGQVLAYGEGIWVTMSYATRK ITTIPAEVMAPYHSEEQTRLPRLPRPDHFDEAVNQTLKPYTVRYFDIDGNGHVNNAHYFD WMLDVLPATFLRAHHPTDVKIRFENEVQYGHQVTSELSQAAALTTQHMIKVGDLTAVKAT IQWDNR |

FIG. 9B

| SEQ ID NO | Organism | GENBANK reference | Amino acid sequence |
|---|---|---|---|
| 5 | Lactobacillus plantarum | CCC78182.1 | MATLGANASLYSEQHRITYYECDRTGRATLTTLIDIAVLASEDQSDALGLTTEMVQSHGV GWVVTQYAIDITRMPRQDEVVTIAVRGSAYNPYFAYREFWIRDADGQQLAYITSIWVNMS QTTRRIVKILPELVAPYQSEVVKRIPRLPRPISFEATDTTITKPYHVRFFDIDPNRHVNN AHYFDWLVDTLPATFLLQHDLVHVDVRYENEVKYGQTVTAHANILPSEVADQVTTSHLIE VDDEKCCEVTIQWRTLPEPIQ |
| 6 | Escherichia coli | AAC76437.1 | MNNIWWQTKGQGNVHLVLLHGWGLNAEVWRCIDEELSHFTLHLVDLPGFGRSRGFGALS LADMAEAVLQQAPDKAIWLGWSLGGLVASQIALTHPERVQALVTVASSPCFSARDEWPGI KPDVLAGFQQQLSDDFQRTVERFLALQTMGTETARQDARALKKTVLALPMPEVDVLNGGL EILKTVDLRQPLQNVSMPFLRLYGYLDGLVPRKVVPMLDKLWPHSESYIFAKAAHAPFIS HPAEFCHLLVALKQRV |

FIG. 9C

| SEQ ID NO | Organism | GENBANK reference | Amino acid sequence |
|---|---|---|---|
| 7 | *Mycobacterium marinum* | ACC40567.1 | MSPITREERLERRIQDLYANDPQFAAAKPATAITAAIERPGLPLPQIIETVMTGYADRPA<br>LAQRSVEFVTDAGTGHTTLRLLPHFETISYGELWDRISALADVLSTEQTVKPGDRVCLLG<br>FNSVDYATIDMTLARLGAVAVPLQTSAAITQLQPIVAETQPTMIAASVDALADATELALS<br>GQTATRVLVFDHHRQVDAHRAAVESARERLAGSAVVETLAEAIARGDVPRGASAGSAPGT<br>DVSDDSLALLIYTSGSTGAPKGAMYPRRNVATFWRKRTWFEGGYEPSITLNFMPMSHVMG<br>RQILYGTLCNGGTAYFVAKSDLSTLFEDLALVRPTELTFVPRVWDMVFDEFQSEVDRRLV<br>DGADRVALEAQVKAEIRNDVLGGRYTSALTGSAPISDEMKAWVEELLDMHLVEGYGSTEA<br>GMILIDGAIRRPAVLDYKLVDVPDLGYFLTDRPHPRGELLVKTDSLFPGYYQRAEVTADV<br>FDADGFYRTGDIMAEVGPEQFVYLDRRNNVLKLSQGEFVTVSKLEAVFGDSPLVRQIYIY<br>GNSARAYLLAVIVPTQEALDAVPVEELKARLGDSLQEVAKAAGLQSYEIPRDFIIETTPW<br>TLENGLLTGIRKLARPQLKKHYGELLEQIYTDLAHGQADELRSLRQSGADAPVLVTVCRA<br>AAALLGGSASDVQPDAHFTDLGGDSLSALSFTNLLHEIFDIEVPVGVIVSPANDLQALAD<br>YVEAARKPGSSRPTFASVHGASNGQVTEVHAGDLSLDKFIDAATLAEAPRLPAANTQVRT<br>VLLTGATGFLGRYLALEWLERMDLVDGKLICLVRAKSDTEARARLDKTFDSGDPELLAHY<br>RALAGDHLEVLAGDKGEADLGLDRQTWQRLADTVDLIVDPAALVNHVLPYSQLFGPNALG<br>TAELLRLALTSKIKPYSYTSTIGVADQIPPSAFTEDADIRVISATRAVDDSYANGYSNSK<br>WAGEVLLREAHDLCGLPVAVFRCDMILADTTWAGQLNVPDMFTRMILSLAATGIAPGSFY<br>ELAADGARQRAHYDGLPVEFIAEAISTLGAQSQDGFHTYHVMNPYDDGIGLDEFVDWLNE<br>SGCPIQRIADYGDWLQRFETALRALPDRQRHSSLLPLLHNYRQPERPVRGSIAPTDRFRA<br>AVQEAKIGPDKDIPHVGAPIIVKYVSDLRLLGLL |

FIG. 9D

| SEQ ID NO | Organism | GENBANK reference | Amino acid sequence |
|---|---|---|---|
| 8 | Mycobacterium smegmatis | ABK71854.1 | MTSDVHDATDGVTETALDDEQSTRRIAELVATDPEFAAAAPLPAVVDAAHKPGLRLAEIL QTLFTGYGDRPALGYRARELATDEGGRTVTFRLLPRFDTLTYAQVWSRVQAVAAALRHNFA QPIYPGDAVATIGFASPDYLTLDLVCAYLGLVSVPLQHNAPVSRLAPILAEVEPRILTVS AEYLDLAVESVRDVNSVSQLVVFDHHPEVDDHRDALAREQLAGKGIAVTTLDAIADEG AGLPAEPIYTADHDQRLAMILYTSGSTGAPKGAMYTEAMVARLWTMSFITGDPTPVINVN FMPLNHLGGRIPISTAVQNGGTSYFVPESDMSTLFEDLALVRPTELGLVPRVADMLYQHH LATVDRLVTQGADELTAEKQAGAELREQVIGGRVITGFVSTAPLAAEMRAFLDITLGAHI VDGYGLTETGAVTRDGVIVRPPVIDYKLIDVPELGYFSTDKPYPRGELLVRSQTLTPGYY KRPEVTASVFDRDGYYHTGDVMAETAPDHLVYVDRRNNVLKLAQGEFVAVANLEAVFSGA ALVRQIFVVGNSERSFLLAVVPTPEALEQYDPAALKAALADSLQRTARDAELQSYEVPA DFIVETEPFSAANGLLSGVGKLLRPNLKDRYGQRLEQMYADIAATQANQLRELRRAAATQ PVIDTLTQAAATILGTGSEVASDAHFTDLGGDSLSALTLSNLLSDFFGFEVPVGTIVNPA TNLAQLAQHIEAQRTAGDRRPSFTTVHGADATEIRASELTLDKFIDAETLRAAPGLPKVT TEPRTVLLSGANGWLGRFLTLQWLERLAPVGGTLITIVRGRDDAAARARLTQAYDTDPEL SRRFAELADRHLRVVAGDIGDPNLGLTPEIWHRLAAEVDLVVHPAALVNHVLPYRQLFGP NVVGTAEVIKLALTERIKPVTYLSTVSVAMGIPDFEEDGDIRTVSPVRPLDGGYANGYGN SKWAGEVLLREAHDLCGLPVATFRSDMILAHPRYRGQVNVPDMFTRLLLSLLITGVAPRS FYIGDGERPRAHYPGLTVDFVAEAVTTLGAQQREGVSYDVMNPHDDGISLDVFVDWLIR AGHPIDRVDDYDYDDWVRRFETALTALPEKRRAQTVLPLLHAFRAPQAPLRGAPEPTEVFHA AVRTAKVGPGDIPHLDEALIDKYIRDLREFGLI |

FIG. 9E

| SEQ ID NO | Organism | GENBANK reference | Amino acid sequence |
|---|---|---|---|
| 9 | Segniliparus rugosus | EFV11917.1 | MGDGEERAKRFFQRIGELSATDPQFAAAAPDPAVVEAVSDPSLSFTRYLDTLMRGYAERP ALAHRVGAGYETISYGELWARVGAIAAAWQADGLAPGDFVATVGFTSPDYVAVDLAAARS GLVSVPLQAGASLAQLVGILEETEPKVLAASASSLEGAVACALAAPSVQRLVVFDLRGPD ASESAADERRGALADAEEQLARAGRAVVVETLADLAARGEALPEAPLFEPAEGEDPLALL IYTSGSTGAPKGAMYSQRLVSQLWGRTPVVPGMPNISLHYMPLSHSYGRAVLAGALSAGG TAHFTANSDLSTLFEDIALARPTFLALVPRVCEMLFQESQRGQDVAELRERVLGGRLLVA VCGSAPLSPEMRAFMEEVLGFPLLDGYGSTEALGVMRNGIIQRPPVIDYKLVDVPELGYR TTDKPYPRGELCIRSTSLISGYYKRPEITAEVFDAQGYYKTGDVMIAEIAPDHLVYVDRSK NVLKLSQGEFVAVAKLEAAYGTSPYVKQIFVYGNSERSFLLAVVVPNAEVLGARDQEEAK PLIAASLQKIAKEAGLQSYEVPRDFLIETEPFTTQNGLLSEVGKLLRPKLKARYGEALEA RYDEIAHGQADELRALRDGAGQRPVVETVVRAAVAISGSEGAEVGPEANFADLGGDSLSA LSLANLLHDVFEVEVPVRIIIGPTASLAGIAKHIEAERAGASAPTAASVHGAGATRIRAS ELTLEKFLPEDLLAAAKGLPAADQVRTVLLTGANGWLGRFLALEQLERLARSGQDGGKLI CLVRGKDAAAARRRIEETLGTDPALAARFAELAEGRLEVVPGDVGEPKFGLDDAAWDRLA EEVDVIVHPAALVNHVLPYHQLFGPNVVGTAEIIRLAITAKRKPVTYLSTVAVAAGVEPS SFEEDGDIRAVVPERPLGDGYANGYGNSKWAGEVLLREAHELVGLPVAVFRSDMILAHTR YTFGQLNVPDQFTRLVLSLLATGIAPKSFYQQGAAGERQRAHYDGIPVDFTAEAITTLGAE PSWFDGGAGFRSFDVFNPHHDGVGLDEFVDWLIEAGHPISRIDDHKEWFARFETAVRGLP EAQRQHSLLPLLRAYSFPHPVDGSVYPTGKFQGAVKAAQVGSDHDVPHLGKALIVKYAD DLKALGLL |

FIG. 9F

| SEQ ID NO | Organism | GENBANK reference | Amino acid sequence |
|---|---|---|---|
| 10 | Mycobacterium smegmatis | ABK75684.1 | MTIETREDRFNRRIDHLFETDPQFAAARPDEAISAAAADPELRLPAAVKQILAGYADRPA LGKRAVEFVTDEEGRTTAKLLPRFDTITYRQLAGRIQAVTNAWHNHPVNAGDRVAILGFT SVDYTTIDIALLELGAVSVPLQTSAPVAQLQPIVAETEPKVIASSVDFLADAVALVESGP APSRLVVFDYSHEVDDQREAFEAAKGKLAGTGVVVETITDALDRGRSLADAPLYVPDEAD PLTLLIYTSGSTGTPKGAMYPESKTATMWQAGSKARWDETLGVMPSITLNFMPMSHVMGR GILCSTLASGGTAYFAARSDLSTFLEDLALVRPTQLNFVPRIWDMLFQEYQSRLDNRRAE GSEDRAEAAVLEEVRTQLLGGRFVSALTGSAPISAEMKSWVEDLLDMHLLEGYGSTEAGA VFIDGQIQRPPVIDYKLVDVPDLGYFATDRPVPRGELLVKSEQMFPGYYKRPEITAEMFD EDGYYRTGDIVAELGPDHLEYLDRRMNVLKLSQGEFVTVSKLEAVFGDSPLVRQIYVYGN SARSYLLAVVPTEEALSRWDGDELKSRISDSLQDAARAAGLQSYEIPRDFLVETTPFTL ENGLLTGIRKLARPKLKAHYGERLEQLYTDLAEGQANELRELRRNGADRPVVETVSRAAV ALLGASVTDLRSDAHFTDLGGDSLSALSFSNLLHEIFDVDVPVGVIVSPATDLAGVAAYI EGELRGSKRPTYASVHGRDATEVRARDLALGKFIDAKTLSAAPGLPRSGTEIRTVLLTGA TGFLGRYLALEWLERMDLVDGKVICLVRARSDDEARARLDATFDTGDATLLEHYRALAAD HLEVIAGDKGEADLGLDHDTWQRLADTVDLIVDPAALVNHVLPYSQMFGPNALGTAELIR IALTTIKPYVYVSTIGVGQGISPEAFVEDADIREISATRRVDDSYANGYGNSKWAGEVL LREAHDWCGLPVSVFRCDMILADTTYSGQLNLPDMFTRIMLSLVATGIAPGSFYELDADG NRQRAHYDGLPVEFIAEAISTIGSQVTDGFETHVMNPYDDGIGLDEYVDWLIEAGYPVH RVDDYATWLSRFETALRALPERQRQASILPLLHNYQQPSPPVCGAMAPTDRFRAAVQQAK IGPDKDIPHVTADVIVKYISNLQMLGLL |

FIG. 9G

| SEQ ID NO | Organism | GENBANK reference | Amino acid sequence |
|---|---|---|---|
| 11 | Mycobacterium massiliense | EIV11143.1 | MTNETNPQQEQLSRRIESLRESDPQFRAAQPDPAVAEQVLRPGLHLSEAIAALMTGYAER PALGERARELVIDQDGRTTLRLLPRFDTTTYGELWSRTTSVAAAWHHDATHPVKAGDLVA TLGFTSIDYTVLDLAIMILGGVAVPLQTSAPASQWTTILAEAEPNTLAVSIELIGAAMES VRATPSIKQVVVFDYTPEVDQREAFEAASTQLAGTGIALETLDAVIARGAALPAAPLYA PSAGDDPLALLIYTSGSTGAPKGAMHSENIVRRWWIREDVMAGTENLPMIGLNFMPMSHH MGRGTLTSTLSTGGTGYFAASSDMSTLFEDMELIRPTALALVPRVCDMVFQRFQTEVDRR LASGDTASAEAVAAEVKADIRDNLFGGRVSAVMVGSAPLSEELGEFIESCFEILNLTDGYG STEAGMVFRDGIVQRPPVIDYKLVDPELGYFSTDKPHPRGELLLKTDGMFLGYYKRPEV TASVFDADGFYMTGDIVAELAHDNIEHDRRNNVLKLSQGEFVAVATLEAEYANSPVVHQ IYVYGSSERSYLLAVVVPTPEAVAAAKGDAAALKTTIADSLQDIAKEIQLQSYEVPRDFI IEPQPFTQGNGLLTGIAKLARPNLKAHYGPRLEQMYAEIAEQQAAELRALHGVDPDKPAL ETVLKAAQALLGVSSAELAADAHFTDLGGDSLSALSFSDLLRDIFAVEVPVGVIVSAAND LGGVAKFVDEQRHSGGTRPTAETVHGAGHTEIRAADLTLDKFIDEATLHAAPSLPKAAGI PHTVLLTGSNGYLGHYLALEWLERLDKTDGKLIVIVRGKNAEAAYGRLEEAFDTGDTELL AHFRSLADKHLEVLAGDIGDPNLGLDADTWQRLADTVDVIVHPAALVNHVLPYNQLFGPN VVGTAEIIKLAITTKIKPVTYLSTVAVAAYVDPTTFDEESDIRLISAVRPIDDGYANGYG NAKWAGEVLLREAHDLCGLPVAVFRSDMILAHSRYTGQLNVPDQFTRLILSLIATGIAPG SFYQAQTTGERPLAHYDGLPGDFTAEAITTLGTQVPEGSEGFVTYDCVNPHADGISLDNF VDWLIEAGYPIARIDNYTEWFTRFDTAIRGLSEKQKQHSLLPLLHAFEQPSAAENHGVVP AKRFQHAVQAAGIGPVGQDGTTDIPHLSRRLIVKYAKDLEQLGLL |

FIG. 9H

| SEQ ID NO | Organism | GENBANK reference | Amino acid sequence |
|---|---|---|---|
| 12 | Segniliparus rotundus | ADG98140.1 | MTQSHTQGPQASAAHSRLARRAAELLATDPQAAATLPDPEVVRQATRPGLRLAERVDAIL SGYADRPALGQRSFQTVKDPITGRSSVELLPTFDTITYRELRERATAIASDLAHHPQAPA KPGDFLASIGFISVDYVVAIDIAGVFAGLTAVPLQTGATLATLTAITAETAPTLFAASIEH LPTAVDAVLATPSVRRLLVFDYRAGSDEDREAVEAAKRKIADAGSSVLVDVLDEVIARGK SAPKAPLPPATDAGDDSLSLLIYTSGSTGTPKGAMYPERNVAHFWGGVWAAAFDEDAAPP VPAINITFLPLSHVASRLSLMPTLARGGLMHFVAKSDLSTLFEDLKLARPTNLFLVPRVV EMLYQHYQSELDRRGVQDGTREAEAVKDDLRTGLLGGRILTAGFGSAPLSAELAGFIESL LQIHLVDGYGSTEAGPVWRDGYLVKPPVTDYKLIDVPELGYFSTDSPHPRGELAIKTQTI LPGYYKRPETTAEVFDEDGFYLTGDVVAQIGPEQFAYVDRRKNVLKLSQGEFVTLAKLEA AYSSSPLVRQLFVVGSSERSYLLAVIVPTPDALKFGVGEAAKAALGESLQKIARDEGLQ SYEVPRDFIIETDPFTVENGLLSDARKSLRPKLKEHYGERLEAMYKELADGQANELRDIR RGVQQRPTLETVRRAAAAMLGASAAEIKPDAHFTDLGGDSLSALTFSNFLHDLFEVDVPV GVIVSAANTLGSVAEHIDAQLAGGRARPTFATVHGKGSTTIKASDLTLDKFIDEQTLEAA KHLPKPADPPRTVLLTGANGWLGRFLAEWLERLAPAGGKLITVRGKDAAQAKARLDAA YESGDPKLAGHYQDLAATTLEVLAGDFSEPRLGLDEATWNRLADEVDFISHPGALVNHVL PYNQLFGPNVAGVAEIIKLAITTRIKPVTYLSTVAVAAGVEPSALDEDGDIRTVSAERSV DEGYANGYGNSKWGGEVLLREAHDRTGLPVRVFRSDMILAHQKYTGQVNATDQFTRLVQS LLATGLAPKSFYELDAQGNRQRAHYDGIPVDFTAESITLGGDGLEGYRSYNVFNPHRDG VGLDEFVDWLIEAGHPITRIDDYDQWLSRFETSLRGLPESKRQASVLPLLHAFARPGPAV DGSPFRNTVFRTDVQKAKIGAEHDIPHLGKALVLKYADDIKQLGLL |

FIG. 9I

| SEQ ID NO | Organism | GENBANK reference | Amino acid sequence |
|---|---|---|---|
| 13 | Chromobacterium violaceum | AAQ59697.1 | MQKQRTTSQWRELDAAHHLHPFTDTASLNQAGARVMTRGEGVYLWDSEGNKILDGMAGLW CVNVGYGRKDFAEAARRQMEELPFYNTFFKTTHPAVVELSSLLAEVTPAGFDRVFYTNSG SESVDTMIRMVRRYWDVQGKPEKKTLIGRWNGYHGSTIGGASLGGMKYMHEQGDLPIPGM AHIEQPWWYKHGKDMTPDEFGVVAARWLEEKILEIGADKVAAFVGEPIQGAGGVIVPPAT YWPEIERICRKYDVLLVADEVICGFGRTGEWFGHQHFGFQPDLFTAAKGLSSGYLPIGAV FVGKRVAEGLIAGGDFNHGFTYSGHPVCAAVAHANVAALRDEGIVQRVKDDIGPYMQKRW RETFSRFEHVDDVRGVGMVQAFTLVKNKAKRELFPDFGEIGTLCRDIFFRNNLIMRACGD HIVSAPPLVMTRAEVDEMLAVAERCLEEFEQTLKARGLA |
| 14 | Pseudomonas aeruginosa | AAG08191.1 | MNARLHATSPLGDADLVRADQAHYMHGYHVFDDHRVNGSLNIAAGDGAYIYDTAGNRYLD AVGGMWCTNIGLGREEMARTVAEQTRLLAYSNPFCDMANPRAIELCRKLAELAPGDLDHV FLTTGGSTAVDTAIRLMHYYQNCRGKRAKKHVITRINAYHGSTFLGMSLGGKSADRPAEF DFLDERIHHLACPYYYRAPEGLGEAEFLDGLVDEFERKILELGADRVGAFISEPVFGSGG VIVPPAGYHRRMWELCQRYDVLYISDEVVTSFGRLGHFFASQAVFGVQPDILLTAKGLTS GYQPLGACIFSRRIWEVIAEPDKGRCFSHGFTYSGHPVACAAALKNEIEREGLLAHAD EVGRYFEERLQSLRDLPIVGDVRGMRFMACVEFVADKASKALFPESLNIGEWVHLRAQKR GLLVRPIVHLNVMSPPLILTREQVDTVVRVLRESIEETVEDLVRAGHR |
| 15 | Pseudomonas syringae | AAY39893.1 | MSANNPQITLEWQALSSEHHLAPFSDYKCLKEKGPRIHTRAEGVYLWDSEGNKILDGMSGL WCVAIGYGREELADAASKQMRELPYYNLFFCQTAHPPVLELAKAISDIAPEGMNHVFFTGS GSEGNDTMLRMVRHYWALKGQPNKKTIISRVNGYHGSTVAGASLGGMTYMHEQGDLPIPG VVHIPQPYWFGEGGDMTPDEFGIWAAEQLEKKILELGVENVGAFIAEPIQGAGGVIVPPD SYWPKIKEILSRYDILFAADEVICGFGRTSEWFGSDFYGLRPDMMTIAKGLTSGYVPMGG LIVRDEIVAVLNEGGDFNHGFTYSGHPVAAAVALENIRILREEKIVERVRSETAPYLQKR LRELSDHPLVGEVRGVGLLGAIELVKDKTTRERYTDKGAGMICRTFCFDNGLIMRAVGDT MIIAPPLVISFAQIDELVEKARTCLDLTLAVLQG |

FIG. 9J

| SEQ ID NO | Organism | GENBANK reference | Amino acid sequence |
|---|---|---|---|
| 16 | Rhodobacter sphaeroides | ABA81135.1 | MTRNDATNAAGAVGAAMRDHILLPAQEMAKLGKSAQPVLTHAEGIVHTEDGRRLIDGPA GMWCAQVGYGRREIVDAMAHQAMVLPYASPWYMATSPAARLAEKIATLTPGDLNRIFFTT GGSTAVDSALRFSEFYNNVLGRPQKKRIIVRYDGYHGSTALTAACTGRTGNWPNFDIAQD RISFLSSPNPRHAGNRSQEAFLDDLVQEFEDRIESLGPDTIAAFLAEPILASGVIIPPA GYHARFKAICEKHDILYISDEVVTGFGRCGEWFASEKVFGVVPDIITFAKGVTSGYVPLG GLAISEAVLARISGENAKGSWFTNGYTYSNQPVACAAALANIELMEREGIVDQAREMADY FAAALASLRDLPGVAETRSVGLVGCVQCLLDPTRADGTAEDKAFTLKIDERCFELGLIVR PLGDLCVISPPLIISRAQIDEMVAIMRQAITEVSAAHGLTAKEPAAV |
| 17 | Escherichia coli | AAA57874.1 | MNRLPSSASALACSAHALNLIEKRTLDHEEMKALNREVIEYFKEHVNPGFLEYRKSVTAG GDYGAVEWCQAGSLNTLVDTQGQEFIDCLGGFGIFNVGHRNPVVVSAVQNQLAKQPLHSQE LLDPLRAMLAKTLAALTPGKLKYSFFCNSGTESVEAALKLAKAYQSPRGKFTFIATSGAF HGKSLGALSATAKSTFRKPFMPLLPGFRHVPFGNIEAMRTALNECKKTGDDVAAVILEPI QGEGGVILPPPGYLTAVRKLCDEFGALMILDEVQTGMGRTGKMFACEHENVQPDILCLAK ALGGGVMPIGATIATEVFSVLFDNPFLHTTTFGGNPLACAAALATINVLLEQNLPAQAE QKGDMLLDGFRQLAREYPDLVQEARGKGMLMAIEFVDNEIGYNFASEMFRQRVLVAGTLN NAKTIRIEPPLTLTIEQCELVIKAARKALAAMRVSVEEA |
| 18 | Vibrio Fluvialis | AEA39183.1 | MNKPQSWEARAETYSLYGFTDMPSLHQRGTVVTHGEGPYIVDVNGRRYLDANSGLWNMV AGFDHKGLIDAAKAQYERFPGYHAFFGRMSDQTVMLSEKLVEVSPFDSGRVFYTNSGSEA NDTMVKMLWFLHAAEGKPQKRKILTRWNAYHGVTAVSASMTGKPYNSVFGLPLPGFVHLT CPHYWRYGEEGETTEEQFVARLARELEETIQREGADTIAGFFAEPVMGAGGVIPPAKGYFQ AILPILRKYDIPVISDEVICGFGRTGNTWGCVTVDFTPDAIISSKNLTAGFFPMGAVILG PELSKRLETAIEAIEEPPHGFTASGHPVGCAIALKAIDVVMNEGLAENVRRLAPRFEERL KHIAERPNIGEYRGIGFMWALEAVKDKASKTPFDGNLSVSERIANTCTDLGLICRPLGQS VVLCPPFILTEAQMDEMFDKLEKALDKVFAEVA |

FIG. 9K

| SEQ ID NO | Organism | GENBANK reference | Amino acid sequence |
|---|---|---|---|
| 19 | Bacillus subtilis | CAA44858.1 | MKIYGIYMDRPLSQEENERFMSFISPEKREKCRRFYHKEDAHRTLLGDVLVRSVISRQYQ LDKSDIRFSTQEYGKPCIPDLPDAHFNISHSGRWVICAFDSQPIGIDIEKTKPISLEIAK RFFSKTEYSDLLAKDKDEQTDYFYHLWSMKESHKQEGKGLSLPLDSFSVRLHQDGQVSI ELPDSHSPCYIKTYEVDPGYKMAVCAAHPDFPEDITMVSYEELL |
| 20 | Nocardia sp. NRRL 5646 | ABI83656.1 | MIETILPAGVESAELLEYPEDLKAHPAEEHLIAKSVEKRRRDFIGARHCARLALAELGEP PVAIGKGERGAPIWPRGVVGSLTHCDGYRAAAVAHKMRFRSIGIDAEPHATLPEGVLDSV SLPPEREWLKTTDSALHLDRLLFCAKEATYKAWWPLTARWLGEEAAHITFEIEDGSADSG NGTFHSELLVPGQTNDGGTPLLSFDGRWLIADGFILTAIAYA |
| 21 | Escherichia coli | AAA24665.1 | MSQALKNLLTLLNLEKIEEGLFRGQSEDLGLRQVFGGQVVGQALYAAKETVPEERLVHSF HSYFLRPGDSKKPIIYDVETLRDGNSFSARRVAAIQNGKPIFYMTASFQAPEAGFEHQKT MPSAPAPDGLPSETQIAQSLAHLLPPVLKDKFICDRPLEVRPVEFHNPLKGHVAEPHRQV WIRANGSVPDDLRVHQYLLGYASDLNFLPVALQPHGIGFLEPGIQIATIDHSMWFHRPFN LNEWLLYSVESTSASSARGFVRGEFYTQDGVLVASTVQEGVMRHHN |
| 22 | Escherichia coli | CAA50321.1 | MKKVWLNRYPADVPTEINPDRYQSILVDMFEQSVARYADQPAFVNMGEVMTFRKLEERSRA FAAYLQQGLIGLKKGDRVALMMPNLLQYPVALFGILRAGMIVVNVNPLYTPRELEHQLNDS GASAIVIVSNFAHTLEKVVDKTAVQHVILTRMGDQLSTAKGTVVNFVVKYIKRLVPKYHL PDAISFRSALHNGYRMQYVKPELVPEDLAFLQYTGGTTGVAKGAMLTHRNMLANLEQVNA TYGPLLHPGKELVVTALPLYHIFALTINCLLFIELGGQNLLITNPRDIPGLVKELAKYPF TAITGVNTLFNALLNNKEFQQLDFSSLHLSAGGGMPVQQVVAERWVKLTGQYLLEGYGLT ECAPLVSVNPYDIDYHSGSIGLPVPSTEAKLVDDDDNEVPPGQPGELCVKGPQVMLGYWQ RPDATDEIIKNGWLHTGDIAVMDEEGFLRIVDRKKDMILVSGFNVYPNEIEDVVMCHPGV QEVAAVGVPSGSSGEAVKIFVVKKDPSLTEESLVTFCRRQLTGYKVPKLVEFRDELPKSN VGKILRRELRDEARGKVDNKA |

FIG. 9L

| SEQ ID NO | Organism | GENBANK reference | Amino acid sequence |
|---|---|---|---|
| 23 | Cupriavidus necator | CAJ95550.1 | MHPHHAQRTPEKPAVIMGGSGAVVTYRELDERSNQVAHLFRSQGLQPGDRVAFMVENHP RLFELCWGAQRSGIVYVCLSTRLNVADAAHINDSGARILVTTHAQAEVAAALAGQTPAL RGRLMLDGTMPGYDAYETALARCPATRIDDEVTGGDMLYSSGTTGRPKGVYAPPSSPNID DPTTLTSLCQRLYGFDAETRYLSPAPLYHAAPLRYNMTVQALGGTAVVMEHFDAEHYLQL VQQHRITHTQLVPTMFSRMLKLPEAQRQAYDVSSLRVAIHAAAPCPVQVKEAMIAWWGPV IWEYYAGTEGNGVTVVSTPEWLERKGTVGRAMVGKLRICGPDGALLPPGESGTIYFAEGR DFSYHNDEAKTAESRHPQQPDWSTIGDVGYVDADGYLYLTDRKANMIISGGVNIYPQEAE NLLMTHPKVMDVAVIGVPNEDFGEEVKAVVQPVDMSQAGPELAAELIAFCRANLSAIKCP RSVDFASELPRLPTGKLLKRLLRDRYWGGHANKLV |
| 24 | Acidaminococcus fermentans | CAA57199.1 | MSKVMTLKDAIAKYVHSGDHIALGGFTTDRKPYAAVFEILRQGITDLTGLGGAAGGDWDM LIGNGRVKAYINCYTANSGVTNVSRRFRKWFEAGKLTMEDYSQDVIYMMWHAAALGLPFL PVTLMQGSGLTDEWGISKEVRKTLDKVPDDKFKYIDNPFKPGEKVVAVPVPQVDVAIIHA CQASPDGTVRIWGGKFQDVDIAEAAKYTIVTCEEIISDEEIRRDPTKNDIPGMCVDAVVL APYGAHPSQCYGLYDYDNPFLKVYDKVSKTQEDFDAFCKEWVFDLKDHDEYLNKLGATRL INLKVVPGLGYHIDMTKEDK |
| 25 | Acidaminococcus fermentans | CAA57200.1 | MADYTNYTNKEMQAVTIAKQIKNGQVVTVGTGLPLIGASVAKRVYAPDCHIIVESGLMDC SPVEVPRSVGDLRFMAHCCGCIWPNVRFVGFEINEYLHKANRLIAFIGGAQIDPYGNVNST SIGDYHHPKTRFTGSGGANGIATYSNTIIMMQHEKRRFMNKIDYVTSPGWIDGPGGRERL GLPGDVGPQLVVTDKGILKFDEKTKRMYLAAYYPTSSPEDVLENTGFDLDVSKAVELEAP DPAVIKLIREEIDPGQAFIQVPTEAK |
| 26 | Treponema denticola | AAS11092.1 | MIVKPMVRNNICLNAHPQGCKKGVEDQIEYTKKRITAEVKAGAKAPKNVLVLGCSNGYGL ASRITAAFGYGAATIGVSFEKAGSETKYGTPGWYNNLAFDEAAKREGLYSVTIDGDAFSD EIKAQVIEEAKKKGIKFDLIVYSLASPVRTDPDTGIMHKSVLKPFGKTFTGKTVDPFTGE LKEISAEPANDEEAAATVKVMGGEDWERWIKQLSKEGLLEEGCITLAYSIGPEATQALY RKGTIGKAKEHLEATAHRLNKENPSIRAFVSVNKGLVTRASAVIPVIPLYLASLFKVMKE KGNHEGCIEQITRLYAERLYRKDGTIPVDEENRIRIDDWELEEDVQKAVSALMEKVTGEN AESLTDLAGYRHDFLASNGFDVEGINYEAEVERFDRI |

FIG. 9M

| SEQ ID NO | Organism | GENBANK reference | Amino acid sequence |
|---|---|---|---|
| 27 | Euglena gracilis | AAW66853.1 | MSCPASPSAAVVSAGALCLCVATVLLATGSNPTALSTASTRSPTSLVRGVDRGLMRPTTA AALTTMREVPQMAEGFSGEATSAWAAAGPQWAAPLVAAASSALALWWWAARRSVRRPLAA LAELPTAVTHLAPPMIAMFTTTAKVIQPKIRGFICTTTHPIGCEKRVQEEIAYARAHPPTS PGPKRVLVIGCSTGYGLSTRITAAFGYQAATLGVFLAGPPTKGRPAAAGWYNTVAFEKAA LEAGLYARSLNGDAFDSTTKARTVEAIKRDLGTVDLVVYSIAAPKRTDPATGVLHKACLK PIGATYTNRTVNTDKAEVTDVSIEPASPEEIADTVKVMGGEDWELWIQALSEAGVLAEGA KTVAYSYIGPEMTWPVYWSGTIGEAKKDVEKAAKRITQQYGCPAYPVVAKALVTQASSAI PVVPLYICLLYRVMKEKGTHEGCIEQMVRLLTTKLYPENGAPIVDEAGRVRVDDWEMAED VQQAVKDLWSQVSTANLKDISDFAGYQITEFLRLFGFGIDGVDYDQPVDVEADLPSAAQQ |
| 28 | Pseudomonas reinekei MT1 | ACZ63623.1 | MKNALIVSPLRTPIGKFGGALAPLTAEHLASFMISQVMARTGVPGHSLDEVIVAQSYASS EAPCIGRYAALSAGLPVEVPGYTLDRRCGSGLQAVIDASMMVKTGNAEAVLVVGVESMSN IEYYSTDMRWGARAGSVRFHDRLERGRERSQPSERFGHISGMPETADNLALDYGISREEA DSFSVRSHQNAAAAWREGRFADEVVAVDVPGKRGAVTRVTIDEGIREDASLESMKALRLI RPEGVCTAGNSSQONDAAAGCLVVSPEYAARHGLTPMARLVDWAAAGCEPSRMGIGPVPA TQKLLMRTGLSLAELDLIELNEAFAAQALAVLKTWGLDDLSRVNVNGSGISLGHPIGATG VRINMTLLHEMRRREARYGLETMCIGGGQGLAALFERV |
| 29 | Pseudomonas putida | AAA85138.1 | MRDVFICDAIRTPIGRFGGALAGVRADDLAAVPLKALIEPNPAVQWDQVDEVFFGCANQA GEDNRRVARMALLLAGLPESIPGVTLNRLCASGMDAIGTAFRAIASGEMELAIAGGVESM SRAPFVMGKAESGYSRNMKLEDTTIGWRFINPLMKSQYGVDSMPETADNVADDYQVSRAD QDAFALRSQQKAAAAQAAGFFAEEIVPVRIAHKKGETIVERDEHLRPETTLEALTKLKPV NGPDKTVTAGNASGVNDGAAALILASAEAVKKHGLTPRARVLGMASGGVAPRVMGIGPVP AVRKLTERLGVAVSDFDVIELNEAFASQGLAVLRELGVADDAPQVNPNGGAIALGHPLGM SGARLVLTALHQLEKSGGRKGLATMCVGVGQGLALAIERV |

FIG. 9N

| SEQ ID NO | Organism | GENBANK reference | Amino acid sequence |
|---|---|---|---|
| 30 | Burkholderia xenovorans | ABE33819.1 | MTEAFLCDAIRTPIGRYAGALSSVRADDLGAVPLKALMERNKEVDWNAIDDVIYGCANQA GEDNRNVARMSLLLAGLPQGVPGTTVNRLCGSGMDAVGIAARAIKSGEAALMVAGGVESM SRAPFVTGKATSAFSRQAEIYDTTIGWRFVNPLMKKLYGVDSMPETGENVATDYNISRAD QDAFALRSQQKAARAQRDGTLAQEIVGVTIACKKGDPVTVSQDEHPRETSLDALAKLKGV VRPDGTVTAGNASGVNDGAAAALLLANEETARRFGLTPRARVLGIATAGVAPRVMGIGPAP ATQKLLARLNMSLDQFDVIELNEAFASQGIAVLRALGVADDDTRVNPNGGAIALGHPLGM SGARLVTTAMYQLHRTQGRFALCTMCIGVGQGIAIAIERV |
| 31 | Arthrobacter sp. | ABK03524.1 | MSFNGQSATGPDESAAAPAATPGAGLLRKAVVGGNRIPFARTGGAYTKSSNQDMLTAAL DGLIARFGLADERIGEVAAGAVLKHSRDFNLTREAVLGSALSAETPAYDLQQACATGLET VLGLANKIKLGQIDSAIAGGVDSASDAPIAVSEGIREVLLDLNRAKTLPQRLKVLGRLRP KDLAPDAPNTGEPRTGLSMGEHQALTTAQWKITREAQDELAYNSHRNLAAAYDAGFFDDL LTPYRGLNRDSNLRADTTREKLSTLKPVFGKNLGAEATMTAGNSTPLITDGASTVLLASEE WADAHELPKLATVVDGEAAAVDPVHGKDGLLMAPAFAVPRLLARNGLTLDDIDFFEIHEA FAGTVLSTLAAWEDEEFGRTRLGLDGPLGSIDRAKLNVNGSSLAAGHPFAATGGRIVATL AKMLHDKGQVDGRPARGLISICAAGGQGVVAILEAS |
| 32 | Burkholderia xenovorans | ABE36495.1 | MTRDTRDVVIVDAVRTPIGKFRGALAGVRADHLGALVIDELIRRAGVKPQAVNDVVFGCV TQIGEQSANIARTSVLGAGWPETIPGLTIDRKCGSGEEAVHIAAGLIAFGAADVIVAGGA ESMSRVPMGSNRDLHGEAFGWMASERFELTSQGEAAERLCDCWALTRAQLDAYSVESHRR AAAAAEGWFAREIVPVPVGQVREKSLEGEAALFAADETIRPGTNADKLATLKSSFRSDG RLTAGNSSQISDGAAAALLMSSDKARELGVKARARVRAVTTVGSDPTLMLTGPILATCQV LEKAGLGLSIDIDLFEINEAFAPVPLVWMKEFGVPHAKLNVNGGAIALGHPLGASGARIMT SMLHELERRGARYGLQAICCAGGMGTATLIERLD |

FIG. 9O

| SEQ ID NO | Organism | GENBANK reference | Amino acid sequence |
|---|---|---|---|
| 33 | Geobacillus kaustophilus | BAD75605.1 | MREAVIVEAVRTPVGKRNGVFRDVHPVHLAAVVLDEVVRRAGMDKGAVEDIVMGCVTPVA EQGYNIGRLAALEAGFPIEVPAVQINRMCGSGQAIHFAAQEIRSGDMDVTIAAGVESMT KVPILSDGNERTIPPSLHEKYEFIHQGVSAERIAKKYGLTREELDAYAYESHQRALAALR EGKFRAEIVPVKGLDRDGREILVTDDEGPRADTSPEALAALKPVFQEDGLITAGNASQMS DGAAAVILMEREAARRFGLKPKARIVAQTVVGSDPTYMLDGVIPATRQVLKKAGLSIDDI DLIEINEAFAPVVLAWQKEIGAPLEKVNVNGGAIALGHPLGATGAKLMTSLVHELERRGG RYGLLTICIGHGMATATHERE |
| 34 | Gordonia bronchialis | ACY20886.1 | MAPCSVKAMPEAVIVAHARSPIGRAGKGSLKDVRPDELSRQMVAAALAKVPELAPSDIED IHWGIGQPGGQGYNIARVIAVELGYDHIPGVTVNRYCSSSLQTTRMALHAIKAGEADVL ISGGVESVSSFGISGGADGAPDSKNPVFDDAQARTAKAAEGGAPAWTDPREQGLIPDVYI AMGQTAENVASFTGISREDQDRWSVLSQNRAEEAINAGFFEREIDPVTLPDGSTVNTDDG PRAGTTYEKVSQLKPVFRPDGTVTAGMACPLNDGAAALVIMSDSKAKQLGLTPLARVVAT AATGLSPEIMGLGPIEAIRKVLRISGMSLSDIDLVEINEAFAVQVLGSANELGIDHDKLN VSGGAIALGHPFGMTGARITTTLLNNLQTRDKTFGIESMCVGGGQGMAMVLERLS |
| 35 | Citrobacter freundii | KFB98168.1 | MEQVVIVDAIRTPMGRSKGGAFRNVRAEDLSAHLMRSLLARNPALDPTALDDIYWGCVQQ TLEQGFNIARNAALLAEIPHSVPAVTVNRLCGSSMQALHDAARMIMTGDAQACLIGGVEH MGHVPMSHGVDFHPGMSRNVAKAAGMMGLTAEMLSRMHGISREMQDAFAARSHARAWAAT QSGAFKNEIIPTGGHDADGVLKQFNYDEVIRPETTVEALSTLRPAFDPVSGTVTAGTSSA LSDGAAAMLVMSESRARELGLTPRARIRSMAVVGCDPSIMGYGPVPASKLALKKAGLSTS DIGLFEMNEAFAAQILPCIKDLGLMEQIDEKINLNGGAIALGHPLGCSGARISTTLNLM ERKDVQFGLATMCIGLGQGIATVFERV |

FIG. 9P

| SEQ ID NO | Organism | GENBANK reference | Amino acid sequence |
|---|---|---|---|
| 36 | Burkholderia sp. | ADG18081.1 | MREAVIVSTARTPLTKAHRGEFNITPGPTLASFAVRAAVERSGVDPDHEDAILGCGYPE GTTGRNVARQSVIRAGLPLSIAGTTVNRFCASGLQAIAMAAGRIVVDGAPAMIAGGVESI SNIQTREDGVSGLDPWIVEHKPSLYTAMIDTADIVARRYGISREAQDQFSVESQRRTAEA QQAGRYADEIIPVTTMAITDKETRAVSYREVTVSADNCNRPGTTYEALAKLAPVKGPDQ FITAGNASQNADGASACVLMEAKAAERANFAPLGAFRGLALAGCEPDEMGIGPVLAVPKL LARHGLTVDDIGLWELNEAFASQAVYCQKRLEIPSERLNVNGGAISIGHPFGMTGSRLVG HVLIEGRRRGVKYAVVTMCMAGGMGAAGLFEIY |
| 37 | Beijerinckia indica | ACB95386.1 | MTKVVIAGYIRSPFTLAKKGELATVRPDDLAAQVVKGLIKKTGIPAEDIEDLLGCAFPE GEQGFNVARLVSFLAGLPLSVGASTVNRFCGSSMTTVHMAAGAIQMNAGNAFIAAGVESM SRVPMMGFNPLPNPELAATMPGAYMGMGDTAENVAAKWTISRKEQEEFALRSHQRATAAQ KEGRLTGEIIPITGRKGTITTDGCIRPDTTLEGLAELKPAFSANGVVTAGTSSPLTDGAA AVLVCSEDYAKHHHLDVLASVKAIAVSGCSPEIMGIGPVAASRKALARAGLEAGQJDIVE LNEAFASQSIACMRELNLSPDRVNIDGGAJALGHPLGATGARIVGKAASLLKREKGKYAL ATQCIGGGQGIATVLEAF |
| 38 | Arthrobacter arilaitensis | CBT74677.1 | MQQAYLYDAIRTPFGKIGGALSSHRPDDLAAHVVRELVARSPKLDVADIDESIFGNANGA GEENRNVARMATLLAGLPTSLPGTTMNRLCGSSLDASIAASRQIATGDADLVLVGGVESM SRAPWVLPKTERPFPMSNLELANTTLGWRLVNPAMPGEWTVSLGEATEQLREKHGISRED QDEFSAASHQRAAAAWOAQGKYDNLVVPVPPANKRGTEVTRDETIRADSTAQTLSKLRTVF RTGENATVTAGNASPMSDGASAAFIGSERGGELLGAAPIARIASNGAAALDPQFFGFAPV EAANKALAKAGILKWSDHAAVELNEAFAAQSLACIRAWDIDPAIVNAWGGAISIGHPLGAS GLRILGTVARRLAESGERYGLAAICIGVGQGLAVVVENIMATK |

FIG. 9Q

| SEQ ID NO | Organism | GENBANK reference | Amino acid sequence |
|---|---|---|---|
| 39 | Cupriavidus necator | AAC38322.1 | MTREVVVVSGVRTAIGTFGGSLKDVAPAELGALVVREALARAQVSGDDVGHVVFGNVIQT EPRDMYLGRVAAVNGGVTINAPALTVNRLCGSGLQAIVSAAQTILLGDTDVAIGGGAESM SRAPYLAPAARWGARMGDAGLVDMMLGALHDPFHRIHMGVTAENVAKEYDISRAQQDEAA LESHRRASAAIKAGYFKDQIVPVVSKGRKGDVTFDTDEHVRHDATIDDMTKLRPVFVKEN GTVTAGNASGLNDAAAAVVMMEREAEAERRGLKPLARLVSYGHAGVDPKAMGIGPVPATKI ALERAGLQVSDLDVIEANEAFAAQACAVTKALGLDPAKVNPNGSGISLGHPIGATGALIT VKALHELNRVCQGRYALVTMCIGGGQGIAAIFERI |
| 40 | Escherichia coli | AAC74479.1 | MREAFICDGIRTPIGRYGGALSSVRADDLAAIPLRELLVRNPRLDAECIDDVILGCANQA GEDNRNVARMATLLAGLPQSVSGTTINRLCGSGLDALGFAARAIKAGDGDLLIAGGVESM SRAPPVMGKAASAFSRQAEMFDTTIGWRFVNPLMAQQFGTDSMPETAENVAELLKISRED QDSFALRSQQRTAKAQSSGILAEEIVPVVLKNKKGVVTEIQHDEHLRPETTLEQLRGLKA PFRANGVITAGNASGVNDGAAALIIASEQMAAAQGLTPRARIVAMATAGVEPRLMGLGPV PATRRVLERAGLSIHDMDVIELNEAFAAQALGVLRELGLPDDAPHVNPNGGAIALGHPLG MSGARLALAASHELHRRNGRYALCTMCIGVGQGIAMILERV |

FIG. 22

| Sample ID | Analyte | Mwt [g/mol] | Peak Retention Time [min] | Peak Area @ 260nm [mAu] | Observed Mass (m/z) Negative mode (M-H) | Observed Mass (m/z) Positive mode (M+H) | Comments |
|---|---|---|---|---|---|---|---|
| Reference Standard | pimeloyl-CoA methyl ester | 923 | 6.161 | 31172.1 | 922 | 924 | |
| Biotransformation at 1 [h] time point #1 | pimeloyl-CoA methyl ester | 923 | nd | nd | nd | nd | No substrate detected after 1 [h] |
| | pimeloyl-CoA | 910 | 5.577 | 3956.1 | 908 | 910 | |
| Biotransformation at 1 [h] time point #2 | pimeloyl-CoA methyl ester | 923 | nd | nd | nd | nd | No substrate detected after 1 [h] |
| | pimeloyl-CoA | 910 | 5.579 | 3974.1 | 908 | 910 | |
| Biotransformation at 1 [h] time point #3 | pimeloyl-CoA methyl ester | 923 | nd | nd | nd | nd | No substrate detected after 1 [h] |
| | pimeloyl-CoA | 910 | 5.577 | 4093.3 | 908 | 910 | |
| Substrate only control (no enzyme) at 1 [h] time point | pimeloyl-CoA methyl ester | 923 | 6.333 | 4577.9 | 922 | 924 | No product detected after 1 [h] |
| | pimeloyl-CoA | 910 | nd | nd | nd | nd | |

SEQUENCE LISTING

<160> NUMBER OF SEQ ID NOS: 40

<210> SEQ ID NO 1
<211> LENGTH: 368
<212> TYPE: PRT
<213> ORGANISM: Mycobacterium marinum

<400> SEQUENCE: 1

Met Pro Arg Glu Ile Arg Leu Pro Glu Ser Ser Val Val Arg Pro
1               5                   10                  15

Ala Pro Met Glu Ser Ala Thr Tyr Ser Gln Ser Ser Arg Leu Gln Ala
            20                  25                  30

Ala Gly Leu Ser Pro Ala Ile Thr Leu Phe Glu Lys Ala Ala Gln Thr
        35                  40                  45

Val Pro Leu Pro Asp Ala Pro Gln Pro Val Val Ile Ala Asp Tyr Gly
    50                  55                  60

Val Ala Thr Gly His Asn Ser Leu Lys Pro Met Met Ala Ala Ile Asn
65                  70                  75                  80

Ala Leu Arg Arg Ile Arg Glu Asp Arg Ala Ile Met Val Ala His
                85                  90                  95

Thr Asp Val Pro Asp Asn Asp Phe Thr Ala Leu Phe Arg Thr Leu Ala
                100                 105                 110

Asp Asp Pro Asp Ser Tyr Leu His His Asp Ser Ala Ser Phe Ala Ser
            115                 120                 125

Ala Val Gly Arg Ser Phe Tyr Thr Gln Ile Leu Pro Ser Asn Thr Val
        130                 135                 140

Ser Leu Gly Trp Ser Ser Trp Ala Ile Gln Trp Leu Ser Arg Ile Pro
145                 150                 155                 160

Ala Gly Ala Pro Glu Leu Thr Asp His Val Gln Val Ala Tyr Ser Lys
            165                 170                 175

Asp Glu Arg Ala Arg Ala Ala Tyr Ala His Gln Ala Ala Thr Asp Trp
            180                 185                 190

Gln Asp Phe Leu Ala Phe Arg Gly Arg Glu Leu Cys Pro Gly Gly Arg
            195                 200                 205

Leu Val Val Leu Thr Met Ala Leu Asp Glu His Gly His Phe Gly Tyr
            210                 215                 220

Arg Pro Met Asn Asp Ala Leu Val Ala Ala Leu Asn Asp Gln Val Arg
225                 230                 235                 240

Asp Gly Leu Leu Arg Pro Glu Glu Leu Arg Arg Met Ala Ile Pro Val
            245                 250                 255

Val Ala Arg Ala Glu Lys Asp Leu Arg Ala Pro Phe Ala Pro Arg Gly
            260                 265                 270

Trp Phe Glu Gly Leu Thr Ile Glu Gln Leu Asp Val Phe Asn Ala Glu
            275                 280                 285

Asp Arg Phe Trp Ala Ala Phe Gln Ser Asp Gly Asp Ala Glu Ser Phe
            290                 295                 300

Gly Ala Gln Trp Ala Gly Phe Ala Arg Ala Ala Leu Phe Pro Thr Leu
305                 310                 315                 320

Ala Ala Ala Leu Asp Cys Gly Thr Gly Asp Pro Arg Ala Thr Ala Phe
            325                 330                 335

Ile Glu Gln Leu Glu Ala Ser Val Ala Asp Arg Leu Ala Ser Gln Pro
            340                 345                 350

Glu Pro Met Arg Ile Pro Leu Ala Ser Leu Val Leu Ala Lys Arg Ala
            355                 360                 365

<210> SEQ ID NO 2
<211> LENGTH: 360
<212> TYPE: PRT
<213> ORGANISM: Mycobacterium smegmatis

<400> SEQUENCE: 2

Met Pro Lys Phe Arg Val Ala Val Asp Pro Glu Pro Asp Asp Pro Thr
1               5                   10                  15

Pro Lys Met Arg Ala Pro Arg Pro His Ala Ala Gly Leu Asn Ser Ala
            20                  25                  30

Ile Ala Leu Leu Glu Glu Ala Ala Arg Thr Val Pro Leu Pro Glu Ala
            35                  40                  45

Pro Tyr Pro Ile Val Ile Ala Asp Tyr Gly Val Gly Thr Gly Arg Asn
    50                  55                  60

Ser Met Arg Pro Ile Ala Ala Ile Ala Ala Leu Arg Gly Arg Thr
65                  70                  75                  80

Arg Pro Glu His Ser Val Leu Val Thr His Thr Asp Asn Ala Asp Asn
            85                  90                  95

Asp Phe Thr Ala Val Phe Arg Gly Leu Ala Asp Asn Pro Asp Ser Tyr
            100                 105                 110

Leu Arg Arg Asp Thr Ser Thr Tyr Pro Ser Ala Val Gly Arg Ser Phe
            115                 120                 125

Tyr Thr Gln Ile Leu Pro Ser Lys Ser Val His Val Gly Trp Ser Ala
            130                 135                 140

Trp Ala Ile Val Arg Val Gly Arg Met Pro Met Pro Val Pro Asp His
145                 150                 155                 160

Val Ala Ala Ser Phe Ser Gly Asp Pro Gln Val Val Ala Ala Tyr Ala

```
                    165                 170                 175
Arg Gln Ala Ala Phe Asp Trp His Glu Phe Val Ala Phe Arg Gly Arg
                180                 185                 190

Glu Leu Ala Ser Gly Ala Gln Leu Val Val Leu Thr Ala Ala Leu Gly
            195                 200                 205

Asp Asp Gly Asp Phe Gly Tyr Arg Pro Leu Phe Ala Ala Val Met Asp
        210                 215                 220

Thr Leu Arg Glu Leu Thr Ala Asp Gly Val Leu Arg Gln Asp Glu Leu
225                 230                 235                 240

His Arg Met Ser Leu Pro Ile Val Gly Arg Arg Ala Asn Asp Phe Met
                245                 250                 255

Ala Pro Phe Ala Pro Ser Gly Arg Phe Glu Arg Leu Ser Ile Ser His
                260                 265                 270

Leu Glu Val Tyr Asp Ala Glu Asp Val Ile Tyr Ser Ser Tyr Gln Lys
                275                 280                 285

Asp Arg Asp Thr Asp Val Phe Gly Leu Arg Trp Ala Asp Phe Cys Arg
            290                 295                 300

Phe Thr Phe Phe Ser Asp Leu Cys Thr Ala Leu Asp Asp Ala Ala
305                 310                 315                 320

Arg Cys Thr Gln Phe Gln Asp Arg Leu His Ala Gly Ile Ala Ala Arg
                325                 330                 335

Leu Ser Ala Gln Pro Glu Gln Met Arg Ile Pro Leu Ala Gln Leu Val
            340                 345                 350

Leu Glu Arg Arg Arg Ser Gly
            355                 360

<210> SEQ ID NO 3
<211> LENGTH: 394
<212> TYPE: PRT
<213> ORGANISM: Pseudomonas putida

<400> SEQUENCE: 3

Met Leu Ala Gln Leu Pro Pro Ala Leu Gln Ser Leu His Leu Pro Leu
1               5                   10                  15

Arg Leu Lys Leu Trp Asp Gly Asn Gln Phe Asp Leu Gly Pro Ser Pro
                20                  25                  30

Gln Val Thr Ile Leu Val Lys Glu Pro Gln Leu Ile Gly Gln Leu Thr
            35                  40                  45

His Pro Ser Met Glu Gln Leu Gly Thr Ala Phe Val Glu Gly Lys Leu
        50                  55                  60

Glu Leu Glu Gly Asp Ile Gly Glu Ala Ile Arg Val Cys Asp Glu Leu
65                  70                  75                  80

Ser Glu Ala Leu Phe Thr Asp Glu Asp Glu Gln Pro Pro Glu Arg Arg
                85                  90                  95

Ser His Asp Lys Arg Thr Asp Ala Glu Ala Ile Ser Tyr His Tyr Asp
                100                 105                 110

Val Ser Asn Ala Phe Tyr Gln Leu Trp Leu Asp Gln Asp Met Ala Tyr
            115                 120                 125

Ser Cys Ala Tyr Phe Arg Glu Pro Asp Asn Thr Leu Asp Gln Ala Gln
        130                 135                 140

Gln Asp Lys Phe Asp His Leu Cys Arg Lys Leu Arg Leu Asn Ala Gly
145                 150                 155                 160

Asp Tyr Leu Leu Asp Val Gly Cys Gly Trp Gly Gly Leu Ala Arg Phe
                165                 170                 175
```

```
Ala Ala Arg Glu Tyr Asp Ala Lys Val Phe Gly Ile Thr Leu Ser Lys
            180                 185                 190

Glu Gln Leu Lys Leu Gly Arg Gln Arg Val Lys Ala Glu Gly Leu Thr
        195                 200                 205

Asp Lys Val Asp Leu Gln Ile Leu Asp Tyr Arg Asp Leu Pro Gln Asp
    210                 215                 220

Gly Arg Phe Asp Lys Val Val Ser Val Gly Met Phe Glu His Val Gly
225                 230                 235                 240

His Ala Asn Leu Ala Leu Tyr Cys Gln Lys Leu Phe Gly Ala Val Arg
                245                 250                 255

Glu Gly Gly Leu Val Met Asn His Gly Ile Thr Ala Lys His Val Asp
            260                 265                 270

Gly Arg Pro Val Gly Arg Gly Ala Gly Glu Phe Ile Asp Arg Tyr Val
        275                 280                 285

Phe Pro His Gly Glu Leu Pro His Leu Ser Met Ile Ser Ala Ser Ile
    290                 295                 300

Cys Glu Ala Gly Leu Glu Val Val Asp Val Glu Ser Leu Arg Leu His
305                 310                 315                 320

Tyr Ala Lys Thr Leu His His Trp Ser Glu Asn Leu Glu Asn Gln Leu
                325                 330                 335

His Lys Ala Ala Ala Leu Val Pro Glu Lys Thr Leu Arg Ile Trp Arg
            340                 345                 350

Leu Tyr Leu Ala Gly Cys Ala Tyr Ala Phe Glu Lys Gly Trp Ile Asn
        355                 360                 365

Leu His Gln Ile Leu Ala Val Lys Pro Tyr Ala Asp Gly His His Asp
    370                 375                 380

Leu Pro Trp Thr Arg Glu Asp Met Tyr Arg
385                 390

<210> SEQ ID NO 4
<211> LENGTH: 246
<212> TYPE: PRT
<213> ORGANISM: Lactobacillus brevis

<400> SEQUENCE: 4

Met Ala Ala Asn Glu Phe Ser Glu Thr His Arg Val Tyr Tyr Glu
1               5                   10                  15

Ala Asp Asp Thr Gly Gln Leu Thr Leu Ala Met Leu Ile Asn Leu Phe
            20                  25                  30

Val Leu Val Ser Glu Asp Gln Asn Asp Ala Leu Gly Leu Ser Thr Ala
        35                  40                  45

Phe Val Gln Ser His Gly Val Gly Trp Val Val Thr Gln Tyr His Leu
    50                  55                  60

His Ile Asp Glu Leu Pro Arg Thr Gly Ala Gln Val Thr Ile Lys Thr
65                  70                  75                  80

Arg Ala Thr Ala Tyr Asn Arg Tyr Phe Ala Tyr Arg Glu Tyr Trp Leu
                85                  90                  95

Leu Asp Asp Ala Gly Gln Val Leu Ala Tyr Gly Glu Gly Ile Trp Val
            100                 105                 110

Thr Met Ser Tyr Ala Thr Arg Lys Ile Thr Thr Ile Pro Ala Glu Val
        115                 120                 125

Met Ala Pro Tyr His Ser Glu Glu Gln Thr Arg Leu Pro Arg Leu Pro
    130                 135                 140

Arg Pro Asp His Phe Asp Glu Ala Val Asn Gln Thr Leu Lys Pro Tyr
145                 150                 155                 160
```

```
Thr Val Arg Tyr Phe Asp Ile Asp Gly Asn Gly His Val Asn Asn Ala
                165                 170                 175

His Tyr Phe Asp Trp Met Leu Asp Val Leu Pro Ala Thr Phe Leu Arg
            180                 185                 190

Ala His His Pro Thr Asp Val Lys Ile Arg Phe Glu Asn Glu Val Gln
        195                 200                 205

Tyr Gly His Gln Val Thr Ser Glu Leu Ser Gln Ala Ala Ala Leu Thr
    210                 215                 220

Thr Gln His Met Ile Lys Val Gly Asp Leu Thr Ala Val Lys Ala Thr
225                 230                 235                 240

Ile Gln Trp Asp Asn Arg
                245

<210> SEQ ID NO 5
<211> LENGTH: 261
<212> TYPE: PRT
<213> ORGANISM: Lactobacillus plantarum

<400> SEQUENCE: 5

Met Ala Thr Leu Gly Ala Asn Ala Ser Leu Tyr Ser Glu Gln His Arg
1               5                   10                  15

Ile Thr Tyr Tyr Glu Cys Asp Arg Thr Gly Arg Ala Thr Leu Thr Thr
            20                  25                  30

Leu Ile Asp Ile Ala Val Leu Ala Ser Glu Asp Gln Ser Asp Ala Leu
        35                  40                  45

Gly Leu Thr Thr Glu Met Val Gln Ser His Gly Val Gly Trp Val Val
    50                  55                  60

Thr Gln Tyr Ala Ile Asp Ile Thr Arg Met Pro Arg Gln Asp Glu Val
65                  70                  75                  80

Val Thr Ile Ala Val Arg Gly Ser Ala Tyr Asn Pro Tyr Phe Ala Tyr
                85                  90                  95

Arg Glu Phe Trp Ile Arg Asp Ala Asp Gly Gln Gln Leu Ala Tyr Ile
            100                 105                 110

Thr Ser Ile Trp Val Met Met Ser Gln Thr Thr Arg Arg Ile Val Lys
        115                 120                 125

Ile Leu Pro Glu Leu Val Ala Pro Tyr Gln Ser Glu Val Val Lys Arg
    130                 135                 140

Ile Pro Arg Leu Pro Arg Pro Ile Ser Phe Glu Ala Thr Asp Thr Thr
145                 150                 155                 160

Ile Thr Lys Pro Tyr His Val Arg Phe Phe Asp Ile Asp Pro Asn Arg
                165                 170                 175

His Val Asn Asn Ala His Tyr Phe Asp Trp Leu Val Asp Thr Leu Pro
            180                 185                 190

Ala Thr Phe Leu Leu Gln His Asp Leu Val His Val Asp Val Arg Tyr
        195                 200                 205

Glu Asn Glu Val Lys Tyr Gly Asn Thr Val Thr Ala His Ala Asn Ile
    210                 215                 220

Leu Pro Ser Glu Val Ala Asp Gln Val Thr Thr Ser His Leu Ile Glu
225                 230                 235                 240

Val Asp Asp Glu Lys Cys Cys Glu Val Thr Ile Gln Trp Arg Thr Leu
                245                 250                 255

Pro Glu Pro Ile Gln
            260
```

<210> SEQ ID NO 6
<211> LENGTH: 256
<212> TYPE: PRT
<213> ORGANISM: Escherichia coli

<400> SEQUENCE: 6

Met Asn Ile Trp Trp Gln Thr Lys Gly Gln Gly Asn Val His Leu
1               5                   10                  15

Val Leu His Gly Trp Gly Leu Asn Ala Glu Val Trp Arg Cys Ile
            20                  25                  30

Asp Glu Glu Leu Ser Ser His Phe Thr Leu His Leu Val Asp Leu Pro
            35                  40                  45

Gly Phe Gly Arg Ser Arg Gly Phe Gly Ala Leu Ser Leu Ala Asp Met
    50                  55                  60

Ala Glu Ala Val Leu Gln Gln Ala Pro Asp Lys Ala Ile Trp Leu Gly
65                  70                  75                  80

Trp Ser Leu Gly Gly Leu Val Ala Ser Gln Ile Ala Leu Thr His Pro
                85                  90                  95

Glu Arg Val Gln Ala Leu Val Thr Val Ala Ser Ser Pro Cys Phe Ser
            100                 105                 110

Ala Arg Asp Glu Trp Pro Gly Ile Lys Pro Asp Val Leu Ala Gly Phe
        115                 120                 125

Gln Gln Gln Leu Ser Asp Asp Phe Gln Arg Thr Val Glu Arg Phe Leu
    130                 135                 140

Ala Leu Gln Thr Met Gly Thr Glu Thr Ala Arg Gln Asp Ala Arg Ala
145                 150                 155                 160

Leu Lys Lys Thr Val Leu Ala Leu Pro Met Pro Glu Val Asp Val Leu
                165                 170                 175

Asn Gly Gly Leu Glu Ile Leu Lys Thr Val Asp Leu Arg Gln Pro Leu
            180                 185                 190

Gln Asn Val Ser Met Pro Phe Leu Arg Leu Tyr Gly Tyr Leu Asp Gly
        195                 200                 205

Leu Val Pro Arg Lys Val Val Pro Met Leu Asp Lys Leu Trp Pro His
    210                 215                 220

Ser Glu Ser Tyr Ile Phe Ala Lys Ala Ala His Ala Pro Phe Ile Ser
225                 230                 235                 240

His Pro Ala Glu Phe Cys His Leu Leu Val Ala Leu Lys Gln Arg Val
                245                 250                 255

<210> SEQ ID NO 7
<211> LENGTH: 1174
<212> TYPE: PRT
<213> ORGANISM: Mycobacterium marinum

<400> SEQUENCE: 7

Met Ser Pro Ile Thr Arg Glu Glu Arg Leu Glu Arg Arg Ile Gln Asp
1               5                   10                  15

Leu Tyr Ala Asn Asp Pro Gln Phe Ala Ala Ala Lys Pro Ala Thr Ala
            20                  25                  30

Ile Thr Ala Ala Ile Glu Arg Pro Gly Leu Pro Leu Pro Gln Ile Ile
        35                  40                  45

Glu Thr Val Met Thr Gly Tyr Ala Asp Arg Pro Ala Leu Ala Gln Arg
    50                  55                  60

Ser Val Glu Phe Val Thr Asp Ala Gly Thr Gly His Thr Thr Leu Arg
65                  70                  75                  80

Leu Leu Pro His Phe Glu Thr Ile Ser Tyr Gly Glu Leu Trp Asp Arg

```
            85                  90                  95
Ile Ser Ala Leu Ala Asp Val Leu Ser Thr Glu Gln Thr Val Lys Pro
            100                 105                 110

Gly Asp Arg Val Cys Leu Leu Gly Phe Asn Ser Val Asp Tyr Ala Thr
            115                 120                 125

Ile Asp Met Thr Leu Ala Arg Leu Gly Ala Val Ala Val Pro Leu Gln
            130                 135                 140

Thr Ser Ala Ala Ile Thr Gln Leu Gln Pro Ile Val Ala Glu Thr Gln
145                 150                 155                 160

Pro Thr Met Ile Ala Ala Ser Val Asp Ala Leu Ala Asp Ala Thr Glu
                165                 170                 175

Leu Ala Leu Ser Gly Gln Thr Ala Thr Arg Val Leu Val Phe Asp His
                180                 185                 190

His Arg Gln Val Asp Ala His Arg Ala Ala Val Glu Ser Ala Arg Glu
                195                 200                 205

Arg Leu Ala Gly Ser Ala Val Val Glu Thr Leu Ala Glu Ala Ile Ala
            210                 215                 220

Arg Gly Asp Val Pro Arg Gly Ala Ser Ala Gly Ser Ala Pro Gly Thr
225                 230                 235                 240

Asp Val Ser Asp Asp Ser Leu Ala Leu Leu Ile Tyr Thr Ser Gly Ser
                245                 250                 255

Thr Gly Ala Pro Lys Gly Ala Met Tyr Pro Arg Arg Asn Val Ala Thr
                260                 265                 270

Phe Trp Arg Lys Arg Thr Trp Phe Glu Gly Gly Tyr Glu Pro Ser Ile
            275                 280                 285

Thr Leu Asn Phe Met Pro Met Ser His Val Met Gly Arg Gln Ile Leu
            290                 295                 300

Tyr Gly Thr Leu Cys Asn Gly Gly Thr Ala Tyr Phe Val Ala Lys Ser
305                 310                 315                 320

Asp Leu Ser Thr Leu Phe Glu Asp Leu Ala Leu Val Arg Pro Thr Glu
                325                 330                 335

Leu Thr Phe Val Pro Arg Val Trp Asp Met Val Phe Asp Glu Phe Gln
                340                 345                 350

Ser Glu Val Asp Arg Arg Leu Val Asp Gly Ala Asp Arg Val Ala Leu
                355                 360                 365

Glu Ala Gln Val Lys Ala Glu Ile Arg Asn Asp Val Leu Gly Gly Arg
            370                 375                 380

Tyr Thr Ser Ala Leu Thr Gly Ser Ala Pro Ile Ser Asp Glu Met Lys
385                 390                 395                 400

Ala Trp Val Glu Glu Leu Leu Asp Met His Leu Val Glu Gly Tyr Gly
                405                 410                 415

Ser Thr Glu Ala Gly Met Ile Leu Ile Asp Gly Ala Ile Arg Arg Pro
                420                 425                 430

Ala Val Leu Asp Tyr Lys Leu Val Asp Val Pro Asp Leu Gly Tyr Phe
            435                 440                 445

Leu Thr Asp Arg Pro His Pro Arg Gly Glu Leu Leu Val Lys Thr Asp
            450                 455                 460

Ser Leu Phe Pro Gly Tyr Tyr Gln Arg Ala Glu Val Thr Ala Asp Val
465                 470                 475                 480

Phe Asp Ala Asp Gly Phe Tyr Arg Thr Gly Asp Ile Met Ala Glu Val
                485                 490                 495

Gly Pro Glu Gln Phe Val Tyr Leu Asp Arg Arg Asn Asn Val Leu Lys
                500                 505                 510
```

```
Leu Ser Gln Gly Glu Phe Val Thr Val Ser Lys Leu Glu Ala Val Phe
            515                 520                 525

Gly Asp Ser Pro Leu Val Arg Gln Ile Tyr Ile Tyr Gly Asn Ser Ala
            530                 535                 540

Arg Ala Tyr Leu Leu Ala Val Ile Val Pro Thr Gln Glu Ala Leu Asp
545                 550                 555                 560

Ala Val Pro Val Glu Glu Leu Lys Ala Arg Leu Gly Asp Ser Leu Gln
            565                 570                 575

Glu Val Ala Lys Ala Ala Gly Leu Gln Ser Tyr Glu Ile Pro Arg Asp
            580                 585                 590

Phe Ile Ile Glu Thr Thr Pro Trp Thr Leu Glu Asn Gly Leu Leu Thr
            595                 600                 605

Gly Ile Arg Lys Leu Ala Arg Pro Gln Leu Lys Lys His Tyr Gly Glu
            610                 615                 620

Leu Leu Glu Gln Ile Tyr Thr Asp Leu Ala His Gly Gln Ala Asp Glu
625                 630                 635                 640

Leu Arg Ser Leu Arg Gln Ser Gly Ala Asp Ala Pro Val Leu Val Thr
            645                 650                 655

Val Cys Arg Ala Ala Ala Leu Leu Gly Gly Ser Ala Ser Asp Val
            660                 665                 670

Gln Pro Asp Ala His Phe Thr Asp Leu Gly Gly Asp Ser Leu Ser Ala
            675                 680                 685

Leu Ser Phe Thr Asn Leu Leu His Glu Ile Phe Asp Ile Glu Val Pro
            690                 695                 700

Val Gly Val Ile Val Ser Pro Ala Asn Asp Leu Gln Ala Leu Ala Asp
705                 710                 715                 720

Tyr Val Glu Ala Ala Arg Lys Pro Gly Ser Ser Arg Pro Thr Phe Ala
            725                 730                 735

Ser Val His Gly Ala Ser Asn Gly Gln Val Thr Glu Val His Ala Gly
            740                 745                 750

Asp Leu Ser Leu Asp Lys Phe Ile Asp Ala Ala Thr Leu Ala Glu Ala
            755                 760                 765

Pro Arg Leu Pro Ala Ala Asn Thr Gln Val Arg Thr Val Leu Leu Thr
            770                 775                 780

Gly Ala Thr Gly Phe Leu Gly Arg Tyr Leu Ala Leu Glu Trp Leu Glu
785                 790                 795                 800

Arg Met Asp Leu Val Asp Gly Lys Leu Ile Cys Leu Val Arg Ala Lys
            805                 810                 815

Ser Asp Thr Glu Ala Arg Ala Arg Leu Asp Lys Thr Phe Asp Ser Gly
            820                 825                 830

Asp Pro Glu Leu Leu Ala His Tyr Arg Ala Leu Ala Gly Asp His Leu
            835                 840                 845

Glu Val Leu Ala Gly Asp Lys Gly Glu Ala Asp Leu Gly Leu Asp Arg
850                 855                 860

Gln Thr Trp Gln Arg Leu Ala Asp Thr Val Asp Leu Ile Val Asp Pro
865                 870                 875                 880

Ala Ala Leu Val Asn His Val Leu Pro Tyr Ser Gln Leu Phe Gly Pro
            885                 890                 895

Asn Ala Leu Gly Thr Ala Glu Leu Leu Arg Leu Ala Leu Thr Ser Lys
            900                 905                 910

Ile Lys Pro Tyr Ser Tyr Thr Ser Thr Ile Gly Val Ala Asp Gln Ile
            915                 920                 925
```

-continued

```
Pro Pro Ser Ala Phe Thr Glu Asp Ala Asp Ile Arg Val Ile Ser Ala
    930                 935                 940

Thr Arg Ala Val Asp Asp Ser Tyr Ala Asn Gly Tyr Ser Asn Ser Lys
945                 950                 955                 960

Trp Ala Gly Glu Val Leu Leu Arg Glu Ala His Asp Leu Cys Gly Leu
                965                 970                 975

Pro Val Ala Val Phe Arg Cys Asp Met Ile Leu Ala Asp Thr Thr Trp
            980                 985                 990

Ala Gly Gln Leu Asn Val Pro Asp Met Phe Thr Arg Met Ile Leu Ser
        995                 1000                1005

Leu Ala Ala Thr Gly Ile Ala Pro Gly Ser Phe Tyr Glu Leu Ala Ala
    1010                1015                1020

Asp Gly Ala Arg Gln Arg Ala His Tyr Asp Gly Leu Pro Val Glu Phe
1025                1030                1035                1040

Ile Ala Glu Ala Ile Ser Thr Leu Gly Ala Gln Ser Gln Asp Gly Phe
                1045                1050                1055

His Thr Tyr His Val Met Asn Pro Tyr Asp Asp Gly Ile Gly Leu Asp
            1060                1065                1070

Glu Phe Val Asp Trp Leu Asn Glu Ser Gly Cys Pro Ile Gln Arg Ile
        1075                1080                1085

Ala Asp Tyr Gly Asp Trp Leu Gln Arg Phe Glu Thr Ala Leu Arg Ala
    1090                1095                1100

Leu Pro Asp Arg Gln Arg His Ser Ser Leu Leu Pro Leu Leu His Asn
1105                1110                1115                1120

Tyr Arg Gln Pro Glu Arg Pro Val Arg Gly Ser Ile Ala Pro Thr Asp
                1125                1130                1135

Arg Phe Arg Ala Ala Val Gln Glu Ala Lys Ile Gly Pro Asp Lys Asp
            1140                1145                1150

Ile Pro His Val Gly Ala Pro Ile Ile Val Lys Tyr Val Ser Asp Leu
        1155                1160                1165

Arg Leu Leu Gly Leu Leu
    1170

<210> SEQ ID NO 8
<211> LENGTH: 1173
<212> TYPE: PRT
<213> ORGANISM: Mycobacterium smegmatis

<400> SEQUENCE: 8

Met Thr Ser Asp Val His Asp Ala Thr Asp Gly Val Thr Glu Thr Ala
1               5                   10                  15

Leu Asp Asp Glu Gln Ser Thr Arg Arg Ile Ala Glu Leu Tyr Ala Thr
            20                  25                  30

Asp Pro Glu Phe Ala Ala Ala Ala Pro Leu Pro Ala Val Val Asp Ala
        35                  40                  45

Ala His Lys Pro Gly Leu Arg Leu Ala Glu Ile Leu Gln Thr Leu Phe
    50                  55                  60

Thr Gly Tyr Gly Asp Arg Pro Ala Leu Gly Tyr Arg Ala Arg Glu Leu
65                  70                  75                  80

Ala Thr Asp Glu Gly Gly Arg Thr Val Thr Arg Leu Leu Pro Arg Phe
                85                  90                  95

Asp Thr Leu Thr Tyr Ala Gln Val Trp Ser Arg Val Gln Ala Val Ala
            100                 105                 110

Ala Ala Leu Arg His Asn Phe Ala Gln Pro Ile Tyr Pro Gly Asp Ala
        115                 120                 125
```

-continued

```
Val Ala Thr Ile Gly Phe Ala Ser Pro Asp Tyr Leu Thr Leu Asp Leu
    130                 135                 140

Val Cys Ala Tyr Leu Gly Leu Val Ser Val Pro Leu Gln His Asn Ala
145                 150                 155                 160

Pro Val Ser Arg Leu Ala Pro Ile Leu Ala Glu Val Glu Pro Arg Ile
                165                 170                 175

Leu Thr Val Ser Ala Glu Tyr Leu Asp Leu Ala Val Glu Ser Val Arg
                180                 185                 190

Asp Val Asn Ser Val Ser Gln Leu Val Val Phe Asp His His Pro Glu
            195                 200                 205

Val Asp Asp His Arg Asp Ala Leu Ala Arg Ala Arg Glu Gln Leu Ala
210                 215                 220

Gly Lys Gly Ile Ala Val Thr Thr Leu Asp Ala Ile Ala Asp Glu Gly
225                 230                 235                 240

Ala Gly Leu Pro Ala Glu Pro Ile Tyr Thr Ala Asp His Asp Gln Arg
                245                 250                 255

Leu Ala Met Ile Leu Tyr Thr Ser Gly Ser Thr Gly Ala Pro Lys Gly
                260                 265                 270

Ala Met Tyr Thr Glu Ala Met Val Ala Arg Leu Trp Thr Met Ser Phe
                275                 280                 285

Ile Thr Gly Asp Pro Thr Pro Val Ile Asn Val Asn Phe Met Pro Leu
            290                 295                 300

Asn His Leu Gly Gly Arg Ile Pro Ile Ser Thr Ala Val Gln Asn Gly
305                 310                 315                 320

Gly Thr Ser Tyr Phe Val Pro Glu Ser Asp Met Ser Thr Leu Phe Glu
                325                 330                 335

Asp Leu Ala Leu Val Arg Pro Thr Glu Leu Gly Leu Val Pro Arg Val
                340                 345                 350

Ala Asp Met Leu Tyr Gln His His Leu Ala Thr Val Asp Arg Leu Val
            355                 360                 365

Thr Gln Gly Ala Asp Glu Leu Thr Ala Glu Lys Gln Ala Gly Ala Glu
370                 375                 380

Leu Arg Glu Gln Val Leu Gly Gly Arg Val Ile Thr Gly Phe Val Ser
385                 390                 395                 400

Thr Ala Pro Leu Ala Ala Glu Met Arg Ala Phe Leu Asp Ile Thr Leu
                405                 410                 415

Gly Ala His Ile Val Asp Gly Tyr Gly Leu Thr Glu Thr Gly Ala Val
                420                 425                 430

Thr Arg Asp Gly Val Ile Val Arg Pro Pro Val Ile Asp Tyr Lys Leu
            435                 440                 445

Ile Asp Val Pro Glu Leu Gly Tyr Phe Ser Thr Asp Lys Pro Tyr Pro
450                 455                 460

Arg Gly Glu Leu Leu Val Arg Ser Gln Thr Leu Thr Pro Gly Tyr Tyr
465                 470                 475                 480

Lys Arg Pro Glu Val Thr Ala Ser Val Phe Asp Arg Asp Gly Tyr Tyr
                485                 490                 495

His Thr Gly Asp Val Met Ala Glu Thr Ala Pro Asp His Leu Val Tyr
            500                 505                 510

Val Asp Arg Arg Asn Asn Val Leu Lys Leu Ala Gln Gly Glu Phe Val
            515                 520                 525

Ala Val Ala Asn Leu Glu Ala Val Phe Ser Gly Ala Ala Leu Val Arg
530                 535                 540
```

```
Gln Ile Phe Val Tyr Gly Asn Ser Glu Arg Ser Phe Leu Leu Ala Val
545                 550                 555                 560

Val Val Pro Thr Pro Glu Ala Leu Glu Gln Tyr Asp Pro Ala Ala Leu
                565                 570                 575

Lys Ala Ala Leu Ala Asp Ser Leu Gln Arg Thr Ala Arg Asp Ala Glu
                580                 585                 590

Leu Gln Ser Tyr Glu Val Pro Ala Asp Phe Ile Val Glu Thr Glu Pro
            595                 600                 605

Phe Ser Ala Ala Asn Gly Leu Ser Gly Val Gly Lys Leu Leu Arg
        610                 615                 620

Pro Asn Leu Lys Asp Arg Tyr Gly Gln Arg Leu Glu Gln Met Tyr Ala
625                 630                 635                 640

Asp Ile Ala Ala Thr Gln Ala Asn Gln Leu Arg Glu Leu Arg Arg Ala
                645                 650                 655

Ala Ala Thr Gln Pro Val Ile Asp Thr Leu Thr Gln Ala Ala Ala Thr
                660                 665                 670

Ile Leu Gly Thr Gly Ser Glu Val Ala Ser Asp Ala His Phe Thr Asp
            675                 680                 685

Leu Gly Gly Asp Ser Leu Ser Ala Leu Thr Leu Ser Asn Leu Leu Ser
690                 695                 700

Asp Phe Phe Gly Phe Glu Val Pro Val Gly Thr Ile Val Asn Pro Ala
705                 710                 715                 720

Thr Asn Leu Ala Gln Leu Ala Gln His Ile Glu Ala Gln Arg Thr Ala
                725                 730                 735

Gly Asp Arg Arg Pro Ser Phe Thr Thr Val His Gly Ala Asp Ala Thr
                740                 745                 750

Glu Ile Arg Ala Ser Glu Leu Thr Leu Asp Lys Phe Ile Asp Ala Glu
            755                 760                 765

Thr Leu Arg Ala Ala Pro Gly Leu Pro Lys Val Thr Thr Glu Pro Arg
            770                 775                 780

Thr Val Leu Leu Ser Gly Ala Asn Gly Trp Leu Gly Arg Phe Leu Thr
785                 790                 795                 800

Leu Gln Trp Leu Glu Arg Leu Ala Pro Val Gly Gly Thr Leu Ile Thr
                805                 810                 815

Ile Val Arg Gly Arg Asp Asp Ala Ala Ala Arg Ala Arg Leu Thr Gln
                820                 825                 830

Ala Tyr Asp Thr Asp Pro Glu Leu Ser Arg Arg Phe Ala Glu Leu Ala
            835                 840                 845

Asp Arg His Leu Arg Val Val Ala Gly Asp Ile Gly Asp Pro Asn Leu
850                 855                 860

Gly Leu Thr Pro Glu Ile Trp His Arg Leu Ala Ala Glu Val Asp Leu
865                 870                 875                 880

Val Val His Pro Ala Ala Leu Val Asn His Val Leu Pro Tyr Arg Gln
                885                 890                 895

Leu Phe Gly Pro Asn Val Val Gly Thr Ala Glu Val Ile Lys Leu Ala
                900                 905                 910

Leu Thr Glu Arg Ile Lys Pro Val Thr Tyr Leu Ser Thr Val Ser Val
            915                 920                 925

Ala Met Gly Ile Pro Asp Phe Glu Glu Asp Gly Asp Ile Arg Thr Val
            930                 935                 940

Ser Pro Val Arg Pro Leu Asp Gly Gly Tyr Ala Asn Gly Tyr Gly Asn
945                 950                 955                 960

Ser Lys Trp Ala Gly Glu Val Leu Leu Arg Glu Ala His Asp Leu Cys
```

-continued

```
                965                 970                 975
Gly Leu Pro Val Ala Thr Phe Arg Ser Asp Met Ile Leu Ala His Pro
            980                 985                 990
Arg Tyr Arg Gly Gln Val Asn Val Pro Asp Met Phe Thr Arg Leu Leu
            995                1000                1005
Leu Ser Leu Leu Ile Thr Gly Val Ala Pro Arg Ser Phe Tyr Ile Gly
           1010                1015                1020
Asp Gly Glu Arg Pro Arg Ala His Tyr Pro Gly Leu Thr Val Asp Phe
1025                1030                1035                1040
Val Ala Glu Ala Val Thr Thr Leu Gly Ala Gln Gln Arg Glu Gly Tyr
                1045                1050                1055
Val Ser Tyr Asp Val Met Asn Pro His Asp Asp Gly Ile Ser Leu Asp
                1060                1065                1070
Val Phe Val Asp Trp Leu Ile Arg Ala Gly His Pro Ile Asp Arg Val
                1075                1080                1085
Asp Asp Tyr Asp Asp Trp Val Arg Arg Phe Glu Thr Ala Leu Thr Ala
                1090                1095                1100
Leu Pro Glu Lys Arg Arg Ala Gln Thr Val Leu Pro Leu Leu His Ala
1105                1110                1115                1120
Phe Arg Ala Pro Gln Ala Pro Leu Arg Gly Ala Pro Glu Pro Thr Glu
                1125                1130                1135
Val Phe His Ala Ala Val Arg Thr Ala Lys Val Gly Pro Gly Asp Ile
                1140                1145                1150
Pro His Leu Asp Glu Ala Leu Ile Asp Lys Tyr Ile Arg Asp Leu Arg
                1155                1160                1165
Glu Phe Gly Leu Ile
                1170

<210> SEQ ID NO 9
<211> LENGTH: 1148
<212> TYPE: PRT
<213> ORGANISM: Segniliparus rugosus

<400> SEQUENCE: 9

Met Gly Asp Gly Glu Glu Arg Ala Lys Arg Phe Phe Gln Arg Ile Gly
1               5                  10                  15
Glu Leu Ser Ala Thr Asp Pro Gln Phe Ala Ala Ala Pro Asp Pro
            20                  25                  30
Ala Val Val Glu Ala Val Ser Asp Pro Ser Leu Ser Phe Thr Arg Tyr
            35                  40                  45
Leu Asp Thr Leu Met Arg Gly Tyr Ala Glu Arg Pro Ala Leu Ala His
        50                  55                  60
Arg Val Gly Ala Gly Tyr Glu Thr Ile Ser Tyr Gly Glu Leu Trp Ala
65                  70                  75                  80
Arg Val Gly Ala Ile Ala Ala Trp Gln Ala Asp Gly Leu Ala Pro
                85                  90                  95
Gly Asp Phe Val Ala Thr Val Gly Phe Thr Ser Pro Asp Tyr Val Ala
            100                 105                 110
Val Asp Leu Ala Ala Ala Arg Ser Gly Leu Val Ser Val Pro Leu Gln
            115                 120                 125
Ala Gly Ala Ser Leu Ala Gln Leu Val Gly Ile Leu Glu Glu Thr Glu
        130                 135                 140
Pro Lys Val Leu Ala Ala Ser Ala Ser Ser Leu Glu Gly Ala Val Ala
145                 150                 155                 160
```

```
Cys Ala Leu Ala Ala Pro Ser Val Gln Arg Leu Val Phe Asp Leu
                165                 170                 175

Arg Gly Pro Asp Ala Ser Glu Ser Ala Ala Asp Glu Arg Arg Gly Ala
            180                 185                 190

Leu Ala Asp Ala Glu Glu Gln Leu Ala Arg Ala Gly Arg Ala Val Val
            195                 200                 205

Val Glu Thr Leu Ala Asp Leu Ala Ala Arg Gly Glu Ala Leu Pro Glu
            210                 215                 220

Ala Pro Leu Phe Glu Pro Ala Glu Gly Glu Asp Pro Leu Ala Leu Leu
225                 230                 235                 240

Ile Tyr Thr Ser Gly Ser Thr Gly Ala Pro Lys Gly Ala Met Tyr Ser
                245                 250                 255

Gln Arg Leu Val Ser Gln Leu Trp Gly Arg Thr Pro Val Val Pro Gly
            260                 265                 270

Met Pro Asn Ile Ser Leu His Tyr Met Pro Leu Ser His Ser Tyr Gly
            275                 280                 285

Arg Ala Val Leu Ala Gly Ala Leu Ser Ala Gly Thr Ala His Phe
            290                 295                 300

Thr Ala Asn Ser Asp Leu Ser Thr Leu Phe Glu Asp Ile Ala Leu Ala
305                 310                 315                 320

Arg Pro Thr Phe Leu Ala Leu Val Pro Arg Val Cys Glu Met Leu Phe
                325                 330                 335

Gln Glu Ser Gln Arg Gly Gln Asp Val Ala Glu Leu Arg Glu Arg Val
            340                 345                 350

Leu Gly Gly Arg Leu Leu Val Ala Val Cys Gly Ser Ala Pro Leu Ser
            355                 360                 365

Pro Glu Met Arg Ala Phe Met Glu Glu Val Leu Gly Phe Pro Leu Leu
            370                 375                 380

Asp Gly Tyr Gly Ser Thr Glu Ala Leu Gly Val Met Arg Asn Gly Ile
385                 390                 395                 400

Ile Gln Arg Pro Pro Val Ile Asp Tyr Lys Leu Val Asp Val Pro Glu
                405                 410                 415

Leu Gly Tyr Arg Thr Thr Asp Lys Pro Tyr Pro Arg Gly Glu Leu Cys
            420                 425                 430

Ile Arg Ser Thr Ser Leu Ile Ser Gly Tyr Tyr Lys Arg Pro Glu Ile
            435                 440                 445

Thr Ala Glu Val Phe Asp Ala Gln Gly Tyr Tyr Lys Thr Gly Asp Val
            450                 455                 460

Met Ala Glu Ile Ala Pro Asp His Leu Val Tyr Val Asp Arg Ser Lys
465                 470                 475                 480

Asn Val Leu Lys Leu Ser Gln Gly Glu Phe Val Ala Val Ala Lys Leu
                485                 490                 495

Glu Ala Ala Tyr Gly Thr Ser Pro Tyr Val Lys Gln Ile Phe Val Tyr
            500                 505                 510

Gly Asn Ser Glu Arg Ser Phe Leu Leu Ala Val Val Pro Asn Ala
            515                 520                 525

Glu Val Leu Gly Ala Arg Asp Gln Glu Glu Ala Lys Pro Leu Ile Ala
            530                 535                 540

Ala Ser Leu Gln Lys Ile Ala Lys Glu Ala Gly Leu Gln Ser Tyr Glu
545                 550                 555                 560

Val Pro Arg Asp Phe Leu Ile Glu Thr Glu Pro Phe Thr Thr Gln Asn
                565                 570                 575

Gly Leu Leu Ser Glu Val Gly Lys Leu Leu Arg Pro Lys Leu Lys Ala
```

-continued

```
            580                 585                 590
Arg Tyr Gly Glu Ala Leu Glu Ala Arg Tyr Asp Glu Ile Ala His Gly
            595                 600                 605
Gln Ala Asp Glu Leu Arg Ala Leu Arg Asp Gly Ala Gly Gln Arg Pro
            610                 615                 620
Val Val Glu Thr Val Val Arg Ala Ala Val Ala Ile Ser Gly Ser Glu
625                 630                 635                 640
Gly Ala Glu Val Gly Pro Glu Ala Asn Phe Ala Asp Leu Gly Gly Asp
                    645                 650                 655
Ser Leu Ser Ala Leu Ser Leu Ala Asn Leu Leu His Asp Val Phe Glu
                    660                 665                 670
Val Glu Val Pro Val Arg Ile Ile Ile Gly Pro Thr Ala Ser Leu Ala
                    675                 680                 685
Gly Ile Ala Lys His Ile Glu Ala Glu Arg Ala Gly Ala Ser Ala Pro
                    690                 695                 700
Thr Ala Ala Ser Val His Gly Ala Gly Ala Thr Arg Ile Arg Ala Ser
705                 710                 715                 720
Glu Leu Thr Leu Glu Lys Phe Leu Pro Glu Asp Leu Leu Ala Ala Ala
                    725                 730                 735
Lys Gly Leu Pro Ala Ala Asp Gln Val Arg Thr Val Leu Leu Thr Gly
                    740                 745                 750
Ala Asn Gly Trp Leu Gly Arg Phe Leu Ala Leu Glu Gln Leu Glu Arg
                    755                 760                 765
Leu Ala Arg Ser Gly Gln Asp Gly Gly Lys Leu Ile Cys Leu Val Arg
                    770                 775                 780
Gly Lys Asp Ala Ala Ala Arg Arg Arg Ile Glu Glu Thr Leu Gly
785                 790                 795                 800
Thr Asp Pro Ala Leu Ala Ala Arg Phe Ala Glu Leu Ala Glu Gly Arg
                    805                 810                 815
Leu Glu Val Val Pro Gly Asp Val Gly Glu Pro Lys Phe Gly Leu Asp
                    820                 825                 830
Asp Ala Ala Trp Asp Arg Leu Ala Glu Glu Val Asp Val Ile Val His
                    835                 840                 845
Pro Ala Ala Leu Val Asn His Val Leu Pro Tyr His Gln Leu Phe Gly
                    850                 855                 860
Pro Asn Val Val Gly Thr Ala Glu Ile Ile Arg Leu Ala Ile Thr Ala
865                 870                 875                 880
Lys Arg Lys Pro Val Thr Tyr Leu Ser Thr Val Ala Val Ala Ala Gly
                    885                 890                 895
Val Glu Pro Ser Ser Phe Glu Glu Asp Gly Asp Ile Arg Ala Val Val
                    900                 905                 910
Pro Glu Arg Pro Leu Gly Asp Gly Tyr Ala Asn Gly Tyr Gly Asn Ser
                    915                 920                 925
Lys Trp Ala Gly Glu Val Leu Leu Arg Glu Ala His Glu Leu Val Gly
                    930                 935                 940
Leu Pro Val Ala Val Phe Arg Ser Asp Met Ile Leu Ala His Thr Arg
945                 950                 955                 960
Tyr Thr Gly Gln Leu Asn Val Pro Asp Gln Phe Thr Arg Leu Val Leu
                    965                 970                 975
Ser Leu Leu Ala Thr Gly Ile Ala Pro Lys Ser Phe Tyr Gln Gln Gly
                    980                 985                 990
Ala Ala Gly Glu Arg Gln Arg Ala His Tyr Asp Gly Ile Pro Val Asp
                    995                 1000                1005
```

Phe Thr Ala Glu Ala Ile Thr Thr Leu Gly Ala Glu Pro Ser Trp Phe
        1010                1015                1020

Asp Gly Gly Ala Gly Phe Arg Ser Phe Asp Val Phe Asn Pro His His
1025                1030                1035                1040

Asp Gly Val Gly Leu Asp Glu Phe Val Asp Trp Leu Ile Glu Ala Gly
                1045                1050                1055

His Pro Ile Ser Arg Ile Asp Asp His Lys Glu Trp Phe Ala Arg Phe
                1060                1065                1070

Glu Thr Ala Val Arg Gly Leu Pro Glu Ala Gln Arg Gln His Ser Leu
            1075                1080                1085

Leu Pro Leu Leu Arg Ala Tyr Ser Phe Pro His Pro Val Asp Gly
        1090                1095                1100

Ser Val Tyr Pro Thr Gly Lys Phe Gln Gly Ala Val Lys Ala Ala Gln
1105                1110                1115                1120

Val Gly Ser Asp His Asp Val Pro His Leu Gly Lys Ala Leu Ile Val
                1125                1130                1135

Lys Tyr Ala Asp Asp Leu Lys Ala Leu Gly Leu Leu
            1140                1145

<210> SEQ ID NO 10
<211> LENGTH: 1168
<212> TYPE: PRT
<213> ORGANISM: Mycobacterium smegmatis

<400> SEQUENCE: 10

Met Thr Ile Glu Thr Arg Glu Asp Arg Phe Asn Arg Arg Ile Asp His
1               5                   10                  15

Leu Phe Glu Thr Asp Pro Gln Phe Ala Ala Ala Arg Pro Asp Glu Ala
            20                  25                  30

Ile Ser Ala Ala Ala Asp Pro Glu Leu Arg Leu Pro Ala Ala Val
        35                  40                  45

Lys Gln Ile Leu Ala Gly Tyr Ala Asp Arg Pro Ala Leu Gly Lys Arg
 50                  55                  60

Ala Val Glu Phe Val Thr Asp Glu Glu Gly Arg Thr Thr Ala Lys Leu
65                  70                  75                  80

Leu Pro Arg Phe Asp Thr Ile Thr Tyr Arg Gln Leu Ala Gly Arg Ile
                85                  90                  95

Gln Ala Val Thr Asn Ala Trp His Asn His Pro Val Asn Ala Gly Asp
            100                 105                 110

Arg Val Ala Ile Leu Gly Phe Thr Ser Val Asp Tyr Thr Thr Ile Asp
        115                 120                 125

Ile Ala Leu Leu Glu Leu Gly Ala Val Ser Val Pro Leu Gln Thr Ser
    130                 135                 140

Ala Pro Val Ala Gln Leu Gln Pro Ile Val Ala Glu Thr Glu Pro Lys
145                 150                 155                 160

Val Ile Ala Ser Ser Val Asp Phe Leu Ala Asp Ala Val Ala Leu Val
                165                 170                 175

Glu Ser Gly Pro Ala Pro Ser Arg Leu Val Val Phe Asp Tyr Ser His
            180                 185                 190

Glu Val Asp Asp Gln Arg Glu Ala Phe Glu Ala Ala Lys Gly Lys Leu
        195                 200                 205

Ala Gly Thr Gly Val Val Val Glu Thr Ile Thr Asp Ala Leu Asp Arg
    210                 215                 220

Gly Arg Ser Leu Ala Asp Ala Pro Leu Tyr Val Pro Asp Glu Ala Asp

```
              225                 230                 235                 240
        Pro Leu Thr Leu Leu Ile Tyr Thr Ser Gly Ser Thr Gly Thr Pro Lys
                            245                 250                 255

Gly Ala Met Tyr Pro Glu Ser Lys Thr Ala Thr Met Trp Gln Ala Gly
                            260                 265                 270

Ser Lys Ala Arg Trp Asp Glu Thr Leu Gly Val Met Pro Ser Ile Thr
                    275                 280                 285

Leu Asn Phe Met Pro Met Ser His Val Met Gly Arg Gly Ile Leu Cys
                    290                 295                 300

Ser Thr Leu Ala Ser Gly Gly Thr Ala Tyr Phe Ala Ala Arg Ser Asp
        305                 310                 315                 320

Leu Ser Thr Phe Leu Glu Asp Leu Ala Leu Val Arg Pro Thr Gln Leu
                            325                 330                 335

Asn Phe Val Pro Arg Ile Trp Asp Met Leu Phe Gln Glu Tyr Gln Ser
                            340                 345                 350

Arg Leu Asp Asn Arg Arg Ala Glu Gly Ser Glu Asp Arg Ala Glu Ala
                    355                 360                 365

Ala Val Leu Glu Glu Val Arg Thr Gln Leu Leu Gly Gly Arg Phe Val
                    370                 375                 380

Ser Ala Leu Thr Gly Ser Ala Pro Ile Ser Ala Glu Met Lys Ser Trp
        385                 390                 395                 400

Val Glu Asp Leu Leu Asp Met His Leu Leu Gly Tyr Gly Ser Thr
                            405                 410                 415

Glu Ala Gly Ala Val Phe Ile Asp Gly Gln Ile Gln Arg Pro Pro Val
                    420                 425                 430

Ile Asp Tyr Lys Leu Val Asp Val Pro Asp Leu Gly Tyr Phe Ala Thr
                    435                 440                 445

Asp Arg Pro Tyr Pro Arg Gly Glu Leu Leu Val Lys Ser Glu Gln Met
                    450                 455                 460

Phe Pro Gly Tyr Tyr Lys Arg Pro Glu Ile Thr Ala Glu Met Phe Asp
        465                 470                 475                 480

Glu Asp Gly Tyr Tyr Arg Thr Gly Asp Ile Val Ala Glu Leu Gly Pro
                            485                 490                 495

Asp His Leu Glu Tyr Leu Asp Arg Arg Asn Asn Val Leu Lys Leu Ser
                    500                 505                 510

Gln Gly Glu Phe Val Thr Val Ser Lys Leu Glu Ala Val Phe Gly Asp
                    515                 520                 525

Ser Pro Leu Val Arg Gln Ile Tyr Val Tyr Gly Asn Ser Ala Arg Ser
        530                 535                 540

Tyr Leu Leu Ala Val Val Pro Thr Glu Glu Ala Leu Ser Arg Trp
        545                 550                 555                 560

Asp Gly Asp Glu Leu Lys Ser Arg Ile Ser Asp Ser Leu Gln Asp Ala
                            565                 570                 575

Ala Arg Ala Ala Gly Leu Gln Ser Tyr Glu Ile Pro Arg Asp Phe Leu
                    580                 585                 590

Val Glu Thr Thr Pro Phe Thr Leu Glu Asn Gly Leu Leu Thr Gly Ile
                    595                 600                 605

Arg Lys Leu Ala Arg Pro Lys Leu Lys Ala His Tyr Gly Glu Arg Leu
        610                 615                 620

Glu Gln Leu Tyr Thr Asp Leu Ala Gly Gln Ala Asn Glu Leu Arg
        625                 630                 635                 640

Glu Leu Arg Arg Asn Gly Ala Asp Arg Pro Val Val Glu Thr Val Ser
                            645                 650                 655
```

```
Arg Ala Ala Val Ala Leu Leu Gly Ala Ser Val Thr Asp Leu Arg Ser
            660                 665                 670

Asp Ala His Phe Thr Asp Leu Gly Asp Ser Leu Ser Ala Leu Ser
        675                 680                 685

Phe Ser Asn Leu Leu His Glu Ile Phe Asp Val Asp Val Pro Val Gly
690                 695                 700

Val Ile Val Ser Pro Ala Thr Asp Leu Ala Gly Val Ala Ala Tyr Ile
705                 710                 715                 720

Glu Gly Glu Leu Arg Gly Ser Lys Arg Pro Thr Tyr Ala Ser Val His
            725                 730                 735

Gly Arg Asp Ala Thr Glu Val Arg Ala Arg Asp Leu Ala Leu Gly Lys
            740                 745                 750

Phe Ile Asp Ala Lys Thr Leu Ser Ala Ala Pro Gly Leu Pro Arg Ser
        755                 760                 765

Gly Thr Glu Ile Arg Thr Val Leu Leu Thr Gly Ala Thr Gly Phe Leu
770                 775                 780

Gly Arg Tyr Leu Ala Leu Glu Trp Leu Glu Arg Met Asp Leu Val Asp
785                 790                 795                 800

Gly Lys Val Ile Cys Leu Val Arg Ala Arg Ser Asp Asp Glu Ala Arg
            805                 810                 815

Ala Arg Leu Asp Ala Thr Phe Asp Thr Gly Asp Ala Thr Leu Leu Glu
            820                 825                 830

His Tyr Arg Ala Leu Ala Ala Asp His Leu Glu Val Ile Ala Gly Asp
        835                 840                 845

Lys Gly Glu Ala Asp Leu Gly Leu Asp His Asp Thr Trp Gln Arg Leu
        850                 855                 860

Ala Asp Thr Val Asp Leu Ile Val Asp Pro Ala Ala Leu Val Asn His
865                 870                 875                 880

Val Leu Pro Tyr Ser Gln Met Phe Gly Pro Asn Ala Leu Gly Thr Ala
            885                 890                 895

Glu Leu Ile Arg Ile Ala Leu Thr Thr Thr Ile Lys Pro Tyr Val Tyr
            900                 905                 910

Val Ser Thr Ile Gly Val Gly Gln Gly Ile Ser Pro Glu Ala Phe Val
        915                 920                 925

Glu Asp Ala Asp Ile Arg Glu Ile Ser Ala Thr Arg Arg Val Asp Asp
930                 935                 940

Ser Tyr Ala Asn Gly Tyr Gly Asn Ser Lys Trp Ala Gly Glu Val Leu
945                 950                 955                 960

Leu Arg Glu Ala His Asp Trp Cys Gly Leu Pro Val Ser Val Phe Arg
            965                 970                 975

Cys Asp Met Ile Leu Ala Asp Thr Thr Tyr Ser Gly Gln Leu Asn Leu
            980                 985                 990

Pro Asp Met Phe Thr Arg Leu Met Leu Ser Leu Val Ala Thr Gly Ile
        995                 1000                1005

Ala Pro Gly Ser Phe Tyr Glu Leu Asp Ala Asp Gly Asn Arg Gln Arg
        1010                1015                1020

Ala His Tyr Asp Gly Leu Pro Val Glu Phe Ile Ala Glu Ala Ile Ser
1025                1030                1035                1040

Thr Ile Gly Ser Gln Val Thr Asp Gly Phe Glu Thr Phe His Val Met
            1045                1050                1055

Asn Pro Tyr Asp Asp Gly Ile Gly Leu Asp Glu Tyr Val Asp Trp Leu
            1060                1065                1070
```

```
Ile Glu Ala Gly Tyr Pro Val His Arg Val Asp Asp Tyr Ala Thr Trp
    1075                1080                1085

Leu Ser Arg Phe Glu Thr Ala Leu Arg Ala Leu Pro Glu Arg Gln Arg
    1090                1095                1100

Gln Ala Ser Leu Leu Pro Leu Leu His Asn Tyr Gln Gln Pro Ser Pro
1105                1110                1115                1120

Pro Val Cys Gly Ala Met Ala Pro Thr Asp Arg Phe Arg Ala Ala Val
            1125                1130                1135

Gln Asp Ala Lys Ile Gly Pro Asp Lys Asp Ile Pro His Val Thr Ala
                1140                1145                1150

Asp Val Ile Val Lys Tyr Ile Ser Asn Leu Gln Met Leu Gly Leu Leu
            1155                1160                1165

<210> SEQ ID NO 11
<211> LENGTH: 1185
<212> TYPE: PRT
<213> ORGANISM: Mycobacterium massiliense

<400> SEQUENCE: 11

Met Thr Asn Glu Thr Asn Pro Gln Gln Glu Gln Leu Ser Arg Arg Ile
1               5                   10                  15

Glu Ser Leu Arg Glu Ser Asp Pro Gln Phe Arg Ala Ala Gln Pro Asp
            20                  25                  30

Pro Ala Val Ala Glu Gln Val Leu Arg Pro Gly Leu His Leu Ser Glu
        35                  40                  45

Ala Ile Ala Ala Leu Met Thr Gly Tyr Ala Glu Arg Pro Ala Leu Gly
    50                  55                  60

Glu Arg Ala Arg Glu Leu Val Ile Asp Gln Asp Gly Arg Thr Thr Leu
65                  70                  75                  80

Arg Leu Leu Pro Arg Phe Asp Thr Thr Thr Tyr Gly Glu Leu Trp Ser
                85                  90                  95

Arg Thr Thr Ser Val Ala Ala Ala Trp His His Asp Ala Thr His Pro
            100                 105                 110

Val Lys Ala Gly Asp Leu Val Ala Thr Leu Gly Phe Thr Ser Ile Asp
        115                 120                 125

Tyr Thr Val Leu Asp Leu Ala Ile Met Ile Leu Gly Gly Val Ala Val
    130                 135                 140

Pro Leu Gln Thr Ser Ala Pro Ser Gln Trp Thr Thr Ile Leu Ala
145                 150                 155                 160

Glu Ala Glu Pro Asn Thr Leu Ala Val Ser Ile Glu Leu Ile Gly Ala
                165                 170                 175

Ala Met Glu Ser Val Arg Ala Thr Pro Ser Ile Lys Gln Val Val Val
            180                 185                 190

Phe Asp Tyr Thr Pro Glu Val Asp Asp Gln Arg Glu Ala Phe Glu Ala
        195                 200                 205

Ala Ser Thr Gln Leu Ala Gly Thr Gly Ile Ala Leu Glu Thr Leu Asp
    210                 215                 220

Ala Val Ile Ala Arg Gly Ala Ala Leu Pro Ala Ala Pro Leu Tyr Ala
225                 230                 235                 240

Pro Ser Ala Gly Asp Asp Pro Leu Ala Leu Leu Ile Tyr Thr Ser Gly
                245                 250                 255

Ser Thr Gly Ala Pro Lys Gly Ala Met His Ser Glu Asn Ile Val Arg
            260                 265                 270

Arg Trp Trp Ile Arg Glu Asp Val Met Ala Gly Thr Glu Asn Leu Pro
        275                 280                 285
```

```
Met Ile Gly Leu Asn Phe Met Pro Met Ser His Ile Met Gly Arg Gly
        290                 295                 300
Thr Leu Thr Ser Thr Leu Ser Thr Gly Gly Thr Gly Tyr Phe Ala Ala
305                 310                 315                 320
Ser Ser Asp Met Ser Thr Leu Phe Glu Asp Met Glu Leu Ile Arg Pro
                325                 330                 335
Thr Ala Leu Ala Leu Val Pro Arg Val Cys Asp Met Val Phe Gln Arg
                340                 345                 350
Phe Gln Thr Glu Val Asp Arg Arg Leu Ala Ser Gly Asp Thr Ala Ser
            355                 360                 365
Ala Glu Ala Val Ala Ala Glu Val Lys Ala Asp Ile Arg Asp Asn Leu
370                 375                 380
Phe Gly Gly Arg Val Ser Ala Val Met Val Gly Ser Ala Pro Leu Ser
385                 390                 395                 400
Glu Glu Leu Gly Glu Phe Ile Glu Ser Cys Phe Glu Leu Asn Leu Thr
                405                 410                 415
Asp Gly Tyr Gly Ser Thr Glu Ala Gly Met Val Phe Arg Asp Gly Ile
                420                 425                 430
Val Gln Arg Pro Pro Val Ile Asp Tyr Lys Leu Val Asp Val Pro Glu
            435                 440                 445
Leu Gly Tyr Phe Ser Thr Asp Lys Pro His Pro Arg Gly Glu Leu Leu
450                 455                 460
Leu Lys Thr Asp Gly Met Phe Leu Gly Tyr Tyr Lys Arg Pro Glu Val
465                 470                 475                 480
Thr Ala Ser Val Phe Asp Ala Asp Gly Phe Tyr Met Thr Gly Asp Ile
                485                 490                 495
Val Ala Glu Leu Ala His Asp Asn Ile Glu Ile Ile Asp Arg Arg Asn
                500                 505                 510
Asn Val Leu Lys Leu Ser Gln Gly Glu Phe Val Ala Val Ala Thr Leu
            515                 520                 525
Glu Ala Glu Tyr Ala Asn Ser Pro Val Val His Gln Ile Tyr Val Tyr
            530                 535                 540
Gly Ser Ser Glu Arg Ser Tyr Leu Leu Ala Val Val Pro Thr Pro
545                 550                 555                 560
Glu Ala Val Ala Ala Lys Gly Asp Ala Ala Ala Leu Lys Thr Thr
                565                 570                 575
Ile Ala Asp Ser Leu Gln Asp Ile Ala Lys Glu Ile Gln Leu Gln Ser
                580                 585                 590
Tyr Glu Val Pro Arg Asp Phe Ile Ile Glu Pro Gln Pro Phe Thr Gln
            595                 600                 605
Gly Asn Gly Leu Leu Thr Gly Ile Ala Lys Leu Ala Arg Pro Asn Leu
            610                 615                 620
Lys Ala His Tyr Gly Pro Arg Leu Glu Gln Met Tyr Ala Glu Ile Ala
625                 630                 635                 640
Glu Gln Gln Ala Ala Glu Leu Arg Ala Leu His Gly Val Asp Pro Asp
                645                 650                 655
Lys Pro Ala Leu Glu Thr Val Leu Lys Ala Ala Gln Ala Leu Leu Gly
                660                 665                 670
Val Ser Ser Ala Glu Leu Ala Ala Asp Ala His Phe Thr Asp Leu Gly
            675                 680                 685
Gly Asp Ser Leu Ser Ala Leu Ser Phe Ser Asp Leu Leu Arg Asp Ile
            690                 695                 700
```

```
Phe Ala Val Glu Val Pro Val Gly Val Ile Val Ser Ala Ala Asn Asp
705                 710                 715                 720

Leu Gly Gly Val Ala Lys Phe Val Asp Glu Gln Arg His Ser Gly Gly
            725                 730                 735

Thr Arg Pro Thr Ala Glu Thr Val His Gly Ala Gly His Thr Glu Ile
            740                 745                 750

Arg Ala Ala Asp Leu Thr Leu Asp Lys Phe Ile Asp Glu Ala Thr Leu
            755                 760                 765

His Ala Ala Pro Ser Leu Pro Lys Ala Ala Gly Ile Pro His Thr Val
            770                 775                 780

Leu Leu Thr Gly Ser Asn Gly Tyr Leu Gly His Tyr Leu Ala Leu Glu
785                 790                 795                 800

Trp Leu Glu Arg Leu Asp Lys Thr Asp Gly Lys Leu Ile Val Ile Val
                805                 810                 815

Arg Gly Lys Asn Ala Glu Ala Ala Tyr Gly Arg Leu Glu Glu Ala Phe
            820                 825                 830

Asp Thr Gly Asp Thr Glu Leu Leu Ala His Phe Arg Ser Leu Ala Asp
            835                 840                 845

Lys His Leu Glu Val Leu Ala Gly Asp Ile Gly Asp Pro Asn Leu Gly
            850                 855                 860

Leu Asp Ala Asp Thr Trp Gln Arg Leu Ala Asp Thr Val Asp Val Ile
865                 870                 875                 880

Val His Pro Ala Ala Leu Val Asn His Val Leu Pro Tyr Asn Gln Leu
                885                 890                 895

Phe Gly Pro Asn Val Val Gly Thr Ala Glu Ile Ile Lys Leu Ala Ile
            900                 905                 910

Thr Thr Lys Ile Lys Pro Val Thr Tyr Leu Ser Thr Val Ala Val Ala
            915                 920                 925

Ala Tyr Val Asp Pro Thr Thr Phe Asp Glu Glu Ser Asp Ile Arg Leu
            930                 935                 940

Ile Ser Ala Val Arg Pro Ile Asp Asp Gly Tyr Ala Asn Gly Tyr Gly
945                 950                 955                 960

Asn Ala Lys Trp Ala Gly Glu Val Leu Leu Arg Glu Ala His Asp Leu
            965                 970                 975

Cys Gly Leu Pro Val Ala Val Phe Arg Ser Asp Met Ile Leu Ala His
            980                 985                 990

Ser Arg Tyr Thr Gly Gln Leu Asn Val Pro Asp Gln Phe Thr Arg Leu
            995                 1000                1005

Ile Leu Ser Leu Ile Ala Thr Gly Ile Ala Pro Gly Ser Phe Tyr Gln
    1010                1015                1020

Ala Gln Thr Thr Gly Glu Arg Pro Leu Ala His Tyr Asp Gly Leu Pro
1025                1030                1035                1040

Gly Asp Phe Thr Ala Glu Ala Ile Thr Thr Leu Gly Thr Gln Val Pro
            1045                1050                1055

Glu Gly Ser Glu Gly Phe Val Tyr Asp Cys Val Asn Pro His Ala
            1060                1065                1070

Asp Gly Ile Ser Leu Asp Asn Phe Val Asp Trp Leu Ile Glu Ala Gly
            1075                1080                1085

Tyr Pro Ile Ala Arg Ile Asp Asn Tyr Thr Glu Trp Phe Thr Arg Phe
            1090                1095                1100

Asp Thr Ala Ile Arg Gly Leu Ser Glu Lys Gln Lys Gln His Ser Leu
1105                1110                1115                1120

Leu Pro Leu Leu His Ala Phe Glu Gln Pro Ser Ala Ala Glu Asn His
```

```
                    1125                1130                1135
Gly Val Val Pro Ala Lys Arg Phe Gln His Ala Val Gln Ala Ala Gly
            1140                1145                1150

Ile Gly Pro Val Gly Gln Asp Gly Thr Thr Asp Ile Pro His Leu Ser
            1155                1160                1165

Arg Arg Leu Ile Val Lys Tyr Ala Lys Asp Leu Glu Gln Leu Gly Leu
            1170                1175                1180

Leu
1185

<210> SEQ ID NO 12
<211> LENGTH: 1186
<212> TYPE: PRT
<213> ORGANISM: Segniliparus rotundus

<400> SEQUENCE: 12

Met Thr Gln Ser His Thr Gln Gly Pro Gln Ala Ser Ala Ala His Ser
  1               5                  10                  15

Arg Leu Ala Arg Arg Ala Ala Glu Leu Leu Ala Thr Asp Pro Gln Ala
             20                  25                  30

Ala Ala Thr Leu Pro Asp Pro Glu Val Val Arg Gln Ala Thr Arg Pro
         35                  40                  45

Gly Leu Arg Leu Ala Glu Arg Val Asp Ala Ile Leu Ser Gly Tyr Ala
     50                  55                  60

Asp Arg Pro Ala Leu Gly Gln Arg Ser Phe Gln Thr Val Lys Asp Pro
 65                  70                  75                  80

Ile Thr Gly Arg Ser Ser Val Glu Leu Leu Pro Thr Phe Asp Thr Ile
                 85                  90                  95

Thr Tyr Arg Glu Leu Arg Glu Arg Ala Thr Ala Ile Ala Ser Asp Leu
            100                 105                 110

Ala His His Pro Gln Ala Pro Ala Lys Pro Gly Asp Phe Leu Ala Ser
        115                 120                 125

Ile Gly Phe Ile Ser Val Asp Tyr Val Ala Ile Asp Ile Ala Gly Val
    130                 135                 140

Phe Ala Gly Leu Thr Ala Val Pro Leu Gln Thr Gly Ala Thr Leu Ala
145                 150                 155                 160

Thr Leu Thr Ala Ile Thr Ala Glu Thr Ala Pro Thr Leu Phe Ala Ala
                165                 170                 175

Ser Ile Glu His Leu Pro Thr Ala Val Asp Ala Val Leu Ala Thr Pro
            180                 185                 190

Ser Val Arg Arg Leu Leu Val Phe Asp Tyr Arg Ala Gly Ser Asp Glu
        195                 200                 205

Asp Arg Glu Ala Val Glu Ala Ala Lys Arg Lys Ile Ala Asp Ala Gly
    210                 215                 220

Ser Ser Val Leu Val Asp Val Leu Asp Glu Val Ile Ala Arg Gly Lys
225                 230                 235                 240

Ser Ala Pro Lys Ala Pro Leu Pro Pro Ala Thr Asp Ala Gly Asp Asp
                245                 250                 255

Ser Leu Ser Leu Leu Ile Tyr Thr Ser Gly Ser Thr Gly Thr Pro Lys
            260                 265                 270

Gly Ala Met Tyr Pro Glu Arg Asn Val Ala His Phe Trp Gly Gly Val
        275                 280                 285

Trp Ala Ala Ala Phe Asp Glu Asp Ala Ala Pro Val Pro Ala Ile
    290                 295                 300
```

```
Asn Ile Thr Phe Leu Pro Leu Ser His Val Ala Ser Arg Leu Ser Leu
305                 310                 315                 320

Met Pro Thr Leu Ala Arg Gly Gly Leu Met His Phe Val Ala Lys Ser
            325                 330                 335

Asp Leu Ser Thr Leu Phe Glu Asp Leu Lys Leu Ala Arg Pro Thr Asn
                340                 345                 350

Leu Phe Leu Val Pro Arg Val Val Glu Met Leu Tyr Gln His Tyr Gln
            355                 360                 365

Ser Glu Leu Asp Arg Arg Gly Val Gln Asp Gly Thr Arg Glu Ala Glu
370                 375                 380

Ala Val Lys Asp Asp Leu Arg Thr Gly Leu Leu Gly Gly Arg Ile Leu
385                 390                 395                 400

Thr Ala Gly Phe Gly Ser Ala Pro Leu Ser Ala Glu Leu Ala Gly Phe
                405                 410                 415

Ile Glu Ser Leu Leu Gln Ile His Leu Val Asp Gly Tyr Gly Ser Thr
                420                 425                 430

Glu Ala Gly Pro Val Trp Arg Asp Gly Tyr Leu Val Lys Pro Pro Val
            435                 440                 445

Thr Asp Tyr Lys Leu Ile Asp Val Pro Glu Leu Gly Tyr Phe Ser Thr
450                 455                 460

Asp Ser Pro His Pro Arg Gly Glu Leu Ala Ile Lys Thr Gln Thr Ile
465                 470                 475                 480

Leu Pro Gly Tyr Tyr Lys Arg Pro Glu Thr Thr Ala Glu Val Phe Asp
                485                 490                 495

Glu Asp Gly Phe Tyr Leu Thr Gly Asp Val Val Ala Gln Ile Gly Pro
                500                 505                 510

Glu Gln Phe Ala Tyr Val Asp Arg Arg Lys Asn Val Leu Lys Leu Ser
            515                 520                 525

Gln Gly Glu Phe Val Thr Leu Ala Lys Leu Glu Ala Ala Tyr Ser Ser
            530                 535                 540

Ser Pro Leu Val Arg Gln Leu Phe Val Tyr Gly Ser Ser Glu Arg Ser
545                 550                 555                 560

Tyr Leu Leu Ala Val Ile Val Pro Thr Pro Asp Ala Leu Lys Lys Phe
                565                 570                 575

Gly Val Gly Glu Ala Ala Lys Ala Ala Leu Gly Glu Ser Leu Gln Lys
            580                 585                 590

Ile Ala Arg Asp Glu Gly Leu Gln Ser Tyr Glu Val Pro Arg Asp Phe
            595                 600                 605

Ile Ile Glu Thr Asp Pro Phe Thr Val Glu Asn Gly Leu Leu Ser Asp
            610                 615                 620

Ala Arg Lys Ser Leu Arg Pro Lys Leu Lys Glu His Tyr Gly Glu Arg
625                 630                 635                 640

Leu Glu Ala Met Tyr Lys Glu Leu Ala Asp Gly Gln Ala Asn Glu Leu
                645                 650                 655

Arg Asp Ile Arg Arg Gly Val Gln Gln Arg Pro Thr Leu Glu Thr Val
                660                 665                 670

Arg Arg Ala Ala Ala Ala Met Leu Gly Ala Ser Ala Ala Glu Ile Lys
            675                 680                 685

Pro Asp Ala His Phe Thr Asp Leu Gly Gly Asp Ser Leu Ser Ala Leu
            690                 695                 700

Thr Phe Ser Asn Phe Leu His Asp Leu Phe Glu Val Asp Val Pro Val
705                 710                 715                 720

Gly Val Ile Val Ser Ala Ala Asn Thr Leu Gly Ser Val Ala Glu His
```

```
              725                 730                 735
Ile Asp Ala Gln Leu Ala Gly Gly Arg Ala Arg Pro Thr Phe Ala Thr
                740                 745                 750

Val His Gly Lys Gly Ser Thr Thr Ile Lys Ala Ser Asp Leu Thr Leu
                755                 760                 765

Asp Lys Phe Ile Asp Glu Gln Thr Leu Glu Ala Ala Lys His Leu Pro
    770                 775                 780

Lys Pro Ala Asp Pro Pro Arg Thr Val Leu Leu Thr Gly Ala Asn Gly
785                 790                 795                 800

Trp Leu Gly Arg Phe Leu Ala Leu Glu Trp Leu Glu Arg Leu Ala Pro
                805                 810                 815

Ala Gly Gly Lys Leu Ile Thr Ile Val Arg Gly Lys Asp Ala Ala Gln
                820                 825                 830

Ala Lys Ala Arg Leu Asp Ala Ala Tyr Glu Ser Gly Asp Pro Lys Leu
                835                 840                 845

Ala Gly His Tyr Gln Asp Leu Ala Ala Thr Thr Leu Glu Val Leu Ala
                850                 855                 860

Gly Asp Phe Ser Glu Pro Arg Leu Gly Leu Asp Glu Ala Thr Trp Asn
865                 870                 875                 880

Arg Leu Ala Asp Glu Val Asp Phe Ile Ser His Pro Gly Ala Leu Val
                885                 890                 895

Asn His Val Leu Pro Tyr Asn Gln Leu Phe Gly Pro Asn Val Ala Gly
                900                 905                 910

Val Ala Glu Ile Ile Lys Leu Ala Ile Thr Thr Arg Ile Lys Pro Val
                915                 920                 925

Thr Tyr Leu Ser Thr Val Ala Val Ala Ala Gly Val Glu Pro Ser Ala
    930                 935                 940

Leu Asp Glu Asp Gly Asp Ile Arg Thr Val Ser Ala Glu Arg Ser Val
945                 950                 955                 960

Asp Glu Gly Tyr Ala Asn Gly Tyr Gly Asn Ser Lys Trp Gly Gly Glu
                965                 970                 975

Val Leu Leu Arg Glu Ala His Asp Arg Thr Gly Leu Pro Val Arg Val
                980                 985                 990

Phe Arg Ser Asp Met Ile Leu Ala His Gln Lys Tyr Thr Gly Gln Val
                995                1000                1005

Asn Ala Thr Asp Gln Phe Thr Arg Leu Val Gln Ser Leu Leu Ala Thr
    1010                1015                1020

Gly Leu Ala Pro Lys Ser Phe Tyr Glu Leu Asp Ala Gln Gly Asn Arg
1025                1030                1035                1040

Gln Arg Ala His Tyr Asp Gly Ile Pro Val Asp Phe Thr Ala Glu Ser
                1045                1050                1055

Ile Thr Thr Leu Gly Gly Asp Gly Leu Glu Gly Tyr Arg Ser Tyr Asn
                1060                1065                1070

Val Phe Asn Pro His Arg Asp Gly Val Gly Leu Asp Glu Phe Val Asp
                1075                1080                1085

Trp Leu Ile Glu Ala Gly His Pro Ile Thr Arg Ile Asp Asp Tyr Asp
                1090                1095                1100

Gln Trp Leu Ser Arg Phe Glu Thr Ser Leu Arg Gly Leu Pro Glu Ser
1105                1110                1115                1120

Lys Arg Gln Ala Ser Val Leu Pro Leu Leu His Ala Phe Ala Arg Pro
                1125                1130                1135

Gly Pro Ala Val Asp Gly Ser Pro Phe Arg Asn Thr Val Phe Arg Thr
                1140                1145                1150
```

Asp Val Gln Lys Ala Lys Ile Gly Ala Glu His Asp Ile Pro His Leu
    1155                1160                1165

Gly Lys Ala Leu Val Leu Lys Tyr Ala Asp Asp Ile Lys Gln Leu Gly
    1170                1175                1180

Leu Leu
1185

<210> SEQ ID NO 13
<211> LENGTH: 459
<212> TYPE: PRT
<213> ORGANISM: Chromobacterium violaceum

<400> SEQUENCE: 13

Met Gln Lys Gln Arg Thr Thr Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Ser Glu
        35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Ala Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
    210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
        275                 280                 285

Gly Leu Ser Ser Gly Tyr Leu Pro Ile Gly Ala Val Phe Val Gly Lys
    290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val

```
            325                 330                 335
Ala Ala Leu Arg Asp Glu Gly Ile Val Gln Arg Val Lys Asp Asp Ile
            340                 345                 350
Gly Pro Tyr Met Gln Lys Arg Trp Arg Glu Thr Phe Ser Arg Phe Glu
            355                 360                 365
His Val Asp Asp Val Arg Gly Val Gly Met Val Gln Ala Phe Thr Leu
            370                 375                 380
Val Lys Asn Lys Ala Lys Arg Glu Leu Phe Pro Asp Phe Gly Glu Ile
385                 390                 395                 400
Gly Thr Leu Cys Arg Asp Ile Phe Phe Arg Asn Asn Leu Ile Met Arg
            405                 410                 415
Ala Cys Gly Asp His Ile Val Ser Ala Pro Leu Val Met Thr Arg
            420                 425                 430
Ala Glu Val Asp Glu Met Leu Ala Val Ala Glu Arg Cys Leu Glu Glu
            435                 440                 445
Phe Glu Gln Thr Leu Lys Ala Arg Gly Leu Ala
            450                 455

<210> SEQ ID NO 14
<211> LENGTH: 468
<212> TYPE: PRT
<213> ORGANISM: Pseudomonas aeruginosa

<400> SEQUENCE: 14

Met Asn Ala Arg Leu His Ala Thr Ser Pro Leu Gly Asp Ala Asp Leu
1               5                   10                  15
Val Arg Ala Asp Gln Ala His Tyr Met His Gly Tyr His Val Phe Asp
            20                  25                  30
Asp His Arg Val Asn Gly Ser Leu Asn Ile Ala Ala Gly Asp Gly Ala
            35                  40                  45
Tyr Ile Tyr Asp Thr Ala Gly Asn Arg Tyr Leu Asp Ala Val Gly Gly
            50                  55                  60
Met Trp Cys Thr Asn Ile Gly Leu Gly Arg Glu Glu Met Ala Arg Thr
65                  70                  75                  80
Val Ala Glu Gln Thr Arg Leu Leu Ala Tyr Ser Asn Pro Phe Cys Asp
                85                  90                  95
Met Ala Asn Pro Arg Ala Ile Glu Leu Cys Arg Lys Leu Ala Glu Leu
                100                 105                 110
Ala Pro Gly Asp Leu Asp His Val Phe Leu Thr Thr Gly Gly Ser Thr
            115                 120                 125
Ala Val Asp Thr Ala Ile Arg Leu Met His Tyr Tyr Gln Asn Cys Arg
            130                 135                 140
Gly Lys Arg Ala Lys Lys His Val Ile Thr Arg Ile Asn Ala Tyr His
145                 150                 155                 160
Gly Ser Thr Phe Leu Gly Met Ser Leu Gly Gly Lys Ser Ala Asp Arg
                165                 170                 175
Pro Ala Glu Phe Asp Phe Leu Asp Glu Arg Ile His His Leu Ala Cys
            180                 185                 190
Pro Tyr Tyr Tyr Arg Ala Pro Glu Gly Leu Gly Glu Ala Glu Phe Leu
            195                 200                 205
Asp Gly Leu Val Asp Glu Phe Glu Arg Lys Ile Leu Glu Leu Gly Ala
            210                 215                 220
Asp Arg Val Gly Ala Phe Ile Ser Glu Pro Val Phe Gly Ser Gly Gly
225                 230                 235                 240
```

```
Val Ile Val Pro Pro Ala Gly Tyr His Arg Arg Met Trp Glu Leu Cys
            245                 250                 255

Gln Arg Tyr Asp Val Leu Tyr Ile Ser Asp Glu Val Val Thr Ser Phe
        260                 265                 270

Gly Arg Leu Gly His Phe Phe Ala Ser Gln Ala Val Phe Gly Val Gln
    275                 280                 285

Pro Asp Ile Ile Leu Thr Ala Lys Gly Leu Thr Ser Gly Tyr Gln Pro
290                 295                 300

Leu Gly Ala Cys Ile Phe Ser Arg Arg Ile Trp Glu Val Ile Ala Glu
305                 310                 315                 320

Pro Asp Lys Gly Arg Cys Phe Ser His Gly Phe Thr Tyr Ser Gly His
                325                 330                 335

Pro Val Ala Cys Ala Ala Leu Lys Asn Ile Glu Ile Ile Glu Arg
            340                 345                 350

Glu Gly Leu Leu Ala His Ala Asp Glu Val Gly Arg Tyr Phe Glu Glu
        355                 360                 365

Arg Leu Gln Ser Leu Arg Asp Leu Pro Ile Val Gly Asp Val Arg Gly
    370                 375                 380

Met Arg Phe Met Ala Cys Val Glu Phe Val Ala Asp Lys Ala Ser Lys
385                 390                 395                 400

Ala Leu Phe Pro Glu Ser Leu Asn Ile Gly Glu Trp Val His Leu Arg
                405                 410                 415

Ala Gln Lys Arg Gly Leu Leu Val Arg Pro Ile Val His Leu Asn Val
            420                 425                 430

Met Ser Pro Pro Leu Ile Leu Thr Arg Glu Gln Val Asp Thr Val Val
        435                 440                 445

Arg Val Leu Arg Glu Ser Ile Glu Glu Thr Val Glu Asp Leu Val Arg
    450                 455                 460

Ala Gly His Arg
465

<210> SEQ ID NO 15
<211> LENGTH: 454
<212> TYPE: PRT
<213> ORGANISM: Pseudomonas syringae

<400> SEQUENCE: 15

Met Ser Ala Asn Asn Pro Gln Thr Leu Glu Trp Gln Ala Leu Ser Ser
1               5                   10                  15

Glu His His Leu Ala Pro Phe Ser Asp Tyr Lys Gln Leu Lys Glu Lys
            20                  25                  30

Gly Pro Arg Ile Ile Thr Arg Ala Glu Gly Val Tyr Leu Trp Asp Ser
        35                  40                  45

Glu Gly Asn Lys Ile Leu Asp Gly Met Ser Gly Leu Trp Cys Val Ala
    50                  55                  60

Ile Gly Tyr Gly Arg Glu Glu Leu Ala Asp Ala Ala Ser Lys Gln Met
65                  70                  75                  80

Arg Glu Leu Pro Tyr Tyr Asn Leu Phe Phe Gln Thr Ala His Pro Pro
                85                  90                  95

Val Leu Glu Leu Ala Lys Ala Ile Ser Asp Ile Ala Pro Glu Gly Met
            100                 105                 110

Asn His Val Phe Phe Thr Gly Ser Gly Ser Glu Gly Asn Asp Thr Met
        115                 120                 125

Leu Arg Met Val Arg His Tyr Trp Ala Leu Lys Gly Gln Pro Asn Lys
    130                 135                 140
```

```
Lys Thr Ile Ile Ser Arg Val Asn Gly Tyr His Gly Ser Thr Val Ala
145                 150                 155                 160

Gly Ala Ser Leu Gly Gly Met Thr Tyr Met His Glu Gln Gly Asp Leu
            165                 170                 175

Pro Ile Pro Gly Val Val His Ile Pro Gln Pro Tyr Trp Phe Gly Glu
        180                 185                 190

Gly Gly Asp Met Thr Pro Asp Glu Phe Gly Ile Trp Ala Ala Glu Gln
            195                 200                 205

Leu Glu Lys Lys Ile Leu Glu Leu Gly Val Glu Asn Val Gly Ala Phe
    210                 215                 220

Ile Ala Glu Pro Ile Gln Gly Ala Gly Gly Val Ile Val Pro Pro Asp
225                 230                 235                 240

Ser Tyr Trp Pro Lys Ile Lys Glu Ile Leu Ser Arg Tyr Asp Ile Leu
                245                 250                 255

Phe Ala Ala Asp Glu Val Ile Cys Gly Phe Gly Arg Thr Ser Glu Trp
            260                 265                 270

Phe Gly Ser Asp Phe Tyr Gly Leu Arg Pro Asp Met Met Thr Ile Ala
        275                 280                 285

Lys Gly Leu Thr Ser Gly Tyr Val Pro Met Gly Gly Leu Ile Val Arg
    290                 295                 300

Asp Glu Ile Val Ala Val Leu Asn Gly Gly Asp Phe Asn His Gly
305                 310                 315                 320

Phe Thr Tyr Ser Gly His Pro Val Ala Ala Val Ala Leu Glu Asn
                325                 330                 335

Ile Arg Ile Leu Arg Glu Glu Lys Ile Val Glu Arg Val Arg Ser Glu
            340                 345                 350

Thr Ala Pro Tyr Leu Gln Lys Arg Leu Arg Glu Leu Ser Asp His Pro
        355                 360                 365

Leu Val Gly Glu Val Arg Gly Val Gly Leu Leu Gly Ala Ile Glu Leu
    370                 375                 380

Val Lys Asp Lys Thr Thr Arg Glu Arg Tyr Thr Asp Lys Gly Ala Gly
385                 390                 395                 400

Met Ile Cys Arg Thr Phe Cys Phe Asp Asn Gly Leu Ile Met Arg Ala
                405                 410                 415

Val Gly Asp Thr Met Ile Ile Ala Pro Pro Leu Val Ile Ser Phe Ala
            420                 425                 430

Gln Ile Asp Glu Leu Val Glu Lys Ala Arg Thr Cys Leu Asp Leu Thr
        435                 440                 445

Leu Ala Val Leu Gln Gly
    450

<210> SEQ ID NO 16
<211> LENGTH: 467
<212> TYPE: PRT
<213> ORGANISM: Rhodobacter sphaeroides

<400> SEQUENCE: 16

Met Thr Arg Asn Asp Ala Thr Asn Ala Ala Gly Ala Val Gly Ala Ala
1               5                   10                  15

Met Arg Asp His Ile Leu Leu Pro Ala Gln Glu Met Ala Lys Leu Gly
            20                  25                  30

Lys Ser Ala Gln Pro Val Leu Thr His Ala Glu Gly Ile Tyr Val His
        35                  40                  45

Thr Glu Asp Gly Arg Arg Leu Ile Asp Gly Pro Ala Gly Met Trp Cys
```

```
        50                  55                  60
Ala Gln Val Gly Tyr Gly Arg Arg Glu Ile Val Asp Ala Met Ala His
 65                  70                  75                  80

Gln Ala Met Val Leu Pro Tyr Ala Ser Pro Trp Tyr Met Ala Thr Ser
                 85                  90                  95

Pro Ala Ala Arg Leu Ala Glu Lys Ile Ala Thr Leu Thr Pro Gly Asp
            100                 105                 110

Leu Asn Arg Ile Phe Phe Thr Thr Gly Gly Ser Thr Ala Val Asp Ser
        115                 120                 125

Ala Leu Arg Phe Ser Glu Phe Tyr Asn Asn Val Leu Gly Arg Pro Gln
    130                 135                 140

Lys Lys Arg Ile Ile Val Arg Tyr Asp Gly Tyr His Gly Ser Thr Ala
145                 150                 155                 160

Leu Thr Ala Ala Cys Thr Gly Arg Thr Gly Asn Trp Pro Asn Phe Asp
                165                 170                 175

Ile Ala Gln Asp Arg Ile Ser Phe Leu Ser Ser Pro Asn Pro Arg His
            180                 185                 190

Ala Gly Asn Arg Ser Gln Glu Ala Phe Leu Asp Asp Leu Val Gln Glu
        195                 200                 205

Phe Glu Asp Arg Ile Glu Ser Leu Gly Pro Asp Thr Ile Ala Ala Phe
    210                 215                 220

Leu Ala Glu Pro Ile Leu Ala Ser Gly Gly Val Ile Pro Pro Ala
225                 230                 235                 240

Gly Tyr His Ala Arg Phe Lys Ala Ile Cys Glu Lys His Asp Ile Leu
                245                 250                 255

Tyr Ile Ser Asp Glu Val Val Thr Gly Phe Gly Arg Cys Gly Glu Trp
            260                 265                 270

Phe Ala Ser Glu Lys Val Phe Gly Val Val Pro Asp Ile Ile Thr Phe
        275                 280                 285

Ala Lys Gly Val Thr Ser Gly Tyr Val Pro Leu Gly Gly Leu Ala Ile
    290                 295                 300

Ser Glu Ala Val Leu Ala Arg Ile Ser Gly Glu Asn Ala Lys Gly Ser
305                 310                 315                 320

Trp Phe Thr Asn Gly Tyr Thr Tyr Ser Asn Gln Pro Val Ala Cys Ala
                325                 330                 335

Ala Ala Leu Ala Asn Ile Glu Leu Met Glu Arg Glu Gly Ile Val Asp
            340                 345                 350

Gln Ala Arg Glu Met Ala Asp Tyr Phe Ala Ala Leu Ala Ser Leu
        355                 360                 365

Arg Asp Leu Pro Gly Val Ala Glu Thr Arg Ser Val Gly Leu Val Gly
    370                 375                 380

Cys Val Gln Cys Leu Leu Asp Pro Thr Arg Ala Asp Gly Thr Ala Glu
385                 390                 395                 400

Asp Lys Ala Phe Thr Leu Lys Ile Asp Glu Arg Cys Phe Glu Leu Gly
                405                 410                 415

Leu Ile Val Arg Pro Leu Gly Asp Leu Cys Val Ile Ser Pro Pro Leu
            420                 425                 430

Ile Ile Ser Arg Ala Gln Ile Asp Glu Met Val Ala Ile Met Arg Gln
        435                 440                 445

Ala Ile Thr Glu Val Ser Ala Ala His Gly Leu Thr Ala Lys Glu Pro
    450                 455                 460

Ala Ala Val
465
```

<210> SEQ ID NO 17
<211> LENGTH: 459
<212> TYPE: PRT
<213> ORGANISM: Escherichia coli

<400> SEQUENCE: 17

```
Met Asn Arg Leu Pro Ser Ser Ala Ser Ala Leu Ala Cys Ser Ala His
1               5                   10                  15

Ala Leu Asn Leu Ile Glu Lys Arg Thr Leu Asp His Glu Glu Met Lys
            20                  25                  30

Ala Leu Asn Arg Glu Val Ile Glu Tyr Phe Lys Glu His Val Asn Pro
        35                  40                  45

Gly Phe Leu Glu Tyr Arg Lys Ser Val Thr Ala Gly Gly Asp Tyr Gly
    50                  55                  60

Ala Val Glu Trp Gln Ala Gly Ser Leu Asn Thr Leu Val Asp Thr Gln
65                  70                  75                  80

Gly Gln Glu Phe Ile Asp Cys Leu Gly Gly Phe Gly Ile Phe Asn Val
                85                  90                  95

Gly His Arg Asn Pro Val Val Ser Ala Val Gln Asn Gln Leu Ala
            100                 105                 110

Lys Gln Pro Leu His Ser Gln Glu Leu Leu Asp Pro Leu Arg Ala Met
        115                 120                 125

Leu Ala Lys Thr Leu Ala Ala Leu Thr Pro Gly Lys Leu Lys Tyr Ser
130                 135                 140

Phe Phe Cys Asn Ser Gly Thr Glu Ser Val Glu Ala Ala Leu Lys Leu
145                 150                 155                 160

Ala Lys Ala Tyr Gln Ser Pro Arg Gly Lys Phe Thr Phe Ile Ala Thr
                165                 170                 175

Ser Gly Ala Phe His Gly Lys Ser Leu Gly Ala Leu Ser Ala Thr Ala
            180                 185                 190

Lys Ser Thr Phe Arg Lys Pro Phe Met Pro Leu Leu Pro Gly Phe Arg
        195                 200                 205

His Val Pro Phe Gly Asn Ile Glu Ala Met Arg Thr Ala Leu Asn Glu
    210                 215                 220

Cys Lys Lys Thr Gly Asp Asp Val Ala Ala Val Ile Leu Glu Pro Ile
225                 230                 235                 240

Gln Gly Glu Gly Gly Val Ile Leu Pro Pro Gly Tyr Leu Thr Ala
                245                 250                 255

Val Arg Lys Leu Cys Asp Glu Phe Gly Ala Leu Met Ile Leu Asp Glu
            260                 265                 270

Val Gln Thr Gly Met Gly Arg Thr Gly Lys Met Phe Ala Cys Glu His
        275                 280                 285

Glu Asn Val Gln Pro Asp Ile Leu Cys Leu Ala Lys Ala Leu Gly Gly
    290                 295                 300

Gly Val Met Pro Ile Gly Ala Thr Ile Ala Thr Glu Glu Val Phe Ser
305                 310                 315                 320

Val Leu Phe Asp Asn Pro Phe Leu His Thr Thr Thr Phe Gly Gly Asn
                325                 330                 335

Pro Leu Ala Cys Ala Ala Ala Leu Ala Thr Ile Asn Val Leu Leu Glu
            340                 345                 350

Gln Asn Leu Pro Ala Gln Ala Glu Gln Lys Gly Asp Met Leu Leu Asp
        355                 360                 365

Gly Phe Arg Gln Leu Ala Arg Glu Tyr Pro Asp Leu Val Gln Glu Ala
```

-continued

```
                370                 375                 380
Arg Gly Lys Gly Met Leu Met Ala Ile Glu Phe Val Asp Asn Glu Ile
385                 390                 395                 400

Gly Tyr Asn Phe Ala Ser Glu Met Phe Arg Gln Arg Val Leu Val Ala
                405                 410                 415

Gly Thr Leu Asn Asn Ala Lys Thr Ile Arg Ile Glu Pro Pro Leu Thr
                420                 425                 430

Leu Thr Ile Glu Gln Cys Glu Leu Val Ile Lys Ala Ala Arg Lys Ala
                435                 440                 445

Leu Ala Ala Met Arg Val Ser Val Glu Glu Ala
                450                 455
```

<210> SEQ ID NO 18
<211> LENGTH: 453
<212> TYPE: PRT
<213> ORGANISM: Vibrio Fluvialis

<400> SEQUENCE: 18

```
Met Asn Lys Pro Gln Ser Trp Glu Ala Arg Ala Glu Thr Tyr Ser Leu
1               5                   10                  15

Tyr Gly Phe Thr Asp Met Pro Ser Leu His Gln Arg Gly Thr Val Val
                20                  25                  30

Val Thr His Gly Glu Gly Pro Tyr Ile Val Asp Val Asn Gly Arg Arg
            35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Phe Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Val His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Arg Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285
```

Ala Gly Phe Phe Pro Met Gly Ala Val Ile Leu Gly Pro Glu Leu Ser
          290                 295                 300

Lys Arg Leu Glu Thr Ala Ile Glu Ala Ile Glu Glu Phe Pro His Gly
305                 310                 315                 320

Phe Thr Ala Ser Gly His Pro Val Gly Cys Ala Ile Ala Leu Lys Ala
                325                 330                 335

Ile Asp Val Val Met Asn Glu Gly Leu Ala Glu Asn Val Arg Arg Leu
                340                 345                 350

Ala Pro Arg Phe Glu Arg Leu Lys His Ile Ala Glu Arg Pro Asn
                355                 360                 365

Ile Gly Glu Tyr Arg Gly Ile Gly Phe Met Trp Ala Leu Glu Ala Val
    370                 375                 380

Lys Asp Lys Ala Ser Lys Thr Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
                420                 425                 430

Gln Met Asp Glu Met Phe Asp Lys Leu Glu Lys Ala Leu Asp Lys Val
                435                 440                 445

Phe Ala Glu Val Ala
    450

<210> SEQ ID NO 19
<211> LENGTH: 224
<212> TYPE: PRT
<213> ORGANISM: Bacillus subtilis

<400> SEQUENCE: 19

Met Lys Ile Tyr Gly Ile Tyr Met Asp Arg Pro Leu Ser Gln Glu Glu
  1               5                  10                  15

Asn Glu Arg Phe Met Ser Phe Ile Ser Pro Glu Lys Arg Glu Lys Cys
                 20                  25                  30

Arg Arg Phe Tyr His Lys Glu Asp Ala His Arg Thr Leu Leu Gly Asp
                 35                  40                  45

Val Leu Val Arg Ser Val Ile Ser Arg Gln Tyr Gln Leu Asp Lys Ser
 50                  55                  60

Asp Ile Arg Phe Ser Thr Gln Glu Tyr Gly Lys Pro Cys Ile Pro Asp
 65                  70                  75                  80

Leu Pro Asp Ala His Phe Asn Ile Ser His Ser Gly Arg Trp Val Ile
                 85                  90                  95

Cys Ala Phe Asp Ser Gln Pro Ile Gly Ile Asp Ile Glu Lys Thr Lys
                100                 105                 110

Pro Ile Ser Leu Glu Ile Ala Lys Arg Phe Phe Ser Lys Thr Glu Tyr
                115                 120                 125

Ser Asp Leu Leu Ala Lys Asp Lys Asp Glu Gln Thr Asp Tyr Phe Tyr
                130                 135                 140

His Leu Trp Ser Met Lys Glu Ser Phe Ile Lys Gln Glu Gly Lys Gly
145                 150                 155                 160

Leu Ser Leu Pro Leu Asp Ser Phe Ser Val Arg Leu His Gln Asp Gly
                165                 170                 175

Gln Val Ser Ile Glu Leu Pro Asp Ser His Ser Pro Cys Tyr Ile Lys
                180                 185                 190

Thr Tyr Glu Val Asp Pro Gly Tyr Lys Met Ala Val Cys Ala Ala His
                195                 200                 205

-continued

Pro Asp Phe Pro Glu Asp Ile Thr Met Val Ser Tyr Glu Glu Leu Leu
    210                 215                 220

<210> SEQ ID NO 20
<211> LENGTH: 222
<212> TYPE: PRT
<213> ORGANISM: Nocardia sp. NRRL 5646

<400> SEQUENCE: 20

Met Ile Glu Thr Ile Leu Pro Ala Gly Val Glu Ser Ala Glu Leu Leu
  1               5                  10                  15

Glu Tyr Pro Glu Asp Leu Lys Ala His Pro Ala Glu Glu His Leu Ile
                 20                  25                  30

Ala Lys Ser Val Glu Lys Arg Arg Asp Phe Ile Gly Ala Arg His
             35                  40                  45

Cys Ala Arg Leu Ala Leu Ala Glu Leu Gly Glu Pro Pro Val Ala Ile
         50                  55                  60

Gly Lys Gly Glu Arg Gly Ala Pro Ile Trp Pro Arg Gly Val Val Gly
 65                  70                  75                  80

Ser Leu Thr His Cys Asp Gly Tyr Arg Ala Ala Val Ala His Lys
                 85                  90                  95

Met Arg Phe Arg Ser Ile Gly Ile Asp Ala Glu Pro His Ala Thr Leu
                100                 105                 110

Pro Glu Gly Val Leu Asp Ser Val Ser Leu Pro Pro Glu Arg Glu Trp
                115                 120                 125

Leu Lys Thr Thr Asp Ser Ala Leu His Leu Asp Arg Leu Leu Phe Cys
130                 135                 140

Ala Lys Glu Ala Thr Tyr Lys Ala Trp Trp Pro Leu Thr Ala Arg Trp
145                 150                 155                 160

Leu Gly Phe Glu Glu Ala His Ile Thr Phe Glu Ile Glu Asp Gly Ser
                165                 170                 175

Ala Asp Ser Gly Asn Gly Thr Phe His Ser Glu Leu Leu Val Pro Gly
                180                 185                 190

Gln Thr Asn Asp Gly Gly Thr Pro Leu Leu Ser Phe Asp Gly Arg Trp
                195                 200                 205

Leu Ile Ala Asp Gly Phe Ile Leu Thr Ala Ile Ala Tyr Ala
    210                 215                 220

<210> SEQ ID NO 21
<211> LENGTH: 286
<212> TYPE: PRT
<213> ORGANISM: Escherichia coli

<400> SEQUENCE: 21

Met Ser Gln Ala Leu Lys Asn Leu Leu Thr Leu Leu Asn Leu Glu Lys
  1               5                  10                  15

Ile Glu Glu Gly Leu Phe Arg Gly Gln Ser Glu Asp Leu Gly Leu Arg
                 20                  25                  30

Gln Val Phe Gly Gly Gln Val Val Gly Gln Ala Leu Tyr Ala Ala Lys
             35                  40                  45

Glu Thr Val Pro Glu Glu Arg Leu Val His Ser Phe His Ser Tyr Phe
         50                  55                  60

Leu Arg Pro Gly Asp Ser Lys Lys Pro Ile Ile Tyr Asp Val Glu Thr
 65                  70                  75                  80

Leu Arg Asp Gly Asn Ser Phe Ser Ala Arg Arg Val Ala Ala Ile Gln
                 85                  90                  95

-continued

Asn Gly Lys Pro Ile Phe Tyr Met Thr Ala Ser Phe Gln Ala Pro Glu
            100                 105                 110

Ala Gly Phe Glu His Gln Lys Thr Met Pro Ser Ala Pro Ala Pro Asp
        115                 120                 125

Gly Leu Pro Ser Glu Thr Gln Ile Ala Gln Ser Leu Ala His Leu Leu
    130                 135                 140

Pro Pro Val Leu Lys Asp Lys Phe Ile Cys Asp Arg Pro Leu Glu Val
145                 150                 155                 160

Arg Pro Val Glu Phe His Asn Pro Leu Lys Gly His Val Ala Glu Pro
                165                 170                 175

His Arg Gln Val Trp Ile Arg Ala Asn Gly Ser Val Pro Asp Asp Leu
            180                 185                 190

Arg Val His Gln Tyr Leu Leu Gly Tyr Ala Ser Asp Leu Asn Phe Leu
        195                 200                 205

Pro Val Ala Leu Gln Pro His Gly Ile Gly Phe Leu Glu Pro Gly Ile
    210                 215                 220

Gln Ile Ala Thr Ile Asp His Ser Met Trp Phe His Arg Pro Phe Asn
225                 230                 235                 240

Leu Asn Glu Trp Leu Leu Tyr Ser Val Glu Ser Thr Ser Ala Ser Ser
                245                 250                 255

Ala Arg Gly Phe Val Arg Gly Glu Phe Tyr Thr Gln Asp Gly Val Leu
            260                 265                 270

Val Ala Ser Thr Val Gln Glu Gly Val Met Arg Asn His Asn
        275                 280                 285

<210> SEQ ID NO 22
<211> LENGTH: 561
<212> TYPE: PRT
<213> ORGANISM: Escherichia coli

<400> SEQUENCE: 22

Met Lys Lys Val Trp Leu Asn Arg Tyr Pro Ala Asp Val Pro Thr Glu
1               5                   10                  15

Ile Asn Pro Asp Arg Tyr Gln Ser Leu Val Asp Met Phe Glu Gln Ser
            20                  25                  30

Val Ala Arg Tyr Ala Asp Gln Pro Ala Phe Val Asn Met Gly Glu Val
        35                  40                  45

Met Thr Phe Arg Lys Leu Glu Glu Arg Ser Arg Ala Phe Ala Ala Tyr
    50                  55                  60

Leu Gln Gln Gly Leu Gly Leu Lys Lys Gly Asp Arg Val Ala Leu Met
65                  70                  75                  80

Met Pro Asn Leu Leu Gln Tyr Pro Val Ala Leu Phe Gly Ile Leu Arg
                85                  90                  95

Ala Gly Met Ile Val Val Asn Val Asn Pro Leu Tyr Thr Pro Arg Glu
            100                 105                 110

Leu Glu His Gln Leu Asn Asp Ser Gly Ala Ser Ala Ile Val Ile Val
        115                 120                 125

Ser Asn Phe Ala His Thr Leu Glu Lys Val Val Asp Lys Thr Ala Val
    130                 135                 140

Gln His Val Ile Leu Thr Arg Met Gly Asp Gln Leu Ser Thr Ala Lys
145                 150                 155                 160

Gly Thr Val Val Asn Phe Val Val Lys Tyr Ile Lys Arg Leu Val Pro
                165                 170                 175

Lys Tyr His Leu Pro Asp Ala Ile Ser Phe Arg Ser Ala Leu His Asn

```
                180                 185                 190
Gly Tyr Arg Met Gln Tyr Val Lys Pro Glu Leu Val Pro Glu Asp Leu
            195                 200                 205

Ala Phe Leu Gln Tyr Thr Gly Thr Thr Gly Val Ala Lys Gly Ala
        210                 215                 220

Met Leu Thr His Arg Asn Met Leu Ala Asn Leu Glu Gln Val Asn Ala
225                 230                 235                 240

Thr Tyr Gly Pro Leu Leu His Pro Gly Lys Glu Leu Val Val Thr Ala
            245                 250                 255

Leu Pro Leu Tyr His Ile Phe Ala Leu Thr Ile Asn Cys Leu Leu Phe
        260                 265                 270

Ile Glu Leu Gly Gly Gln Asn Leu Leu Ile Thr Asn Pro Arg Asp Ile
            275                 280                 285

Pro Gly Leu Val Lys Glu Leu Ala Lys Tyr Pro Phe Thr Ala Ile Thr
        290                 295                 300

Gly Val Asn Thr Leu Phe Asn Ala Leu Leu Asn Asn Lys Glu Phe Gln
305                 310                 315                 320

Gln Leu Asp Phe Ser Ser Leu His Leu Ser Ala Gly Gly Met Pro
            325                 330                 335

Val Gln Gln Val Val Ala Glu Arg Trp Val Lys Leu Thr Gly Gln Tyr
        340                 345                 350

Leu Leu Glu Gly Tyr Gly Leu Thr Glu Cys Ala Pro Leu Val Ser Val
            355                 360                 365

Asn Pro Tyr Asp Ile Asp Tyr His Ser Gly Ser Ile Gly Leu Pro Val
370                 375                 380

Pro Ser Thr Glu Ala Lys Leu Val Asp Asp Asp Asn Glu Val Pro
385                 390                 395                 400

Pro Gly Gln Pro Gly Glu Leu Cys Val Lys Gly Pro Gln Val Met Leu
            405                 410                 415

Gly Tyr Trp Gln Arg Pro Asp Ala Thr Asp Glu Ile Ile Lys Asn Gly
        420                 425                 430

Trp Leu His Thr Gly Asp Ile Ala Val Met Asp Glu Glu Gly Phe Leu
        435                 440                 445

Arg Ile Val Asp Arg Lys Lys Asp Met Ile Leu Val Ser Gly Phe Asn
    450                 455                 460

Val Tyr Pro Asn Glu Ile Glu Asp Val Val Met Gln His Pro Gly Val
465                 470                 475                 480

Gln Glu Val Ala Ala Val Gly Val Pro Ser Gly Ser Ser Gly Glu Ala
            485                 490                 495

Val Lys Ile Phe Val Val Lys Asp Pro Ser Leu Thr Glu Glu Ser
        500                 505                 510

Leu Val Thr Phe Cys Arg Arg Gln Leu Thr Gly Tyr Lys Val Pro Lys
        515                 520                 525

Leu Val Glu Phe Arg Asp Glu Leu Pro Lys Ser Asn Val Gly Lys Ile
        530                 535                 540

Leu Arg Arg Glu Leu Arg Asp Glu Ala Arg Gly Lys Val Asp Asn Lys
545                 550                 555                 560

Ala

<210> SEQ ID NO 23
<211> LENGTH: 515
<212> TYPE: PRT
<213> ORGANISM: Cupriavidus necator
```

<400> SEQUENCE: 23

```
Met His Pro His Ile His Ala Gln Arg Thr Pro Glu Lys Pro Ala Val
1               5                   10                  15

Ile Met Gly Gly Ser Gly Ala Val Val Thr Tyr Arg Glu Leu Asp Glu
            20                  25                  30

Arg Ser Asn Gln Val Ala His Leu Phe Arg Ser Gln Gly Leu Gln Pro
        35                  40                  45

Gly Asp Arg Val Ala Phe Met Val Glu Asn His Pro Arg Leu Phe Glu
    50                  55                  60

Leu Cys Trp Gly Ala Gln Arg Ser Gly Ile Val Tyr Val Cys Leu Ser
65                  70                  75                  80

Thr Arg Leu Asn Val Ala Asp Ala Ala His Ile Ile Asn Asp Ser Gly
                85                  90                  95

Ala Arg Leu Leu Val Thr Thr His Ala Gln Ala Glu Val Ala Ala Ala
            100                 105                 110

Leu Ala Gly Gln Thr Pro Ala Leu Arg Gly Arg Leu Met Leu Asp Gly
        115                 120                 125

Thr Met Pro Gly Tyr Asp Ala Tyr Glu Thr Ala Leu Ala Arg Cys Pro
130                 135                 140

Ala Thr Arg Ile Asp Asp Glu Val Thr Gly Gly Asp Met Leu Tyr Ser
145                 150                 155                 160

Ser Gly Thr Thr Gly Arg Pro Lys Gly Val Tyr Ala Pro Pro Ser Ser
                165                 170                 175

Pro Asn Ile Asp Asp Pro Thr Thr Leu Thr Ser Leu Cys Gln Arg Leu
            180                 185                 190

Tyr Gly Phe Asp Ala Glu Thr Arg Tyr Leu Ser Pro Ala Pro Leu Tyr
        195                 200                 205

His Ala Ala Pro Leu Arg Tyr Asn Met Thr Val Gln Ala Leu Gly Gly
    210                 215                 220

Thr Ala Val Val Met Glu His Phe Asp Ala Glu His Tyr Leu Gln Leu
225                 230                 235                 240

Val Gln Gln His Arg Ile Thr His Thr Gln Leu Val Pro Thr Met Phe
                245                 250                 255

Ser Arg Met Leu Lys Leu Pro Glu Ala Gln Arg Gln Ala Tyr Asp Val
            260                 265                 270

Ser Ser Leu Arg Val Ala Ile His Ala Ala Pro Cys Pro Val Gln
        275                 280                 285

Val Lys Glu Ala Met Ile Ala Trp Trp Gly Pro Val Ile Trp Glu Tyr
    290                 295                 300

Tyr Ala Gly Thr Glu Gly Asn Gly Val Thr Val Val Ser Thr Pro Glu
305                 310                 315                 320

Trp Leu Glu Arg Lys Gly Thr Val Gly Arg Ala Met Val Gly Lys Leu
                325                 330                 335

Arg Ile Cys Gly Pro Asp Gly Ala Leu Leu Pro Pro Gly Glu Ser Gly
            340                 345                 350

Thr Ile Tyr Phe Ala Glu Gly Arg Asp Phe Ser Tyr His Asn Asp Glu
        355                 360                 365

Ala Lys Thr Ala Glu Ser Arg His Pro Gln Gln Pro Asp Trp Ser Thr
    370                 375                 380

Ile Gly Asp Val Gly Tyr Val Asp Ala Asp Gly Tyr Leu Tyr Leu Thr
385                 390                 395                 400

Asp Arg Lys Ala Asn Met Ile Ile Ser Gly Gly Val Asn Ile Tyr Pro
                405                 410                 415
```

```
Gln Glu Ala Glu Asn Leu Leu Met Thr His Pro Lys Val Met Asp Val
                420                 425                 430

Ala Val Ile Gly Val Pro Asn Glu Asp Phe Gly Glu Val Lys Ala
            435                 440                 445

Val Val Gln Pro Val Asp Met Ser Gln Ala Gly Pro Glu Leu Ala Ala
    450                 455                 460

Glu Leu Ile Ala Phe Cys Arg Ala Asn Leu Ser Ala Ile Lys Cys Pro
465                 470                 475                 480

Arg Ser Val Asp Phe Ala Ser Glu Leu Pro Arg Leu Pro Thr Gly Lys
                485                 490                 495

Leu Leu Lys Arg Leu Leu Arg Asp Arg Tyr Trp Gly Gly His Ala Asn
                500                 505                 510

Lys Leu Val
        515

<210> SEQ ID NO 24
<211> LENGTH: 320
<212> TYPE: PRT
<213> ORGANISM: Acidaminococcus fermentans

<400> SEQUENCE: 24

Met Ser Lys Val Met Thr Leu Lys Asp Ala Ile Ala Lys Tyr Val His
1               5                   10                  15

Ser Gly Asp His Ile Ala Leu Gly Gly Phe Thr Thr Asp Arg Lys Pro
                20                  25                  30

Tyr Ala Ala Val Phe Glu Ile Leu Arg Gln Gly Ile Thr Asp Leu Thr
            35                  40                  45

Gly Leu Gly Gly Ala Ala Gly Gly Asp Trp Asp Met Leu Ile Gly Asn
    50                  55                  60

Gly Arg Val Lys Ala Tyr Ile Asn Cys Tyr Thr Ala Asn Ser Gly Val
65                  70                  75                  80

Thr Asn Val Ser Arg Arg Phe Arg Lys Trp Phe Glu Ala Gly Lys Leu
                85                  90                  95

Thr Met Glu Asp Tyr Ser Gln Asp Val Ile Tyr Met Met Trp His Ala
                100                 105                 110

Ala Ala Leu Gly Leu Pro Phe Leu Pro Val Thr Leu Met Gln Gly Ser
            115                 120                 125

Gly Leu Thr Asp Glu Trp Gly Ile Ser Lys Glu Val Arg Lys Thr Leu
    130                 135                 140

Asp Lys Val Pro Asp Asp Lys Phe Lys Tyr Ile Asp Asn Pro Phe Lys
145                 150                 155                 160

Pro Gly Glu Lys Val Val Ala Val Pro Val Pro Gln Val Asp Val Ala
                165                 170                 175

Ile Ile His Ala Gln Gln Ala Ser Pro Asp Gly Thr Val Arg Ile Trp
            180                 185                 190

Gly Gly Lys Phe Gln Asp Val Asp Ile Ala Glu Ala Ala Lys Tyr Thr
    195                 200                 205

Ile Val Thr Cys Glu Glu Ile Ile Ser Asp Glu Glu Ile Arg Arg Asp
210                 215                 220

Pro Thr Lys Asn Asp Ile Pro Gly Met Cys Val Asp Ala Val Val Leu
225                 230                 235                 240

Ala Pro Tyr Gly Ala His Pro Ser Gln Cys Tyr Gly Leu Tyr Asp Tyr
                245                 250                 255

Asp Asn Pro Phe Leu Lys Val Tyr Asp Lys Val Ser Lys Thr Gln Glu
```

```
                260                 265                 270
Asp Phe Asp Ala Phe Cys Lys Glu Trp Val Phe Asp Leu Lys Asp His
                275                 280                 285

Asp Glu Tyr Leu Asn Lys Leu Gly Ala Thr Arg Leu Ile Asn Leu Lys
                290                 295                 300

Val Val Pro Gly Leu Gly Tyr His Ile Asp Met Thr Lys Glu Asp Lys
305                 310                 315                 320

<210> SEQ ID NO 25
<211> LENGTH: 266
<212> TYPE: PRT
<213> ORGANISM: Acidaminococcus fermentans

<400> SEQUENCE: 25

Met Ala Asp Tyr Thr Asn Tyr Thr Asn Lys Glu Met Gln Ala Val Thr
1               5                   10                  15

Ile Ala Lys Gln Ile Lys Asn Gly Gln Val Val Thr Val Gly Thr Gly
                20                  25                  30

Leu Pro Leu Ile Gly Ala Ser Val Ala Lys Arg Val Tyr Ala Pro Asp
                35                  40                  45

Cys His Ile Ile Val Glu Ser Gly Leu Met Asp Cys Ser Pro Val Glu
            50                  55                  60

Val Pro Arg Ser Val Gly Asp Leu Arg Phe Met Ala His Cys Gly Cys
65                  70                  75                  80

Ile Trp Pro Asn Val Arg Phe Val Gly Phe Glu Ile Asn Glu Tyr Leu
                85                  90                  95

His Lys Ala Asn Arg Leu Ile Ala Phe Ile Gly Gly Ala Gln Ile Asp
                100                 105                 110

Pro Tyr Gly Asn Val Asn Ser Thr Ser Ile Gly Asp Tyr His His Pro
            115                 120                 125

Lys Thr Arg Phe Thr Gly Ser Gly Gly Ala Asn Gly Ile Ala Thr Tyr
130                 135                 140

Ser Asn Thr Ile Ile Met Met Gln His Glu Lys Arg Arg Phe Met Asn
145                 150                 155                 160

Lys Ile Asp Tyr Val Thr Ser Pro Gly Trp Ile Asp Gly Pro Gly Gly
                165                 170                 175

Arg Glu Arg Leu Gly Leu Pro Gly Asp Val Gly Pro Gln Leu Val Val
                180                 185                 190

Thr Asp Lys Gly Ile Leu Lys Phe Asp Glu Lys Thr Lys Arg Met Tyr
            195                 200                 205

Leu Ala Ala Tyr Tyr Pro Thr Ser Ser Pro Glu Asp Val Leu Glu Asn
210                 215                 220

Thr Gly Phe Asp Leu Asp Val Ser Lys Ala Val Glu Leu Glu Ala Pro
225                 230                 235                 240

Asp Pro Ala Val Ile Lys Leu Ile Arg Glu Glu Ile Asp Pro Gly Gln
                245                 250                 255

Ala Phe Ile Gln Val Pro Thr Glu Ala Lys
                260                 265

<210> SEQ ID NO 26
<211> LENGTH: 397
<212> TYPE: PRT
<213> ORGANISM: Treponema denticola

<400> SEQUENCE: 26

Met Ile Val Lys Pro Met Val Arg Asn Asn Ile Cys Leu Asn Ala His
```

```
              1               5                  10                 15
        Pro Gln Gly Cys Lys Lys Gly Val Glu Asp Gln Ile Glu Tyr Thr Lys
                         20                  25                 30

Lys Arg Ile Thr Ala Glu Val Lys Ala Gly Ala Lys Ala Pro Lys Asn
                         35                  40                 45

Val Leu Val Leu Gly Cys Ser Asn Gly Tyr Gly Leu Ala Ser Arg Ile
             50                      55                 60

Thr Ala Ala Phe Gly Tyr Gly Ala Ala Thr Ile Gly Val Ser Phe Glu
        65                      70                 75                 80

Lys Ala Gly Ser Glu Thr Lys Tyr Gly Thr Pro Gly Trp Tyr Asn Asn
                             85                 90                 95

Leu Ala Phe Asp Glu Ala Ala Lys Arg Glu Gly Leu Tyr Ser Val Thr
                         100                 105                110

Ile Asp Gly Asp Ala Phe Ser Asp Glu Ile Lys Ala Gln Val Ile Glu
                         115                 120                 125

Glu Ala Lys Lys Lys Gly Ile Lys Phe Asp Leu Ile Val Tyr Ser Leu
        130                     135                 140

Ala Ser Pro Val Arg Thr Asp Pro Asp Thr Gly Ile Met His Lys Ser
        145                     150                 155                160

Val Leu Lys Pro Phe Gly Lys Thr Phe Thr Gly Lys Thr Val Asp Pro
                            165                 170                 175

Phe Thr Gly Glu Leu Lys Glu Ile Ser Ala Glu Pro Ala Asn Asp Glu
                        180                 185                 190

Glu Ala Ala Ala Thr Val Lys Val Met Gly Gly Glu Asp Trp Glu Arg
                        195                 200                 205

Trp Ile Lys Gln Leu Ser Lys Glu Gly Leu Leu Glu Glu Gly Cys Ile
        210                     215                 220

Thr Leu Ala Tyr Ser Tyr Ile Gly Pro Glu Ala Thr Gln Ala Leu Tyr
        225                     230                 235                 240

Arg Lys Gly Thr Ile Gly Lys Ala Lys Glu His Leu Glu Ala Thr Ala
                        245                 250                 255

His Arg Leu Asn Lys Glu Asn Pro Ser Ile Arg Ala Phe Val Ser Val
                        260                 265                 270

Asn Lys Gly Leu Val Thr Arg Ala Ser Ala Val Ile Pro Val Ile Pro
                        275                 280                 285

Leu Tyr Leu Ala Ser Leu Phe Lys Val Met Lys Glu Lys Gly Asn His
                        290                 295                 300

Glu Gly Cys Ile Glu Gln Ile Thr Arg Leu Tyr Ala Glu Arg Leu Tyr
        305                     310                 315                 320

Arg Lys Asp Gly Thr Ile Pro Val Asp Glu Asn Arg Ile Arg Ile
                            325                 330                 335

Asp Asp Trp Glu Leu Glu Asp Val Gln Lys Ala Val Ser Ala Leu
                        340                 345                 350

Met Glu Lys Val Thr Gly Glu Asn Ala Glu Ser Leu Thr Asp Leu Ala
                        355                 360                 365

Gly Tyr Arg His Asp Phe Leu Ala Ser Asn Gly Phe Asp Val Glu Gly
                        370                 375                 380

Ile Asn Tyr Glu Ala Glu Val Glu Arg Phe Asp Arg Ile
        385                     390                 395
```

<210> SEQ ID NO 27
<211> LENGTH: 539
<212> TYPE: PRT
<213> ORGANISM: Euglena gracilis

<400> SEQUENCE: 27

```
Met Ser Cys Pro Ala Ser Pro Ser Ala Ala Val Val Ser Ala Gly Ala
 1               5                  10                  15

Leu Cys Leu Cys Val Ala Thr Val Leu Leu Ala Thr Gly Ser Asn Pro
                20                  25                  30

Thr Ala Leu Ser Thr Ala Ser Thr Arg Ser Pro Thr Ser Leu Val Arg
                35                  40                  45

Gly Val Asp Arg Gly Leu Met Arg Pro Thr Thr Ala Ala Leu Thr
 50                  55                  60

Thr Met Arg Glu Val Pro Gln Met Ala Glu Gly Phe Ser Gly Glu Ala
65                   70                  75                  80

Thr Ser Ala Trp Ala Ala Gly Pro Gln Trp Ala Ala Pro Leu Val
                85                  90                  95

Ala Ala Ala Ser Ser Ala Leu Ala Leu Trp Trp Ala Ala Arg Arg
                100                 105                 110

Ser Val Arg Arg Pro Leu Ala Ala Leu Ala Glu Leu Pro Thr Ala Val
                115                 120                 125

Thr His Leu Ala Pro Pro Met Ala Met Phe Thr Thr Thr Ala Lys Val
130                  135                 140

Ile Gln Pro Lys Ile Arg Gly Phe Ile Cys Thr Thr His Pro Ile
145                  150                 155                 160

Gly Cys Glu Lys Arg Val Gln Glu Glu Ile Ala Tyr Ala Arg Ala His
                165                 170                 175

Pro Pro Thr Ser Pro Gly Pro Lys Arg Val Leu Val Ile Gly Cys Ser
                180                 185                 190

Thr Gly Tyr Gly Leu Ser Thr Arg Ile Thr Ala Ala Phe Gly Tyr Gln
                195                 200                 205

Ala Ala Thr Leu Gly Val Phe Leu Ala Gly Pro Pro Thr Lys Gly Arg
                210                 215                 220

Pro Ala Ala Ala Gly Trp Tyr Asn Thr Val Ala Phe Glu Lys Ala Ala
225                  230                 235                 240

Leu Glu Ala Gly Leu Tyr Ala Arg Ser Leu Asn Gly Asp Ala Phe Asp
                245                 250                 255

Ser Thr Thr Lys Ala Arg Thr Val Glu Ala Ile Lys Arg Asp Leu Gly
                260                 265                 270

Thr Val Asp Leu Val Val Tyr Ser Ile Ala Ala Pro Lys Arg Thr Asp
                275                 280                 285

Pro Ala Thr Gly Val Leu His Lys Ala Cys Leu Lys Pro Ile Gly Ala
                290                 295                 300

Thr Tyr Thr Asn Arg Thr Val Asn Thr Asp Lys Ala Glu Val Thr Asp
305                  310                 315                 320

Val Ser Ile Glu Pro Ala Ser Pro Glu Glu Ile Ala Asp Thr Val Lys
                325                 330                 335

Val Met Gly Gly Glu Asp Trp Glu Leu Trp Ile Gln Ala Leu Ser Glu
                340                 345                 350

Ala Gly Val Leu Ala Glu Gly Ala Lys Thr Val Ala Tyr Ser Tyr Ile
                355                 360                 365

Gly Pro Glu Met Thr Trp Pro Val Tyr Trp Ser Gly Thr Ile Gly Glu
                370                 375                 380

Ala Lys Lys Asp Val Glu Lys Ala Ala Lys Arg Ile Thr Gln Gln Tyr
385                  390                 395                 400

Gly Cys Pro Ala Tyr Pro Val Val Ala Lys Ala Leu Val Thr Gln Ala
```

```
              405                 410                 415
Ser Ser Ala Ile Pro Val Val Pro Leu Tyr Ile Cys Leu Leu Tyr Arg
            420                 425                 430

Val Met Lys Glu Lys Gly Thr His Glu Gly Cys Ile Glu Gln Met Val
            435                 440                 445

Arg Leu Leu Thr Thr Lys Leu Tyr Pro Glu Asn Gly Ala Pro Ile Val
            450                 455                 460

Asp Glu Ala Gly Arg Val Arg Val Asp Asp Trp Glu Met Ala Glu Asp
465                 470                 475                 480

Val Gln Gln Ala Val Lys Asp Leu Trp Ser Gln Val Ser Thr Ala Asn
            485                 490                 495

Leu Lys Asp Ile Ser Asp Phe Ala Gly Tyr Gln Thr Glu Phe Leu Arg
            500                 505                 510

Leu Phe Gly Phe Gly Ile Asp Gly Val Asp Tyr Asp Gln Pro Val Asp
            515                 520                 525

Val Glu Ala Asp Leu Pro Ser Ala Ala Gln Gln
            530                 535

<210> SEQ ID NO 28
<211> LENGTH: 398
<212> TYPE: PRT
<213> ORGANISM: Pseudomonas reinekei MT1

<400> SEQUENCE: 28

Met Lys Asn Ala Leu Ile Val Ser Pro Leu Arg Thr Pro Ile Gly Lys
1               5                   10                  15

Phe Gly Gly Ala Leu Ala Pro Leu Thr Ala Glu His Leu Ala Ser Phe
            20                  25                  30

Met Ile Ser Gln Val Met Ala Arg Thr Gly Val Pro Gly His Ser Leu
        35                  40                  45

Asp Glu Val Ile Val Ala Gln Ser Tyr Ala Ser Ser Glu Ala Pro Cys
    50                  55                  60

Ile Gly Arg Tyr Ala Ala Leu Ser Ala Gly Leu Pro Val Glu Val Pro
65                  70                  75                  80

Gly Tyr Thr Leu Asp Arg Arg Cys Gly Ser Gly Leu Gln Ala Val Ile
                85                  90                  95

Asp Ala Ser Met Met Val Lys Thr Gly Asn Ala Glu Ala Val Leu Val
            100                 105                 110

Val Gly Val Glu Ser Met Ser Asn Ile Glu Tyr Tyr Ser Thr Asp Met
        115                 120                 125

Arg Trp Gly Ala Arg Ala Gly Ser Val Arg Phe His Asp Arg Leu Glu
130                 135                 140

Arg Gly Arg Glu Arg Ser Gln Pro Ser Glu Arg Phe Gly His Ile Ser
145                 150                 155                 160

Gly Met Pro Glu Thr Ala Asp Asn Leu Ala Leu Asp Tyr Gly Ile Ser
                165                 170                 175

Arg Glu Glu Ala Asp Ser Phe Ser Val Arg Ser His Gln Asn Ala Ala
            180                 185                 190

Ala Ala Trp Arg Glu Gly Arg Phe Ala Asp Glu Val Val Ala Val Asp
        195                 200                 205

Val Pro Gly Lys Arg Gly Ala Val Thr Arg Val Thr Ile Asp Glu Gly
    210                 215                 220

Ile Arg Glu Asp Ala Ser Leu Glu Ser Met Lys Ala Leu Arg Leu Ile
225                 230                 235                 240
```

```
Arg Pro Glu Gly Val Cys Thr Ala Gly Asn Ser Ser Gln Gln Asn Asp
                245                 250                 255

Ala Ala Ala Gly Cys Leu Val Val Ser Pro Glu Tyr Ala Ala Arg His
            260                 265                 270

Gly Leu Thr Pro Met Ala Arg Leu Val Asp Trp Ala Ala Gly Cys
        275                 280                 285

Glu Pro Ser Arg Met Gly Ile Gly Pro Val Pro Ala Thr Gln Lys Leu
    290                 295                 300

Leu Met Arg Thr Gly Leu Ser Leu Ala Glu Leu Asp Leu Ile Glu Leu
305                 310                 315                 320

Asn Glu Ala Phe Ala Ala Gln Ala Leu Ala Val Leu Lys Thr Trp Gly
                325                 330                 335

Leu Asp Asp Leu Ser Arg Val Asn Val Asn Gly Ser Gly Ile Ser Leu
                340                 345                 350

Gly His Pro Ile Gly Ala Thr Gly Val Arg Ile Met Thr Thr Leu Leu
            355                 360                 365

His Glu Met Arg Arg Glu Ala Arg Tyr Gly Leu Glu Thr Met Cys
        370                 375                 380

Ile Gly Gly Gly Gln Gly Leu Ala Ala Leu Phe Glu Arg Val
385                 390                 395

<210> SEQ ID NO 29
<211> LENGTH: 400
<212> TYPE: PRT
<213> ORGANISM: Pseudomonas putida

<400> SEQUENCE: 29

Met Arg Asp Val Phe Ile Cys Asp Ala Ile Arg Thr Pro Ile Gly Arg
  1               5                  10                  15

Phe Gly Gly Ala Leu Ala Gly Val Arg Ala Asp Asp Leu Ala Ala Val
                 20                  25                  30

Pro Leu Lys Ala Leu Ile Glu Pro Asn Pro Ala Val Gln Trp Asp Gln
             35                  40                  45

Val Asp Glu Val Phe Phe Gly Cys Ala Asn Gln Ala Gly Glu Asp Asn
 50                  55                  60

Arg Asn Val Ala Arg Met Ala Leu Leu Leu Ala Gly Leu Pro Glu Ser
 65                  70                  75                  80

Ile Pro Gly Val Thr Leu Asn Arg Leu Cys Ala Ser Gly Met Asp Ala
                 85                  90                  95

Ile Gly Thr Ala Phe Arg Ala Ile Ala Ser Gly Glu Met Glu Leu Ala
            100                 105                 110

Ile Ala Gly Gly Val Glu Ser Met Ser Arg Ala Pro Phe Val Met Gly
        115                 120                 125

Lys Ala Glu Ser Gly Tyr Ser Arg Asn Met Lys Leu Glu Asp Thr Thr
130                 135                 140

Ile Gly Trp Arg Phe Ile Asn Pro Leu Met Lys Ser Gln Tyr Gly Val
145                 150                 155                 160

Asp Ser Met Pro Glu Thr Ala Asp Asn Val Ala Asp Tyr Gln Val
                165                 170                 175

Ser Arg Ala Asp Gln Asp Ala Phe Ala Leu Arg Ser Gln Gln Lys Ala
            180                 185                 190

Ala Ala Ala Gln Ala Ala Gly Phe Phe Ala Glu Glu Ile Val Pro Val
        195                 200                 205

Arg Ile Ala His Lys Lys Gly Glu Thr Ile Val Glu Arg Asp Glu His
210                 215                 220
```

```
Leu Arg Pro Glu Thr Thr Leu Glu Ala Leu Thr Lys Leu Lys Pro Val
225                 230                 235                 240

Asn Gly Pro Asp Lys Thr Val Thr Ala Gly Asn Ala Ser Gly Val Asn
            245                 250                 255

Asp Gly Ala Ala Ala Leu Ile Leu Ala Ser Ala Glu Ala Val Lys Lys
        260                 265                 270

His Gly Leu Thr Pro Arg Ala Arg Val Leu Gly Met Ala Ser Gly Gly
    275                 280                 285

Val Ala Pro Arg Val Met Gly Ile Gly Pro Val Pro Ala Val Arg Lys
290                 295                 300

Leu Thr Glu Arg Leu Gly Val Ala Val Ser Asp Phe Asp Val Ile Glu
305                 310                 315                 320

Leu Asn Glu Ala Phe Ala Ser Gln Gly Leu Ala Val Leu Arg Glu Leu
                325                 330                 335

Gly Val Ala Asp Asp Ala Pro Gln Val Asn Pro Asn Gly Gly Ala Ile
            340                 345                 350

Ala Leu Gly His Pro Leu Gly Met Ser Gly Ala Arg Leu Val Leu Thr
        355                 360                 365

Ala Leu His Gln Leu Glu Lys Ser Gly Gly Arg Lys Gly Leu Ala Thr
    370                 375                 380

Met Cys Val Gly Val Gly Gln Gly Leu Ala Leu Ala Ile Glu Arg Val
385                 390                 395                 400

<210> SEQ ID NO 30
<211> LENGTH: 400
<212> TYPE: PRT
<213> ORGANISM: Burkholderia xenovorans

<400> SEQUENCE: 30

Met Thr Glu Ala Phe Leu Cys Asp Ala Ile Arg Thr Pro Ile Gly Arg
 1               5                  10                  15

Tyr Ala Gly Ala Leu Ser Ser Val Arg Ala Asp Asp Leu Gly Ala Val

```
                195                 200                 205
Thr Ile Ala Gln Lys Lys Gly Asp Pro Val Thr Val Ser Gln Asp Glu
210                 215                 220

His Pro Arg Glu Thr Ser Leu Asp Ala Leu Ala Lys Leu Lys Gly Val
225                 230                 235                 240

Val Arg Pro Asp Gly Thr Val Thr Ala Gly Asn Ala Ser Gly Val Asn
            245                 250                 255

Asp Gly Ala Ala Ala Leu Leu Leu Ala Asn Glu Glu Thr Ala Arg Arg
            260                 265                 270

Phe Gly Leu Thr Pro Arg Ala Arg Val Leu Gly Ile Ala Thr Ala Gly
            275                 280                 285

Val Ala Pro Arg Val Met Gly Ile Gly Pro Ala Pro Ala Thr Gln Lys
290                 295                 300

Leu Leu Ala Arg Leu Asn Met Ser Leu Asp Gln Phe Asp Val Ile Glu
305                 310                 315                 320

Leu Asn Glu Ala Phe Ala Ser Gln Gly Ile Ala Val Leu Arg Ala Leu
                325                 330                 335

Gly Val Ala Asp Asp Asp Thr Arg Val Asn Pro Asn Gly Gly Ala Ile
                340                 345                 350

Ala Leu Gly His Pro Leu Gly Met Ser Gly Ala Arg Leu Val Thr Thr
                355                 360                 365

Ala Met Tyr Gln Leu His Arg Thr Gln Gly Arg Phe Ala Leu Cys Thr
370                 375                 380

Met Cys Ile Gly Val Gly Gln Gly Ile Ala Ile Ala Ile Glu Arg Val
385                 390                 395                 400

<210> SEQ ID NO 31
<211> LENGTH: 456
<212> TYPE: PRT
<213> ORGANISM: Arthrobacter sp.

<400> SEQUENCE: 31

Met Ser Phe Asn Gly Gln Ser Ala Thr Gly Pro Asp Glu Ser Ala Ala
1               5                   10                  15

Ala Pro Ala Thr Pro Gly Ala Gly Leu Leu Arg Lys Ala Val Val
            20                  25                  30

Val Gly Gly Asn Arg Ile Pro Phe Ala Arg Thr Gly Gly Ala Tyr Thr
        35                  40                  45

Lys Ser Ser Asn Gln Asp Met Leu Thr Ala Ala Leu Asp Gly Leu Ile
50                  55                  60

Ala Arg Phe Gly Leu Ala Asp Glu Arg Ile Gly Glu Val Ala Ala Gly
65                  70                  75                  80

Ala Val Leu Lys His Ser Arg Asp Phe Asn Leu Thr Arg Glu Ala Val
                85                  90                  95

Leu Gly Ser Ala Leu Ser Ala Glu Thr Pro Ala Tyr Asp Leu Gln Gln
            100                 105                 110

Ala Cys Ala Thr Gly Leu Glu Thr Val Leu Gly Leu Ala Asn Lys Ile
            115                 120                 125

Lys Leu Gly Gln Ile Asp Ser Ala Ile Ala Gly Val Asp Ser Ala
130                 135                 140

Ser Asp Ala Pro Ile Ala Val Ser Glu Gly Leu Arg Glu Val Leu Leu
145                 150                 155                 160

Asp Leu Asn Arg Ala Lys Thr Leu Pro Gln Arg Leu Lys Val Leu Gly
                165                 170                 175
```

```
Arg Leu Arg Pro Lys Asp Leu Ala Pro Asp Ala Pro Asn Thr Gly Glu
            180                 185                 190

Pro Arg Thr Gly Leu Ser Met Gly Glu His Gln Ala Leu Thr Thr Ala
        195                 200                 205

Gln Trp Lys Ile Thr Arg Glu Ala Gln Asp Glu Leu Ala Tyr Asn Ser
    210                 215                 220

His Arg Asn Leu Ala Ala Ala Tyr Asp Ala Gly Phe Phe Asp Asp Leu
225                 230                 235                 240

Leu Thr Pro Tyr Arg Gly Leu Asn Arg Asp Ser Asn Leu Arg Ala Asp
                245                 250                 255

Thr Thr Arg Glu Lys Leu Ser Thr Leu Lys Pro Val Phe Gly Lys Asn
            260                 265                 270

Leu Gly Ala Glu Ala Thr Met Thr Ala Gly Asn Ser Thr Pro Leu Thr
        275                 280                 285

Asp Gly Ala Ser Thr Val Leu Leu Ala Ser Glu Glu Trp Ala Asp Ala
    290                 295                 300

His Glu Leu Pro Lys Leu Ala Thr Val Val Asp Gly Glu Ala Ala Ala
305                 310                 315                 320

Val Asp Phe Val His Gly Lys Asp Gly Leu Leu Met Ala Pro Ala Phe
                325                 330                 335

Ala Val Pro Arg Leu Leu Ala Arg Asn Gly Leu Thr Leu Asp Asp Ile
            340                 345                 350

Asp Phe Phe Glu Ile His Glu Ala Phe Ala Gly Thr Val Leu Ser Thr
        355                 360                 365

Leu Ala Ala Trp Glu Asp Glu Phe Gly Arg Thr Arg Leu Gly Leu
    370                 375                 380

Asp Gly Pro Leu Gly Ser Ile Asp Arg Ala Lys Leu Asn Val Asn Gly
385                 390                 395                 400

Ser Ser Leu Ala Ala Gly His Pro Phe Ala Ala Thr Gly Gly Arg Ile
                405                 410                 415

Val Ala Thr Leu Ala Lys Met Leu His Asp Lys Gly Gln Val Asp Gly
            420                 425                 430

Arg Pro Ala Arg Gly Leu Ile Ser Ile Cys Ala Ala Gly Gly Gln Gly
        435                 440                 445

Val Val Ala Ile Leu Glu Ala Ser
    450                 455

<210> SEQ ID NO 32
<211> LENGTH: 394
<212> TYPE: PRT
<213> ORGANISM: Burkholderia xenovorans

<400> SEQUENCE: 32

Met Thr Arg Asp Thr Arg Asp Val Val Ile Val Asp Ala Val Arg Thr
 1               5                  10                  15

Pro Ile Gly Lys Phe Arg Gly Ala Leu Ala Gly Val Arg Ala Asp His
            20                  25                  30

Leu Gly Ala Leu Val Ile Asp Glu Leu Ile Arg Arg Ala Gly Val Lys
        35                  40                  45

Pro Gln Ala Val Asn Asp Val Val Phe Gly Cys Val Thr Gln Ile Gly
    50                  55                  60

Glu Gln Ser Ala Asn Ile Ala Arg Thr Ser Val Leu Gly Ala Gly Trp
65                  70                  75                  80

Pro Glu Thr Ile Pro Gly Leu Thr Ile Asp Arg Lys Cys Gly Ser Gly
                85                  90                  95
```

```
Glu Glu Ala Val His Ile Ala Ala Gly Leu Ile Ala Phe Gly Ala Ala
            100                 105                 110

Asp Val Ile Val Ala Gly Gly Ala Glu Ser Met Ser Arg Val Pro Met
            115                 120                 125

Gly Ser Asn Arg Asp Leu His Gly Glu Ala Phe Gly Trp Met Ala Ser
            130                 135                 140

Glu Arg Phe Glu Leu Thr Ser Gln Gly Glu Ala Ala Glu Arg Leu Cys
145                 150                 155                 160

Asp Cys Trp Ala Leu Thr Arg Ala Gln Leu Asp Ala Tyr Ser Val Glu
                165                 170                 175

Ser His Arg Arg Ala Ala Ala Ala Ala Glu Gly Trp Phe Ala Arg
            180                 185                 190

Glu Ile Val Pro Val Pro Val Gly Gln Val Arg Glu Lys Ser Leu Glu
            195                 200                 205

Gly Glu Ala Ala Leu Phe Ala Ala Asp Glu Thr Ile Arg Pro Gly Thr
            210                 215                 220

Asn Ala Asp Lys Leu Ala Thr Leu Lys Ser Ser Phe Arg Ser Asp Gly
225                 230                 235                 240

Arg Leu Thr Ala Gly Asn Ser Ser Gln Ile Ser Asp Gly Ala Ala Ala
                245                 250                 255

Leu Leu Leu Met Ser Ser Asp Lys Ala Arg Glu Leu Gly Val Lys Ala
            260                 265                 270

Arg Ala Arg Val Arg Ala Val Thr Thr Val Gly Ser Asp Pro Thr Leu
            275                 280                 285

Met Leu Thr Gly Pro Ile Leu Ala Thr Cys Gln Val Leu Glu Lys Ala
            290                 295                 300

Gly Leu Gly Leu Ser Asp Ile Asp Leu Phe Glu Ile Asn Glu Ala Phe
305                 310                 315                 320

Ala Pro Val Pro Leu Val Trp Met Lys Glu Phe Gly Val Pro His Ala
                325                 330                 335

Lys Leu Asn Val Asn Gly Gly Ala Ile Ala Leu Gly His Pro Leu Gly
            340                 345                 350

Ala Ser Gly Ala Arg Ile Met Thr Ser Met Leu His Glu Leu Glu Arg
            355                 360                 365

Arg Gly Ala Arg Tyr Gly Leu Gln Ala Ile Cys Cys Ala Gly Gly Met
            370                 375                 380

Gly Thr Ala Thr Leu Ile Glu Arg Leu Asp
385                 390

<210> SEQ ID NO 33
<211> LENGTH: 382
<212> TYPE: PRT
<213> ORGANISM: Geobacillus kaustophilus

<400> SEQUENCE: 33

Met Arg Glu Ala Val Ile Val Glu Ala Val Arg Thr Pro Val Gly Lys
1               5                   10                  15

Arg Asn Gly Val Phe Arg Asp Val His Pro Val His Leu Ala Ala Val
            20                  25                  30

Val Leu Asp Glu Val Val Arg Arg Ala Gly Met Asp Lys Gly Ala Val
            35                  40                  45

Glu Asp Ile Val Met Gly Cys Val Thr Pro Val Ala Glu Gln Gly Tyr
            50                  55                  60

Asn Ile Gly Arg Leu Ala Ala Leu Glu Ala Gly Phe Pro Ile Glu Val
```

```
                65                  70                  75                  80
Pro Ala Val Gln Ile Asn Arg Met Cys Gly Ser Gly Gln Gln Ala Ile
                    85                  90                  95

His Phe Ala Ala Gln Glu Ile Arg Ser Gly Asp Met Asp Val Thr Ile
                    100                 105                 110

Ala Ala Gly Val Glu Ser Met Thr Lys Val Pro Ile Leu Ser Asp Gly
                    115                 120                 125

Asn Glu Arg Thr Ile Pro Pro Ser Leu His Glu Lys Tyr Glu Phe Ile
                    130                 135                 140

His Gln Gly Val Ser Ala Glu Arg Ile Ala Lys Lys Tyr Gly Leu Thr
145                 150                 155                 160

Arg Glu Glu Leu Asp Ala Tyr Ala Tyr Glu Ser His Gln Arg Ala Leu
                    165                 170                 175

Ala Ala Leu Arg Glu Gly Lys Phe Arg Ala Glu Ile Val Pro Val Lys
                    180                 185                 190

Gly Leu Asp Arg Asp Gly Arg Glu Ile Leu Val Thr Asp Asp Glu Gly
                    195                 200                 205

Pro Arg Ala Asp Thr Ser Pro Glu Ala Leu Ala Ala Leu Lys Pro Val
                    210                 215                 220

Phe Gln Glu Asp Gly Leu Ile Thr Ala Gly Asn Ala Ser Gln Met Ser
225                 230                 235                 240

Asp Gly Ala Ala Ala Val Leu Leu Met Glu Arg Glu Ala Ala Arg Arg
                    245                 250                 255

Phe Gly Leu Lys Pro Lys Ala Arg Ile Val Ala Gln Thr Val Val Gly
                    260                 265                 270

Ser Asp Pro Thr Tyr Met Leu Asp Gly Val Ile Pro Ala Thr Arg Gln
                    275                 280                 285

Val Leu Lys Lys Ala Gly Leu Ser Ile Asp Asp Ile Asp Leu Ile Glu
                    290                 295                 300

Ile Asn Glu Ala Phe Ala Pro Val Val Leu Ala Trp Gln Lys Glu Ile
305                 310                 315                 320

Gly Ala Pro Leu Glu Lys Val Asn Val Asn Gly Gly Ala Ile Ala Leu
                    325                 330                 335

Gly His Pro Leu Gly Ala Thr Gly Ala Lys Leu Met Thr Ser Leu Val
                    340                 345                 350

His Glu Leu Glu Arg Arg Gly Gly Arg Tyr Gly Leu Leu Thr Ile Cys
                    355                 360                 365

Ile Gly His Gly Met Ala Thr Ala Thr Ile Ile Glu Arg Glu
370                 375                 380

<210> SEQ ID NO 34
<211> LENGTH: 415
<212> TYPE: PRT
<213> ORGANISM: Gordonia bronchialis

<400> SEQUENCE: 34

Met Ala Pro Cys Ser Val Lys Ala Met Pro Glu Ala Val Ile Val Ala
1               5                   10                  15

His Ala Arg Ser Pro Ile Gly Arg Ala Gly Lys Gly Ser Leu Lys Asp
                    20                  25                  30

Val Arg Pro Asp Glu Leu Ser Arg Gln Met Val Ala Ala Leu Ala
                    35                  40                  45

Lys Val Pro Glu Leu Ala Pro Ser Asp Ile Glu Asp Ile His Trp Gly
                    50                  55                  60
```

```
Ile Gly Gln Pro Gly Gln Gly Gly Tyr Asn Ile Ala Arg Val Ile
 65                  70                  75                  80

Ala Val Glu Leu Gly Tyr Asp His Ile Pro Gly Val Thr Val Asn Arg
                 85                  90                  95

Tyr Cys Ser Ser Ser Leu Gln Thr Thr Arg Met Ala Leu His Ala Ile
            100                 105                 110

Lys Ala Gly Glu Ala Asp Val Leu Ile Ser Gly Val Glu Ser Val
        115                 120                 125

Ser Ser Phe Gly Ile Ser Gly Ala Asp Gly Ala Pro Asp Ser Lys
130                 135                 140

Asn Pro Val Phe Asp Asp Ala Gln Ala Arg Thr Ala Lys Ala Ala Glu
145                 150                 155                 160

Gly Gly Ala Pro Ala Trp Thr Asp Pro Arg Glu Gln Gly Leu Ile Pro
                165                 170                 175

Asp Val Tyr Ile Ala Met Gly Gln Thr Ala Glu Asn Val Ala Ser Phe
            180                 185                 190

Thr Gly Ile Ser Arg Glu Asp Gln Asp Arg Trp Ser Val Leu Ser Gln
        195                 200                 205

Asn Arg Ala Glu Glu Ala Ile Asn Ala Gly Phe Phe Glu Arg Glu Ile
    210                 215                 220

Asp Pro Val Thr Leu Pro Asp Gly Ser Thr Val Asn Thr Asp Asp Gly
225                 230                 235                 240

Pro Arg Ala Gly Thr Thr Tyr Glu Lys Val Ser Gln Leu Lys Pro Val
                245                 250                 255

Phe Arg Pro Asp Gly Thr Val Thr Ala Gly Asn Ala Cys Pro Leu Asn
            260                 265                 270

Asp Gly Ala Ala Ala Leu Val Ile Met Ser Asp Ser Lys Ala Lys Gln
        275                 280                 285

Leu Gly Leu Thr Pro Leu Ala Arg Val Val Ala Thr Ala Ala Thr Gly
    290                 295                 300

Leu Ser Pro Glu Ile Met Gly Leu Gly Pro Ile Glu Ala Ile Arg Lys
305                 310                 315                 320

Val Leu Arg Ile Ser Gly Met Ser Leu Ser Asp Ile Asp Leu Val Glu
                325                 330                 335

Ile Asn Glu Ala Phe Ala Val Gln Val Leu Gly Ser Ala Asn Glu Leu
            340                 345                 350

Gly Ile Asp His Asp Lys Leu Asn Val Ser Gly Gly Ala Ile Ala Leu
        355                 360                 365

Gly His Pro Phe Gly Met Thr Gly Ala Arg Ile Thr Thr Thr Leu Leu
    370                 375                 380

Asn Asn Leu Gln Thr Arg Asp Lys Thr Phe Gly Ile Glu Ser Met Cys
385                 390                 395                 400

Val Gly Gly Gly Gln Gly Met Ala Met Val Leu Glu Arg Leu Ser
                405                 410                 415

<210> SEQ ID NO 35
<211> LENGTH: 387
<212> TYPE: PRT
<213> ORGANISM: Citrobacter freundii

<400> SEQUENCE: 35

Met Glu Gln Val Val Ile Val Asp Ala Ile Arg Thr Pro Met Gly Arg
  1               5                  10                  15

Ser Lys Gly Gly Ala Phe Arg Asn Val Arg Ala Glu Asp Leu Ser Ala
             20                  25                  30
```

His Leu Met Arg Ser Leu Leu Ala Arg Asn Pro Ala Leu Asp Pro Thr
                35                  40                  45

Ala Leu Asp Asp Ile Tyr Trp Gly Cys Val Gln Gln Thr Leu Glu Gln
 50                  55                  60

Gly Phe Asn Ile Ala Arg Asn Ala Ala Leu Leu Ala Glu Ile Pro His
 65                  70                  75                  80

Ser Val Pro Ala Val Thr Val Asn Arg Leu Cys Gly Ser Ser Met Gln
                 85                  90                  95

Ala Leu His Asp Ala Ala Arg Met Ile Met Thr Gly Asp Ala Gln Ala
            100                 105                 110

Cys Leu Ile Gly Gly Val Glu His Met Gly His Val Pro Met Ser His
        115                 120                 125

Gly Val Asp Phe His Pro Gly Met Ser Arg Asn Val Ala Lys Ala Ala
    130                 135                 140

Gly Met Met Gly Leu Thr Ala Glu Met Leu Ser Arg Met His Gly Ile
145                 150                 155                 160

Ser Arg Glu Met Gln Asp Ala Phe Ala Ala Arg Ser His Ala Arg Ala
                165                 170                 175

Trp Ala Ala Thr Gln Ser Gly Ala Phe Lys Asn Glu Ile Ile Pro Thr
            180                 185                 190

Gly Gly His Asp Ala Asp Gly Val Leu Lys Gln Phe Asn Tyr Asp Glu
        195                 200                 205

Val Ile Arg Pro Glu Thr Thr Val Glu Ala Leu Ser Thr Leu Arg Pro
    210                 215                 220

Ala Phe Asp Pro Val Ser Gly Thr Val Thr Ala Gly Thr Ser Ser Ala
225                 230                 235                 240

Leu Ser Asp Gly Ala Ala Ala Met Leu Val Met Ser Glu Ser Arg Ala
                245                 250                 255

Arg Glu Leu Gly Leu Thr Pro Arg Ala Arg Ile Arg Ser Met Ala Val
            260                 265                 270

Val Gly Cys Asp Pro Ser Ile Met Gly Tyr Gly Pro Val Pro Ala Ser
        275                 280                 285

Lys Leu Ala Leu Lys Lys Ala Gly Leu Ser Thr Ser Asp Ile Gly Leu
    290                 295                 300

Phe Glu Met Asn Glu Ala Phe Ala Ala Gln Ile Leu Pro Cys Ile Lys
305                 310                 315                 320

Asp Leu Gly Leu Met Glu Gln Ile Asp Glu Lys Ile Asn Leu Asn Gly
                325                 330                 335

Gly Ala Ile Ala Leu Gly His Pro Leu Gly Cys Ser Gly Ala Arg Ile
            340                 345                 350

Ser Thr Thr Leu Leu Asn Leu Met Glu Arg Lys Asp Val Gln Phe Gly
        355                 360                 365

Leu Ala Thr Met Cys Ile Gly Leu Gly Gln Gly Ile Ala Thr Val Phe
    370                 375                 380

Glu Arg Val
385

<210> SEQ ID NO 36
<211> LENGTH: 393
<212> TYPE: PRT
<213> ORGANISM: Burkholderia sp.

<400> SEQUENCE: 36

Met Arg Glu Ala Val Ile Val Ser Thr Ala Arg Thr Pro Leu Thr Lys

```
  1               5                  10                  15
Ala His Arg Gly Glu Phe Asn Ile Thr Pro Gly Pro Thr Leu Ala Ser
             20                  25                  30

Phe Ala Val Arg Ala Ala Val Glu Arg Ser Gly Val Asp Pro Asp Ile
             35                  40                  45

Ile Glu Asp Ala Ile Leu Gly Cys Gly Tyr Pro Glu Gly Thr Thr Gly
 50                  55                  60

Arg Asn Val Ala Arg Gln Ser Val Ile Arg Ala Gly Leu Pro Leu Ser
 65                  70                  75                  80

Ile Ala Gly Thr Thr Val Asn Arg Phe Cys Ala Ser Gly Leu Gln Ala
             85                  90                  95

Ile Ala Met Ala Ala Gly Arg Ile Val Val Asp Gly Ala Pro Ala Met
            100                 105                 110

Ile Ala Gly Gly Val Glu Ser Ile Ser Asn Ile Gln Thr Arg Glu Asp
            115                 120                 125

Gly Val Ser Gly Leu Asp Pro Trp Ile Val Glu His Lys Pro Ser Leu
130                 135                 140

Tyr Thr Ala Met Ile Asp Thr Ala Asp Ile Val Ala Arg Arg Tyr Gly
145                 150                 155                 160

Ile Ser Arg Glu Ala Gln Asp Gln Phe Ser Val Glu Ser Gln Arg Arg
            165                 170                 175

Thr Ala Glu Ala Gln Gln Ala Gly Arg Tyr Ala Asp Glu Ile Ile Pro
            180                 185                 190

Val Thr Thr Thr Met Ala Ile Thr Asp Lys Glu Thr Arg Ala Val Ser
            195                 200                 205

Tyr Arg Glu Val Thr Val Ser Ala Asp Asn Cys Asn Arg Pro Gly Thr
210                 215                 220

Thr Tyr Glu Ala Leu Ala Lys Leu Ala Pro Val Lys Gly Pro Asp Gln
225                 230                 235                 240

Phe Ile Thr Ala Gly Asn Ala Ser Gln Asn Ala Asp Gly Ala Ser Ala
            245                 250                 255

Cys Val Leu Met Glu Ala Lys Ala Ala Glu Arg Ala Asn Phe Ala Pro
            260                 265                 270

Leu Gly Ala Phe Arg Gly Leu Ala Leu Ala Gly Cys Glu Pro Asp Glu
            275                 280                 285

Met Gly Ile Gly Pro Val Leu Ala Val Pro Lys Leu Leu Ala Arg His
            290                 295                 300

Gly Leu Thr Val Asp Asp Ile Gly Leu Trp Glu Leu Asn Glu Ala Phe
305                 310                 315                 320

Ala Ser Gln Ala Val Tyr Cys Gln Lys Arg Leu Glu Ile Pro Ser Glu
            325                 330                 335

Arg Leu Asn Val Asn Gly Gly Ala Ile Ser Ile Gly His Pro Phe Gly
            340                 345                 350

Met Thr Gly Ser Arg Leu Val Gly His Val Leu Ile Glu Gly Arg Arg
            355                 360                 365

Arg Gly Val Lys Tyr Ala Val Val Thr Met Cys Met Ala Gly Gly Met
            370                 375                 380

Gly Ala Ala Gly Leu Phe Glu Ile Tyr
385                 390

<210> SEQ ID NO 37
<211> LENGTH: 378
<212> TYPE: PRT
<213> ORGANISM: Beijerinckia indica
```

<400> SEQUENCE: 37

```
Met Thr Lys Val Val Ile Ala Gly Tyr Ile Arg Ser Pro Phe Thr Leu
 1               5                  10                 15

Ala Lys Lys Gly Glu Leu Ala Thr Val Arg Pro Asp Asp Leu Ala Ala
             20                  25                  30

Gln Val Val Lys Gly Leu Ile Lys Lys Thr Gly Ile Pro Ala Glu Asp
         35                  40                  45

Ile Glu Asp Leu Leu Leu Gly Cys Ala Phe Pro Gly Glu Gln Gly
 50                  55                  60

Phe Asn Val Ala Arg Leu Val Ser Phe Leu Ala Gly Leu Pro Leu Ser
 65                  70                  75                  80

Val Gly Ala Ser Thr Val Asn Arg Phe Cys Gly Ser Ser Met Thr Thr
                 85                  90                  95

Val His Met Ala Ala Gly Ala Ile Gln Met Asn Ala Gly Asn Ala Phe
                100                 105                 110

Ile Ala Ala Gly Val Glu Ser Met Ser Arg Val Pro Met Met Gly Phe
                115                 120                 125

Asn Pro Leu Pro Asn Pro Glu Leu Ala Ala Thr Met Pro Gly Ala Tyr
130                 135                 140

Met Gly Met Gly Asp Thr Ala Glu Asn Val Ala Ala Lys Trp Thr Ile
145                 150                 155                 160

Ser Arg Lys Glu Gln Glu Glu Phe Ala Leu Arg Ser His Gln Arg Ala
                165                 170                 175

Thr Ala Ala Gln Lys Glu Gly Arg Leu Thr Gly Glu Ile Ile Pro Ile
                180                 185                 190

Thr Gly Arg Lys Gly Thr Ile Thr Thr Asp Gly Cys Ile Arg Pro Asp
                195                 200                 205

Thr Thr Leu Glu Gly Leu Ala Glu Leu Lys Pro Ala Phe Ser Ala Asn
210                 215                 220

Gly Val Val Thr Ala Gly Thr Ser Ser Pro Leu Thr Asp Gly Ala Ala
225                 230                 235                 240

Ala Val Leu Val Cys Ser Glu Asp Tyr Ala Lys His His Leu Asp
                245                 250                 255

Val Leu Ala Ser Val Lys Ala Ile Ala Val Ser Gly Cys Ser Pro Glu
                260                 265                 270

Ile Met Gly Ile Gly Pro Val Ala Ala Ser Arg Lys Ala Leu Ala Arg
                275                 280                 285

Ala Gly Leu Glu Ala Gly Gln Ile Asp Ile Val Glu Leu Asn Glu Ala
            290                 295                 300

Phe Ala Ser Gln Ser Ile Ala Cys Met Arg Glu Leu Asn Leu Ser Pro
305                 310                 315                 320

Asp Arg Val Asn Ile Asp Gly Gly Ala Ile Ala Leu Gly His Pro Leu
                325                 330                 335

Gly Ala Thr Gly Ala Arg Ile Val Gly Lys Ala Ala Ser Leu Leu Lys
                340                 345                 350

Arg Glu Lys Gly Lys Tyr Ala Leu Ala Thr Gln Cys Ile Gly Gly Gly
                355                 360                 365

Gln Gly Ile Ala Thr Val Leu Glu Ala Phe
                370                 375
```

<210> SEQ ID NO 38
<211> LENGTH: 403
<212> TYPE: PRT

<213> ORGANISM: Arthrobacter arilaitensis

<400> SEQUENCE: 38

```
Met Gln Gln Ala Tyr Leu Tyr Asp Ala Ile Arg Thr Pro Phe Gly Lys
  1               5                  10                  15
Ile Gly Gly Ala Leu Ser Ser His Arg Pro Asp Asp Leu Ala Ala His
                 20                  25                  30
Val Val Arg Glu Leu Val Ala Arg Ser Pro Lys Leu Asp Val Ala Asp
             35                  40                  45
Ile Asp Glu Ser Ile Phe Gly Asn Ala Asn Gly Ala Gly Glu Glu Asn
 50                  55                  60
Arg Asn Val Ala Arg Met Ala Thr Leu Leu Ala Gly Leu Pro Thr Ser
 65                  70                  75                  80
Leu Pro Gly Thr Thr Met Asn Arg Leu Cys Gly Ser Ser Leu Asp Ala
                 85                  90                  95
Ser Ile Ala Ala Ser Arg Gln Ile Ala Thr Gly Asp Ala Asp Leu Val
                100                 105                 110
Leu Val Gly Gly Val Glu Ser Met Ser Arg Ala Pro Trp Val Leu Pro
            115                 120                 125
Lys Thr Glu Arg Pro Phe Pro Met Ser Asn Leu Glu Leu Ala Asn Thr
130                 135                 140
Thr Leu Gly Trp Arg Leu Val Asn Pro Ala Met Pro Gly Glu Trp Thr
145                 150                 155                 160
Val Ser Leu Gly Glu Ala Thr Glu Gln Leu Arg Glu Lys His Gly Ile
                165                 170                 175
Ser Arg Glu Asp Gln Asp Glu Phe Ala Ala Ser His Gln Arg Ala
                180                 185                 190
Ala Ala Ala Trp Gln Ala Gly Lys Tyr Asp Asn Leu Val Val Pro Val
            195                 200                 205
Pro Pro Ala Asn Lys Arg Gly Thr Glu Val Thr Arg Asp Glu Thr Ile
210                 215                 220
Arg Ala Asp Ser Thr Ala Gln Thr Leu Ser Lys Leu Arg Thr Val Phe
225                 230                 235                 240
Arg Thr Gly Glu Asn Ala Thr Val Thr Ala Gly Asn Ala Ser Pro Met
                245                 250                 255
Ser Asp Gly Ala Ser Ala Ala Phe Ile Gly Ser Glu Arg Gly Gly Glu
            260                 265                 270
Leu Leu Gly Ala Ala Pro Ile Ala Arg Ile Ala Ser Asn Gly Ala Ala
            275                 280                 285
Ala Leu Asp Pro Gln Phe Phe Gly Phe Ala Pro Val Glu Ala Ala Asn
            290                 295                 300
Lys Ala Leu Ala Lys Ala Gly Leu Lys Trp Ser Asp Ile Ala Ala Val
305                 310                 315                 320
Glu Leu Asn Glu Ala Phe Ala Ala Gln Ser Leu Ala Cys Ile Arg Ala
                325                 330                 335
Trp Asp Ile Asp Pro Ala Ile Val Asn Ala Trp Gly Gly Ala Ile Ser
                340                 345                 350
Ile Gly His Pro Leu Gly Ala Ser Gly Leu Arg Ile Leu Gly Thr Val
                355                 360                 365
Ala Arg Arg Leu Ala Glu Ser Gly Glu Arg Tyr Gly Leu Ala Ala Ile
            370                 375                 380
Cys Ile Gly Val Gly Gln Gly Leu Ala Val Val Val Glu Asn Ile Asn
385                 390                 395                 400
```

Ala Thr Lys

<210> SEQ ID NO 39
<211> LENGTH: 394
<212> TYPE: PRT
<213> ORGANISM: Cupriavidus necator

<400> SEQUENCE: 39

```
Met Thr Arg Glu Val Val Val Ser Gly Val Arg Thr Ala Ile Gly
 1               5                  10                  15

Thr Phe Gly Gly Ser Leu Lys Asp Val Ala Pro Ala Glu Leu Gly Ala
                20                  25                  30

Leu Val Val Arg Glu Ala Leu Ala Arg Ala Gln Val Ser Gly Asp Asp
            35                  40                  45

Val Gly His Val Val Phe Gly Asn Val Ile Gln Thr Glu Pro Arg Asp
        50                  55                  60

Met Tyr Leu Gly Arg Val Ala Ala Val Asn Gly Gly Val Thr Ile Asn
65                  70                  75                  80

Ala Pro Ala Leu Thr Val Asn Arg Leu Cys Gly Ser Gly Leu Gln Ala
                85                  90                  95

Ile Val Ser Ala Ala Gln Thr Ile Leu Leu Gly Asp Thr Asp Val Ala
            100                 105                 110

Ile Gly Gly Gly Ala Glu Ser Met Ser Arg Ala Pro Tyr Leu Ala Pro
        115                 120                 125

Ala Ala Arg Trp Gly Ala Arg Met Gly Asp Ala Gly Leu Val Asp Met
    130                 135                 140

Met Leu Gly Ala Leu His Asp Pro Phe His Arg Ile His Met Gly Val
145                 150                 155                 160

Thr Ala Glu Asn Val Ala Lys Glu Tyr Asp Ile Ser Arg Ala Gln Gln
                165                 170                 175

Asp Glu Ala Ala Leu Glu Ser His Arg Arg Ala Ser Ala Ala Ile Lys
            180                 185                 190

Ala Gly Tyr Phe Lys Asp Gln Ile Val Pro Val Val Ser Lys Gly Arg
        195                 200                 205

Lys Gly Asp Val Thr Phe Asp Thr Asp Glu His Val Arg His Asp Ala
    210                 215                 220

Thr Ile Asp Asp Met Thr Lys Leu Arg Pro Val Phe Val Lys Glu Asn
225                 230                 235                 240

Gly Thr Val Thr Ala Gly Asn Ala Ser Gly Leu Asn Asp Ala Ala Ala
                245                 250                 255

Ala Val Val Met Met Glu Arg Ala Glu Ala Glu Arg Arg Gly Leu Lys
            260                 265                 270

Pro Leu Ala Arg Leu Val Ser Tyr Gly His Ala Gly Val Asp Pro Lys
        275                 280                 285

Ala Met Gly Ile Gly Pro Val Pro Ala Thr Lys Ile Ala Leu Glu Arg
    290                 295                 300

Ala Gly Leu Gln Val Ser Asp Leu Asp Val Ile Glu Ala Asn Glu Ala
305                 310                 315                 320

Phe Ala Ala Gln Ala Cys Ala Val Thr Lys Ala Leu Gly Leu Asp Pro
                325                 330                 335

Ala Lys Val Asn Pro Asn Gly Ser Gly Ile Ser Leu Gly His Pro Ile
            340                 345                 350

Gly Ala Thr Gly Ala Leu Ile Thr Val Lys Ala Leu His Glu Leu Asn
        355                 360                 365
```

```
Arg Val Gln Gly Arg Tyr Ala Leu Val Thr Met Cys Ile Gly Gly Gly
    370                 375                 380

Gln Gly Ile Ala Ala Ile Phe Glu Arg Ile
385                 390
```

<210> SEQ ID NO 40
<211> LENGTH: 401
<212> TYPE: PRT
<213> ORGANISM: Escherichia coli

<400> SEQUENCE: 40

```
Met Arg Glu Ala Phe Ile Cys Asp Gly Ile Arg Thr Pro Ile Gly Arg
  1               5                  10                  15

Tyr Gly Gly Ala Leu Ser Ser Val Arg Ala Asp Leu Ala Ala Ile
             20                  25                  30

Pro Leu Arg Glu Leu Leu Val Arg Asn Pro Arg Leu Asp Ala Glu Cys
         35                  40                  45

Ile Asp Asp Val Ile Leu Gly Cys Ala Asn Gln Ala Gly Glu Asp Asn
 50                  55                  60

Arg Asn Val Ala Arg Met Ala Thr Leu Leu Ala Gly Leu Pro Gln Ser
 65                  70                  75                  80

Val Ser Gly Thr Thr Ile Asn Arg Leu Cys Gly Ser Gly Leu Asp Ala
             85                  90                  95

Leu Gly Phe Ala Ala Arg Ala Ile Lys Ala Gly Asp Gly Asp Leu Leu
        100                 105                 110

Ile Ala Gly Gly Val Glu Ser Met Ser Arg Ala Pro Phe Val Met Gly
        115                 120                 125

Lys Ala Ala Ser Ala Phe Ser Arg Gln Ala Glu Met Phe Asp Thr Thr
130                 135                 140

Ile Gly Trp Arg Phe Val Asn Pro Leu Met Ala Gln Gln Phe Gly Thr
145                 150                 155                 160

Asp Ser Met Pro Glu Thr Ala Glu Asn Val Ala Glu Leu Leu Lys Ile
                165                 170                 175

Ser Arg Glu Asp Gln Asp Ser Phe Ala Leu Arg Ser Gln Gln Arg Thr
            180                 185                 190

Ala Lys Ala Gln Ser Ser Gly Ile Leu Ala Glu Glu Ile Val Pro Val
        195                 200                 205

Val Leu Lys Asn Lys Lys Gly Val Val Thr Glu Ile Gln His Asp Glu
    210                 215                 220

His Leu Arg Pro Glu Thr Thr Leu Glu Gln Leu Arg Gly Leu Lys Ala
225                 230                 235                 240

Pro Phe Arg Ala Asn Gly Val Ile Thr Ala Gly Asn Ala Ser Gly Val
                245                 250                 255

Asn Asp Gly Ala Ala Ala Leu Ile Ile Ala Ser Glu Gln Met Ala Ala
            260                 265                 270

Ala Gln Gly Leu Thr Pro Arg Ala Arg Ile Val Ala Met Ala Thr Ala
        275                 280                 285

Gly Val Glu Pro Arg Leu Met Gly Leu Gly Pro Val Pro Ala Thr Arg
    290                 295                 300

Arg Val Leu Glu Arg Ala Gly Leu Ser Ile His Asp Met Asp Val Ile
305                 310                 315                 320

Glu Leu Asn Glu Ala Phe Ala Ala Gln Ala Leu Gly Val Leu Arg Glu
                325                 330                 335

Leu Gly Leu Pro Asp Asp Ala Pro His Val Asn Pro Asn Gly Gly Ala
            340                 345                 350
```

```
Ile Ala Leu Gly His Pro Leu Gly Met Ser Gly Ala Arg Leu Ala Leu
        355                 360                 365

Ala Ala Ser His Glu Leu His Arg Arg Asn Gly Arg Tyr Ala Leu Cys
    370                 375                 380

Thr Met Cys Ile Gly Val Gly Gln Gly Ile Ala Met Ile Leu Glu Arg
385                 390                 395                 400

Val
```

METHODS, REAGENTS AND CELLS FOR BIOSYNTHESIZING COMPOUNDS

CROSS-REFERENCE TO RELATED APPLICATIONS

This application claims the benefit of U.S. Application Nos. 62/012,674 and 62/012,735, both of which were filed on Jun. 16, 2014, the disclosures of which are incorporated by reference herein in their entireties.

TECHNICAL FIELD

This invention relates to methods of shielding a carbon chain aliphatic backbone, functionalized with terminal carboxyl groups, in a recombinant host using a polypeptide having the activity of a fatty acid O-methyltransferase. This invention also relates to methods for biosynthesizing heptenedioyl-CoA methyl ester in a host using one or more of (i) a polypeptide having fatty acid O-methyltransferase activity (ii) a polypeptide having thioesterase activity or CoA-transferase activity, or (iii) a polypeptide having CoA ligase activity, and to recombinant host cells expressing one or more such enzymes. In addition, this invention also relates to methods for enzymatically converting hept-2-enedioyl-CoA methyl ester to pimeloyl-CoA using a polypeptide having trans-enoyl-CoA reductase activity and/or a polypeptide having pimeloyl-[acp] methyl ester esterase activity, and enzymatically converting pimeloyl-CoA to one or more of pimelic acid, 7-aminoheptanoic acid, heptamethylenediamine, 7-hydroxyheptanoic acid, and 1,7-heptanediol (hereafter "C7 building blocks"), and recombinant hosts that produce such C7 building blocks.

BACKGROUND

Nylons are polyamides which are sometimes synthesized by the condensation polymerisation of a diamine with a dicarboxylic acid. Similarly, nylons may be produced by the condensation polymerisation of lactams. A ubiquitous nylon is Nylon 6,6, which is produced by reaction of hexamethylenediamine (HMD) and adipic acid. Nylon 6 is produced by a ring opening polymerisation of caprolactam (Anton & Baird, Polyamides Fibers, Encyclopedia of Polymer Science and Technology, 2001).

Nylon 7 and Nylon 7,7 represent novel polyamides with value-added characteristics compared to Nylon 6 and Nylon 6,6. Nylon 7 is produced by polymerisation of 7-aminoheptanoic acid, whereas Nylon 7,7 is produced by condensation polymerisation of pimelic acid and heptamethylenediamine. No economically viable petrochemical routes exist to producing the monomers for Nylon 7 and Nylon 7,7.

Given no economically viable petrochemical monomer feedstocks, biotechnology offers an alternative approach via biocatalysis. Biocatalysis is the use of biological catalysts, such as enzymes, to perform biochemical transformations of organic compounds.

Both bioderived feedstocks and petrochemical feedstocks are viable starting materials for the biocatalysis processes.

Accordingly, against this background, it is clear that there is a need for methods for producing pimelic acid, 7-aminoheptanoic acid, heptamethylenediamine, 7-hydroxyheptanoic acid and 1,7-heptanediol (hereafter "C7 building blocks") wherein the methods are biocatalyst-based.

However, no wild-type prokaryote or eukaryote naturally overproduces or excretes C7 building blocks to the extracellular environment. Nevertheless, the metabolism of pimelic acid has been reported.

The dicarboxylic acid, pimelic acid, is converted efficiently as a carbon source by a number of bacteria and yeasts via β-oxidation into central metabolites. β-oxidation of CoEnzyme A (CoA) activated pimelate to CoA-activated 3-oxopimelate facilitates further catabolism via, for example, pathways associated with aromatic substrate degradation. The catabolism of 3-oxopimeloyl-CoA to acetyl-CoA and glutaryl-CoA by several bacteria has been characterized comprehensively (Harwood and Parales, *Annual Review of Microbiology*, 1996, 50, 553-590).

The optimality principle states that microorganisms regulate their biochemical networks to support maximum biomass growth. Beyond the need to express heterologous pathways in a host organism, directing carbon flux towards C7 building blocks that serve as carbon sources rather than to biomass growth constituents, contradicts the optimality principle. For example, transferring the 1-butanol pathway from *Clostridium* species into other production strains has often fallen short by an order of magnitude compared to the production performance of native producers (Shen et al., *Appl. Environ. Microbiol.*, 2011, 77(9), 2905-2915).

The efficient synthesis of the seven carbon aliphatic backbone precursor is a key consideration in synthesizing C7 building blocks prior to forming terminal functional groups, such as carboxyl, amine or hydroxyl groups, on the C7 aliphatic backbone.

SUMMARY

This document is based at least in part on the discovery that it is possible to construct biochemical pathways via hept-2-enedioyl-CoA (also referred to as 2-heptenedioyl-CoA)methyl ester for producing a seven carbon chain aliphatic backbone precursor such as pimeloyl-CoA, in which one or two functional groups, i.e., carboxyl, amine, or hydroxyl, can be formed, leading to the synthesis of one or more of pimelic acid, 7-aminoheptanoate, 7-hydroxyheptanoate, heptamethylenediamine, and 1,7-heptanediol (hereafter "C7 building blocks). Pimelic acid and pimelate, 7-hydroxyheptanoic acid and 7-hydroxyheptanoate, and 7-aminoheptanoic and 7-aminoheptanoate are used interchangeably herein to refer to the compound in any of its neutral or ionized forms, including any salt forms thereof. It is understood by those skilled in the art that the specific form will depend on pH. These pathways, metabolic engineering and cultivation strategies described herein rely on producing 2(E)-heptenedioate methyl ester from 2(E)-heptenedioate using, for example, a fatty acid O-methyltransferase and producing 2(E)-heptenedioyl-CoA methyl ester from 2(E)-heptenedioate methyl ester using, for example, a CoA ligase. Pimeloyl-CoA can be produced from 2(E)-heptenedioyl-CoA methyl ester using, for example, a trans-2-enoyl-CoA reductase and a pimelyl-[acp] methyl ester esterase. 2(E)-heptenedioate can be produced, for example, from 2-oxoglutarate, acetyl-CoA or succinate semialdehyde as shown in FIGS. 1, 2, and 3, respectively.

In the face of the optimality principle, it surprisingly has been discovered that appropriate non-natural pathways, feedstocks, host microorganisms, attenuation strategies to the host's biochemical network and cultivation strategies may be combined to efficiently produce one or more C7 building blocks.

In some embodiments, a terminal carboxyl group can be enzymatically formed using a thioesterase, an aldehyde dehydrogenase, a 7-oxoheptanoate dehydrogenase, a 6-oxohexanoate dehydrogenase, a 5-oxopentanoate dehydrogenase, a reversible CoA-ligase (e.g., a reversible succinyl-CoA-ligase), or a CoA-transferase (e.g., a glutaconate CoA-transferase). See, FIG. 4.

In some embodiments, a terminal amine group can be enzymatically formed using a ω-transaminase or a deacetylase. See, FIGS. 5 and 6.

In some embodiments, a terminal hydroxyl group can be enzymatically formed using a 4-hydroxybutyrate dehydrogenase, 5-hydroxypentanoate dehydrogenase, a 6-hydroxyhexanoate dehydrogenase, or an alcohol dehydrogenase. See, FIGS. 7 and 8.

The two terminal functional groups can be the same (e.g., amine or hydroxyl) or can be different (e.g., a terminal amine and a terminal carboxyl group; or a terminal hydroxyl group and a terminal carboxyl group).

Any of the methods can be performed in a recombinant host by fermentation. The host can be subjected to a cultivation strategy under anaerobic, micro-aerobic or mixed oxygen/denitrification cultivation conditions. The host can be cultured under conditions of nutrient limitation. The host can be retained using a ceramic membrane to maintain a high cell density during fermentation. The final electron acceptor can be an alternative to oxygen such as nitrates.

In any of the methods, the host's tolerance to high concentrations of a C7 building block can be improved through continuous cultivation in a selective environment.

The principal carbon source fed to the fermentation can derive from biological or non-biological feedstocks. In some embodiments, the biological feedstock is, includes, or derives from, monosaccharides, disaccharides, lignocellulose, hemicellulose, cellulose, lignin, levulinic acid and formic acid, triglycerides, glycerol, fatty acids, agricultural waste, condensed distillers' solubles, or municipal waste.

In some embodiments, the non-biological feedstock is or derives from natural gas, syngas, $CO_2/H_2$, methanol, ethanol, benzoate, non-volatile residue (NVR) or a caustic wash waste stream from cyclohexane oxidation processes, or a terephthalic acid/isophthalic acid mixture waste stream.

This document features a recombinant host that includes at least one exogenous nucleic acid encoding (i) a fatty acid O-methyltransferase; and (ii) a thioesterase or CoA-transferase, the host producing 2(E)-heptenedioate methyl ester. The host can further include an exogenous CoA ligase, the host further producing 2(E)-heptenedioyl-CoA methyl ester. In some embodiments, the host can further include an exogenous trans-2-enoyl-CoA reductase and/or an exogenous pimeloyl-[acp] methyl ester methylesterase, and produce pimeloyl-CoA.

This document also features a recombinant host that includes at least one exogenous nucleic acid encoding (i) a fatty acid O-methyltransferase; and (ii) a CoA ligase, the host producing 2(E)-heptenedioyl-CoA methyl ester. Such a host further can include an exogenous thioesterase or CoA-transferase. In some embodiments, the host can further include an exogenous trans-2-enoyl-CoA reductase and/or an exogenous pimeloyl-[acp] methyl ester methylesterase, and produce pimeloyl-CoA.

A recombinant host producing pimeloyl-CoA further can include at least one exogenous nucleic acid encoding one or more of a thioesterase, an aldehyde dehydrogenase, a 7-oxoheptanoate dehydrogenase, a 6-oxohexanoate dehydrogenase, a 5-oxopentanoate dehydrogenase, a CoA-transferase, a reversible CoA-ligase (e.g., a reversible succinyl-CoA-ligase), an acetylating aldehyde dehydrogenase, or a carboxylate reductase, the host producing pimelic acid or pimelate semialdehyde. In any of the recombinant hosts expressing a carboxylate reductase, a phosphopantetheinyl transferase also can be expressed to enhance the activity of the carboxylate reductase.

A recombinant host producing pimelate semialdehyde further can include at least one exogenous nucleic acid encoding a ω-transaminase, and further produce 7-aminoheptanoate.

A recombinant host producing pimelate semialdehyde further can include at least one exogenous nucleic acid encoding a 4-hydroxybutyrate dehydrogenase, a 5-hydroxypentanoate dehydrogenase or a 6-hydroxyhexanoate dehydrogenase, the host further producing 7-hydroxyheptanoic acid.

A recombinant host producing pimelate semialdehyde, 7-aminoheptanoate, or 7-hydroxyheptanoic acid further can include a carboxylate reductase, a ω-transaminase, a deacetylase, an N-acetyl transferase, or an alcohol dehydrogenase, the host further producing heptamethylenediamine.

A recombinant host producing 7-hydroxyheptanoic acid further can include at least one exogenous nucleic acid encoding a carboxylate reductase or an alcohol dehydrogenase, the host further producing 1,7-heptanediol.

The recombinant host can be a prokaryote, e.g., from the genus *Escherichia* such as *Escherichia coli*; from the genus *Clostridia* such as *Clostridium ljungdahlii*, *Clostridium autoethanogenum* or *Clostridium kluyveri*; from the genus *Corynebacteria* such as *Corynebacterium glutamicum*; from the genus *Cupriavidus* such as *Cupriavidus necator* or *Cupriavidus metallidurans*; from the genus *Pseudomonas* such as *Pseudomonas fluorescens*, *Pseudomonas putida* or *Pseudomonas oleavorans*; from the genus *Delftia acidovorans*, from the genus *Bacillus* such as *Bacillus subtillis*; from the genes *Lactobacillus* such as *Lactobacillus delbrueckii*; from the genus *Lactococcus* such as *Lactococcus lactis* or from the genus *Rhodococcus* such as *Rhodococcus equi*.

The recombinant host can be an eukaryote, e.g., a eukaryote from the genus *Aspergillus* such as *Aspergillus niger*; from the genus *Saccharomyces* such as *Saccharomyces cerevisiae*; from the genus *Pichia* such as *Pichia pastoris*; from the genus *Yarrowia* such as *Yarrowia lipolytica*, from the genus *Issatchenkia* such as *Issathenkia orientalis*, from the genus *Debaryomyces* such as *Debaryomyces hansenii*, from the genus *Arxula* such as *Arxula adenoinivorans*, or from the genus *Kluyveromyces* such as *Kluyveromyces lactis*.

Any of the recombinant hosts described herein further can include one or more of the following attenuated enzymes: polyhydroxyalkanoate synthase, an acetyl-CoA thioesterase, an acetyl-CoA specific β-ketothiolase, a phosphotransacetylase forming acetate, an acetate kinase, a lactate dehydrogenase, a menaquinol-fumarate oxidoreductase, an alcohol dehydrogenase forming ethanol, a triose phosphate isomerase, a pyruvate decarboxylase, a glucose-6-phosphate isomerase, a transhydrogenase dissipating the NADPH imbalance, an glutamate dehydrogenase dissipating the NADPH imbalance, a NADH/NADPH-utilizing glutamate dehydrogenase, a pimeloyl-CoA dehydrogenase; an acyl-CoA dehydrogenase accepting C7 building blocks and central precursors as substrates; a glutaryl-CoA dehydrogenase; or a pimeloyl-CoA synthetase.

Any of the recombinant hosts described herein further can overexpress one or more genes encoding: an acetyl-CoA synthetase, a 6-phosphogluconate dehydrogenase; a transketolase; a puridine nucleotide transhydrogenase; a formate dehydrogenase; a glyceraldehyde-3P-dehydrogenase; a malic enzyme; a glucose-6-phosphate dehydrogenase; a fructose 1,6 diphosphatase; a L-alanine dehydrogenase; a PEP carboxylase, a pyruvate carboxylase, PEP carboxykinase, PEP synthase, a L-glutamate dehydrogenase specific to the NADPH used to generate the imbalance; a methanol dehydrogenase, a formaldehyde dehydrogenase, a lysine transporter; a dicarboxylate transporter; an S-adenosylmethionine synthetase, a 3-phosphoglycerate dehydrogenase, a 3-phosphoserine aminotransferase, a phosphoserine phosphatase, and/or a multidrug transporter.

The reactions of the pathways described herein can be performed in one or more cell (e.g., host cell) strains (a) naturally expressing one or more relevant enzymes, (b) genetically engineered to express one or more relevant enzymes, or (c) naturally expressing one or more relevant enzymes and genetically engineered to express one or more relevant enzymes. Alternatively, relevant enzymes can be extracted from any of the above types of host cells and used in a purified or semi-purified form. Extracted enzymes can optionally be immobilized to a solid substrate such as the floors and/or walls of appropriate reaction vessels. Moreover, such extracts include lysates (e.g., cell lysates) that can be used as sources of relevant enzymes. In the methods provided by the document, all the steps can be performed in cells (e.g., host cells), all the steps can be performed using extracted enzymes, or some of the steps can be performed in cells and others can be performed using extracted enzymes.

Many of the enzymes described herein catalyze reversible reactions, and the reaction of interest may be the reverse of the described reaction. The schematic pathways shown in FIGS. 1 to 8 illustrate the reaction of interest for each of the intermediates.

In one aspect, this document features a method for producing a bioderived seven carbon compound. The method for producing a bioderived seven carbon compound can include culturing or growing a recombinant host as described herein under conditions and for a sufficient period of time to produce the bioderived seven carbon compound, wherein, optionally, the bioderived seven carbon compound is selected from the group consisting of pimelic acid, 7-aminoheptanoate, 7-hydroxyheptanoate, heptamethylenediamine, 1,7-heptanediol, and combinations thereof.

In one aspect, this document features composition comprising a bioderived seven carbon compound as described herein and a compound other than the bioderived seven carbon compound, wherein the bioderived seven carbon compound is selected from the group consisting of pimelic acid, 7-aminoheptanoate, 7-hydroxyheptanoate, heptamethylenediamine, 1,7-heptanediol, and combinations thereof. For example, the bioderived seven carbon compound is a cellular portion of a host cell or an organism.

This document also features a biobased polymer comprising the bioderived pimelic acid, 7-aminoheptanoate, 7-hydroxyheptanoate, heptamethylenediamine, 1,7-heptanediol, and combinations thereof.

This document also features a biobased resin comprising the bioderived pimelic acid, 7-aminoheptanoate, 7-hydroxyheptanoate, heptamethylenediamine, 1,7-heptanediol, and combinations thereof, as well as a molded product obtained by molding a biobased resin.

In another aspect, this document features a process for producing a biobased polymer that includes chemically reacting the bioderived pimelic acid, 7-aminoheptanoate, 7-hydroxyheptanoate, heptamethylenediamine, or 1,7-heptanediol, with itself or another compound in a polymer producing reaction.

In another aspect, this document features a process for producing a biobased resin that includes chemically reacting the bioderived pimelic acid, 7-aminoheptanoate, 7-hydroxyheptanoate, heptamethylenediamine, or 1,7-heptanediol, with itself or another compound in a resin producing reaction.

Also, described herein is a biochemical network comprising a polypeptide having fatty acid O-methyltransferase activity, wherein the polypeptide having fatty acid O-methyltransferase activity enzymatically converts 2(E) heptenedioic acid to 2(E) heptenedioate methyl ester. The biochemical network can further include a polypeptide having CoA ligase activity, wherein the polypeptide having CoA ligase activity enzymatically converts 2(E) heptenedioate methyl ester to 2(E) heptenedioyl-CoA methyl ester. The biochemical network can further include a polypeptide having trans-2-enoyl-CoA reductase activity, wherein the polypeptide having trans-2-enoyl-CoA reductase activity enzymatically converts 2(E) heptenedioyl-CoA methyl ester to pimeloyl-CoA methyl ester. The biochemical network can further include a polypeptide having pimelyl-[acp] methyl ester esterase activity, wherein the polypeptide having pimelyl-[acp] methyl ester esterase activity enzymatically converts pimeloyl-CoA methyl ester to pimeloyl-CoA.

The biochemical network can further include one or more polypeptides having thioesterase, reversible CoA-ligase, glutaconate CoA-transferase, ω-transaminase, 6-hydroxyhexanoate dehydrogenase, 5-hydroxypentanoate dehydrogenase, 4-hydroxybutyrate dehydrogenase, alcohol dehydrogenase, carboxylate reductase, or alcohol dehydrogenase activity, wherein the one or more polypeptides having thioesterase, reversible CoA-ligase, glutaconate CoA-transferase, ω-transaminase, 6-hydroxyhexanoate dehydrogenase, 5-hydroxypentanoate dehydrogenase, 4-hydroxybutyrate dehydrogenase, alcohol dehydrogenase, carboxylate reductase, or alcohol dehydrogenase activity enzymatically convert pimeloyl-CoA to a product selected from the group consisting of pimelic acid, 7-aminoheptanoate, 7-hydroxyheptanoate, heptamethylenediamine, and 1,7-heptanediol.

Also, described herein is a means for obtaining 2(E)-heptenedioate methyl ester, 2-heptenedioyl-CoA methyl ester, pimelic acid, 7-aminoheptanoate, 7-hydroxyheptanoate, heptamethylenediamine, and 1,7-heptanediol using one or more polypeptides having thioesterase, reversible CoA-ligase, glutaconate CoA-transferase, ω-transaminase, 6-hydroxyhexanoate dehydrogenase, 5-hydroxypentanoate dehydrogenase, 4-hydroxybutyrate dehydrogenase, alcohol dehydrogenase, carboxylate reductase or alcohol dehydrogenase activity.

In another aspect, this document features a composition comprising one or more polypeptides having fatty acid O-methyltransferase, thioesterase, reversible CoA-ligase, glutaconate CoA-transferase, ω-transaminase, 6-hydroxyhexanoate dehydrogenase, 5-hydroxypentanoate dehydrogenase, 4-hydroxybutyrate dehydrogenase, alcohol dehydrogenase, carboxylate reductase, or alcohol dehydrogenase activity and at least one of 2(E)-heptenedioate methyl ester, 2-heptenedioyl-CoA methyl ester, pimelic acid, 7-aminoheptanoate, 7-hydroxyheptanoate, heptamethylenediamine, and 1,7-heptanediol. The composition can be cellular.

One of skill in the art understands that compounds containing carboxylic acid groups (including, but not limited to, organic monoacids, hydroxyacids, aminoacids, and dicarboxylic acids) are formed or converted to their ionic salt form when an acidic proton present in the parent compound either is replaced by a metal ion, e.g., an alkali metal ion, an alkaline earth ion, or an aluminum ion; or coordinates with an organic base. Acceptable organic bases include, but are not limited to, ethanolamine, diethanolamine, triethanolamine, tromethamine, N-methylglucamine, and the like. Acceptable inorganic bases include, but are not limited to, aluminum hydroxide, calcium hydroxide, potassium hydroxide, sodium carbonate, sodium hydroxide, and the like. A salt of the present invention is isolated as a salt or converted to the free acid by reducing the pH to below the pKa, through addition of acid or treatment with an acidic ion exchange resin.

One of skill in the art understands that compounds containing amine groups (including, but not limited to, organic amines, aminoacids, and diamines) are formed or converted to their ionic salt form, for example, by addition of an acidic proton to the amine to form the ammonium salt, formed with inorganic acids such as hydrochloric acid, hydrobromic acid, sulfuric acid, nitric acid, phosphoric acid, and the like; or formed with organic acids including, but not limited to, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. Acceptable inorganic bases include, but are not limited to, aluminum hydroxide, calcium hydroxide, potassium hydroxide, sodium carbonate, sodium hydroxide, and the like. A salt of the present invention is isolated as a salt or converted to the free amine by raising the pH to above the pKb through addition of base or treatment with a basic ion exchange resin.

One of skill in the art understands that compounds containing both amine groups and carboxylic acid groups (including, but not limited to, aminoacids) are formed or converted to their ionic salt form by either 1) acid addition salts, formed with inorganic acids including, but not limited to, hydrochloric acid, hydrobromic acid, sulfuric acid, nitric acid, phosphoric acid, and the like; or formed with organic acids including, but not limited to, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. Acceptable inorganic bases include, but are not limited to, aluminum hydroxide, calcium hydroxide, potassium hydroxide, sodium carbonate, sodium hydroxide, and the like, or 2) when an acidic proton present in the parent compound either is replaced by a metal ion, e.g., an alkali metal ion, an alkaline earth ion, or an aluminum ion; or coordinates with an organic base. Acceptable organic bases include, but are not limited to, ethanolamine, diethanolamine, triethanolamine, tromethamine, N-methylglucamine, and the like. Acceptable inorganic bases include, but are not limited to, aluminum hydroxide, calcium hydroxide, potassium hydroxide, sodium carbonate, sodium hydroxide, and the like. A salt can of the present invention is isolated as a salt or converted to the free acid by reducing the pH to below the pKa through addition of acid or treatment with an acidic ion exchange resin.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein including GenBank and NCBI submissions with accession numbers are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and the drawings, and from the claims. The word "comprising" in the claims may be replaced by "consisting essentially of" or with "consisting of," according to standard practice in patent law.

DESCRIPTION OF DRAWINGS

FIGS. 9A-9Q contains the amino acid sequences of a *Mycobacterium marimum* fatty acid O-methyltransferase (GenBank Accession No. ACC41782.1; SEQ ID NO: 1), a *Mycobacterium smegmatis* str. MC2 fatty acid O-methyltransferase (GenBank Accession No. ABK73223.1; SEQ ID NO: 2), a *Pseudomonas putida* fatty acid O-methyltransferase (GenBank Accession No. CAA39234.1; SEQ ID NO: 3), a *Lactobacillus brevis* acyl-[acp] thioesterase (GenBank Accession No. ABJ63754.1, SEQ ID NO: 4), a *Lactobacillus plantarum* acyl-[acp] thioesterase (GenBank Accession No. CCC78182.1, SEQ ID NO: 5), an *Escherichia coli* pimelyl-[acp] methyl ester esterase (see GenBank Accession No. AAC76437.1, SEQ ID NO: 6), a *Mycobacterium marinum* carboxylate reductase (See Genbank Accession No. ACC40567.1, SEQ ID NO: 7), a *Mycobacterium smegmatis* carboxylate reductase (See Genbank Accession No. ABK71854.1, SEQ ID NO: 8), a *Segniliparus rugosus* carboxylate reductase (See Genbank Accession No. EFV11917.1, SEQ ID NO: 9), a *Mycobacterium smegmatis* carboxylate reductase (See Genbank Accession No. ABK75684.1, SEQ ID NO: 10), a *Mycobacterium massiliense* carboxylate reductase (See Genbank Accession No. EIV11143.1, SEQ ID NO: 11), a *Segniliparus rotundus* carboxylate reductase (See Genbank Accession No. ADG98140.1, SEQ ID NO: 12), a *Chromobacterium violaceum* ω-transaminase (See Genbank Accession No. AAQ59697.1, SEQ ID NO: 13), a *Pseudomonas aeruginosa* ω-transaminase (See Genbank Accession No. AAG08191.1, SEQ ID NO: 14), a *Pseudomonas syringae* ω-transaminase (See Genbank Accession No. AAY39893.1, SEQ ID NO: 15), a *Rhodobacter sphaeroides* ω-transaminase (see Genbank Accession No. ABA81135.1, SEQ ID NO: 16), an *Escherichia coli* ω-transaminase (see Genbank Accession No. AAA57874.1, SEQ ID NO: 17), a *Vibrio fluvialis* ω(-transaminase (see Genbank Accession No. AEA39183.1, SEQ ID NO: 18), a *Bacillus subtilis* phosphopantetheinyl transferase (see Genbank Accession No. CAA44858.1, SEQ ID NO: 19), a *Nocardia* sp. NRRL 5646 phosphopantetheinyl transferase (see Genbank Accession No. ABI83656.1, SEQ ID NO: 20), an *Escherichia coli* thioesterase encoded by tesB (See GenBank Accession No. AAA24665.1, SEQ ID NO: 21), an *Escherichia coli* long-chain-fatty-acid-CoA ligase (Genbank Accession No. CAA50321.1, SEQ ID NO: 22), a *Cupriavidus necator* long-chain-fatty-acid-CoA ligase (Genbank Accession No. CAJ95550.1, SEQ ID NO: 23), an *Acidaminococcus fermentans* glutaconate CoA-transferase (see, e.g., Genbank Accession No. CAA57199.1 (GctA) and CAA57200.1 (GctB), SEQ ID NOs: 24 and 25, respectively), a *Treponema denticola* enoyl-CoA reductase (see, e.g., Genbank Accession No. AAS11092.1, SEQ ID NO: 26), an *Euglena gracilis* enoyl-CoA reductase (see, e.g., Genbank Accession No. AAW66853.1, SEQ ID NO: 27), a *Pseudomonas reinekei* MT1 β-ketothiolase (see, e.g., Genbank Accession No. ACZ63623.1, SEQ ID NO: 28), a *Pseudomonas putida* β-ketothiolase (see, e.g., Genbank Accession No. AAA85138.1, SEQ ID NO: 29), a *Burkholderia xenovorans* β-ketothiolase (see, e.g., Genbank Accession No. ABE33819.1, SEQ ID NO: 30), an *Arthrobacter* sp. β-ketothiolase (see, e.g., Genbank Accession No. ABK03524.1, SEQ ID NO: 31), a *Burkholderia xenovorans* β-ketothiolase (see, e.g., Genbank Accession No. ABE36495.1, SEQ ID NO: 32), a *Geobacillus kaustophilus* β-ketothiolase (see, e.g., Genbank Accession No. BAD75605.1, SEQ ID NO: 33), a *Gordonia bronchialis* β-kelothiolase (see, e.g., Genbank Accession ACY20886.1, SEQ ID NO: 34), a *Citrobacter freundii* β-ketothiolase (see, e.g., Genbank Accession KFB98168.1, SEQ ID NO: 35), a *Burkholderia* sp. β-ketothiolase (see, e.g., Genbank Accession ADG18081.1, SEQ ID NO: 36), a *Beijerinckia indica* β-ketothiolase (see, e.g., Genbank Accession ACB95386.1, SEQ ID NO: 37), an *Arthrobacter arilaitensis* β-ketothiolase (see, e.g., Genbank Accession CBT74677.1, SEQ ID NO: 38), a *Cupriavidus necator* β-ketothiolase (see, e.g., Genbank Accession AAC38322.1, SEQ ID NO: 39), and an *Escherichia coli* β-ketothiolase (see, e.g., Genbank Accession AAC74479.1, SEQ ID NO: 40).

Figure 10:
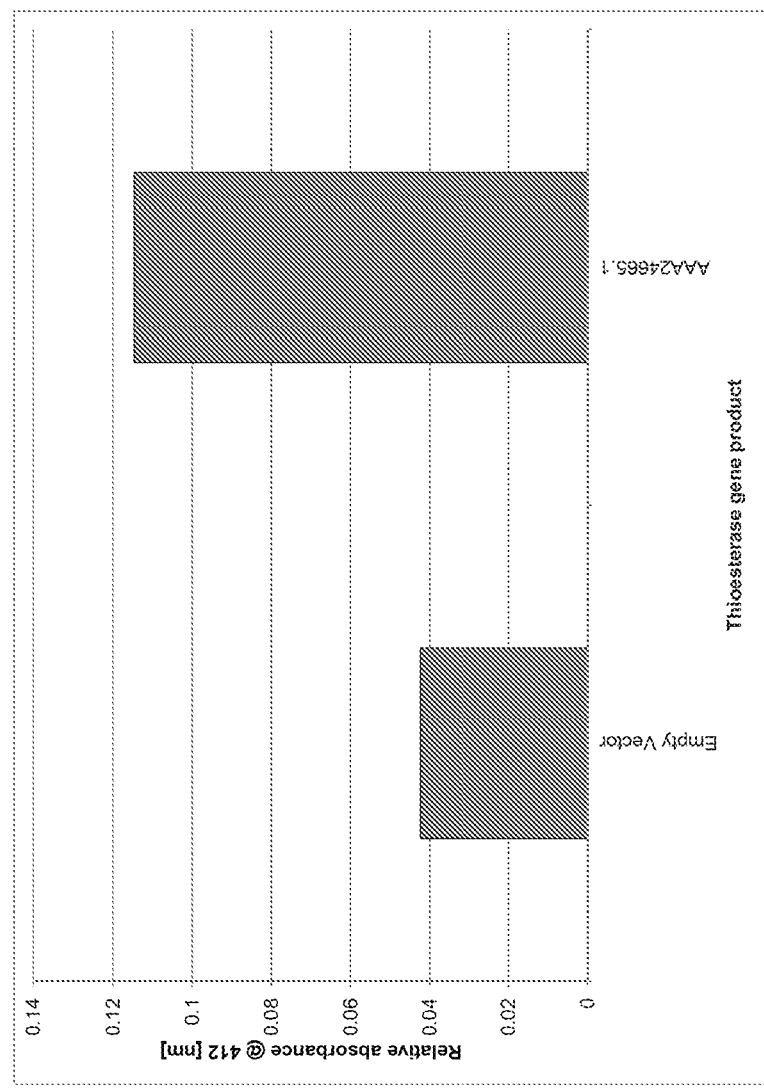

FIG. 10 is a bar graph of the relative absorbance at 412 nm after 20 minutes of released CoA as a measure of the activity of a thioesterase for converting pimeloyl-CoA to pimelate relative to the empty vector control.

Figure 11:
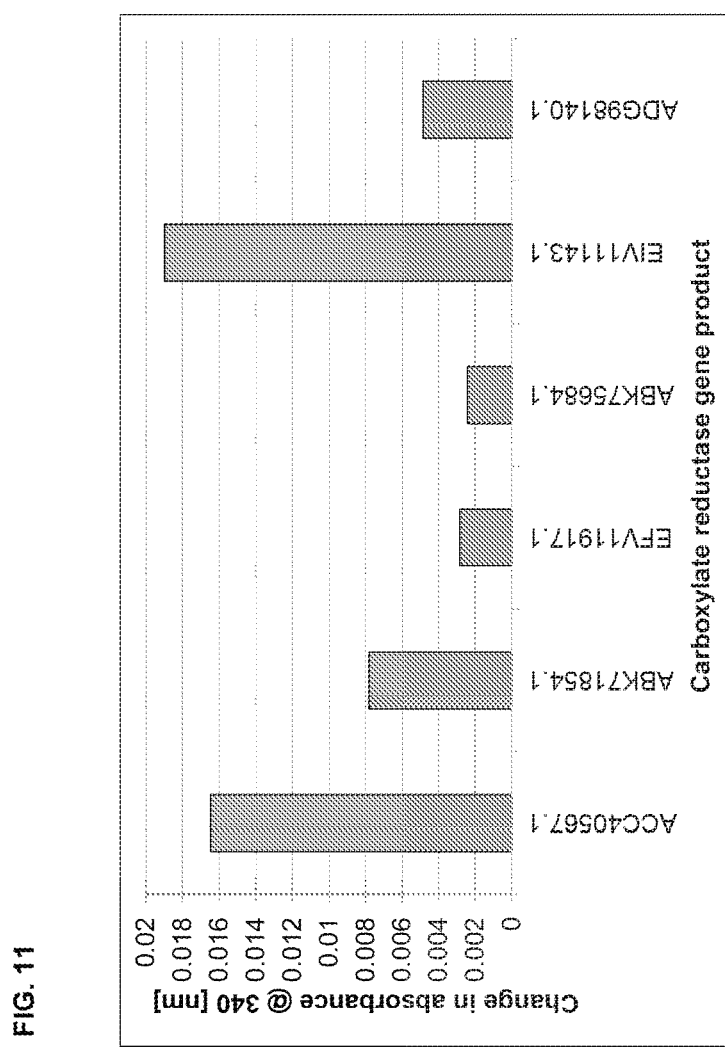

FIG. 11 is a bar graph summarizing the change in absorbance at 340 nm after 20 minutes, which is a measure of the consumption of NADPH and activity of carboxylate reductases relative to the enzyme only controls (no substrate).

Figure 12:
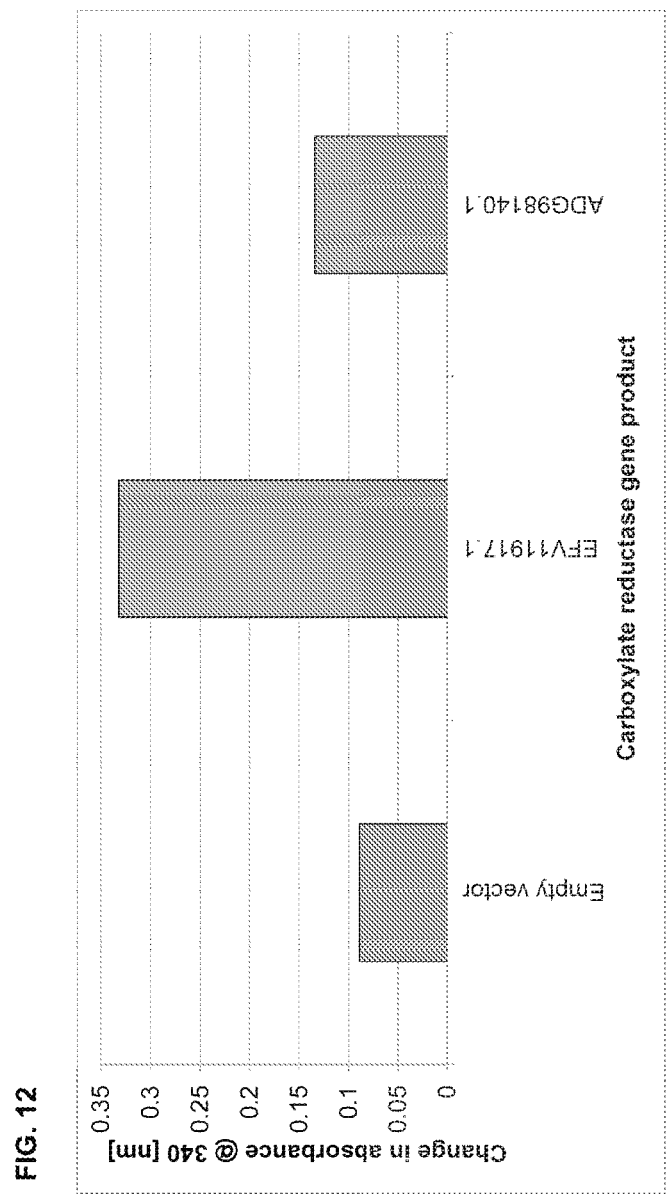

FIG. 12 is a bar graph of the change in absorbance at 340 nm after 20 minutes, which is a measure of the consumption of NADPH and the activity of carboxylate reductases for converting pimelate to pimelate semialdehyde relative to the empty vector control.

Figure 13:
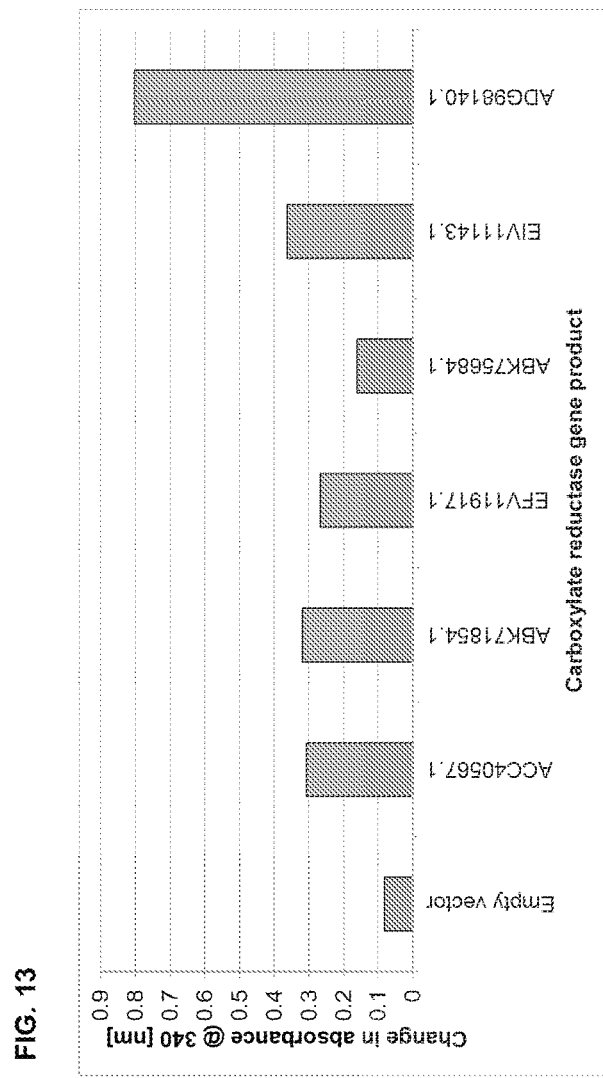

FIG. 13 is a bar graph of the change in absorbance at 340 nm after 20 minutes, which is a measure of the consumption of NADPH and the activity of carboxylate reductases for converting 7-hydroxyheptanoate to 7-hydroxyheptanal relative to the empty vector control.

Figure 14:
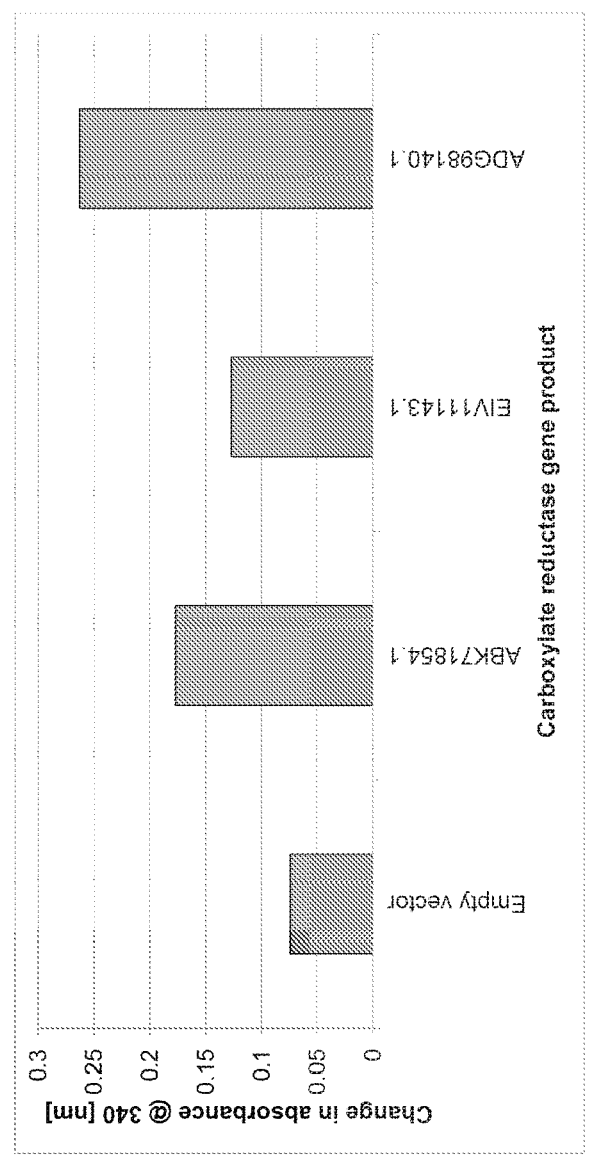

FIG. 14 is a bar graph of the change in absorbance at 340 nm after 20 minutes, which is a measure of the consumption of NADPH and the activity of carboxylate reductases for converting N7-acetyl-7-aminoheptanoate to N7-acetyl-7-aminoheptanal relative to the empty vector control.

Figure 15:
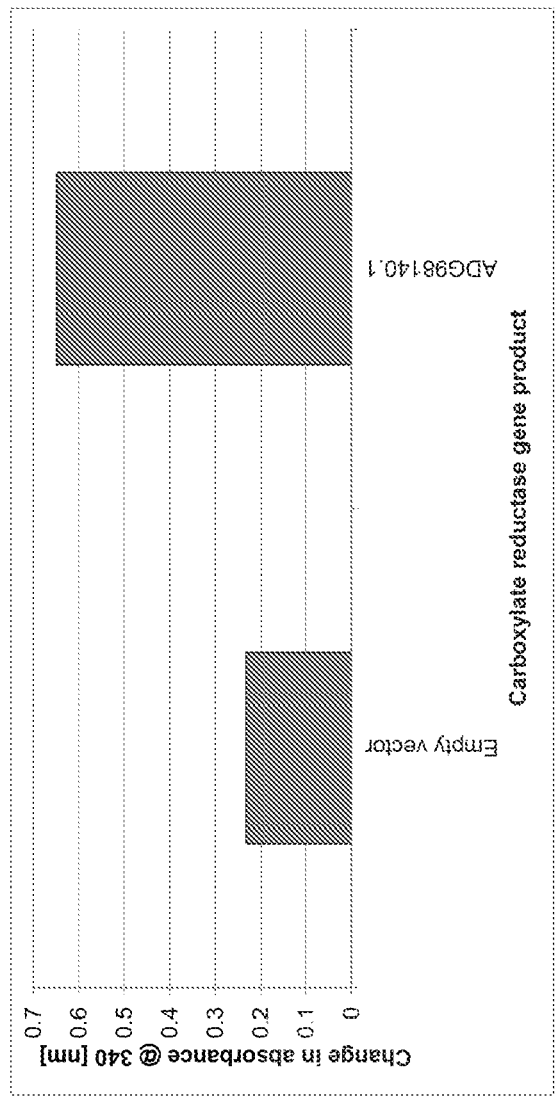

FIG. 15 is a bar graph of the change in absorbance at 340 nm after 20 minutes, which is a measure of the consumption of NADPH and activity of carboxylate reductases for converting pimelate semialdehyde to heptanedial relative to the empty vector control.

Figure 16:
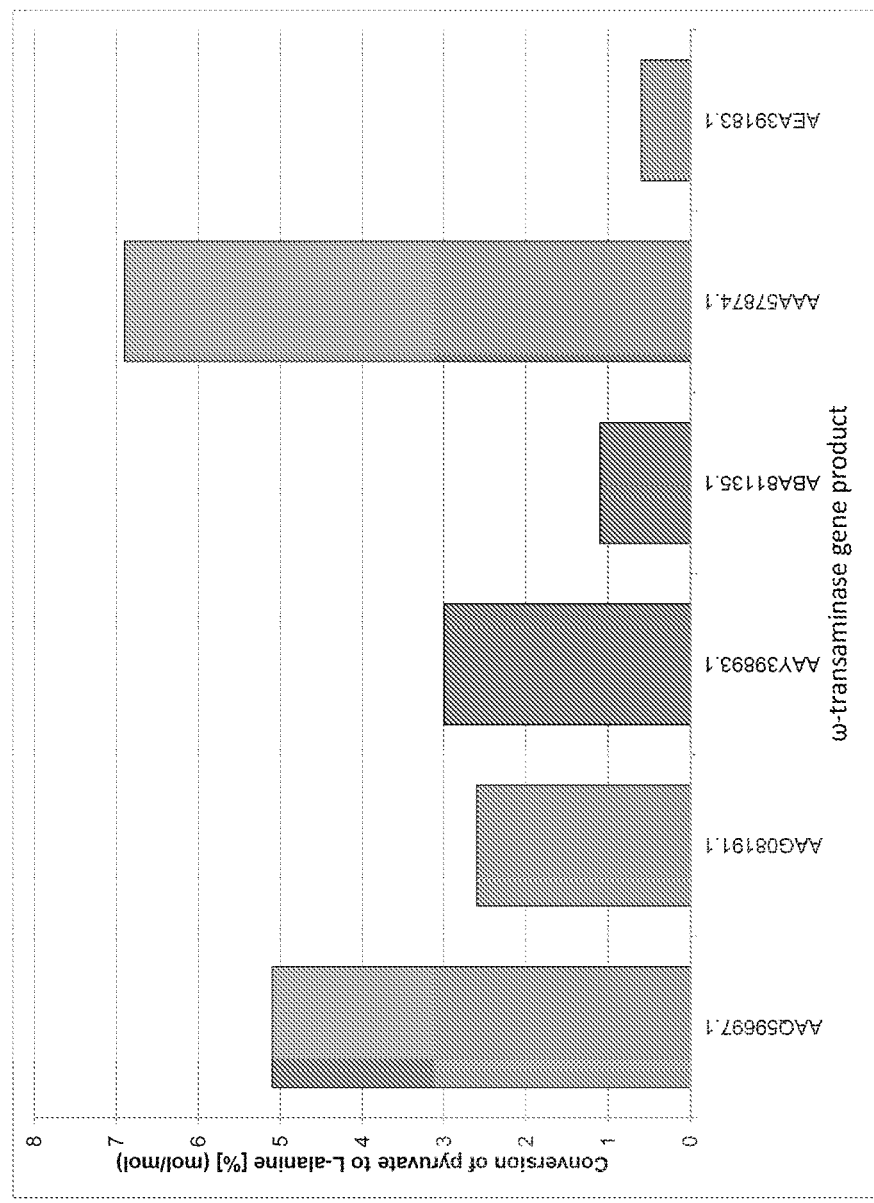

FIG. 16 is a bar graph summarizing the percent conversion after 4 hours of pyruvate to L-alanine (mol/mol) as a measure of the ω-transaminase activity of the enzyme only controls (no substrate).

Figure 17:
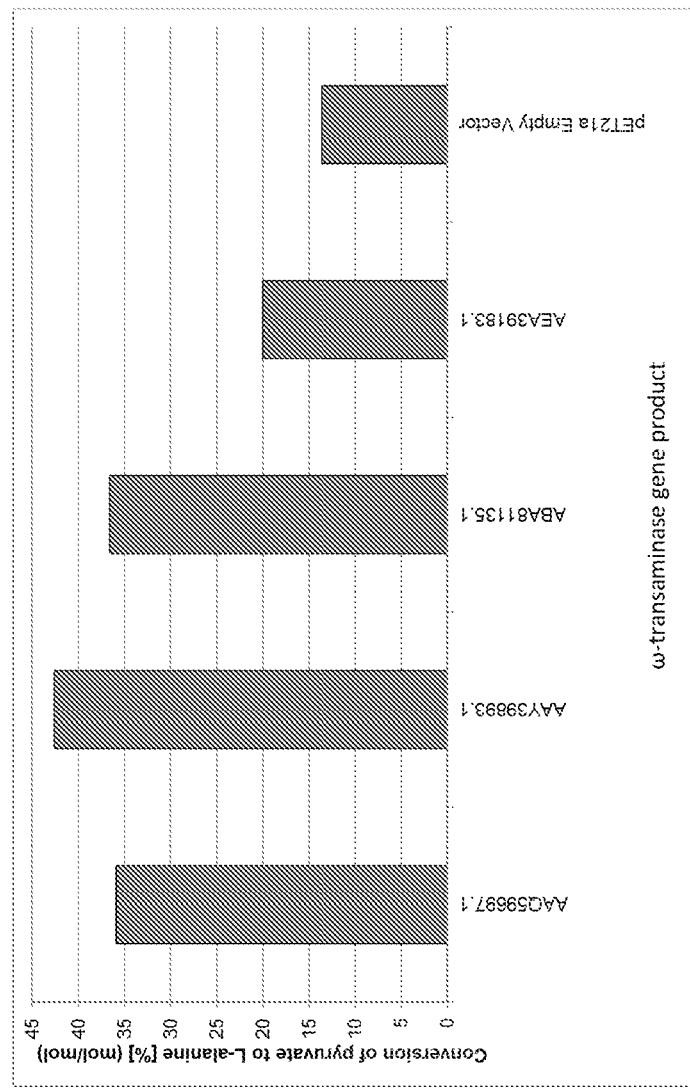

FIG. 17 is a bar graph of the percent conversion after 4 hours of pyruvate to L-alanine (mol/mol) as a measure of the ω-transaminase activity for converting 7-aminoheptanoate to pimelate semialdehyde relative to the empty vector control.

Figure 18:
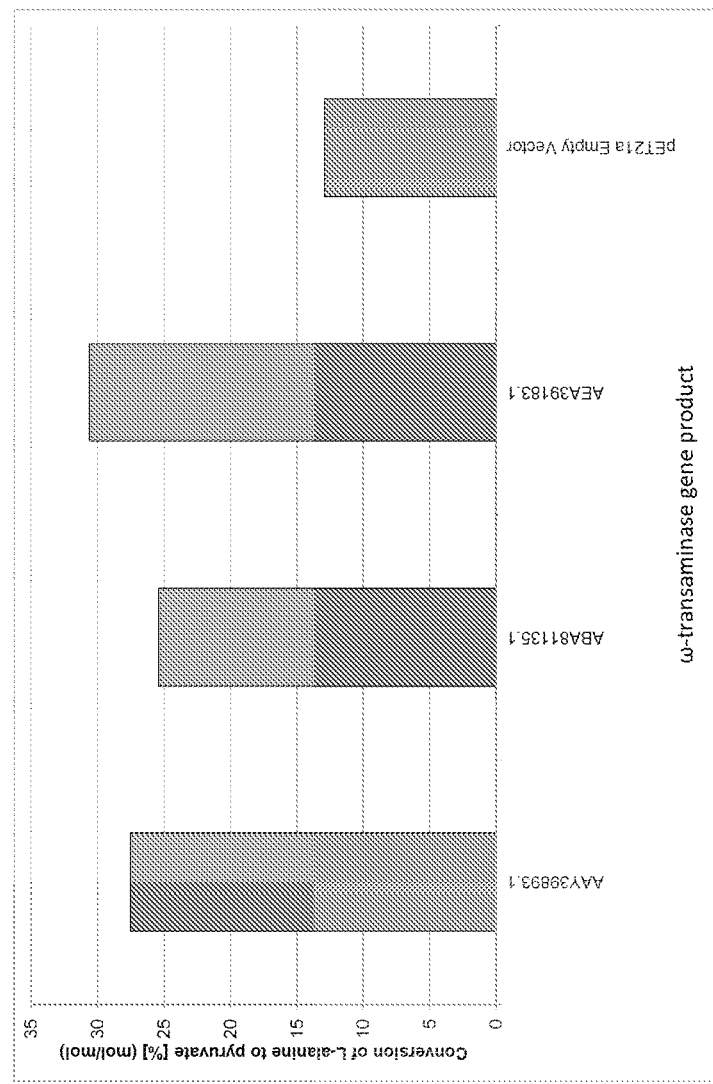

FIG. 18 is a bar graph of the percent conversion after 4 hours of L-alanine to pyruvate (mol/mol) as a measure of the a-transaminase activity for converting pimelate semialdehyde to 7-aminoheptanoate relative to the empty vector control.

Figure 19:
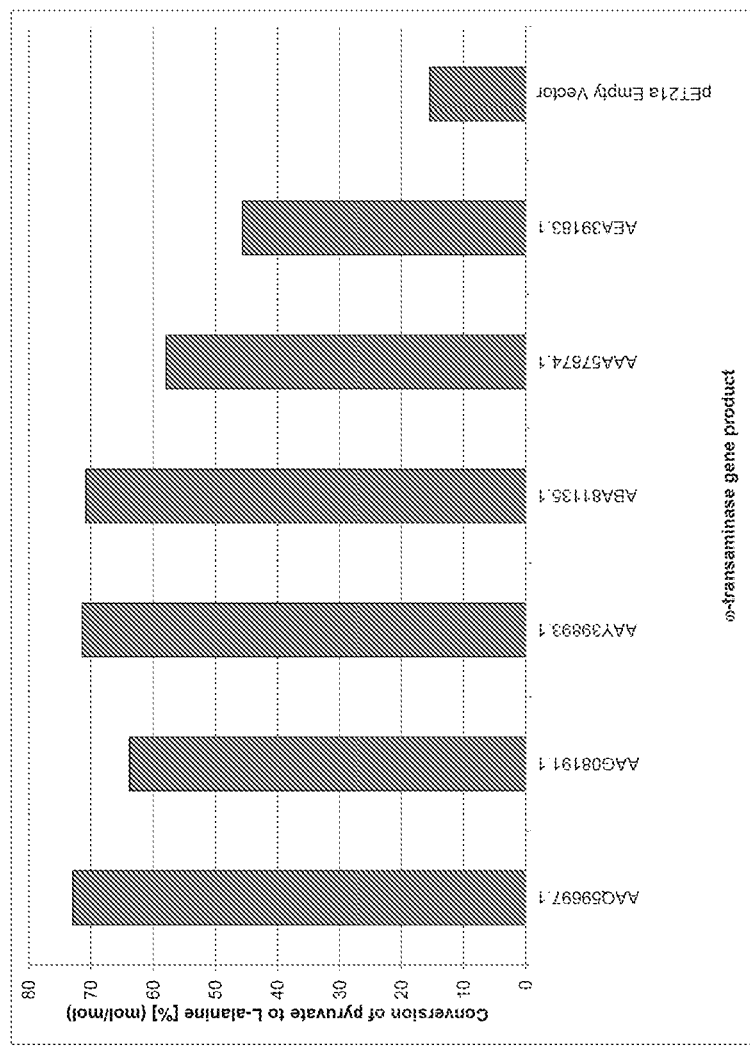

FIG. 19 is a bar graph of the percent conversion after 4 hours of pyruvate to L-alanine (mol/mol) as a measure of the ω-transaminase activity for converting heptamethylenediamine to 7-aminoheptanal relative to the empty vector control.

Figure 20:
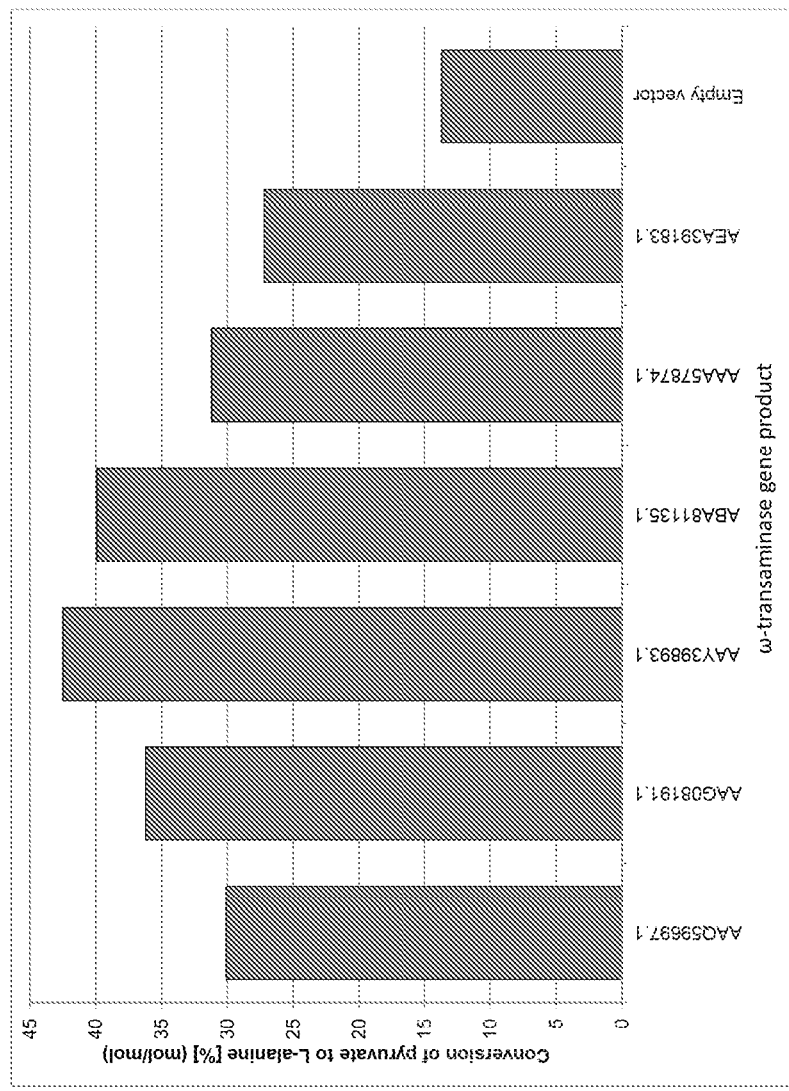

FIG. 20 is a bar graph of the percent conversion after 4 hours of pyruvate to L-alanine (mol/mol) as a measure of the ω-transaminase activity for converting N7-acetyl-1,7-diaminoheptane to N7-acetyl-7-aminoheptanal relative to the empty vector control.

Figure 21:
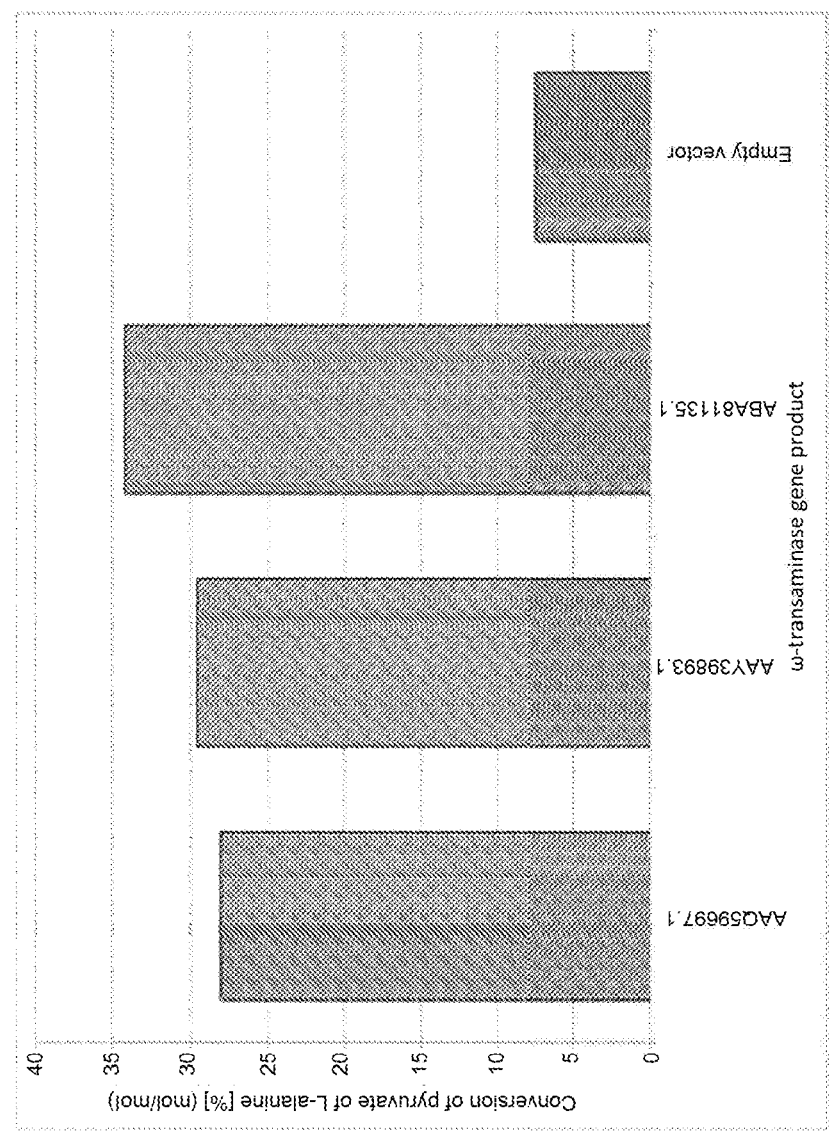

FIG. 21 is a bar graph of the percent conversion after 4 hours of pyruvate to L-alanine (mol/mol) as a measure of the ω-transaminase activity for converting 7-aminoheptanol to 7-oxoheptanol relative to the empty vector control.

FIG. 22 is a table of the conversion after 1 hour of pimeloyl-CoA methyl ester to pimeloyl-CoA by a pimeloyl-[acp] methyl ester methylesterase.

Figure 23:
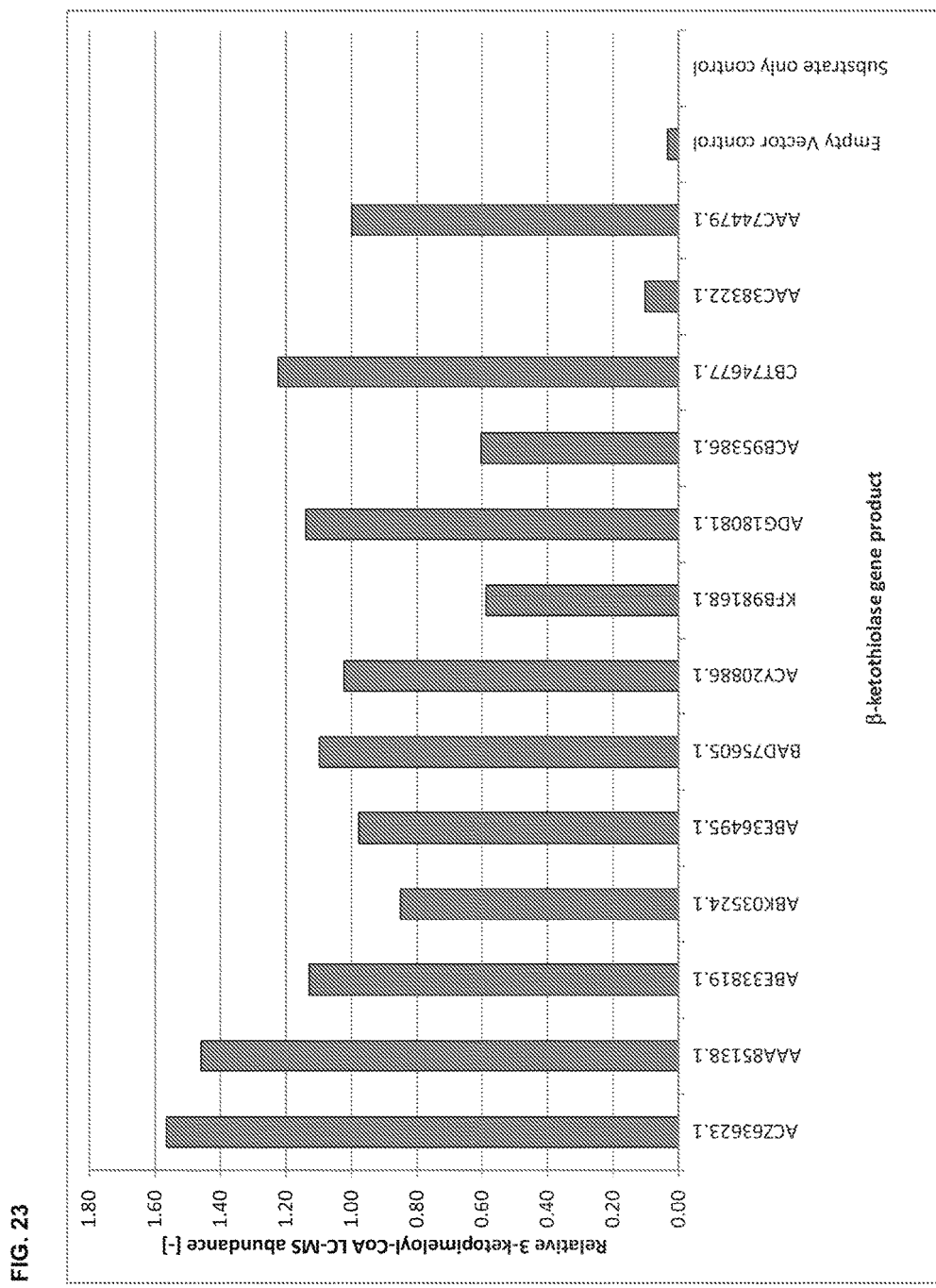

FIG. 23 is a table of the conversion after three hours of glutaryl-CoA and acetyl-CoA to 3-keotpimeloyl-CoA by a β-ketothiolase.

DETAILED DESCRIPTION

This document provides enzymes, non-natural pathways, cultivation strategies, feedstocks, host microorganisms and attenuations to the host's biochemical network, which generates a seven carbon chain aliphatic backbone from central metabolites in which one or two terminal functional groups may be formed leading to the synthesis of pimelic acid, 7-aminoheptanoic acid, heptamethylenediamine, 7-hydroxyheptanoic acid, or 1,7-heptanediol (referred to as "C7 building blocks" herein). As used herein, the term "central precursor" is used to denote any metabolite in any metabolic pathway shown herein leading to the synthesis of a C7 building block. The term "central metabolite" is used herein to denote a metabolite that is produced in all microorganisms to support growth.

Host microorganisms described herein can include endogenous pathways that can be manipulated such that one or more C7 building blocks can be produced. In an endogenous pathway, the host microorganism naturally expresses all of the enzymes catalyzing the reactions within the pathway. A host microorganism containing an engineered pathway does not naturally express all of the enzymes catalyzing the reactions within the pathway but has been engineered such that all of the enzymes within the pathway are expressed in the host.

The term "exogenous" as used herein with reference to a nucleic acid (or a protein) and a host refers to a nucleic acid that does not occur in (and cannot be obtained from) a cell of that particular type as it is found in nature or a protein encoded by such a nucleic acid. Thus, a non-naturally-occurring nucleic acid is considered to be exogenous to a host once in the host. It is important to note that non-naturally-occurring nucleic acids can contain nucleic acid subsequences or fragments of nucleic acid sequences that are found in nature provided the nucleic acid as a whole does not exist in nature. For example, a nucleic acid molecule containing a genomic DNA sequence within an expression vector is non-naturally-occurring nucleic acid, and thus is exogenous to a host cell once introduced into the host, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid. A nucleic acid that is naturally-occurring can be exogenous to a particular host microorganism. For example, an entire chromosome isolated from a cell of yeast x is an exogenous nucleic acid with respect to a cell of yeast y once that chromosome is introduced into a cell of yeast y.

In contrast, the term "endogenous" as used herein with reference to a nucleic acid (e.g., a gene) (or a protein) and a host refers to a nucleic acid (or protein) that does occur in (and can be obtained from) that particular host as it is found in nature. Moreover, a cell "endogenously expressing" a nucleic acid (or protein) expresses that nucleic acid (or protein) as does a host of the same particular type as it is found in nature. Moreover, a host "endogenously producing" or that "endogenously produces" a nucleic acid, protein, or other compound produces that nucleic acid, protein, or compound as does a host of the same particular type as it is found in nature.

For example, depending on the host and the compounds produced by the host, a recombinant host can express an exogenous polypeptide having fatty acid O-methyltransferase activity.

For example, depending on the host and the compounds produced by the host, one or more of the following polypeptides may be expressed in the host in addition to a polypeptide having (i)fatty acid O-methyltransferase activity, (ii) thioesterase activity or a CoA-transferase activity, and (iii) CoA ligase activity: a pimelyl-[acp] methyl ester esterae, a (homo)$_n$citrate synthase, a (homo)$_n$citrate dehydratave, a (homo)aconitate hydratase, an iso(homo)$_n$citrate dehydrogenase, an decarboxylase such as an indolepyruvate decarboxylase, a β-ketothiolase, an acetyl-carboxylase, an acetoacetyl-CoA synthase, a 3-hydroxybutyryl-CoA dehydrogenase, an enoyl-CoA hydratase, a glutaryl-CoA dehydrogenase, an enoyl-CoA reductase, a trans-2-enoyl-CoA reductase, a glutaconyl-CoA decarboxylase, a β-ketoacyl-[acp] synthase, a 3-hydroxybutyryl-CoA dehydrogenase, a 2-hydroxyglutarate dehydrogenase, a 2-hydroxyglutaryl-CoA dehydratase, a glutarate semialdehyde dehydrogenase, a 4-hydroxy-2-oxoheptanedioate aldolase, a 2-oxo-hept-3-ene-1,7-dioate hydratase, a 2-enoate reductase, a 2-hydroxyglutarate dehydrogenase, a 2-hydroxyglutaryl-CoA dehydratase, a thioesterase, an aldehyde dehydrogenase, a 6-oxohexanoate dehydrogenase, a 7-oxoheptanoate dehydrogenase, a reversible CoA-ligase (e.g., a reversible succinyl-CoA-ligase), a CoA-transferase (e.g., a glutaconate CoA-transferase), an acetylating aldehyde dehydrogenase, a carboxylate reductase, 4-hydroxybutyrate dehydrogenase, a 5-hydroxypentanoate dehydrogenase, a 6-hydroxyhexanoate dehydrogenase, a ω-transaminase, a N-acetyl transferase, an alcohol dehydrogenase, or a deacetylase. In recombinant hosts expressing a carboxylate reductase, a phosphopantetheinyl transferase also can be expressed as it enhances activity of the carboxylate reductase.

For example, a recombinant host can include at least one exogenous nucleic acid encoding a (i) fatty acid O-methyltransferase, (ii) a thioesterase or CoA-transferase, and/or (iii) a CoA ligase. In some embodiments, a recombinant host includes an exogenous nucleic acid encoding a (i) fatty acid O-methyltransferase and a (ii) thioesterase or CoA-transferase, wherein the host produces 2(E)-heptenedioate methyl ester. In some embodiments, a recombinant host includes an exogenous nucleic acid encoding a fatty acid O-methyltransferase and a CoA ligase, wherein the host produces hept-2-enedioyl CoA methyl ester. In some embodiments, the recombinant host includes an exogenous nucleic acid encoding (i) a fatty acid O-methyltransferase, (ii) a thioesterase, and (iii) a CoA ligase, and produces hept-2-enedioyl CoA methyl ester. Such a host further can include an exogenous trans-2-enoyl-CoA reductase and an exogenous pimeloyl-[acp] methyl ester methylesterase, and further produce pimeloyl-CoA.

In some embodiments, the host can include one or more of the following exogenous enzymes used to produce glutaryl-CoA from 2-oxo-glutarate: (a) a homocitrate synthase, (b) a homocitrate dehydratase, (c) a homoaconitate hydratase, an (d) isohomocitrate dehydrogenase, (e) a decarboxylase such as indolepyruvate decarboxylase, (f) a glutarate-semialdehyde dehydrogenase, and (g) a glutarate:CoA ligase or CoA-transferase.

In some embodiments, the host can include one or more of the following exogenous enzymes used to produce glutaryl CoA from acetyl CoA: (a) a β-ketothiolase or an acetyl-carboxylase in combination with an acetoacetyl-CoA synthase. (b) a 3-hydroxybutyryl-CoA dehydrogenase, (c)

an enoyl-CoA hydratase, and either (d) a glutaryl-CoA dehydrogenase in combination with an enoyl-CoA reductase or (e) a glutaconyl-CoA decarboxylase.

In some embodiments, the host can include one or more of the following exogenous enzymes used to produce 2-heptenedioyl-CoA from glutaryl CoA: a β-ketoacyl-[acp] synthase or β-ketothiolase, a 3-hydroxyacyl-CoA dehydrogenase, and an enoyl-CoA hydratase.

Figure 2:
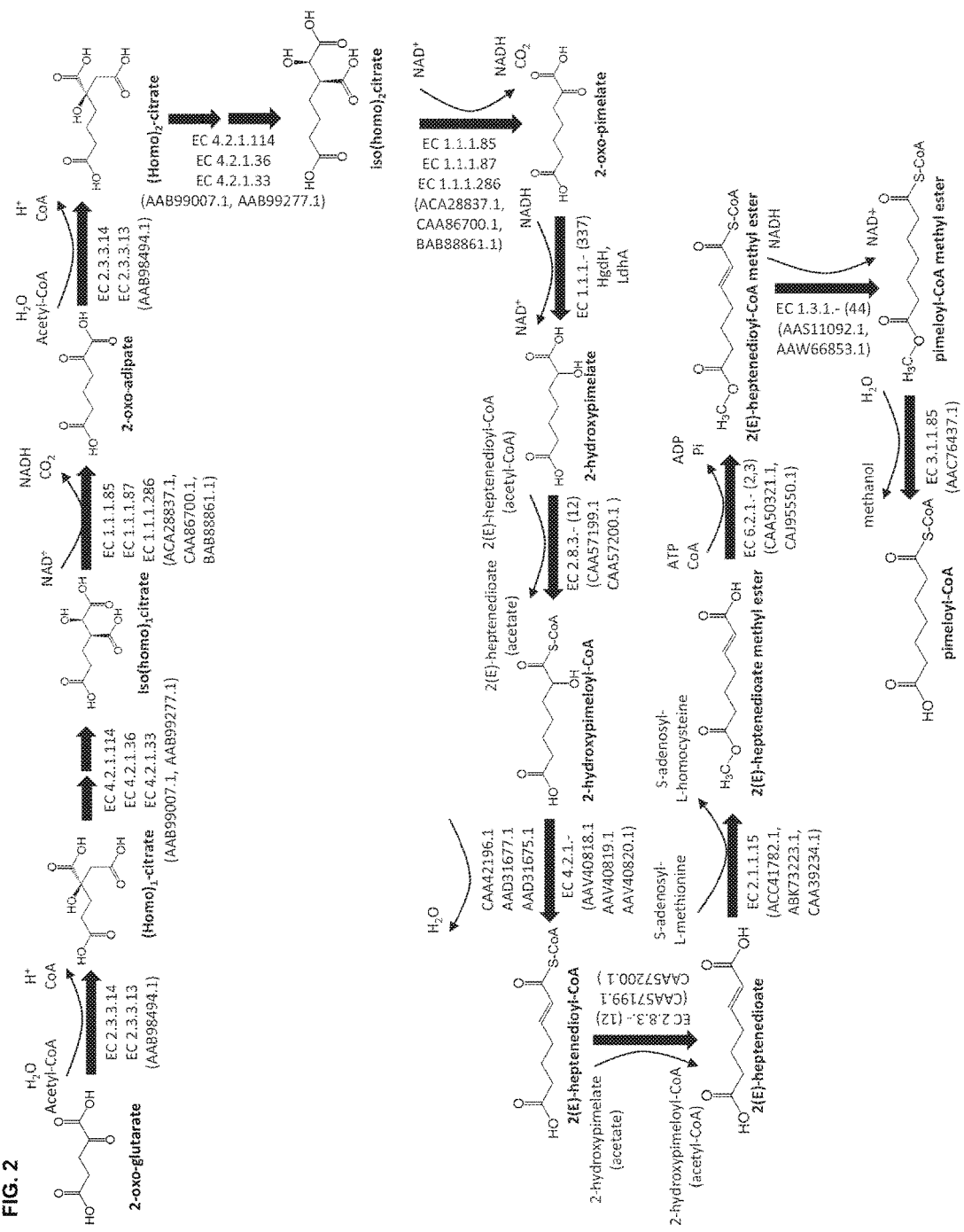
FIG. 2 is a schematic of an exemplary biochemical pathway leading to pimeloyl-CoA from 2-oxo-glutarate via a hept-2-enedioyl-CoA methyl ester.

In some embodiments, the host can include one or more of the following exogenous enzymes used to convert 2-oxo-glutarate to hept-2-enedioyl-CoA via 2-oxo-pimelate as shown in FIG. 2: a homocitrate synthase, a homocitrate dehydratase, a homoaconitate hydratase, an isohomocitrate dehydrogenase, a 2-hydroxyglutarate dehydrogenase, a glutaconate CoA-transferase, and a 2-hydroxyglutaryl-CoA dehydratase.

Figure 3:
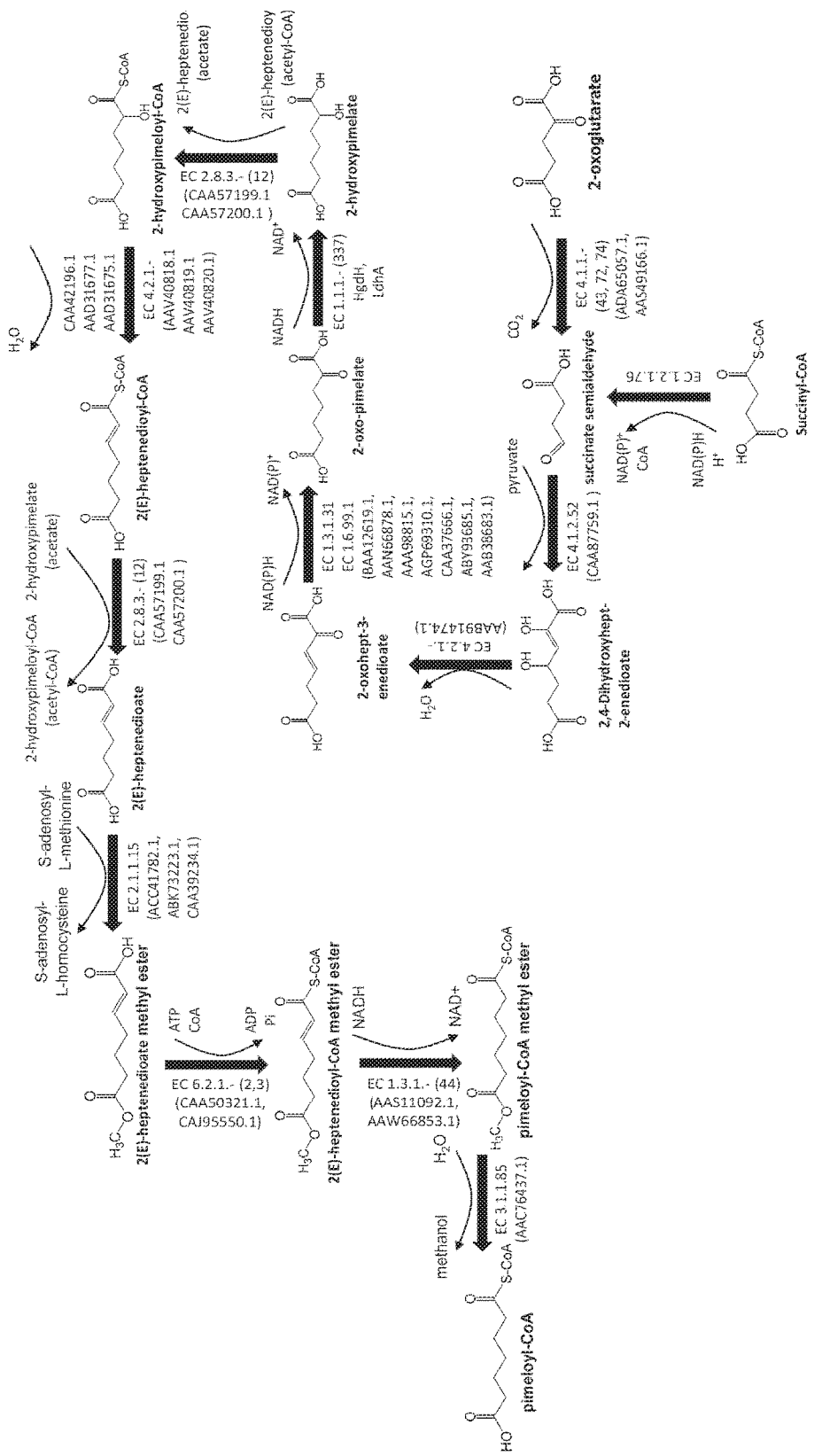
FIG. 3 is a schematic of exemplary biochemical pathways leading to pimeloyl-CoA from succinyl-CoA or 2-oxo-glutarate via a hept-2-enedioyl-CoA methyl ester.

In some embodiments, the host can include one or more of the following exogenous enzymes used to convert succinate semialdehyde to hept-2-enedioyl-CoA via 2-oxo-pimelate as shown in FIG. 3: a glutarate semialdehyde dehydrogenase, a 4-hydroxy-2-oxoheptanedioate aldolase, a 2-oxo-hept-3-ene-1,7-dioate hydratase, a 2-enoate reductase, a 2-hydroxyglutarate dehydrogenase, a glutaconate CoA-transferase, and a 2-hydroxyglutaryl-CoA dehydratase.

Such recombinant hosts further can include at least one exogenous nucleic acid encoding one or more of a thioesterase, an aldehyde dehydrogenase, a 7-oxoheptanoate dehydrogenase, a 6-oxohexanoate dehydrogenase, a 5-oxopentanoate dehydrogenase, a CoA-transferase, a reversible CoA-ligase, an acetylating aldehyde dehydrogenase, or a carboxylate reductase and produce pimelic acid or pimelate semialdehyde. For example, a recombinant host producing pimeloyl-CoA further can include a thioesterase, a reversible Co-ligase (e.g., a reversible succinyl-CoA ligase), or a CoA transferase (e.g., a glutaconate CoA-transferase) and produce pimelic acid. For example, a recombinant host producing pimeloyl-CoA further can include an acetylating aldehyde dehydrogenase and produce pimelate semilaldehyde. For example, a recombinant host producing pimelate further can include a carboxylate reductase and produce pimelate semialdehyde.

A recombinant hosts producing pimelic acid or pimelate semialdehyde further can include at least one exogenous nucleic acid encoding a ω-transaminase and produce 7-aminoheptanoate. In some embodiments, a recombinant host producing pimelate includes a carboxylate reductase and a ω-transaminase to produce 7-aminoheptanoate.

A recombinant host producing pimelate or pimelate semialdehyde further can include at least one exogenous nucleic acid encoding a 6-hydroxyhexanoate dehydrogenase, a 5-hydroxypentanoate dehydrogenase or a 4-hydroxybutyrate dehydrogenase, and produce 7-hydroxyheptanoic acid. In some embodiments, a recombinant host producing pimeloyl-CoA includes an acetylating aldehyde dehydrogenase, and a 6-hydroxyhexanoate dehydrogenase, a 5-hydroxypentanoate dehydrogenase or a 4-hydroxybutyrate dehydrogenase to produce 7-hydroxyheptanoate. In some embodiments, a recombinant host producing pimelate includes a carboxylate reductase and a 6-hydroxyhexanoate dehydrogenase, a 5-hydroxypentanoate dehydrogenase or a 4-hydroxybutyrate dehydrogenase to produce 7-hydroxyheptanoate.

A recombinant hosts producing 7-aminoheptanoate, 7-hydroxyheptanoate or pimelate semialdehyde further can include at least one exogenous nucleic acid encoding a ω-transaminase, a deacetylase, a N-acetyl transferase, or an alcohol dehydrogenase, and produce heptamethylenediamine. For example, a recombinant host producing 7-hydroxyheptanoate can include a carboxylate reductase with a phosphopantetheine transferase enhancer, a ω-transaminase and an alcohol dehydrogenase.

A recombinant host producing 7-hydroxyheptanoic acid further can include one or more of a carboxylate reductase with a phosphopantetheine transferase enhancer and an alcohol dehydrogenase, and produce 1,7-heptanediol.

Within an engineered pathway, the enzymes can be from a single source, i.e., from one species or genus, or can be from multiple sources, i.e., different species or genera. Nucleic acids encoding the enzymes described herein have been identified from various organisms and are readily available in publicly available databases such as GenBank or EMBL.

Any of the enzymes described herein that can be used for production of one or more C7 building blocks can have at least 70% sequence identity (homology) (e.g., at least 75%, 80%, 85%, 90%, 91%, 92%, 93%, 94%, 95%, 96%, 97%, 98%, 99%, or 1000%) to the amino acid sequence of the corresponding wild-type enzyme. It will be appreciated that the sequence identity can be determined on the basis of the mature enzyme (e.g., with any signal sequence removed) or on the basis of the immature enzyme (e.g., with any signal sequence included). It also will be appreciated that the initial methionine residue may or may not be present on any of the enzyme sequences described herein.

For example, a polypeptide having fatty acid O-methyl-transferase activity described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Mycobacterium marinum* (see GenBank Accession No. ACC41782.1, SEQ ID NO: 1), a *Mycobacterium smegmatis* (see GenBank Accession No. ABK73223.1, SEQ ID NO: 2), or a *Pseudomonas putida* (see GenBank Accession No. CAA39234.1, SEQ ID NO: 3) methyltransferase. See, FIG. 9A.

For example, a polypeptide having thioesterase activity described herein can have at least 70% sequence identity (homology) (e.g., at least 75%, 80%, 85%, 90%, 91%, 92%, 93%, 94%0, 95%, 96%, 97%, 98%, 99%, or 100%) to the amino acid sequence of a *Lactobacillus brevis* (GenBank Accession No. ABJ63754.1, SEQ ID NO: 4) or a *Lactobacillus plantarum* (GenBank Accession No. CCC78182.1, SEQ ID NO: 5) acyl-[acp] thioesterase. See, FIGS. 9A and 9B.

For example, a polypeptide having pimelyl-[acp] methyl ester esterase activity described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of an *Escherichia coli* pimelyl-[acp] methyl ester esterase (see GenBank Accession No. AAC76437.1, SEQ ID NO: 6). See, FIG. 9B.

For example, a polypeptide having carboxylate reductase activity described herein can have at least 700% sequence identity (homology) (e.g., at least 75%, 80%, 85%, 90%, 91%, 92%, 93%, 94%, 95%, 96%, 97%, 98%, 99%, or 100%) to the amino acid sequence of a *Mycobacterium marinum* (see Genbank Accession No. ACC40567.1, SEQ ID NO: 7), a *Mycobacterium smegmatis* (see Genbank Accession No. ABK71854.1, SEQ ID NO: 8), a *Segniliparus rugoslis* (see Genbank Accession No. EFV11917.1, SEQ ID NO: 9), a *Mycobacterium smegmatis* (see Genbank Accession No. ABK75684.1, SEQ ID NO: 10), a *Mycobacterium massiliense* (see Genbank Accession No. EIV11143.1, SEQ ID NO: 11), or a *Segniliparus rotundus* (see Genbank Accession No. ADG98140.1, SEQ ID NO: 12) carboxylate reductase. See, FIGS. 9C-9H.

For example, a polypeptide having ω-transaminase activity described herein can have at least 70% sequence identity (homology) (e.g., at least 75%, 80%, 85%, 90%, 91%, 920%, 93%, 94%, 95%, 96%, 97%, 98%, 99%, or 100%) to the amino acid sequence of a *Chromobacterium violaceum* (see Genbank Accession No. AAQ59697.1, SEQ ID NO: 13), a *Pseudomonas aeruginosa* (see Genbank Accession No. AAG08191.1, SEQ ID NO: 14), a *Pseudomonas syringae* (see Genbank Accession No. AAY39893.1, SEQ ID NO: 15), a *Rhodobacter sphaeroides* (see Genbank Accession No. ABA81135.1, SEQ ID NO: 16), an *Escherichia coli* (see Genbank Accession No. AAA57874.1, SEQ ID NO: 17), or a *Vibrio fluvialis* (see Genbank Accession No. AEA39183.1, SEQ ID NO: 18) ω-transaminase. See FIGS. 9I and 9J. Some of these ω-transaminases are diamine ω-transaminases.

For example, a polypeptide having phosphopantetheinyl transferase activity described herein can have at least 700 sequence identity (homology) (e.g., at least 75%, 80%, 85%, 90%, 91%, 92%, 93%, 94%, 95%, 96%, 97%, 98%, 99%, or 100%) to the amino acid sequence of a *Bacillus subtilis* phosphopantetheinyl transferase (see Genbank Accession No. CAA44858.1, SEQ ID NO: 19) or a *Nocardia* sp. NRRL 5646 phosphopantetheinyl transferase (see Genbank Accession No. AB183656.1, SEQ ID NO: 20). See, FIG. 9K.

For example, a polypeptide having thioesterase activity described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of an *Escherichia coli* thioesterase encoded by tesB (see GenBank Accession No. AAA24665.1, SEQ ID NO: 21). See, FIG. 9K.

For example, a polypeptide having long-chain-fatty-acid-CoA ligase activity described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of an *Escherichia coli* long-chain-fatty-acid-CoA ligase (see Genbank Accession No. CAA50321.1, SEQ ID NO: 22), or a *Cupriavidus necator* long-chain-fatty-acid-CoA ligase (see Genbank Accession No. CAJ95550.1, SEQ ID NO: 23).

For example, a polypeptide having glutaconate CoA-transferase activity described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of an *Acidaminococcus fermentans* glutaconate CoA-transferase (see, e.g., Genbank Accession No. CAA57199.1 (GctA) and CAA57200.1 (GctB), SEQ ID NOs: 24 and 25, respectively).

For example, a polypeptide having enoyl-CoA reductase activity described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Treponema denticola* enoyl-CoA reductase (see, e.g., Genbank Accession No. AAS11092.1, SEQ ID NO: 26) or to the amino acid sequence of an *Euglena gracilis* enoyl-CoA reductase (see, e.g., Genbank Accession No. AAW66853.1, SEQ ID NO: 27).

For example, a polypeptide having enoyl-CoA reductase activity described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Pseudomonas reinekei* MTI β-ketothiolase (see, e.g., Genbank Accession No. ACZ63623.1, SEQ ID NO: 28), a *Pseudomonas putida* β-ketothiolase (see, e.g., Genbank Accession No. AAA85138.1, SEQ ID NO: 29), a *Burkholderia xenovorans* β-ketothiolase (see, e.g., Genbank Accession No. ABE33819.1, SEQ ID NO: 30), an *Arthrobacter* sp. β-ketothiolase (see, e.g., Genbank Accession No. ABK03524.1, SEQ ID NO: 31), a *Burkholderia xenovorans* β-ketothiolase (see, e.g., Genbank Accession No. ABE36495.1, SEQ ID NO: 32), a *Geobacillus kaustophilus* β-ketothiolase (see, e.g., Genbank Accession No. BAD75605.1, SEQ ID NO: 33), a *Gordonia bronchialis* β-ketothiolase (see, e.g., Genbank Accession ACY20886.1, SEQ ID NO: 34), a *Citrobacter freundii* β-ketothiolase (see, e.g., Genbank Accession KFB98168.1, SEQ ID NO: 35), a *Burkholderia* sp. β-ketothiolase (see, e.g., Genbank Accession ADG18081.1, SEQ ID NO: 36), a *Beijerinckia indica* β-ketothiolase (see, e.g., Genbank Accession ACB95386.1, SEQ ID NO: 37), an *Arthrobacter arilaitensis* β-ketothiolase (see, e.g., Genbank Accession CBT74677.1, SEQ ID NO: 38), a *Cupriavidus necator* β-ketothiolase (see, e.g., Genbank Accession AAC38322.1, SEQ ID NO: 39), and an *Escherichia coli* β-ketothiolase (see, e.g., Genbank Accession AAC74479.1, SEQ ID NO: 40).

The percent identity (homology) between two amino acid sequences can be determined as follows. First, the amino acid sequences are aligned using the BLAST 2 Sequences (Bl2seq) program from the stand-alone version of BLASTZ containing BLASTP version 2.0.14. This stand-alone version of BLASTZ can be obtained from Fish & Richardson's web site (e.g., www.fr.com/blast/) or the U.S. government's National Center for Biotechnology Information web site (www.ncbi.nlm.nih.gov). Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq -i c:\seq1.txt -j c:\seq2.txt -p blastp -o c:\output.txt. If the two compared sequences share homology (identity), then the designated output file will present those regions of homology as aligned sequences. If the two compared sequences do not share homology (identity), then the designated output file will not present aligned sequences. Similar procedures can be following for nucleic acid sequences except that blastn is used.

Once aligned, the number of matches is determined by counting the number of positions where an identical amino acid residue is presented in both sequences. The percent identity (homology) is determined by dividing the number of matches by the length of the full-length polypeptide amino acid sequence followed by multiplying the resulting value by 100. It is noted that the percent identity (homology) value is rounded to the nearest tenth. For example, 78.11, 78.12, 78.13, and 78.14 is rounded down to 78.1, while 78.15, 78.16, 78.17, 78.18, and 78.19 is rounded up to 78.2. It also is noted that the length value will always be an integer.

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid. For example, codons in the coding sequence for a given enzyme can be modified such that optimal expression in a particular species (e.g., bacteria or fungus) is obtained, using appropriate codon bias tables for that species.

Functional fragments of any of the enzymes described herein can also be used in the methods of the document. The term "functional fragment" as used herein refers to a peptide fragment of a protein that has at least 25% (e.g., at least: 30%; 40%; 50%; 60%; 70%; 75%; 80%; 85%; 90%; 91%; 92%; 93%; 94%; 95%; 96%; 97%; 98%; 99%; 100%; or even greater than 100%) of the activity of the corresponding mature, full-length, wild-type protein. The functional fragment can generally, but not always, be comprised of a continuous region of the protein, wherein the region has functional activity. Functional fragments are shorter than corresponding mature proteins but are generally at least 25 (e.g., at least: 30; 40; 50; 60; 70; 80, 90; 100; 120; 150; 200; 250; 300; 450; 500; 800; or more) amino acids long.

This document also provides (i) functional variants of the enzymes used in the methods of the document and (ii) functional variants of the functional fragments described above. Functional variants of the enzymes and functional fragments can contain additions, deletions, or substitutions relative to the corresponding wild-type sequences. Enzymes with substitutions will generally have not more than 50 (e.g., not more than one, two, three, four, five, six, seven, eight, nine, ten, 12, 15, 20, 25, 30, 35, 40, or 50) amino acid substitutions (e.g., conservative substitutions). This applies to any of the enzymes described herein and functional fragments. A conservative substitution is a substitution of one amino acid for another with similar characteristics. Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The nonpolar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic or acidic groups by another member of the same group can be deemed a conservative substitution. By contrast, a nonconservative substitution is a substitution of one amino acid for another with dissimilar characteristics.

Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids. Additions (addition variants) include fusion proteins containing: (a) any of the enzymes described herein or a fragment thereof; and (b) internal or terminal (C or N) irrelevant or heterologous amino acid sequences. In the context of such fusion proteins, the term "heterologous amino acid sequences" refers to an amino acid sequence other than (a). A heterologous sequence can be, for example a sequence used for purification of the recombinant protein (e.g., FLAG, polyhistidine (e.g., hexahistidine), hemagglutinin (HA), glutathione-S-transferase (GST), or maltose binding protein (MBP)). Heterologous sequences also can be proteins useful as detectable markers, for example, luciferase, green fluorescent protein (GFP), or chloramphenicol acetyl transferase (CAT). In some embodiments, the fusion protein contains a signal sequence from another protein. In certain host cells (e.g., yeast host cells), expression and/or secretion of the target protein can be increased through use of a heterologous signal sequence. In some embodiments, the fusion protein can contain a carrier (e.g., KLH) useful, e.g., in eliciting an immune response for antibody generation) or ER or Golgi apparatus retention signals. Heterologous sequences can be of varying length and in some cases can be a longer sequences than the full-length target proteins to which the heterologous sequences are attached.

Engineered hosts can naturally express none or some (e.g., one or more, two or more, three or more, four or more, five or more, or six or more) of the enzymes of the pathways described herein. Thus, a pathway within an engineered host can include all exogenous enzymes, or can include both endogenous and exogenous enzymes. Endogenous genes of the engineered hosts also can be disrupted to prevent the formation of undesirable metabolites or prevent the loss of intermediates in the pathway through other enzymes acting on such intermediates. Engineered hosts can be referred to as recombinant hosts or recombinant host cells. As described herein recombinant hosts can include nucleic acids encoding one or more of a methyltransferase, an esterase, a synthase, a dehydratase, a hydratase, a dehydrogenase, a thioesterase, a reversible CoA-ligase, a CoA-transferase, a reductase, deacetylase, N-acetyl transferase or a ω-transaminase as described in more detail below.

In addition, the production of one or more C7 building blocks can be performed in vitro using the isolated enzymes described herein, using a lysate (e.g., a cell lysate) from a host microorganism as a source of the enzymes, or using a plurality of lysates from different host microorganisms as the source of the enzymes.

Biosynthetic Methods

The present document provides methods of shielding a carbon chain aliphatic backbone, functionalized with terminal carboxyl groups, in a recombinant host. The method can include enzymatically converting a n-carboxy-2-enoic acid to a n-carboxy-2-enoate methyl ester in the host using a polypeptide having the activity of a fatty acid O-methyltransferase, wherein n+1 reflects length of the carbon chain aliphatic backbone. For example, the n-carboxy-2-enoic acid can be four to 18, four to 16, four to 14, four to 12, four to 10, five to 10, five to nine, or five to eight carbons in length such as 2(E)-heptenedioic acid, and can be enzymatically converted to the corresponding methyl ester, e.g., 2(E)-heptenedioate methyl ester, The polypeptide having fatty acid O-methyltransferase activity can be classified under EC 2.1.1.15. In some embodiments, the polypeptide having fatty acid O-methyltransferase activity has at least 70% sequence identity to an amino acid sequence set forth in SEQ ID NO: 1, SEQ ID NO: 2, or SEQ ID NO: 3.

In some embodiments, the method further includes enzymatically converting 2(E)-heptenedioate methyl ester to pimeloyl-CoA. For example, the method further can include enzymatically converting pimeloyl-CoA to a product selected from the group consisting of pimelic acid, 7-aminoheptanoate, 7-hydroxyheptanoate, heptamethylenediamine, and 1,7-heptanediol, for example, using one or more polypeptides having thioesterase, reversible CoA-ligase, glutaconate CoA-transferase, ω-transaminase, 6-hydroxyhexanoate dehydrogenase, 5-hydroxypentanoate dehydrogenase, 4-hydroxybutyrate dehydrogenase, alcohol dehydrogenase, carboxylate reductase or alcohol dehydrogenase activity.

The present document further provides methods of producing 2(E)-heptenedioyl-CoA methyl ester in a recombinant host. The method can include enzymatically converting 2(E)-heptenedioate to 2(E)-heptenedioate methyl ester in the recombinant host using a polypeptide having fatty acid O-methyltransferase activity. The polypeptide having fatty acid O-methyltransferase activity can be classified under EC 2.1.1.15. In some embodiments, the polypeptide having fatty acid O-methyltransferase activity has at least 70% sequence identity to an amino acid sequence set forth in SEQ ID NO: 1, SEQ ID NO: 2, or SEQ ID NO: 3. The method further can include enzymatically converting 2(E)-heptenedioate methyl ester to pimeloyl-CoA methyl ester.

In some embodiments, 2(E)-heptenedioate is enzymatically produced from 2(E)-heptenedioyl-CoA. For example, a polypeptide having thioesterase or CoA-transferase activity can enzymatically convert 2(E)-heptenedioyl-CoA to 2(E)-heptenedioate. In some embodiments, the polypeptide having thioesterase activity has at least 70% sequence identity to an amino acid sequence set forth in SEQ ID NO: 4 or SEQ ID NO: 5. In some embodiments, the polypeptide having CoA-transferase activity has at least 70% sequence identity to an amino acid sequence set forth in SEQ ID NO: 24 or SEQ ID NO: 25.

In some embodiments, 2(E)-heptenedioate methyl ester is enzymatically converted to 2(E)-heptenedioyl-CoA methyl ester using a polypeptide having CoA ligase activity classified under EC 6.2.1.-, e.g., EC 6.2.1.2 or EC 6.2.1.3.

In some embodiments, the method further includes enzymatically converting 2(E)-heptenedioyl-CoA methyl ester to pimeloyl-CoA methyl ester. In some embodiments, a polypeptide having trans-2-enoyl-CoA reductase activity enzymatically converts 2(E)-heptenedioyl-CoA methyl ester to pimeloyl-CoA methyl ester.

In some embodiments, the method further includes enzymatically converting pimeloyl-CoA methyl ester to pimeloyl-CoA. In some embodiments, a polypeptide having pimelyl-[acp] methyl ester esterase activity enzymatically converts pimeloyl-CoA methyl ester to pimeloyl-CoA. In some embodiments, the polypeptide having pimelyl-[acp] methyl ester esterase activity has at least 70% sequence identity to the amino acid sequence set forth in SEQ ID NO: 6.

In some embodiments, the method further includes enzymatically converting pimeloyl-CoA to a product selected from the group consisting of pimelic acid, 7-aminoheptanoate, 7-hydroxyheptanoate, heptamethylenediamine, and 1,7-heptanediol. In some embodiments, the method comprises enzymatically converting pimeloyl-CoA to pimelic acid using a polypeptide having thioesterase, reversible CoA-ligase, or glutaconate CoA-transferase activity.

In some embodiments, the method further includes enzymatically converting pimelic acid to pimelate semialdehyde using a polypeptide having carboxylate reductase activity. In some embodiments, the polypeptide having carboxylate reductase activity has at least 70% sequence identity to an amino acid sequence set forth in SEQ ID NOs: 7 to 12.

In some embodiments, the method includes enzymatically converting pimeloyl-CoA to pimelate semialdehyde using a polypeptide having acetylating aldehyde dehydrogenase activity. In some embodiments, the method further includes enzymatically converting pimelate semialdehyde to pimelic acid using a polypeptide having 5-oxopentanoate dehydrogenase, 6-oxohexanoale dehydrogenase, 7-oxoheptanoate dehydmrgenase, or aldehyde dehydrogenase activity.

In some embodiments, the method further includes enzymatically converting pimelate semialdehyde to 7-aminoheptanoate using a polypeptide having ω-transaminase activity. In some embodiments, the polypeptide having ω-transaminase activity has at least 70% sequence identity to an amino acid sequence set forth in SEQ ID NOs: 13 to 18.

In some embodiments, the method further includes enzymatically converting pimelate semialdehyde to heptamethylenediamine using a polypeptide having ω-transaminase activity.

In some embodiments, the method further includes enzymatically converting pimelate semialdehyde to 7-hydroxyheptanoate using a polypeptide having 6-hydroxyhexanoate dehydrogenase, 5-hydroxypentanoate dehydrogenase, 4-hydroxybutyrate dehydrogenase, or alcohol dehydrogenase activity.

In some embodiments, the method further includes enzymatically converting 7-hydroxyheptanoate to 1,7-heptanediol using a polypeptide having carboxylate reductase or alcohol dehydrogenase activity.

In some embodiments, one or more steps of the method are performed by fermentation. In some embodiments, the host is subjected to a cultivation strategy under aerobic, anaerobic, micro-aerobic, or mixed oxygen/denitrification cultivation conditions. In some embodiments, the host is cultured under conditions of phosphate, oxygen, and/or nitrogen limitation. In some embodiments, the host is retained using a ceramic membrane to maintain a high cell density during fermentation.

In some embodiments, the principal carbon source fed to the fermentation derives from biological or non-biological feedstocks. In some embodiments, the biological feedstock is, or derives from, monosaccharides, disaccharides, lignocellulose, hemicellulose, cellulose, lignin, levulinic acid, formic acid, triglycerides, glycerol, fatty acids, agricultural waste, condensed distillers' solubles, or municipal waste. In some embodiments, the non-biological feedstock is, or derives from, natural gas, syngas, $CO_2/H_2$, methanol, ethanol, benzoate, non-volatile residue (NVR) caustic wash waste stream from cyclohexane oxidation processes, or terephthalic acid/isophthalic acid mixture waste streams.

In some embodiments, the host comprises one or more polypeptides having attenuated polyhydroxyalkanoate synthase, acetyl-CoA thioesterase, acetyl-CoA specific β-ketothiolase, phosphotransacetylase forming acetate, acetate kinase, lactate dehydrogenase, menaquinol-fumarate oxidoreductase, 2-oxoacid decarboxylase producing isobutanol, alcohol dehydrogenase forming ethanol, triose phosphate isomerase, pyruvate decarboxylase, glucose-6-phosphate isomerase, transhydrogenase dissipating the NADPH imbalance, glutamate dehydrogenase dissipating the NADPH imbalance, NADH/NADPH-utilizing glutamate dehydrogenase, pimeloyl-CoA dehydrogenase; acyl-CoA dehydrogenase accepting C7 building blocks and central precursors as substrates; glutaryl-CoA dehydrogenase; or pimeloyl-CoA synthetase activity.

In some embodiments, the host overexpresses one or more genes encoding a polypeptide having acetyl-CoA synthetase; 6-phosphogluconate dehydrogenase; transketolase; puridine nucleotide transhydrogenase; formate dehydrogenase; glyceraldehyde-3P-dehydrogenase; malic enzyme; glucose-6-phosphate dehydrogenase; fructose 1,6 diphosphatase; L-alanine dehydrogenase; PEP carboxylase, pyruvate carboxylase; PEP carboxykinase; PEP synthase; L-glutamate dehydrogenase specific to the NADPH used to generate a co-factor imbalance; methanol dehydrogenase, formaldehyde dehydrogenase, lysine transporter; dicarboxylate transporter; S-adenosylmethionine synthetase; 3-phosphoglycerate dehydrogenase; 3-phosphoserine aminotransferase; phosphoserine phosphatase; or a multidrug transporter activity.

In some embodiments, the host is a prokaryote, e.g., *Escherichia coli, Clostridium ljungdahlii, Clostridium autoethanogenum, Clostridium kluyveri, Corynebacterium glutamicum, Cupriavidus necator, Cupriavidus metallidurans, Pseudomonas fluorescens, Pseudomonas putida, Pseudomonas oleavorans, Delftia acidovorans, Bacillus subtillis, Lactobacillus delbrueckii, Lactococcus lactis*, and *Rhodococcus equi*.

In some embodiments, the host is a eukaryote, e.g., *Aspergillus niger, Saccharomyces cerevisiae, Pichia pastoris, Yarrowia lipolytica, Issathenkia orientalis, Debaryomyces hansenii, Arxula adenoinivorans*, and *Kluyveromyces lactis*.

Enzymes Converting 2(E)-heptenedioyl-CoA to 2(E)-heptenedioyl-CoA methyl ester

Figure 1:
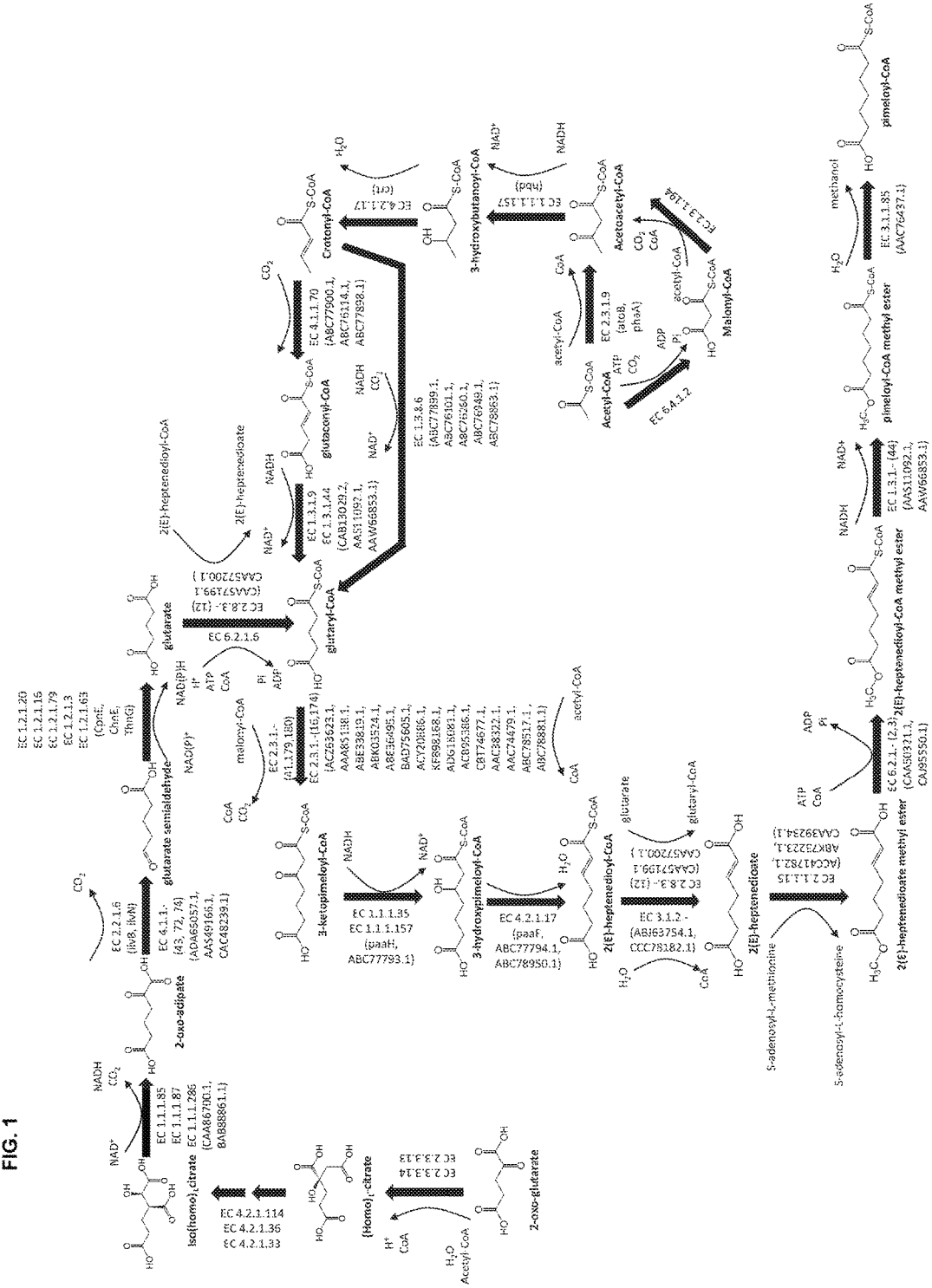
FIG. 1 is a schematic of exemplary biochemical pathways leading to pimeloyl-CoA from 2-oxo-glutarate or acetyl-CoA, via a hept-2-enedioyl-CoA methyl ester.

As depicted in FIGS. 1 to 3, a 2(E)-heptenedioate methyl ester can be formed from 2(E)-heptenedioate using a fatty acid O-methyltransferase, such as the fatty acid O-methyltransferase classified, for example, under EC 2.1.1.15. For example, the fatty acid O-methyltransferase can be obtained from *Mycobacterium marinum* M (GenBank Accession No. ACC41782.1. SEQ ID NO: 1); *Mycobacterium smegmatis* (see GenBank Accession No. ABK73223.1, SEQ ID NO: 2), or *Pseudomonas putida* (see GenBank Accession No. CAA39234.1, SEQ ID NO: 3).

2(E)-heptenedioate methyl ester can be converted to 2(E)-heptenedioyl-CoA methyl ester using, for example, a CoA ligase classified, for example, under EC 6.2.1.-. In some embodiments, a butyrate-CoA ligase classified under EC 6.2.1.2 or a long-chain-fatty-acid-CoA ligase classified under EC 6.2.1.3 such as the long chain fatty acid CoA-ligase from *Escherichia coli* (Genbank Accession No. CAA50321.1, SEQ ID NO: 22) or *Cupriavidus necator* (Genbank Accession No. CAJ95550.1, SEQ ID NO: 23) can be used to convert 2(E)-heptenedioate methyl ester to 2(E)-heptendioyl-CoA methyl ester. See, FIGS. 1 to 3.

In some embodiments, 2(E)-heptenedioate can be formed from 2(E)-heptenedioyl-CoA (also known as 2,3-dehydropimeloyl-CoA) using, for example, a thioesterase classified under EC 3.1.2.-, such as the acyl-[acp] thioesterase from *Lactobacillus brevis* (GenBank Accession No. ABJ63754.1, SEQ ID NO: 4) or from *Lactobacillus plantarum* (GenBank Accession No. CCC78182.1, SEQ ID NO: 5). Such acyl-[acp] thioesterases have C6-C8 chain length specificity (see, for example, Jing et al., 2011, *BMC Biochemistry*, 12(44)). See, e.g., FIG. 1.

In some embodiments, 2(E)-heptenedioate can be formed from 2(E)-heptenedioyl-CoA using, for example, a CoA-transferase (e.g., a glutaconate CoA-transferase) classified, for example, under EC 2.8.3.12 such as the gene product of GctAB from *Acidaminococcus fermentans* (Genbank Accession No. CAA57199.1 (GctA) & CAA57200.1 (GctB), SEQ ID NOs: 24 and 25, respectively). See, for example, Buckel et al., 1981, *Eur. J. Biochem.*, 118:315-321. See, e.g., FIGS. 2 and 3.

Enzymes Producing 2(E)-Heptenedioyl-CoA from Glutaryl-CoA

As depicted in FIG. 1, glutaryl-CoA can be formed from the central metabolites 2-oxoglutarate or acetyl-CoA via carbon chain elongation (i) associated with lysine biosynthesis via α-aminoadipate or (ii) associated with cyclohexane carboxylate biosynthesis in *Synthrophus aciditrophicus*. Glutaryl-CoA can be converted to 2(E)-heptenedioyl-CoA using a (i) β-ketoacyl-[acp] synthase or β-ketothiolase, (ii) a 3-hydroxybutyryl-CoA dehydrogenase, and a (iii) an enoyl-CoA hydratase.

For example, glutaryl-CoA can be formed via C1 carbon chain elongation associated with lysine biosynthesis via α-aminoadipate, which comprises using (i) a homocitrate synthase, (ii) a homocitrate dehydratase and a homoaconitate hydratase, (iii) an isohomocitrate dehydrogenase, (iv) an decarboxylase such as an indolepyruvate decarboxylase, (vi) a glutarate-semialdehyde dehydrogenase and (v) a glutarate:CoA ligase. See, e.g., FIG. 1.

For example, glutaryl-CoA can be formed via CoA-dependent carbon chain elongation associated with cyclohexane carboxylate biosynthesis in *Synthrophus aciditrophicus* which comprises using (i) a β-ketothiolase or an acetyl-carboxylase in combination with an acetoacetyl-CoA synthase, (ii) a 3-hydroxybutyl-CoA dehydrogenase, (iii) an enoyl-CoA hydratave, and either (iv) a glutaryl-CoA dehydrogenase in combination with an enoyl-CoA reductase or a trans-2-enoyl-CoA reductase or (v) a glutaconyl-CoA decarboxylase. See, e.g., FIG. 1.

In some embodiments, a (homo)$_n$citrate synthase can be classified, for example, under EC 2.3.3.14 or EC 2.3.3.13, such as the gene product of aksA from *Methanocaldococcus jannaschii* (see Genbank Accession No. AAB98494.1).

In some embodiments, the combination of (homo)$_n$citrate dehydratase and (homo)$_n$aconitate hydratase can be classified, for example, under EC 4.2.1.- (e.g., EC 4.2.1.114, EC 4.2.1.36 or EC 4.2.1.33), such as the gene product of aksD from *Methanocaldococcus jannaschii* (see, Genbank Accession No. AAB99007.1) or gene product of aksE from *Methanocaldococcus jannaschii* (see, Genbank Accession No. AAB99277.1). The gene products of aksD and aksE are subunits of an enzyme classified under EC 4.2.1.114. The gene products of LeuC and LeuD are subunits of an enzyme classified under EC 4.2.1.33.

In some embodiments, an iso(homo)$_n$citrate dehydrogenase can be classified, for example, under EC 1.1.1.- such as EC 1.1.1.85, EC 1.1.1.87 or EC 1.1.1.286, such as the gene product of aksF from *Methanocaldococcus jannaschii* (see, Genbank Accession No. ACA28837.1), the gene product of LYS12 from *Saccharomyces cerevisiae* (See Genbank Accession No. CAA86700.1) or hicdh from *Thermus thermophiles* (see Genbank Accession No. BAB88861.1).

In some embodiments, 2-oxo-adipate can be decarboxylated by a decarboxylase classified, for example, under EC 4.1.1.43, EC 4.1.1.72, or EC 4.1.1.74 such as the indole-3-pyruvate decarboxylase from *Salmonella typhimurium* (see, for example. Genbank Accession No. CAC48239.1). A mutant variant of the indolepyruvate decarboxylase from *Salmonella typhimurium* was engineered successfully to selectively accept longer chain length substrates. The L544A mutation of the sequence provided in Genbank Accession No. CAC48239.1 allowed for 567 times higher selectivity towards the C7 2-oxoacid than towards the C5 2-oxoacid (see, Xiong et al., 2012, *Scientific Reports*, 2: 311). The 2-oxoglutarate dehydrogenase complex has demonstrated activity for 2-oxoglutarate and 2-oxoadipate (Bunik et al., 2000, *Eur. J. Biochem.*, 267, 3583-3591).

2-oxo-adipate also can be decarboxylated by a 2-oxoglutarate dehydrogenase complex comprised of enzymes homologous to enzymes classified, for example, under EC 1.2.4.2, EC 1.8.1.4, and EC 2.3.1.61. The 2-oxoglutarate dehydrogenase complex contains multiple copies of a 2-oxoglutarate dehydrogenase classified, for example, under EC 1.2.4.2 bound to a core of dihydrolipoyllysine-residue succinyltransferases classified, for example, under EC 2.3.1.61, which also binds multiple copies of a dihydrolipoyl dehydrogenase classified, for example, under EC 1.8.1.4.

In some embodiments, a 5-oxopentanoate dehydrogenase (e.g., a glutarate semialdehyde dehydrogenase) can be classified, for example under EC 1.2.1.- (e.g., EC 1.2.1.20, EC 1.2.1.16 or EC 1.2.1.79) such as the gene product of CpnE (see, for example, Iwaki et al., 2002, *Appl. Environ. Microbiol.*, 68(11):5671-5684).

In some embodiments, a glularate CoA ligase can be classified, for example, under EC 6.2.1.6.

In some embodiments, a β-ketothiolase can be classified under EC 2.3.1.- (e.g., EC 2.3.1.9, EC 2.3.1.16, or EC 2.3.174). For example, a β-ketothiolase can be classified under EC 2.3.1.9, such as the gene product of atoB or phaA. The β-ketothiolase encoded by atoB or phaA accepts acetyl-CoA as substrates, forming acetoacetyl-CoA (see, Haywood et al., 1988, supra; Slater et al., 1998, supra). The β-ketothiolase encoded by paaJ (see, e.g., Genbank Accession No. AAC74479.1), catF and pcaF can be classified under, for example, EC 2.3.1.174. The β-ketothiolase encoded by paaJ condenses acetyl-CoA and succinyl-CoA to 3-oxoadipyl-CoA (see, for example, Fuchs et al., 2011, *Nature Reviews Microbiology*, 9, 803-816; Göbel et al., 2002, *J. Bacteriol.*, 184(1), 216-223). A homologue of paaJ in *Synthrophus aciditrophicus* catalyses the condensation of acetyl-CoA and glutaryl-CoA to 3-oxopimeloyl-CoA such as Genbank Accession No. ABC78517.1 or Genbank Accession No. ABC78881.1. Alternately, a β-ketoacyl-[acp]homologue of paaJ in *S. aciditrophicus* catalyses the condensation of acetyl-CoA and glutaryl-CoA to 3-oxopimeloyl-CoA.

An acetyl-CoA carboxylase can be classified under EC 6.4.1.2 and an acetoacetyl-CoA synthase can be classified under EC 2.3.1.194. Conversion of acetyl-CoA to malonyl-CoA by an acetyl-CoA carboxylase has been shown to increase the rate of fatty acid synthesis (Davis et al., *J. Biol. Chem.*, 2000, 275(37), 28593-28598). It has been demonstrated that acetoacetyl-CoA synthase may be used as an irreversible substitute for the gene product of phaA in the carbon chain elongation associated with polyhydroxybutyrate synthesis (Matsumoto et al., *Biosci. Biotechnol. Biochem.*, 2011, 75(2), 364-366).

In some embodiments, a 3-hydroxybutyryl-CoA dehydrogenase (also can be referred to as a 3-hydroxyacyl-CoA dehydrogenase) can be classified under EC 1.1.1.157 such as the gene product hbd (see, for example, Shen et al., *Appl. Environ. Microbiol.*, 2011, 77(9), 2905-2915; Budde et al., *J. Bacteriol.*, 2010, 192(20), 5319-5328) or the gene product of paaH (Teufel et al., 2010, *Proc. Natl. Acad Sci.* 107(32), 14390-14395).

In some embodiments, an enoyl-CoA hydratase can be classified under EC 4.2.1.17, such as the gene product of crt (see, for example, Shen et al., 2011, supra; Fukui et al., *J. Bacteriol.*, 1998, 180(3), 667-673) or the gene product of paaF (see, for example, Fuchs et al., 2011, supra). Homologs of paaF in *S. acidiirophicus* include the enoyl-CoA hydratase of Genbank Accession No. ABC77794.1 or the enoyl-CoA dehydratase of Genbank Accession No. ABC78950.1.

In some embodiments, a reversible glutaconyl-CoA decarboxylase that relies on a Na$^+$ membrane pump can be classified, for example, under EC 4.1.1.70 (see Mouttaki et al., *Appl. Environ. Microbiol.*, 2007, 73(3), 930-938). The EC 4.1.1.70 enzyme activity is associated with the following subunits in *S. aciditrophicus*, viz. Genbank Accession Nos. (1) ABC77900.1, (2) ABC76114.1 and (3) ABC77898.1.

In some embodiments, an enoyl-[acp] reductase can be classified under EC 1.3.1.- (e.g., EC 1.3.1.9) such as the enoyl-[acp] reductase obtained from *S. aciditrophicus* or the gene product of FabI (Genbank Accession No: CAB13029.2) from *Bacillus subtillis* (see, for example, Heath et al., 2000, *J. Biol. Chem.*, 275(51), 40128-33). The enovl-[acp] reductase involved in fatty acid synthesis in *S. aciditrophicus* likely accepts CoA activated dicarboxylic acids (Mouttaki et al., 2007, supra).

In some embodiments, a trans-2-enoyl-CoA reductase can be classified, for example, under EC 1.3.1.44, such as the gene product of ter (Genbank Accession No. AAW66853.1) (Hoffmeister et al., 2005, *J. Biol. Chem.*, 280(6), 4329-4338; Shen et al., 2011, supra) or tdter (Genbank Accession No. AAS 11092.1) (Bond-Watts et al., *Biochemistry*, 2012, 51, 6827-6837).

A β-ketoacyl-[acp] synthase can be classified, for example, under, EC 2.3.1.41, EC 2.3.1.179, or EC 2.3.1.180. The β-ketothiolases and β-ketoacyl-[acp] synthases involved in fatty acid synthesis in *S. aciditrophicus* likely accept CoA activated dicarboxylic acids (Mouttaki et al., *Appl. Environ. Microbiol.*, 2007, 73(3), 930-938).

Enzymes Producing 2(E)-Heptenedioyl-CoA from 2-Oxo-Pimelate

As depicted in FIG. 2, 2-oxo-pimelate can be formed from the central metabolite 2-oxoglutarate via two rounds of carbon chain elongation associated with lysine biosynthesis via α-aminoadipate, where each round of elongation comprises using (i) a homocitrate synthase, (ii) a homocitrate dehydratase and a homoaconitate hydratase, and (iii) an isohomocitrate dehydrogenase. The homocitrate synthase, a homocitrate dehydratase, homoaconitate hydratase, and isohomocitrate dehydrogenase are described above. 2-oxo-pimelate also can be formed from succinate semialdehyde using a 4-hydroxy-2-oxoheptanedioate aldolase, a 2-oxo-hept-3-ene-1, 7-dioate hydratase, and a 2-enoate reductase as shown in FIG. 3.

2-oxo-pimelate can be converted to 2(E)-heptenedioyl-CoA using (i) a 2-hydroxyglutarate dehydrogenase or (ii) a lactate dehydrogenase. (ii) a CoA-transferase such as a glutaconate CoA-transferase, and (iii) a 2-hydroxyglutaryl-CoA dehydratase or a 2-hydroxvisocaproyl-CoA dehydratase. See, FIGS. 2 and 3.

A 2-hydroxyglutarate dehydrogenase can be classified, for example under EC 1.1.1.-(337) such as the gene product of HgdH or IdhA. See, Djurdjevic et al, 2011, *Appl. Environ. Microbiol.*, 77(1), 320-322 and Kim et al., 2005, *FEBS Journal*, 272, 550-561.

A CoA-transferase such as a glutaconate CoA-transferase can be classified, for example, under EC 2.8.3.12 and can be obtained from *Acidaminococcus fermentans* (see, e.g., SEQ ID NOs: 24 and 25). See, for example, Buckel et al., 1981, *Eur. J. Biochem.*, 118:315-321.

A 2-hydroxyglutaryl-CoA dehydratase can be classified, for example, under EC 4.2.1.- such as the gene product of HgdAB (Genbank Accession Nos. AAD31677.1 and AAD31675.1) in combination with an activator, the gene product of HgdC (Genbank Accession No. CAA42196.1). The HgdAB gene product contains subunits A and B. See, Djurdjevic et al, 2011, supra. A 2-hydroxyisocaproyl-CoA dehydratase can be classified, for example, under EC 4.2.1.- such as the gene product of hadBC (Genbank Accession Nos. AAV40819.1 & AAV40820.1) or hadI (Genbank Accession No. AAV40818.1).

A 4-hydroxy-2-oxoheptanedioate aldolase can be classified, for example, under EC 4.1.2.52 such as the gene product of HpaI. See Genbank Accession No. CAA87759.1.

A 2-oxo-hept-3-ene-1,7-dioate hydratase can be classified, for example, under EC 4.2.1.- such as the gene product of HpaH. See GenBank Accession No. AAB91474.1.

In some embodiments, a 2-enoate reductase may be classified under EC 1.3.1.- such as EC 1.3.1.31 or EC 1.6.99.1 such as originating from *Bacillus subtilis* (Genbank Accession No. BAA12619.1), *Pseudomonas putida* Genbank Accession No. AAN66878.1), *Kluyveromyces lactis* (Genbank Accession No. AAA98815.1), *Lactobacillus casei* (Genbank Accession No. AGP69310.1), *Saccharomyces pastorianus* (Genbank Accession No. CAA37666.1), *Thermoanaerobacter pseudethanolicus* (Genbank Accession No. ABY93685.1), or *Enterobacter cloacae* (Genbank Accession No. AAB38683.1) (Gao et al., 2012, *Enzyme Microb. Technol.*, 51(1), 26-34).

Enzymes Facilitating Introduction of Terminal Functional Groups in the Biosynthesis of a C7 Building Block In some embodiments, a carboxylate reductase facilitates the generation of a terminal aldehyde group for subsequent conversion to an amine group by an ω-transaminase or to a hydroxyl group by an alcohol dehydrogenase. The carboxylate reductase can be obtained, for example, from *Mycobacterium marinum* (Genbank Accession No. ACC40567.1, SEQ ID NO: 7), *Mycobacterium smegmatis* (Genbank Accession No. ABK71854.1, SEQ ID NO: 8), *Segniliparus rugosus* (Genbank Accession No. EFV11917.1, SEQ ID NO: 9), *Mycobacterium smegmatis* (Genbank Accession No. ABK75684.1, SEQ ID NO: 10), *Mycobacterium massiliense* (Genbank Accession No. EIV11143.1, SEQ ID NO: 11), or *Segniliparus rotundus* (Genbank Accession No. ADG98140.1, SEQ ID NO: 12). See, e.g., FIGS. 4 to 8.

The carboxylate reductase encoded by the gene product of car and enhancer npt has broad substrate specificity, including terminal difunctional C4 and C5 carboxylic acids (Venkitasubramanian et al., *Enzyme and Microbial Technology*, 2008, 42, 130-137).

Figure 4:
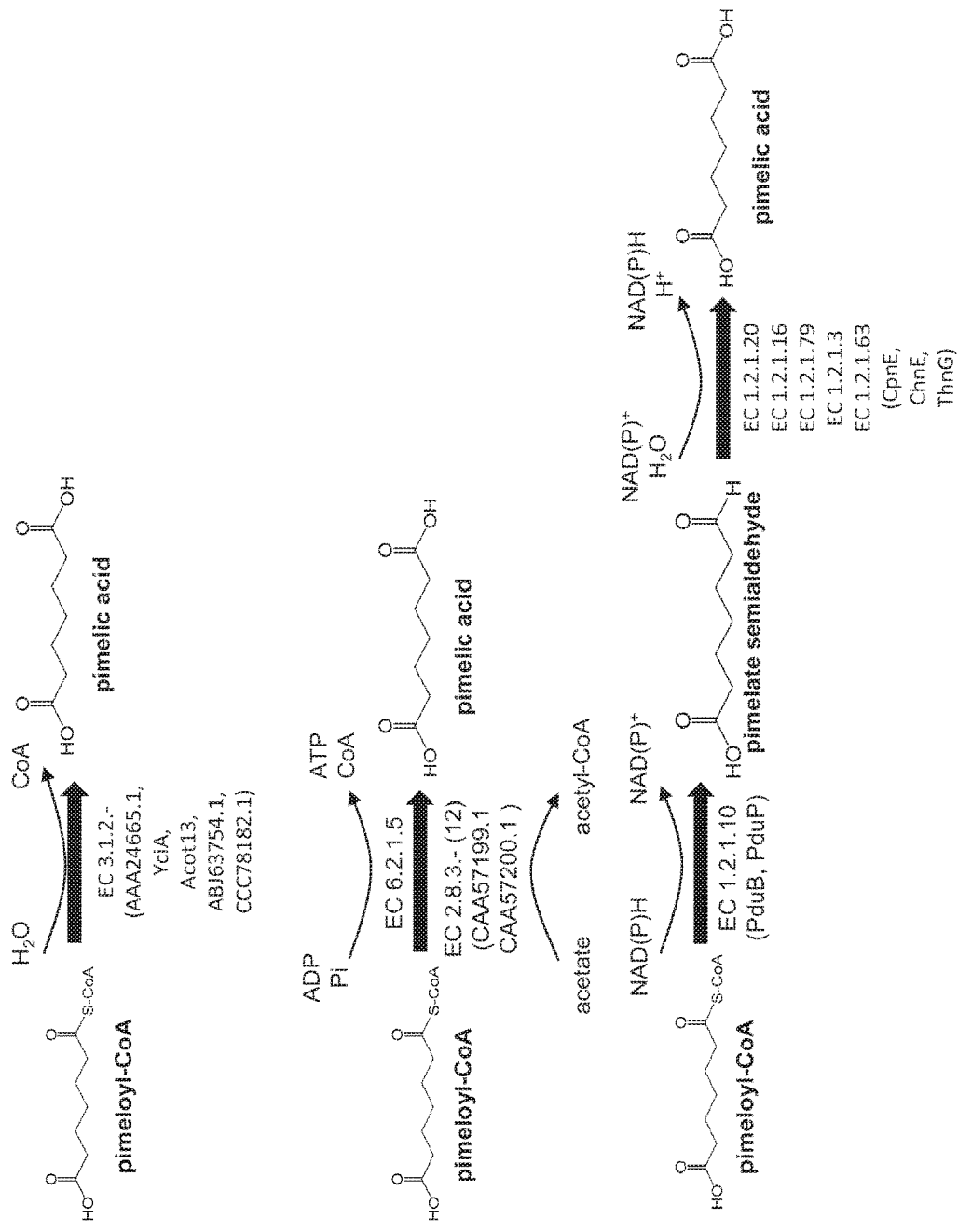
FIG. 4 is schematic of exemplary biochemical pathways leading to pimelic acid using pimeloyl-CoA as a central precursor.

Enzymes Generating the Terminal Carboxyl Groups in the Biosynthesis of C7 Building Blocks As depicted in FIG. 4, a terminal carboxyl group can be enzymatically formed using a thioesterase, an aldehyde dehydrogenase, a 7-oxoheptanoate dehydrogenase, a 6-oxohexanoate dehydrogenase, a CoA-transferase or a reversible CoA-ligase.

In some embodiments, the first terminal carboxyl group leading to the synthesis of a C7 building block is enzymatically formed by a pimelyl-[acp] methyl ester esterase classified, for example, under EC 3.1.1.85 such as the gene product of bioH (GenBank Accession No. AAC76437.1, SEQ ID NO: 6). See, FIGS. 1 and 2.

In some embodiments, the second terminal carboxyl group leading to the synthesis of a C7 building block is enzymatically formed by a thioesterase classified under EC 3.1.2.-, such as the gene product of YciA, tesB (Genbank Accession No. AAA24665.1, SEQ ID NO: 21), Acot13 or originating from *Lactobacillus brevis* (GenBank Accession No. ABJ63754.1, SEQ ID NO: 4) or from *Lactobacillus plantarum* (GenBank Accession No. CCC78182.1, SEQ ID NO: 5) (see, for example, Cantu et al., *Protein Science*, 2010, 19, 1281-1295; Zhuang et al., *Biochemistry*, 2008, 47(9), 2789-2796; Naggert et al., *J. Biol. Chem.*, 1991, 266(17), 11044-11050; or Jing et al., 2011, *BMC Biochemistry*, 12(44)).

In some embodiments, the second terminal carboxyl group leading to the synthesis of pimelic acid is enzymatically formed by an aldehyde dehydrogenase classified, for example, under EC 1.2.1.3 (see, for example, Guerrillot & Vandecasteele, *Eur. J. Biochem.*, 1977, 81, 185-192).

In some embodiments, the second terminal carboxyl group leading to the synthesis of pimelic acid is enzymatically formed by a dehydrogenase classified under EC 1.2.1.- (.g., EC 1.2.1.16, EC 1.2.1.20, EC 1.2.1.79, EC 1.2.1.3 or EC 1.2.1.63) such as 5-oxopentanoate dehydrogenase (e.g., the gene product of CpnE from *Comamonas* sp.), 6-oxohexanoate dehydrogenase (e.g., the gene product of ChnE from *Acinetobacter* sp.) or a 7-oxoheptanoate dehydrogenase (e.g., the gene product of ThnG from *Sphingomonas macrogolitabida*). See, for example, Iwaki et al., *Appl. Environ. Microbiol.*, 1999, 65(11), 5158-5162; Iwaki et al., *Appl. Environ. Microbiol.*, 2002, 68(11), 5671-5684; or López-Sánchez et al., *Appl. Environ. Microbiol.*, 2010, 76(1), 110-118. For example, a 6-oxohexanoate dehydrogenase can be classified under EC 1.2.1.63. For example, a 7-oxoheptanoate dehydrogenase can be classified under EC 1.2.1.-.

In some embodiments, the second terminal carboxyl group leading to the synthesis of pimelic acid is enzymatically formed by a CoA-transferase such as a glutaconate CoA-transferase classified, for example, under EC 2.8.3.12 such as from *Acidaminococcus fermentans*. See, for example, Buckel et al., 1981, *Eur. J. Biochem.*, 118:315-321.

In some embodiments, the second terminal carboxyl group leading to the synthesis of pimelic acid is enzymatically formed by a reversible CoA-ligase such as a succinate-CoA ligase classified, for example, under EC 6.2.1.5 such as from *Thermococcus kodakaraensis*. See, for example, Shikata et al., 2007, *J. Biol. Chem.*, 282(37):26963-26970.

Figure 5:
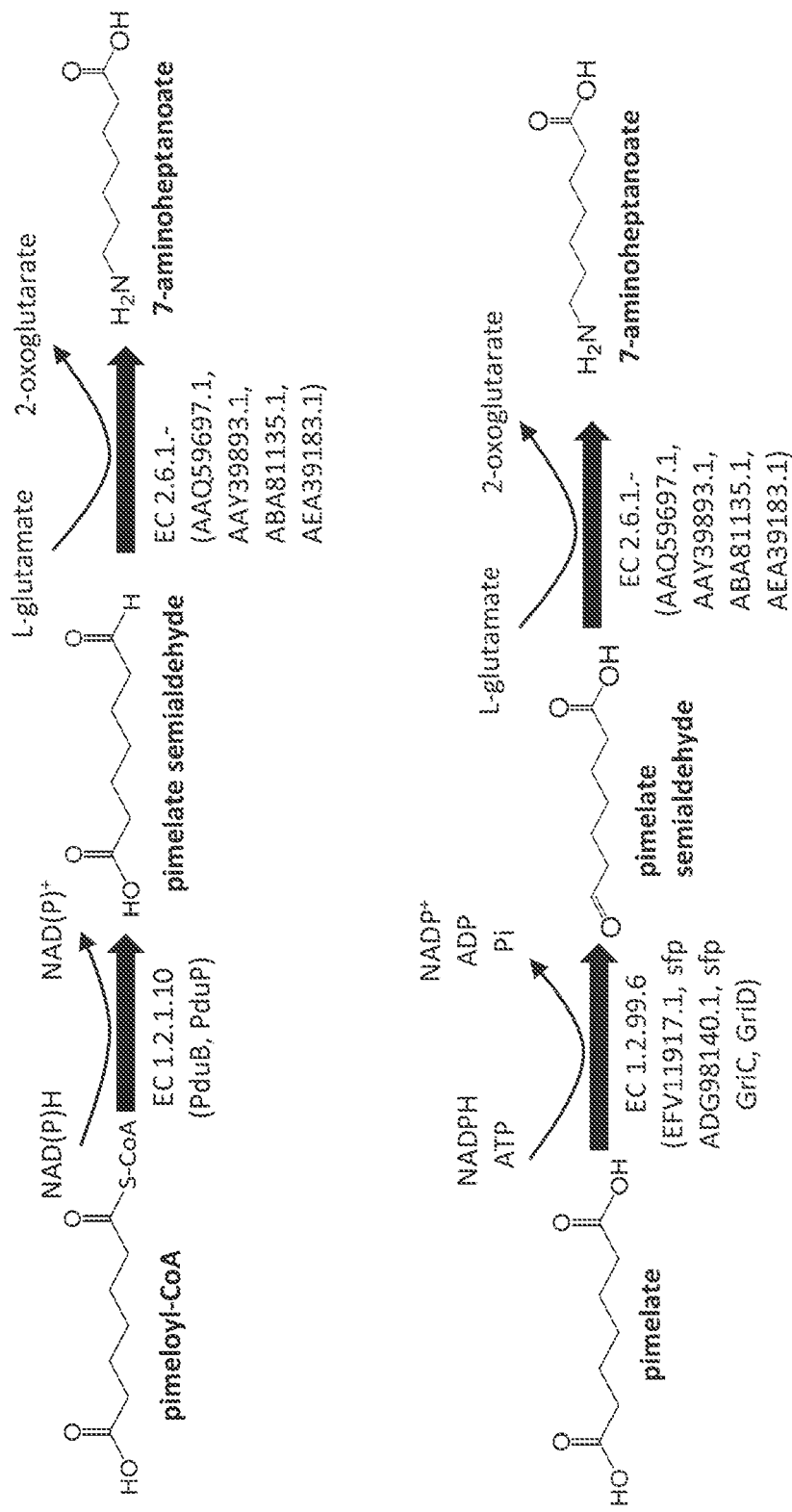
FIG. 5 is a schematic of exemplary biochemical pathways leading to 7-aminoheptanoate using pimeloyl-CoA or pimelate as a central precursor.
Figure 6:
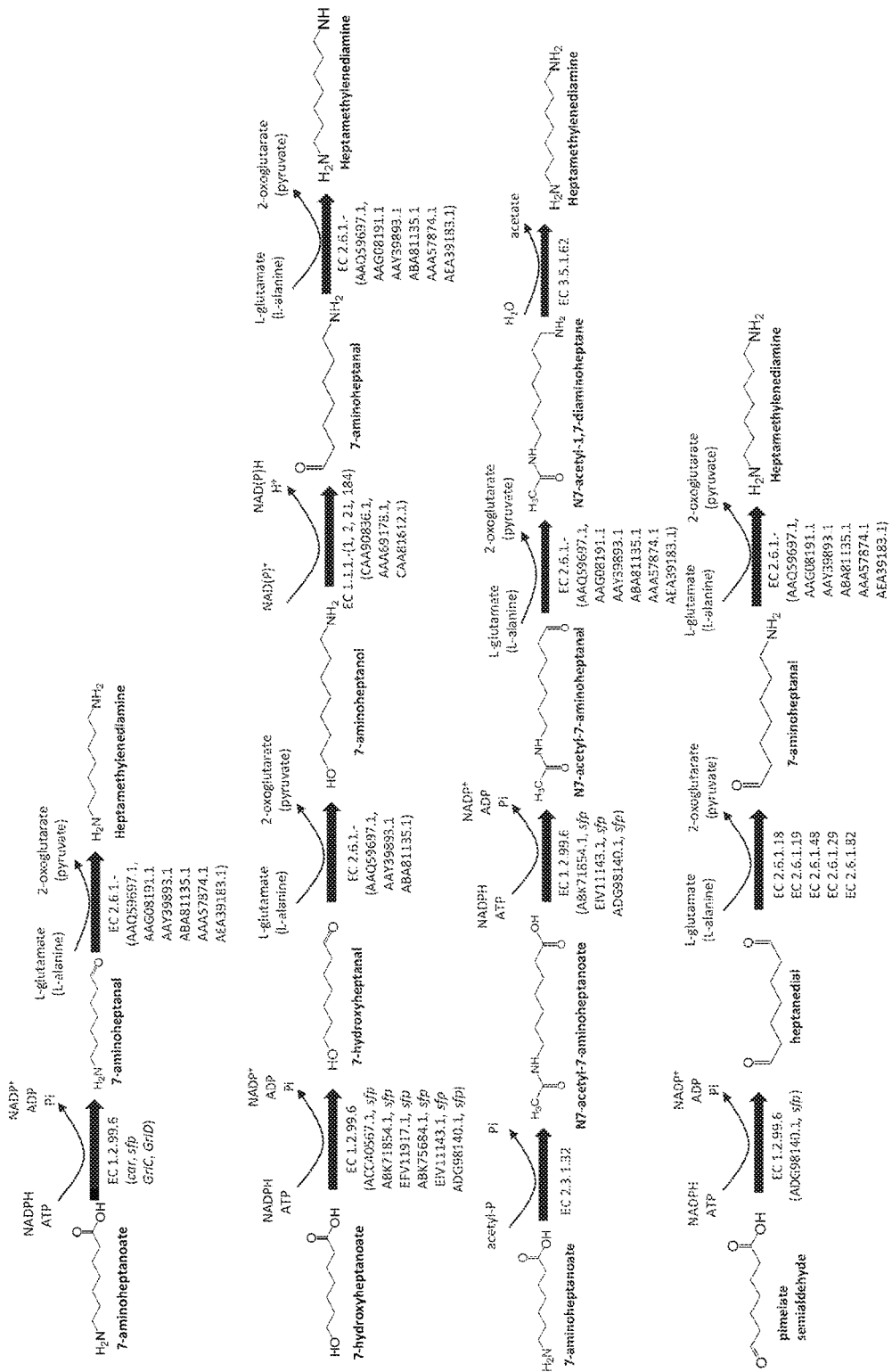
FIG. 6 is a schematic of exemplary biochemical pathways leading to heptamethylenediamine using 7-aminoheptanoate, 7-hydroxyheptanoate, or pimelate semialdehyde as a central precursor.

Enzymes Generating the Terminal Amine Groups in the Biosynthesis of C7 Building Blocks As depicted in FIGS. 5 and 6, terminal amine groups can be enzymatically formed using a ω-transaminase or a deacetylase.

In some embodiments, the first or second terminal amine group leading to the synthesis of 7-aminoheptanoic acid is enzymatically formed by a ω-transaminase classified, for example, under EC 2.6.1.18, EC 2.6.1.19, EC 2.6.1.29, EC 2.6.1.48, or EC 2.6.1.82 such as that obtained from *Chromobacterium violaceum* (Genbank Accession No. AAQ59697.1, SEQ ID NO: 13), *Pseudomonas aeruginosa* (Genbank Accession No. AAG08191.1, SEQ ID NO: 14), *Pseudomonas syringae* (Genbank Accession No. AAY39893.1, SEQ ID NO: 15), *Rhodobacter sphaeroides* (Genbank Accession No. ABA81135.1, SEQ ID NO: 16), *Escherichia coli* (Genbank Accession No. AAA57874.1, SEQ ID NO: 17), *Vibrio fluvialis* (Genbank Accession No. AEA39183.1, SEQ ID NO: 18), *Streptomyces griseus*, or *Clostridium viride*. Some of these ω-transaminases are diamine ω-transaminases (e.g., SEQ ID NO: 17). For example, the ω-transaminases classified, for example, under EC 2.6.1.29 or EC 2.6.1.82 may be diamine ω-transaminases.

The reversible ω-transaminase from *Chromobacterium violaceum* (Genbank Accession No. AAQ59697.1, SEQ ID NO: 13) has demonstrated analogous activity accepting 6-aminohexanoic acid as amino donor, thus forming the first terminal amine group in adipate semialdehyde (Kaulmann et al., *Enzyme and Microbial Technology*, 2007, 41, 628-637).

The reversible 4-aminobubvrate:2-oxoglutarate transaminase from *Streptomyces griseus* has demonstrated analogous activity for the conversion of 6-aminohexanoate to adipate semialdehyde (Yonaha et al., *Eur. J. Biochem.*, 1985, 146: 101-106).

The reversible 5-aminovalerate transaminase from *Clostridium viride* has demonstrated analogous activity for the conversion of 6-aminohexanoate to adipate semialdehyde (Barker et al., *J. Biol. Chem.*, 1987, 262(19), 8994-9003).

In some embodiments, a terminal amine group leading to the synthesis of 7-aminoheptanoate or heptamethylenediamine is enzymatically formed by a diamine ω-transaminase. For example, the second terminal amino group can be enzymatically formed by a diamine ω-transaminase classified, for example, under EC 2.6.1.29 or classified, for example, under EC 2.6.1.82, such as the gene product of YgjG from *E. coli* (Genbank Accession No. AAA57874.1, SEQ ID NO: 17).

The gene product of ygjG accepts a broad range of diamine carbon chain length substrates, such as putrescine, cadaverine and spermidine (see, for example, Samsonova et al., *BMC Microbiology*, 2003, 3:2).

The diamine ω-transaminase from *E. coli* strain B has demonstrated activity for 1,7 diaminoheptane (Kim, *The Journal of Chemistry*, 1964, 239(3), 783-786).

In some embodiments, the second terminal amine group leading to the synthesis of heptamethylenediamine is enzymatically formed by a deacetylase such as an acyl-lysine deacylase classified, for example, under EC 3.5.1.17 or such as acetylputrescine deacetylase classified, for example, under EC 3.5.1.62. The acetylputrescine deacetylase from *Micrococcus luteus* K-11 accepts a broad range of carbon chain length substrates, such as acetylputrescine, acetylcadaverine and $N^8$-acetylspermidine (see, for example, Suzuki et al., 1986, *BBA—General Subjects*, 882(1): 140-142).

Figure 7:
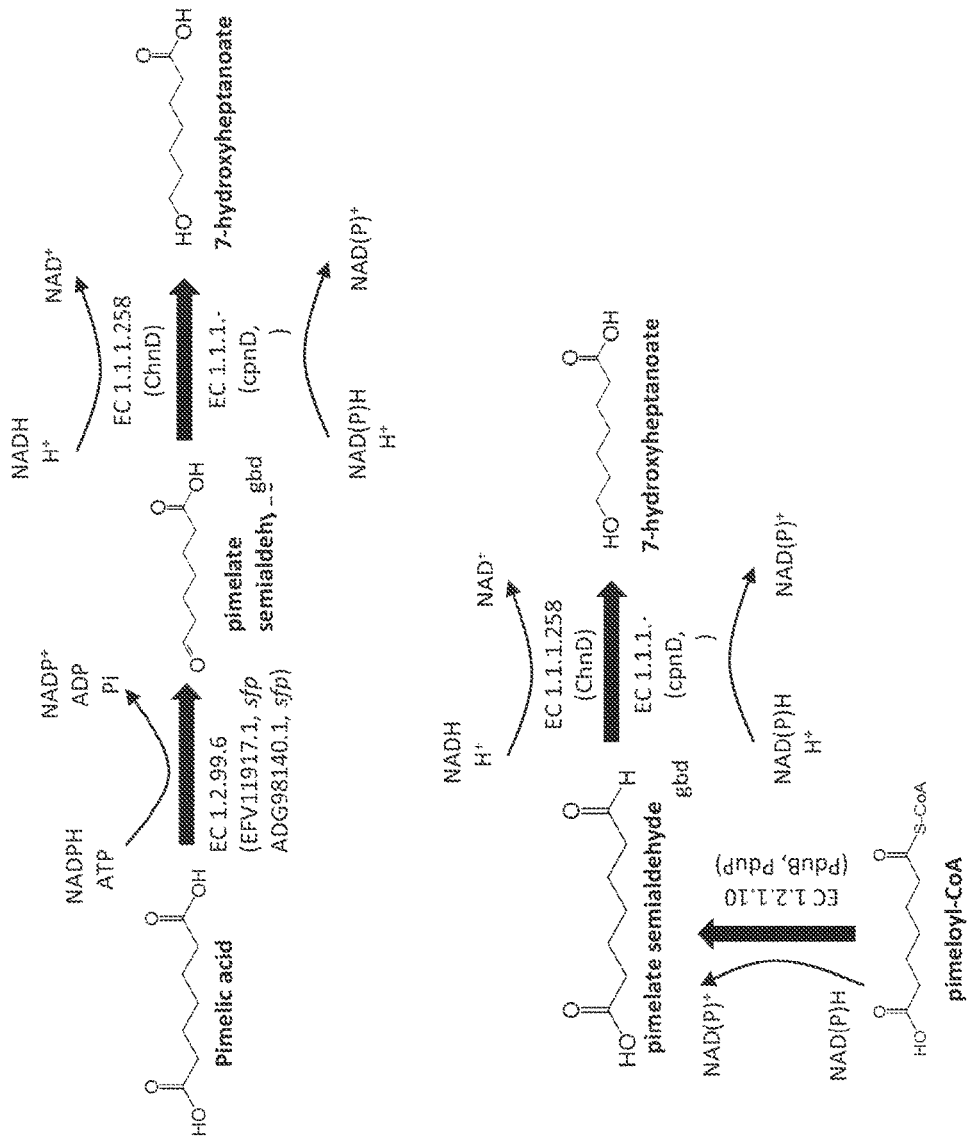
FIG. 7 is a schematic of exemplary biochemical pathways leading to 7-hydroxyheptanoate using pimelate, pimeloyl-CoA or pimelate semialdehyde as a central precursor.
Figure 8:
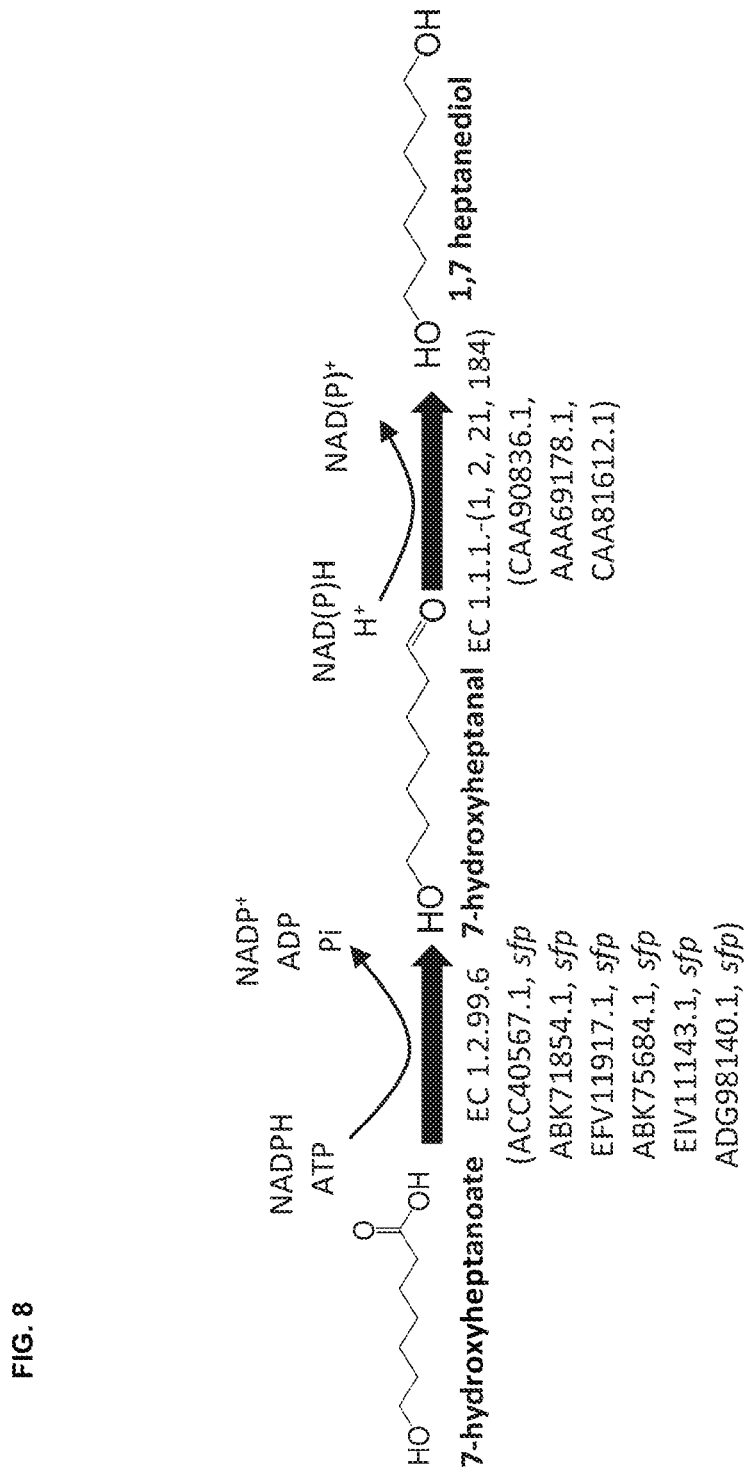
FIG. 8 is a schematic of an exemplary biochemical pathway leading to 1,7-heptanediol using 7-hydroxyheptanoate as a central precursor.

Enzymes Generating the Terminal Hydroxyl Groups in the Biosynthesis of C7 Building Blocks As depicted in FIGS. 7 and 8, a terminal hydroxyl group can be enzymatically formed using 6-hydroxyhexanoate dehydrogenase, a 5-hydroxypentanoate dehydrogenase, 4-hydroxybutyrate dehydrogenase, or an alcohol dehydrogenase.

For example, a terminal hydroxyl group leading to the synthesis of 7-hydroxyheptanoic acid can be enzymatically formed by a dehydrogenase classified, for example, under EC 1.1.1.- such as a 6-hydroxyhexanoate dehydrogenase classified, for example, under EC 1.1.1.258 (e.g., the gene from of ChnD), a 5-hydroxypentanoate dehydrogenase classified, for example, under EC 1.1.1.- such as the gene product of CpnD (see, for example, Iwaki et al., 2002, *Appl. Environ. Microbiol.*, 68(11):5671-5684), a 5-hydroxypentanoate dehydrogenase from *Clostridium viride*, or a 4-hydroxybutyrate dehydrogenase such as gbd. See, FIG. 7.

In some embodiments, the second terminal hydroxyl group leading to the synthesis of 1,7 heptanediol is enzymatically formed by an alcohol dehydrogenase classified, for example, under EC 1.1.1.- (e.g., EC 1.1.1.1, EC 1.1.1.2, EC 1.1.1.21, or EC 1.1.1.184).

Biochemical Pathways

Pathway using acetyl-CoA or 2-oxo-glutarate as Central Metabolite in the Biosynthesis of C7 Backbone In some embodiments, glutaryl-CoA is synthesized from the central metabolite, acetyl-CoA, by conversion of acetyl-CoA to acetoacetyl-CoA by a β-ketothiolase classified, for example, under EC 2.3.1.9 such as the gene product of atoB or phaA or by an acetyl-CoA carboxylase classified under, for example, EC 6.4.1.2 and an acetoacelyl-CoA synthase classified, for example, under EC 2.3.1.194; followed by conversion to 3-hydroxybutanoyl-CoA by a 3-hydroxyacyl-CoA dehydrogenase classified, for example, under EC 1.1.1.- such as EC 1.1.1.157 or EC 1.1.1.35 such as the gene product of hbd; followed by conversion to crotonyl-CoA by an enoyl-CoA reductase classified, for example, under EC 4.2.1.- (e.g., EC 4.2.1.17) such as the gene product of crt, followed by conversion to either a) glutaconyl-CoA by a glutaconyl-CoA decarboxylase classified, for example, under EC 4.1.1.70; followed by conversion to glutaryl-CoA by either (i) an enoyl-[acp] reductase classified, for example, under EC 1.3.1.9 or (ii) a trans-2-enoyl-CoA reductase classified, for example, under EC 1.3.1.44 such as the gene product of ter or tdter or (b) glutaryl-CoA by a glutaryl-CoA dehydrogenase subject to electron bifurcation from *Synthrophus aciditrophicus* such as the dehydrogenases of Genbank Accession Nos. (1) ABC77899.1, (2) ABC76101.1, (3) ABC76260.1, (4) ABC76949.1 or (5) ABC78863.1. See, FIG. 1.

In some embodiments, glutaryl-CoA can be synthesized from the central metabolite, 2-oxo-glutarate, by conversion of 2-oxo-glutarate to (Homo)$_1$citrate by a homocitrate synthase classified, for example, under EC 2.3.3.14 or EC 2.3.3.13 such as the gene product of LYS20 and LYS21 from *Saccharomyces cerevisiae* or hcs from *Thermus thermophiles*; followed by conversion to iso(homo)$_1$citrate by a homocitrate dehydratase and a homoaconitate hydratase classified, for example, under EC 4.2.1.114, EC 4.2.1.36 or EC 4.2.1.33 such as the gene product of LYS4 from *Saccharomyces cerevisiae* or lysT and LysU from *Thermus thermophiles*; followed by conversion to 2-oxoadipate by an iso(homo)$_n$citrate dehydrogenase classified, for example, under EC 1.1.1.85, EC 1.1.1.87 or EC 1.1.1.286 such as the gene product of LYS12 from *Saccharomyces cerevisiae* or hicdh from *Thermus thermophiles*; followed by conversion to glutarate semialdehyde by a decarboxylase classified, for example under EC 4.1.1.43, EC 4.1.1.74, EC 4.1.1.72 such as an indolepyruvale decarboxylase (e.g., GenBank Accession No. CAC48239.1), a branched-chain alpha-ketoacid decarboxylase (e.g., Genbank Accession No. AAS49166.1) or an alpha-ketoisovalerate decarboxylase (e.g., Genbank Accession No. ADA65057.1); followed by conversion to glutarate by a glutarate semialdehyde dehydrogenase classified, for example, under EC 1.2.1.20, EC 1.2.1.16, EC 1.2.1.79, EC 1.2.1.3, or EC 1.2.1.63 such as the gene product of CpnE, ChnE, or ThnG; followed by conversion to glutaryl-CoA by a glutarate:CoA ligase classified, for example, under EC 6.2.1.6 or by a CoA-transferase classified, for example, under EC 2.8.3.12. See, e.g., FIG. 1.

In some embodiments, pimeloyl-CoA can be synthesized from glutaryl-CoA produced as described above by conversion of glutaryl-CoA to 3-ketopimeloyl-CoA by a β-ketothiolase classified under EC 2.3.1.-, e.g., EC 2.3.1.174 or EC 2.3.1.16 such as the gene product of paaJ or homologs of paaJ (e.g., Genbank Accession No. ABC78517.1, AAC74479.1, or ABC78881.1) or by a β-ketoacyl-[acp] synthase classified, for example, under EC 2.3.1.41, EC 2.3.1.179, EC 2.3.1.180; followed by conversion to 3-hydroxypimeloyl-CoA by a 3-hydroxyadipyl-CoA dehydrogenase classified, for example, under EC 1.1.1.157 such as the gene product of paaH or homologs of paaH (e.g., Genbank Accession No. ABC77793.1); followed by conversion to 2(E)-heptenedioyl-CoA (also known as 2,3-dehydropimeloyl-CoA) by an enoyl-CoA hydratase such as the gene product of paaF or homologs of paaF (e.g., Genbank Accession No. ABC77794.1 or Genbank Accession No. ABC78950.1); followed by conversion to 2(E)-heptenedioate by an acyl-[acp] thioesterase classified under EC 3.1.2.-, such as the acyl-[acp] thioesterase from *Lactobacillus brevis* (GenBank Accession No. ABJ63754.1, SEQ ID NO: 4) or from *Lactobacillus plantarum* (GenBank Accession No. CCC78182.1, SEQ ID NO: 5) or CoA-transferase classified under EC 2.8.3.- such as EC 2.8.3.12 (see, e.g., Genbank Accession No. CAA57199.1 (GctA) and CAA57200.1 (GctB), SEQ ID NOs: 24 and 25, respectively), followed by conversion to 2(E)-heptenedioate methyl ester using a fatty acid O-methyltransferase classified, for example, under EC 2.1.1.15 such as the fatty acid O-methyltransferase from *Mycobacterium marinum* M (GenBank Accession No. ACC41782.1, SEQ ID NO: 1); *Mycobacterium smegmatis* (see GenBank Accession No. ABK73223.1, SEQ ID NO: 2), or *Pseudomonas putida* (see GenBank Accession No. CAA39234.1, SEQ ID NO: 3); followed by conversion to 2(E)-heptenedioyl-CoA methyl ester by a CoA ligase classified, for example, under EC 6.2.1.- (e.g., a butyrate-CoA ligase classified under EC 6.2.1.2 or a long-chain-fatty-acid-CoA ligase classified under EC 6.2.1.3); followed by conversion to pimeloyl-CoA methyl ester using a trans-2-enoyl-CoA reductase classified, for example, under EC 1.3.1.44 such as the gene product of ter or tdter; followed by conversion to pimeloyl-CoA by a pimelyl-[acp] methyl ester esterase classified, for example, under EC 3.1.1.85 such as the gene product of bioH from *E. coli*. (GenBank Accession No. AAC76437.1, SEQ ID NO: 6). See, e.g., FIG. 1.

In some embodiments, pimeloyl-CoA can be synthesized from the central metabolite, 2-oxo-glutarate, by two cycles of 2-oxoacid chain elongation by conversion of 2-oxoglutrate to (Homo)$_1$citrate by a (Homo)$_n$citrate synthase classified, for example, under EC 2.3.3.14 or EC 2.3.3.13 (see, e.g., AksA, Genbank Accession No. AAB98494.1); followed by conversion to iso(homo)$_1$citrate by a (homo)$_n$citrate dehydratase and a (homo)$_n$aconitate hydratase classified, for example, under EC 4.2.1.114, EC 4.2.1.36 or EC 4.2.1.33 (see, e.g., AksD and AksE, Genbank Accession Nos. AAB99007.1 and AAB99277.1); followed by conversion to 2-oxoadipate by an iso(homo)$_n$citrate dehydrogenase classified, for example, under EC 1.1.1.85, EC 1.1.1.87 or EC 1.1.1.286 (see, e.g., AksF, Genbank Accession No. ACA28837.1); followed by conversion to (Homo)$_2$citrate by a (Homo)$_n$citrate synthase classified, for example, under EC 2.3.3.14 or EC 2.3.3.13 (see, e.g., AksA, Genbank Accession No. AAB98494.1); followed by conversion to iso(homo)$_2$citrate (also known as 1-hydroxypentane-1,2,5-tricarboxylate or threo-iso(homo)$_2$citrate) by a (homo)$_n$citrate dehydratase and a (homo),aconitate hydratase classified, for example, under EC 4.2.1.114, EC 4.2.1.36 or EC 4.2.1.33 (see, e.g., Genbank Accession Nos. AAB99007.1 and AAB99277.1); followed by conversion to 2-oxo-pimelate by an iso(homo)$_n$citrate dehydrogenase classified under, for example, EC 1.1.1.85, EC 1.1.1.87, or EC 1.1.1.286 (see, e.g., AksF, Genbank Accession No. ACA28837.1); followed by conversion to 2-oxo-pimelate using an alcohol dehydrogenase classified under EC 1.1.1.- such as the gene product of HgdH (see Djurdjevic et al, 2011, supra) or LdhA (see Kim et al., 2005, *FEBS Journal*, 272, 550-561); followed by conversion to 2-hydroxypimeloyl-CoA by a CoA-transferase such as a glutaconate CoA-transferase classified, for example, under EC 2.8.3.12 (e.g., the gene product of GctAB); followed by conversion to 2(E)-heptenedioyl-CoA by a 2-hydroxyglutaryl-CoA dehydratase classified, for example, under EC 4.2.1.- such as the gene product of HgdAB in combination with its activator, the gene product of HgdC (see Djurdjevic et al, 2011, supra) or a 2-hydroxyisocaproyl-CoA dehydratase classified, for example, under EC 4.2.1.- such as the gene product of hadBC in combination with its activator, the gene product of hadI (Kim et al., 2005, supra); followed by conversion to 2(E)-heptenedioate by a CoA-transferase such as a glutaconate CoA-transferase classified, for example, under EC 2.8.3.12 (e.g., the gene product of GctAB); followed by conversion to 2(E)-heptenedioate methyl ester using a fatty acid O-methyltransferase classified, for example, under EC 2.1.1.15 such as the fatty acid O-methyltransferase from *Mycobacterium marimum* MA (GenBank Accession No. ACC41782.1, SEQ ID NO: 1); *Mycobacterium smegmatis* (see GenBank Accession No. ABK73223.1, SEQ ID NO: 2), or *Pseudomonas putida* (see GenBank Accession No. CAA39234.1, SEQ ID NO: 3); followed by conversion to 2(E)-heptenedioyl-CoA methyl ester by a CoA ligase classified, for example, under EC 6.2.1.- (e.g., a butyrate-CoA ligase classified under EC 6.2.1.2 or a long-chain-fatty-acid-CoA ligase classified under EC 6.2.1.3); followed by conversion to pimeloyl-CoA methyl ester using a trans-2-enoyl-CoA reductase classified, for example, under EC 1.3.1.44 such as the gene product of ter or tdter; followed by conversion to pimeloyl-CoA by a pimelyl-[acp] methyl ester esterase classified, for example, under EC 3.1.1.85 such as the gene product of bioH from *E. coli*. (GenBank Accession No. AAC76437.1, SEQ ID NO: 6). See, e.g., FIG. 2.

Pathway Using Succinate Semialdehyde as Central Metabolite in the Biosynthesis of C7 Backbone In some embodiments, pimeloyl-CoA can be synthesized from (i) the central metabolite 2-oxoglutarate by conversion of 2-oxoglutarate to succinate semialdehyde by a branched-chain alpha-ketoacid decarboxylase (e.g., Genbank Accession No. AAS49166.1) classified, for example, under EC 4.1.1.72 or an alpha-ketoisovalerate decarboxylase (e.g., Genbank Accession No. ADA65057.1) classified, for example, under EC 4.1.1.74 or from (ii) the central metabolite succinyl-CoA by conversion of succinyl-CoA to succinate semialdehyde by a succinate-semialdehyde dehydrogenase classified, for example, under EC 1.2.1.76; followed by conversion to 2,4-dihydroxyhept-2-enedioate by a 4-hydroxy-2-oxoheptanedioate aldolase classified, for example, under EC 4.1.2.52 (e.g., the gene product of HpaI); followed by conversion to 2-oxohept-3-enedioate by a 2-oxo-hept-3-ene-1, 7-dioate hydratase classified, for example, under EC 4.2.1.- such as the gene product of HpaH (e.g., Genbank Accession No. AAB91474.1); followed by conversion to 2-oxopimelate by a 2-enoate reductase classified under EC 1.3.1.- such as EC 1.3.1.31 or EC 1.6.99.- such as EC 1.6.99.1 (e.g., encoded by Genbank Accession Nos. BAA12619.1, AAN66878.1, AAA98815.1, AGP69310.1, CAA37666.1, ABY93685.1, or AAB38683.1); followed by conversion to 2-hydroxypimelate by a 2-hydroxyglutarate dehydrogenase classified, for example under EC 1.1.1.- such as EC 1.1.1.337 (e.g., the gene product of HgdH or IdhA); followed by conversion to 2-hydroxypimeloyl-CoA by a CoA-transferase such as a glutaconate CoA-transferase classified, for example, under EC 2.8.3.12 (e.g., the gene product of GctAB); followed by conversion to 2(E)-heptenedioyl-CoA by a 2-hydroxyglutaryl-CoA dehydratase classified, for example, under EC 4.2.1.- such as the gene product of HgdAB in combination with its activator, the gene product of HgdC (see, Djurdjevic et al, 2011, supra) or a 2-hydroxyisocaproyl-CoA dehydratase classified, for example, under EC 4.2.1.- such as the gene product of hadBC in combination with its activator, the gene product of hadI (Kim et al., 2005, supra); followed by conversion to 2(E)-heptenedioate by a CoA-transferase such as a glutaconate CoA-transferase classified, for example, under EC 2.8.3.12 (e.g., the gene product of GctAB); followed by conversion to 2(E)-heptenedioate methyl ester using a fatty acid O-methyltransferase classified, for example, under EC 2.1.1.15 such as the fatty acid O-methyltransferase from *Mycobacterium marinum* (GenBank Accession No. ACC41782.1. SEQ ID NO: 1); *Mycobacterium smegmatis*

(see GenBank Accession No. ABK73223.1, SEQ ID NO: 2), or *Pseudomonas putida* (see GenBank Accession No. CAA39234.1, SEQ ID NO: 3); followed by conversion to 2(E)-heptenedioyl-CoA methyl ester by a CoA ligase classified, for example, under EC 6.2.1.- such as a butyrate-CoA ligase classified, for example, under EC 6.2.1.2 or a long-chain-fatty-acid-CoA ligase classified, for example, under EC 6.2.1.3 (e.g. Genbank Accession No. CAA50321.1 or CAJ95550.1); followed by conversion to pimeloyl-CoA methyl ester using a trans-2-enoyl-CoA reductase classified, for example, under EC 1.3.1.44 such as the gene product of ter (e.g., Genbank Accession No. AAW66853.1) or tdter (Genbank Accessio No. AAS11092.1); followed by conversion to pimeloyl-CoA by a pimelyl-[acp] methyl ester esterase classified, for example, under EC 3.1.1.85 such as the gene product of bioH from *E. coli*. (GenBank Accession No. AAC76437.1, SEQ ID NO: 6). See, e.g., FIG. 3.

Pathways Using Pimeloyl-CoA or Pimelate Semialdehyde as Central Precursors to Pimelate In some embodiments, pimelic acid is synthesized from the central precursor pimeloyl-CoA by conversion of pimeloyl-CoA to pimelate semialdehyde by an acetylating aldehyde dehydrogenase classified, for example, under EC 1.2.1.10 such as the gene product of PduB or PduP (see, for example, Lan et al., 2013, *Energy Environ. Sci.*, 6:2672-2681); followed by conversion to pimelic acid by a 7-oxoheptanoate dehydrogenase classified, for example, under EC 1.2.1.- such as the gene product of ThnG, a 6-oxohexanoate dehydrogenase classified, for example, under EC 1.2.1.63 such as the gene product of ChnE, a 5-oxopentanoate dehydrogenase classified, for example, under EC 1.2.1.- such as the gene product of CpnE, or an aldehyde dehydrogenase (classified, for example, under EC 1.2.1.3). See, FIG. 4.

In some embodiments, pimelic acid is synthesized from the central precursor pimeloyl-CoA by conversion of pimeloyl-CoA to pimelate by a thioesterase classified, for example, under EC 3.1.2.- such as the gene products of YciA, tesB (Genbank Accession No. AAA24665.1, SEQ ID NO: 21), Acot13, an acyl-[acp] thioesterase from *Lactobacillus brevis* (GenBank Accession No. ABJ63754.1, SEQ ID NO: 4), or an acyl-[acp] thioesterase from *Lactobacillus plantarum* (GenBank Accession No. CCC78182.1, SEQ ID NO: 5). See, FIG. 4.

In some embodiments, pimelate is synthesized from the central precursor pimeloyl-CoA by conversion of pimeloyl-CoA to pimelate by a CoA-transferase such as a glutaconate CoA-transferase classified, for example, under EC 2.8.3.12. See, FIG. 4.

In some embodiments, pimelate is synthesized from the central precursor pimeloyl-CoA by conversion of pimeloyl-CoA to pimelate by a reversible CoA-ligase such as a reversible succinate CoA-ligase classified, for example, under EC 6.2.1.5. See, FIG. 4.

Pathways Using Pimeloyl-CoA or Pimelate Semialdehyde as Central Precursor to 7-aminoheptanoate In some embodiments, 7-aminoheptanoate is synthesized from the central precursor pimeloyl-CoA by conversion of pimeloyl-CoA to pimelate semialdehyde by an acetylating aldehyde dehydrogenase classified, for example, EC 1.2.1.10, such as the gene product of PduB or PduP; followed by conversion of pimelate semialdehyde to 7-aminoheptanoate by a ω-transaminase classified, for example, under EC 2.6.1.- such as EC 2.6.1.18, EC 2.6.1.19, EC 2.6.1.29, EC 2.6.1.48, or EC 2.6.1.82 such as from a *Chromobacterium violaceum* (see Genbank Accession No. AAQ59697.1, SEQ ID NO: 13), a *Pseudomonas syringae* (see Genbank Accession No. AAY39893.1, SEQ ID NO: 15), a *Rhodobacter sphaeroides* (see Genbank Accession No. ABA81135.1, SEQ ID NO: 16), or a *Vibrio fluvialis* (see Genbank Accession No. AEA39183.1, SEQ ID NO: 18). See, FIG. 5.

In some embodiments, 7-aminoheptanoate is synthesized from the central precursor pimelate by conversion of pimelate to pimelate semialdehyde by a carboxylate reductase classified, for example, under EC 1.2.99.6 such as from *Segniliparus rugosus* (Genbank Accession No. EFV11917.1, SEQ ID NO: 9) or *Segniliparus rotundus* (Genbank Accession No. ADG98140.1, SEQ ID NO: 12), in combination with a phosphopantetheine transferase enhancer (e.g., encoded by a sfp (Genbank Accession No. CAA44858.1, SEQ ID NO: 19) gene from *Bacillus subtilis* or npt (Genbank Accession No. ABI83656.1, SEQ ID NO: 20) gene from *Nocardia*), or the gene products of GriC and GriD from *Streptomyces griseus* (Suzuki et al., J. Antibiot., 2007, 60(6), 380-387); followed by conversion of pimelate semialdehyde to 7-aminoheptanoate by a ω-transaminase classified, for example, under EC 2.6.1.- such as EC 2.6.1.18, EC 2.6.1.19, EC 2.6.1.48, EC 2.6.1.29, EC 2.6.1.82 such as from a Chromobacterium *violaceum* (see Genbank Accession No. AAQ59697.1, SEQ ID NO: 13), a *Pseudomonas syringae* (see Genbank Accession No. AAY39893.1, SEQ ID NO: 15), a *Rhodobacter sphaeroides* (see Genbank Accession No. ABA81135.1, SEQ ID NO: 16), or a *Vibrio fluvialis* (see Genbank Accession No. AEA39183.1, SEQ ID NO: 18). See, FIG. 5.

Pathway Using 7-Aminoheptanoate, 7-Hydroxyheptanoate or Pimelate Semialdehyde as Central Precursor to Heptamethylenediamine In some embodiments, heptamethylenediamine is synthesized from the central precursor 7-aminoheptanoate by conversion of 7-aminoheptanoate to 7-aminoheptanal by a carboxylate reductase classified, for example, under EC 1.2.99.6 such as the gene product of car (see above) in combination with a phosphopantetheine transferase enhancer (e.g., encoded by a sfp (Genbank Accession No. CAA44858.1, SEQ ID NO: 19) gene from *Bacillus subtilis* or npt (Genbank Accession No. ABI83656.1, SEQ ID NO: 20) gene from *Nocardia*) or the gene product of GriC & GriD (Suzuki et al., *J. Antibiot.*, 2007, 60(6), 380-387); followed by conversion of 7-aminoheptanal to heptamethylenediamine by a ω-transaminase classified, for example, under EC 2.6.1.-such as 2.6.1.18, EC 2.6.1.19, EC 2.6.1.29, EC 2.6.1.48, or EC 2.6.1.82 such as from a *Chromobacterium violaceum* (see Genbank Accession No. AAQ59697.1, SEQ ID NO: 13), a *Pseudomonas aeruginosa* (see Genbank Accession No. AAG08191.1, SEQ ID NO: 14), a *Pseudomonas syringae* (see Genbank Accession No. AAY39893.1, SEQ ID NO: 15), a *Rhodobacter sphaeroides* (see Genbank Accession No. ABA81135.1, SEQ ID NO: 16), an *Escherichia coli* (see Genbank Accession No. AAA57874.1, SEQ ID NO: 17), or a *Vibrio fluvialis* (see Genbank Accession No. AEA39183.1, SEQ ID NO: 18). See FIG. 6.

The carboxylate reductase encoded by the gene product of car and the phosphopantetheine transferase enhancer npt or sfp has broad substrate specificity, including terminal difunctional C4 and C5 carboxylic acids (Venkitasubramanian et al., *Enzyme and Microbial Technology*, 2008, 42, 130-137).

In some embodiments, heptamethylenediamine is synthesized from the central precursor 7-hydroxyheptanoate (which can be produced as described in FIG. 7), by conversion of 7-hydroxyheptanoate to 7-hydroxyheptanal by a carboxylate reductase classified, for example, under EC 1.2.99.6 such as from a *Mycobacterium marinum* (see Genbank Accession No. ACC40567.1, SEQ ID NO: 7), a *Mycobacterium smegmatis* (see Genbank Accession No. ABK71854.1, SEQ ID NO: 8), a *Segniliparus rugosus* (see Genbank Accession No. EFV1917.1, SEQ ID NO: 9), a *Mycobacterium smegmatis* (see Genbank Accession No. ABK75684.1, SEQ ID NO: 10), a *Mycobacterium massiliense* (see Genbank Accession No. EIV11143.1, SEQ ID NO: 11), or a *Segniliparus rotundus* (see Genbank Accession No. ADG98140.1, SEQ ID NO: 12), in combination with a phosphopantetheine transferase enhancer (e.g., encoded by a sfp (Genbank Accession No. CAA44858.1, SEQ ID NO: 19) gene from *Bacillus subtilis* or npt (Genbank Accession No. ABI83656.1, SEQ ID NO: 20) gene from *Nocardia*), or the gene product of GriC & GriD (Suzuki et al., *J. Antibiot.*, 2007, 60(6), 380-387); followed by conversion of 7-aminoheptanal to 7-aminoheptanol by a ω-transaminase classified, for example, under EC 2.6.1.- such as EC 2.6.1.18, EC 2.6.1.19, EC 2.6.1.29, EC 2.6.1.48, or EC 2.6.1.82 from a *Chromobacterium violaceum* (see Genbank Accession No. AAQ59697.1, SEQ ID NO: 13), a *Pseudomonas syringae* (see Genbank Accession No. AAY39893.1, SEQ ID NO: 15), or a *Rhodobacter sphaeroides* (see Genbank Accession No. ABA81135.1, SEQ ID NO: 16); followed by conversion to 7-aminoheptanal by an alcohol dehydrogenase classified, for example, under EC 1.1.1.- (e.g., EC 1.1.1.1, EC 1.1.1.2, EC 1.1.1.21, or EC 1.1.1.184) such as the gene product of YMR318C (classified, for example, under EC 1.1.1.2, see Genbank Accession No. CAA90836.1) (classified, for example, under EC 1.1.1.2, see Genbank Accession No. CAA90836.1) or YqhD (from *E. coli*, GenBank Accession No. AAA69178.1) (Liu et al., *Microbiology*, 2009, 155, 2078-2085; Larroy et al., 2002, *Biochem J.*, 361(Pt 1), 163-172; Jarboe, 2011, *Appl. Microbiol. Biotechnol.*, 89(2), 249-257) or the protein having GenBank Accession No. CAA81612.1 (from *Geobacillus stearothermophilus*); followed by conversion to heptamethylenediamine by a ω-transaminase classified, for example, under EC 2.6.1.- such as 2.6.1.18, EC 2.6.1.19, EC 2.6.1.29, EC 2.6.1.48, or EC 2.6.1.82 such as from a *Chromobacterium violaceum* (see Genbank Accession No. AAQ59697.1, SEQ ID NO: 13), a *Pseudomonas aeruginosa* (see Genbank Accession No. AAG08191.1, SEQ ID NO: 14), a *Pseudomonas syringae* (see Genbank Accession No. AAY39893.1, SEQ ID NO: 15), a *Rhodobacter sphaeroides* (see Genbank Accession No. ABA81135.1, SEQ ID NO: 16), an *Escherichia coli* (see Genbank Accession No. AAA57874.1, SEQ ID NO: 17), or a *Vibrio fluvialis* (see Genbank Accession No. AEA39183.1, SEQ ID NO: 18). See FIG. 6.

In some embodiments, heptamethylenediamine is synthesized from the central precursor 7-aminoheptanoate by conversion of 7-aminoheptanoate to N7-acetyl-7-aminoheptanoate by a N-acetyltrasferase such as a lysine N-acetyltransferase classified, for example, under EC 2.3.1.32; followed by conversion to N7-acetyl-7-aminoheptanal by a carboxylate reductase classified, for example, under EC 1.2.99.6 such as from a *Mycobacterium smegmatis* (see Genbank Accession No. ABK71854.1, SEQ ID NO: 8), a *Mycobacterium massiliense* (see Genbank Accession No. EIV1143.1, SEQ ID NO: 11), or a *Segniliparus rotundus* (see Genbank Accession No. ADG98140.1, SEQ ID NO: 12), in combination with a phosphopantetheine transferase enhancer (e.g., encoded by a sfp (Genbank Accession No. CAA44858.1, SEQ ID NO: 19) gene from *Bacillus subtilis* or npt (Genbank Accession No. ABI83656.1, SEQ ID NO: 20) gene from *Nocardia*), or the gene product of GriC & GriD (Suzuki et al., *J. Antibiot.*, 2007, 60(6), 380-387); followed by conversion to N7-acetyl-1,7-diaminoheptane by a ω-transaminase classified, for example, under EC 2.6.1.- such as EC 2.6.1.18, EC 2.6.1.19, EC 2.6.1.29, EC 2.6.1.48, EC 2.6.1.46, or EC 2.6.1.82 such as from a *Chromobacterium violaceum* (see Genbank Accession No. AAQ59697.1, SEQ ID NO: 13), a *Pseudomonas aeruginosa* (see Genbank Accession No. AAG08191.1, SEQ ID NO: 14), a *Pseudomonas syringae* (see Genbank Accession No. AAY39893.1, SEQ ID NO: 15), a *Rhodobacter sphaeroides* (see Genbank Accession No. ABA81135.1, SEQ ID NO: 16), an *Escherichia coli* (see Genbank Accession No. AAA57874.1, SEQ ID NO: 17), or a *Vibrio fluvialis* (see Genbank Accession No. AEA39183.1, SEQ ID NO: 18); followed by conversion to heptamethylenediamine by an acetylputrescine deacetylase classified, for example, under EC 3.5.1.62 or EC 3.5.1.17. See, FIG. 6.

In some embodiments, heptamethylenediamine is synthesized from the central precursor pimelate semialdehyde by conversion of pimelate semialdehyde to heptanedial by a carboxylate reductase classified, for example, under EC 1.2.99.6 such as from a *Segniliparus rotundus* (see Genbank Accession No. ADG98140.1, SEQ ID NO: 12), in combination with a phosphopantetheine transferase enhancer (e.g., encoded by a sfp (Genbank Accession No. CAA44858.1, SEQ ID NO: 19) gene from *Bacillus subtilis* or npt (Genbank Accession No. ABI83656.1, SEQ ID NO: 20) gene from *Nocardia*), or the gene product of GriC & GriD (Suzuki et al., *J. Antibiot.*, 2007, 60(6), 380-387); followed by conversion to 7-aminoheptanal by a ω-transaminase classified, for example, under EC 2.6.1.18, EC 2.6.1.19, EC 2.6.1.29, EC 2.6.1.48, or EC 2.6.1.82; followed by conversion to heptamethylenediamine by a ω-transaminase classified, for example, under EC 2.6.1.- such as 2.6.1.18, EC 2.6.1.19, EC 2.6.1.29, EC 2.6.1.48, or EC 2.6.1.82 such as from a *Chromobacterium violaceum* (see Genbank Accession No. AAQ59697.1, SEQ ID NO: 13), a *Pseudomonas aeruginosa* (see Genbank Accession No. AAG08191.1, SEQ ID NO: 14), a *Pseudomonas syringae* (see Genbank Accession No. AAY39893.1, SEQ ID NO: 15), a *Rhodobacter sphaeroides* (see Genbank Accession No. ABA81135.1, SEQ ID NO: 16), an *Escherichia coli* (see Genbank Accession No. AAA57874.1, SEQ ID NO: 17), or a *Vibrio fluvialis* (see Genbank Accession No. AEA39183.1, SEQ ID NO: 18). See FIG. 6.

Pathways Using Pimelate or Pimelate Semialdehyde as Central Precursor to 7-Hydroxyheptanoic Acid and 1,7-Heptanediol In some embodiments, 7-hydroxyheptanoate is synthesized from the central precursor pimelate by conversion of pimelate to pimelate semialdehyde by a carboxylate reductase classified, for example, under EC 1.2.99.6 such as from *Segniliparus rugosus* (Genbank Accession No. EFV11917.1, SEQ ID NO: 9) or *Segniliparus rotundus* (Genbank Accession No. ADG98140.1, SEQ ID NO: 12), in combination with a phosphopantetheine transferase enhancer (e.g., encoded by a sfp (Genbank Accession No. CAA44858.1, SEQ ID NO: 19) gene from *Bacillus subtilis* or npt (Genbank Accession No. ABI83656.1, SEQ ID NO: 20) gene from *Nocardia*), or the gene products of GriC and GriD from *Streptomyces griseus*; followed by conversion to 7-hydroxyheptanoate by an alcohol dehydrogenase classified, for example, under EC 1.1.1.- such as a 6-hydroxyhexanoate dehydrogenase classified, for example, under EC 1.1.1.258 (e.g., the gene from of ChnD), a 5-hydroxypentanoate dehydrogenase classified, for example, under EC 1.1.1.- such as the gene product of CpnD (see, for example, Iwaki et al., 2002, *Appl. Environ. Microbiol.*, 68(11):5671-

5684), a 5-hydroxypentanoate dehydrogenase from *Clostridium viride*, or a 4-hydroxybutyrate dehydrogenase such as gbd. See, FIG. 7.

In some embodiments, 7-hydroxyheptanoate is synthesized from the central precursor pimeloyl-CoA by conversion of pimeloyl-CoA to pimelate semialdehyde by an acetylating aldehyde dehydrogenase classified, for example, under EC 1.2.1.10 such as the gene product of PduB or PduP; followed by conversion to 7-hydroxyheptanoate by an alcohol dehydrogenase classified, for example, under EC 1.1.1.- such as a 6-hydroxyhexanoate dehydrogenase classified, for example, under EC 1.1.1.258 (e.g., the gene from of ChnD)), a 5-hydroxypentanoate dehydrogenase classified, for example, under EC 1.1.1.- such as the gene product of CpnD, a 5-hydroxypentanoate dehydrogenase from *Clostridium viride*, or a 4-hydroxybutyrate dehydrogenase such as gbd. See, also FIG. 7.

In some embodiments, 1,7 heptanediol is synthesized from the central precursor 7-hydroxyheptanoate by conversion of 7-hydroxyheptanoate to 7-hydroxyheptanal by a carboxylate reductase classified, for example, under EC 1.2.99.6 such as from a *Mycobacterium marinum* (see Genbank Accession No. ACC40567.1, SEQ ID NO: 7), a *Mycobacterium smegmatis* (see Genbank Accession No. ABK71854.1, SEQ ID NO: 8), a *Segniliparus rugosus* (see Genbank Accession No. EFV11917.1, SEQ ID NO: 9), a *Mycobacterium smegmatis* (see Genbank Accession No. ABK75684.1, SEQ ID NO: 10), a *Mycobacterium massiliense* (see Genbank Accession No. EIV11143.1, SEQ ID NO: 11), or a *Segniliparus rotundus* (see Genbank Accession No. ADG98140.1, SEQ ID NO: 12), in combination with a phosphopantetheine transferase enhancer (e.g., encoded by a sfp (Genbank Accession No. CAA44858.1, SEQ ID NO: 19) gene from *Bacillus subtilis* or npt (Genbank Accession No. ABI83656.1, SEQ ID NO: 20) gene from *Nocardia*). or the gene product of GriC & GriI) (Suzuki et al., *J. Antibiot.*, 2007, 60(6), 380-387; followed by conversion of 7-hydroxyheptanal to 1,7 heptanediol by an alcohol dehydrogenase classified, for example, under EC 1.1.1.- (e.g., EC 1.1.1.1, EC 1.1.1.2, EC 1.1.1.21, or EC 1.1.1.184) such as the gene product of YMR318C (classified, for example, under EC 1.1.1.2, see Genbank Accession No. CAA90836.1) or YqhD (from *E. coli*, GenBank Accession No. AAA69178.1) (Liu et al., *Microbiology*, 2009, 155, 2078-2085; Larroy et al., 2002, *Biochem J.*, 361(Pt 1), 163-172; Jarboe, 2011, *Appl. Microbiol. Biotechnol.*, 89(2), 249-257) or the protein having GenBank Accession No. CAA81612.1 (from *Geobacillus stearothermophilus*). See, FIG. 8.

Cultivation Strategy

In some embodiments, the cultivation strategy entails achieving an aerobic, anaerobic, micro-aerobic, or mixed oxygen/denitrification cultivation condition. Enzymes characterized in vitro as being oxygen sensitive require a micro-aerobic cultivation strategy maintaining a very low dissolved oxygen concentration (See, for example, Chayabatra & Lu-Kwang, *Appl. Environ. Microbiol.*, 2000, 66(2), 493-498; Wilson and Bouwer, 1997, *Journal of Industrial Microbiology and Biotechnology*, 18(2-3), 116-130).

In some embodiments, the cultivation strategy entails nutrient limitation such as nitrogen, phosphate or oxygen limitation.

In some embodiments, a final electron acceptor other than oxygen such as nitrates can be utilized.

In some embodiments, a cell retention strategy using, for example, ceramic membranes can be employed to achieve and maintain a high cell density during either fed-batch or continuous fermentation.

In some embodiments, the principal carbon source fed to the fermentation in the synthesis of one or more C7 building blocks can derive from biological or non-biological feedstocks.

In some embodiments, the biological feedstock can be, can include, or can derive from, monosaccharides, disaccharides, lignocellulose, hemicellulose, cellulose, lignin, levulinic acid and formic acid, triglycerides, glycerol, fatty acids, agricultural waste, condensed distillers' solubles, or municipal waste.

The efficient catabolism of crude glycerol stemming from the production of biodiesel has been demonstrated in several microorganisms such as *Escherichia coli, Cupriavidus necator, Pseudomonas oleamwrans, Pseudomonas putida* and *Yarrowia lipolytica* (Lee et al., *Appl. Biochem. Biotechnol.*, 2012, 166, 1801-1813; Yang et al., *Biotechnology for Biofuels*, 2012, 5: 13; Meijnen et al., *Appl. Microbiol. Biotechnol.*, 2011, 90, 885-893).

The efficient catabolism of lignocellulosic-derived levulinic acid has been demonstrated in several organisms such as *Cupriavidus necator* and *Pseudomonas putida* in the synthesis of 3-hydroxyvalerate via the precursor propanoyl-CoA (Jaremko and Yu, *Journal of Biotechnology*, 2011, 155, 2011, 293-298; Martin and Prather, *Journal of Biotechnology*, 2009, 139, 61-67).

The efficient catabolism of lignin-derived aromatic compounds such as benzoate analogues has been demonstrated in several microorganisms such as *Pseudomonas putida, Cupriavidus necator* (Bugg et al., *Current Opinion in Biotechnology*, 2011, 22, 394-400; Pérez-Pantoja et al., *FEMS Microbiol. Rev.*, 2008, 32, 736-794).

The efficient utilization of agricultural waste, such as olive mill waste water has been demonstrated in several microorganisms, including *Yarrowia lipolytica* (Papanikolaou et al., *Bioresour. Technol.*, 2008, 99(7), 2419-2428).

The efficient utilization of fermentable sugars such as monosaccharides and disaccharides derived from cellulosic, hemicellulosic, cane and beet molasses, cassava, corn and other agricultural sources has been demonstrated for several microorganism such as *Escherichia coli, Corynebacterium glutamicum* and *Lactobacillus delbrueckii* and *Lactococcus lactis* (see, e.g., Hermann et al, *Journal of Biotechnology*, 2003, 104, 155-172; Wee et al., *Food Technol. Biotechnol.*, 2006, 44(2), 163-172; Ohashi et al., *Journal of Bioscience and Bioengineering*, 1999, 87(5), 647-654).

The efficient utilization of furfural, derived from a variety of agricultural lignocellulosic sources, has been demonstrated for *Cupriavidus necator* (Li et al., *Biodegradation*, 2011, 22, 1215-1225).

In some embodiments, the non-biological feedstock can be or can derive from natural gas, syngas, $CO_2/H_2$, methanol, ethanol, benzoic acid, non-volatile residue (NVR), a caustic wash waste stream from cyclohexane oxidation processes, or terephthalic acid/isophthalic acid mixture waste streams.

The efficient catabolism of methanol has been demonstrated for the methylotrophic yeast *Pichia pastoris*.

The efficient catabolism of ethanol has been demonstrated for *Clostridium kluyveri* (Seedorf et al., *Proc. Natl. Acad. Sci. USA*, 2008, 105(6) 2128-2133).

The efficient catabolism of $CO_2$ and $H_2$, which may be derived from natural gas and other chemical and petrochemical sources, has been demonstrated for *Cupriavidus necator* (Prybylski et al., *Energy, Sustainability and Society*, 2012, 2:11).

The efficient catabolism of syngas has been demonstrated for numerous microorganisms, such as *Clostridium jungdahlii* and *Clostridium autoethanogenum* (Köpke et al., *Applied and Environmental Microbiology*, 2011, 77(15), 5467-5475).

The efficient catabolism of the non-volatile residue waste stream from cyclohexane processes has been demonstrated for numerous microorganisms, such as *Delftia acidovorans* and *Cupriavidus necalor* (Ramsay et al., *Applied and Environmental Microbiology*, 1986, 52(1), 152-156). In some embodiments, the host microorganism is a prokaryote. For example, the prokaryote can be a bacterium from the genus *Escherichia* such as *Escherichia coli*; from the genus *Clostridia* such as *Clostridium ljungdahlii, Clostridium autoethanogenum* or *Clostridium kluyveri*; from the genus *Corynebacteria* such as *Corynebacterium glutamicum*; from the genus *Cupriavidus* such as *Cupriavidus necator* or *Cupriavidus metallidurans*; from the genus *Pseudomonas* such as *Pseudomonas fluorescens, Pseudomonas putida* or *Pseudomonas oleavorans*; from the genus *Delftia* such as *Delftia acidovorans*; from the genus *Bacillus* such as *Bacillus subtillis*; from the genus *Lactobacillus* such as *Lactobacillus delbrueckii*; or from the genus *Lactococcus* such as *Lactococcus lactis*. Such prokaryotes also can be a source of genes to construct recombinant host cells described herein that are capable of producing one or more C7 building blocks.

In some embodiments, the host microorganism is a eukaryote. For example, the eukaryote can be a filamentous fungus, e.g., one from the genus *Aspergillus* such as *Aspergillus niger*. Alternatively, the eukaryote can be a yeast, e.g., one from the genus *Saccharomyces* such as *Saccharomyces cerevisiae*; from the genus *Pichia* such as *Pichia pastoris*; or from the genus *Yarrowia* such as *Yarrowia lipolytica*; from the genus *Issatchenkia* such as *Issatchenkia orientalis*; from the genus *Debaryomyces* such as *Debaryomyces hansenii*; from the genus *Arxula* such as *Arxula adenoinivorans*; or from the genus *Kluvveromyces* such as *Kluyveromyces lactis*. Such eukaryotes also can be a source of genes to construct recombinant host cells described herein that are capable of producing one or more C7 building blocks.

Metabolic Engineering

The present document provides methods involving less than all the steps described for all the above pathways. Such methods can involve, for example, one, two, three, four, five, six, seven, eight, nine, ten, eleven, twelve or more of such steps. Where less than all the steps are included in such a method, the first, and in some embodiments the only, step can be any one of the steps listed.

Furthermore, recombinant hosts described herein can include any combination of the above enzymes such that one or more of the steps, e.g., one, two, three, four, five, six, seven, eight, nine, ten, or more of such steps, can be performed within a recombinant host. This document provides host cells of any of the genera and species listed and genetically engineered to express one or more (e.g., two, three, four, five, six, seven, eight, nine, 10, 11, 12 or more) recombinant forms of any of the enzymes recited in the document. Thus, for example, the host cells can contain exogenous nucleic acids encoding enzymes catalyzing one or more of the steps of any of the pathways described herein.

In addition, this document recognizes that where enzymes have been described as accepting CoA-activated substrates, analogous enzyme activities associated with [acp]-bound substrates exist that are not necessarily in the same enzyme class.

Also, this document recognizes that where enzymes have been described accepting (R)-enantiomers of substrate, analogous enzyme activities associated with (S)-enantiomer substrates exist that are not necessarily in the same enzyme class.

This document also recognizes that where an enzyme is shown to accept a particular co-factor, such as NADPH, or a co-substrate, such as acetyl-CoA, many enzymes are promiscuous in terms of accepting a number of different co-factors or co-substrates in catalyzing a particular enzyme activity. Also, this document recognizes that where enzymes have high specificity for e.g., a particular co-factor such as NADH, an enzyme with similar or identical activity that has high specificity for the co-factor NADPH may be in a different enzyme class.

In some embodiments, the enzymes in the pathways outlined herein are the result of enzyme engineering via non-direct or rational enzyme design approaches with aims of improving activity, improving specificity, reducing feedback inhibition, reducing repression, improving enzyme solubility, changing stereo-specificity, or changing co-factor specificity.

In some embodiments, the enzymes in the pathways outlined herein can be gene dosed (i.e., overexpressed by having a plurality of copies of the gene in the host organism), into the resulting genetically modified organism via episomal or chromosomal integration approaches.

In some embodiments, genome-scale system biology techniques such as Flux Balance Analysis can be utilized to devise genome scale attenuation or knockout strategies for directing carbon flux to a C7 building block.

Attenuation strategies include, but are not limited to; the use of transposons, homologous recombination (double cross-over approach), mutagenesis, enzyme inhibitors and RNA interference (RNAi).

In some embodiments, fluxomic, metabolomic and transcriptomal data can be utilized to inform or support genome-scale system biology techniques, thereby devising genome scale attenuation or knockout strategies in directing carbon flux to a C7 building block.

In some embodiments, the host microorganism's tolerance to high concentrations of a C7 building block can be improved through continuous cultivation in a selective environment.

In some embodiments (see, e.g., FIGS. 1 to 3), the host microorganism's endogenous biochemical network can be attenuated or augmented (1) to ensure the intracellular availability of 2-oxo-glutarate and acetyl-CoA; (2) to create an NADPH imbalance that may be balanced via the formation of a C7 building block; (3) to prevent degradation of central metabolites or central precursors leading to and including C7 building blocks; and/or (4) to ensure efficient efflux from the cell.

In some embodiments requiring the intracellular availability of 2-oxo-glutarate, a PEP carboxykinase or PEP carboxylase can be overexpressed in the host to generate anaplerotic carbon flux into the Krebs cycle towards 2-oxo-glutarate (Schwartz et al., 2009, *Proteomics*, 9, 5132-5142).

In some embodiments requiring the intracellular availability of 2-oxo-glutarate, a pyruvate carboxylase can be overexpressed in the host to generated anaplerotic carbon flux into the Krebs cycle towards 2-oxoglutarate (Schwartz et al., 2009, *Proteomics*, 9, 5132-5142).

In some embodiments requiring the intracellular availability of 2-oxo-glutarate, a PEP synthase can be overexpressed in the host to enhance the flux from pyruvate to PEP, thus increasing the carbon flux into the Krebs cycle via PEP carboxykinase or PEP carboxylase (Schwartz et al., 2009, *Proteomics*, 9, 5132-5142).

In some embodiments requiring the intracellular availability of 2-oxoglutarate for C6 building block synthesis, anaplerotic reactions enzymes such asphosphoenolpyruvate carboxylase (e.g., the gene product of pck), phosphoenolpyruvate carboxykinase (e.g., the gene product ofppc), the malic enzyme (e.g., the gene product of sfcA) and/or pyruvate carboxylase are overexpressed in the host organisms (Song and Lee, 2006, Enzyme Micr. Technol., 39, 352-361).

In some embodiments requiring intracellular availability of acetyl-CoA, endogenous enzymes catalyzing the hydrolysis of acetyl-CoA such as short-chain length thioesterases (e.g., an acetyl-CoA thioesterase) can be attenuated in the host organism.

In some embodiments requiring condensation of acetyl-CoA for C7 building block synthesis, one or more endogenous β-ketothiolases catalyzing the condensation of only acetyl-CoA to acetoacetyl-CoA such as the endogenous gene products of AtoB or phaA can be attenuated.

In some embodiments requiring the intracellular availability of acetyl-CoA, an endogenous phosphotransacetylase generating acetate such as pta can be attenuated (Shen et al., *Appl. Environ. Microbiol.*, 2011, 77(9):2905-2915).

In some embodiments requiring the intracellular availability of acetyl-CoA, an endogenous gene in an acetate synthesis pathway encoding an acetate kinase, such as ack, can be attenuated.

In some embodiments requiring the intracellular availability of acetyl-CoA and NADH for C7 building block synthesis, an endogenous gene encoding an enzyme that catalyzes the degradation of pyruvate to lactate such as a lactate dehydrogenase encoded by ldhA can be attenuated (Shen et al., 2011, supra).

In some embodiments requiring the intracellular availability of Krebs cycle intermediates for C6 building block synthesis, 2-oxogltarate dehydrogenase is attenuated in one or more of its subunits.

In some embodiments requiring intracellular availability of Krebs cycle intermediates for C6 building block synthesis, the regulator of 2-oxoglutarate dehydrogenase is overexpressed by induction in the host microorganism.

In some embodiments requiring the intracellular availability of acetyl-CoA and NADH for C7 building block synthesis, endogenous genes encoding enzymes, such as menaquinol-fumarate oxidoreductase, that catalyze the degradation of phophoenolpyruvate to succinate such as frdBC can be attenuated (see, e.g., Shen et al., 2011, supra).

In some embodiments requiring the intracellular availability of acetyl-CoA and NADH for C7 building block synthesis, an endogenous gene encoding an enzyme that catalyzes the degradation of acetyl-CoA to ethanol such as the alcohol dehydrogenase encoded by adhE can be attenuated (Shen et al., 2011, supra).

In some embodiments where the host microorganism uses the lysine biosynthesis pathway via meso-2,6-diaminopimelate, the genes encoding the synthesis of 2-oxoadipate from 2-oxoglutarate are gene dosed into the host.

In some embodiments where the host microorganism uses the lysine biosynthesis pathway via 2-oxoadipate, the genes encoding the synthesis of lysine via meso-2,6-diaminopimelate are gene dosed into the host.

In some embodiments, an endogenous gene encoding an enzyme that catalyzes the degradation of pyruvate to ethanol such as pyruvate decarboxylase is attenuated.

In some embodiments, where pathways require excess NADPH or NADH co-factor for C7 building block synthesis, an endogenous transhydrogenase such as one classified under EC 1.6.1.1, EC 1.6.1.2, or EC 1.6.1.3, dissipating the co-factor imbalance can be attenuated.

In some embodiments, where pathways require excess NADPH co-factor for C7 building block synthesis, an exogenous transhydrogenase such as one classified under EC 1.6.1.1, EC 1.6.1.2 or EC 1.6.1.3, converting NADH to NADPH can be overexpressed.

In some embodiments using hosts that naturally accumulate polyhydroxyalkanoates, an endogenous gene encoding a polyhydroxyalkanoate synthase enzyme can be attenuated in the host strain.

In some embodiments using hosts that naturally accumulate lipid bodies, the genes encoding enzymes involved with lipid body synthesis are attenuated.

In some embodiments requiring the intracellular availability of acetyl-CoA for C7 building block synthesis, a recombinant acetyl-CoA synthetase such as the gene product of acs can be overexpressed in the microorganism (Satoh et al., *J. Bioscience and Bioengineering*, 2003, 95(4):335-341).

In some embodiments, an L-alanine dehydrogenase can be overexpressed in the host to regenerate L-alanine from pyruvate as amino donor for ω-transaminase reactions.

In some embodiments, a NADH-specific L-glutamate dehydrogenase can be overexpressed in the host to regenerate L-glutamate from 2-oxo-glutarate as amino donor for ω-transaminase reactions.

In some embodiments, enzymes such as pimeloyl-CoA dehydrogenase classified under, for example, EC 1.3.1.62; an acyl-CoA dehydrogenase classified under, for example, EC 1.3.8.7 or EC 1.3.8.1; and/or a glutaryl-CoA dehydrogenase classified under, for example, EC 1.3.8.6 that degrade central metabolites and central precursors leading to and including C7 building blocks can be attenuated.

In some embodiments, endogenous enzymes activating C7 building blocks via Coenzyme A esterification such as CoA-ligases such as pimeloyl-CoA synthetase classified under, for example, EC 6.2.1.14 can be attenuated.

In some embodiments, carbon flux can be directed into the pentose phosphate cycle to increase the supply of NADPH by attenuating an endogenous glucose-6-phosphate isomerase (EC 5.3.1.9).

In some embodiments, carbon flux can be redirected into the pentose phosphate cycle to increase the supply of NADPH by overexpression a 6-phosphogluconate dehydrogenase and/or a transketolase (Lee et al., 2003, *Biotechnology Progress*, 19(5), 1444-1449).

In some embodiments, where pathways require excess NADPH co-factor in the synthesis of a C7 building block, a gene such as UdhA encoding a puridine nucleotide transhydrogenase can be overexpressed in the host organisms (Brigham et al., *Advanced Biofuels and Bioproducts*, 2012, Chapter 39, 1065-1090).

In some embodiments, where pathways require excess NADPH co-factor in the synthesis of a C7 Building Block, a recombinant glyceraldehyde-3-phosphate-dehydrogenase gene such as GapN can be overexpressed in the host organisms (Brigham et al., 2012, supra).

In some embodiments, where pathways require excess NADPH co-factor in the synthesis of a C7 building block, a recombinant malic enzyme gene such as maeA or maeB can be overexpressed in the host organisms (Brigham et al., 2012, supra).

In some embodiments, where pathways require excess NADPH co-factor in the synthesis of a C7 building block, a recombinant glucose-6-phosphate dehydrogenase gene such as zwf can be overexpressed in the host organisms (Lim et al., *J. Bioscience and Bioengineering*, 2002, 93(6), 543-549).

In some embodiments, where pathways require excess NADPH co-factor in the synthesis of a C7 building block, a recombinant fructose 1,6 diphosphatase gene such as fbp can be overexpressed in the host organisms (Becker et al., *J. Biotechnol.*, 2007, 132:99-109).

In some embodiments, where pathways require excess NADPH co-factor in the synthesis of a C7 building block, endogenous triose phosphate isomerase (EC 5.3.1.1) can be attenuated.

In some embodiments, where pathways require excess NADPH co-factor in the synthesis of a C7 building block, a recombinant glucose dehydrogenase such as the gene product of gdh can be overexpressed in the host organism (Satoh et al., *J. Bioscience and Bioengineering*, 2003, 95(4):335-341).

In some embodiments, endogenous enzymes facilitating the conversion of NADPH to NADH can be attenuated, such as the NADH generation cycle that may be generated via inter-conversion of glutamate dehydrogenases classified under EC 1.4.1.2 (NADH-specific) and EC 1.4.1.4 (NADPH-specific). For example, avoiding dissipation of an NADPH imbalance towards C7 building blocks, a NADH-specific glutamate dehydrogenase can be attenuated.

In some embodiments, an endogenous glutamate dehydrogenase (EC 1.4.1.3) that utilizes both NADH and NADPH as co-factors can be attenuated.

In some embodiments, a methanol dehydrogenase or a formaldehyde dehydrogenase can be overexpressed in the host to allow methanol catabolism via formate.

In some embodiments, a S-adenosylmethionine synthetase can be overexpressed in the host to generate S-Adenosyl-L-methionine as a co-factor for a fatty acid O-methyltransferase.

In some embodiments, one or more of 3-phosphoglycerate dehydrogenase, 3-phosphoserine aminotransferase and phosphoserine phosphatase can be overexpressed in the host to generate serine as a methyl donor for the S-Adenosyl-L-methionine cycle.

In some embodiments, a membrane-bound enoyl-CoA reductases can be solubilized via expression as a fusion protein to a small soluble protein such as a maltose binding protein (Gloerich et al., *FEBS Letters*, 2006, 580, 2092-2096).

In some embodiments, the efflux of a C7 building block across the cell membrane to the extracellular media can be enhanced or amplified by genetically engineering structural modifications to the cell membrane or increasing any associated transporter activity for a C7 building block.

The efflux of heptamethylenediamine can be enhanced or amplified by overexpressing broad substrate range multi-drug transporters such as Blt from *Bacillus subtilis* (Woolridge et al., 1997, *J. Biol. Chem.*, 272(14):8864-8866); AcrB and AcrD from *Escherichia coli* (Elkins & Nikaido, 2002, *J. Bacteriol.*, 184(23), 6490-6499) or NorA from *Staphylococcus aereus* (Ng et al., 1994, *Antimicrob Agents Chemother*, 38(6), 1345-1355) or Bmr from *Bacillus subtilis* (Neyfakh, 1992, *Antimicrob Agents Chemother*, 36(2), 484-485).

The efflux of 7-aminoheptanoate and heptamethylenediamine can be enhanced or amplified by overexpressing the solute transporters such as the lysE transporter from *Corynebacterium glutamicum* (Bellmann et al., 2001, *Microbiology*, 147, 1765-1774).

The efflux of pimelic acid can be enhanced or amplified by overexpressing a dicarboxylate transporter such as the SucE transporter from *Corynebacterium glutamicum* (Huhn et al., *Appl. Microbiol. & Biotech.*, 89(2), 327-335).

Producing C7 Building Blocks Using a Recombinant Host

Typically, one or more C7 building blocks can be produced by providing a host microorganism and culturing the provided microorganism with a culture medium containing a suitable carbon source as described above. In general, the culture media and/or culture conditions can be such that the microorganisms grow to an adequate density and produce a C7 building block efficiently. For large-scale production processes, any method can be used such as those described elsewhere (Manual of Industrial Microbiology and Biotechnology, 2$^{nd}$ Edition, Editors: A. L. Demain and J. E. Davies, ASM Press; and Principles of Fermentation Technology, P. F. Stanbury and A. Whitaker, Pergamon). Briefly, a large tank (e.g., a 100 gallon, 200 gallon, 500 gallon, or more tank) containing an appropriate culture medium is inoculated with a particular microorganism. After inoculation, the microorganism is incubated to allow biomass to be produced. Once a desired biomass is reached, the broth containing the microorganisms can be transferred to a second tank. This second tank can be any size. For example, the second tank can be larger, smaller, or the same size as the first tank. Typically, the second tank is larger than the first such that additional culture medium can be added to the broth from the first tank. In addition, the culture medium within this second tank can be the same as, or different from, that used in the first tank.

Once transferred, the microorganisms can be incubated to allow for the production of a C7 building block. Once produced, any method can be used to isolate C7 building blocks. For example, C7 building blocks can be recovered selectively from the fermentation broth via adsorption processes. In the case of pimelic acid and 7-aminoheptanoic acid, the resulting eluate can be further concentrated via evaporation, crystallized via evaporative and/or cooling crystallization, and the crystals recovered via centrifugation. In the case of heptamethylenediamine and 1,7-heptanediol, distillation may be employed to achieve the desired product purity.

Accordingly, the methods provided herein can be performed in a recombinant host. In some embodiments, the methods provided herein can be performed in a recombinant host by fermentation. In some embodiments, the recombinant host is subjected to a cultivation strategy under aerobic, anaerobic or, micro-aerobic cultivation conditions. In some embodiments, the recombinant host is cultured under conditions of nutrient limitation such as phosphate, nitrogen and oxygen limitation. In some embodiments, the recombinant host is retained using a ceramic membrane to maintain a high cell density during fermentation.

In some embodiments, the principal carbon source fed to the fermentation derives from biological or non-biological feedstocks. In some embodiments, the biological feedstock is, or derives from, monosaccharides, disaccharides, lignocellulose, hemicellulose, cellulose, lignin, levulinic acid, formic acid, triglycerides, glycerol, fatty acids, agricultural waste, condensed distillers' solubles, or municipal waste. In some embodiments, the non-biological feedstock is, or derives from, natural gas, syngas, $CO_2/H_2$, methanol, ethanol, benzoate, non-volatile residue (NVR) caustic wash waste stream from cyclohexane oxidation processes, or terephthalic acid/isophthalic acid mixture waste streams.

In some embodiments, the recombinant host is a prokaryote. In some embodiments, the prokaryote is from the genus *Escherichia* such as *Escherichia coli*; from the genus *Clostridia* such as *Clostridium ljungdahlii, Clostridium autoethanogenum* or *Clostridium kluyveri*; from the genus *Corynebacteria* such as *Corynebacterium glutamicum*; from the genus *Cupriavidus* such as *Cupriavidus necalor* or *Cupriavidus metallidurans*; from the genus *Pseudomonas* such as *Pseudomonas fluorescens, Pseudomonas putida* or *Pseudomonas oleavorans*; from the genus *Delftia acidovorans*, from the genus *Bacillus* such as *Bacillus subtillis*; from the genes *Lactobacillus* such as *Lactobacillus delbrueckii*; from the genus *Lactococcus* such as *Lactococcus lactis*; or from the genus *Rhodococcus* such as *Rhodococcus equi*.

In some embodiments, the recombinant host is a eukaryote. In some embodiments, the eukaryote is from the genus *Aspergillus* such as *Aspergillus niger*; from the genus *Saccharomyces* such as *Saccharomyces cerevisiae*; from the genus *Pichia* such as *Pichia pastoris*; from the genus *Yarrowia* such as *Yarrowia lipolytica*, from the genus *Issatchenkia* such as *Issathenkia orientalis*, from the genus *Debaryomyces* such as *Debaryomyces hansenii*, from the genus *Arxula* such as *Arxula adenoinivorans*, or from the genus *Kluyveromyces* such as *Kluyveromyces lactis*.

In some embodiments, the recombinant host includes one or more of the following polypeptides having attenuated activity: polyhydroxyalkanoate synthase activity, acetyl-CoA thioesterase activity, acetyl-CoA specific β-ketothiolase activity, phosphotransacetylase forming acetate activity, acetate kinase activity, lactate dehydrogenase activity, menaquinol-fumarate oxidoreductase activity, 2-oxoacid decarboxylase producing isobutanol, alcohol dehydrogenase activity forming ethanol, triose phosphate isomerase activity, pyruvate decarboxylase activity, glucose-6-phosphate isomerase activity, transhydrogenase activity dissipating the NADPH imbalance, glutamate dehydrogenase activity dissipating the NADPH imbalance, NADH/NADPH-utilizing glutamate dehydrogenase activity, pimeloyl-CoA dehydrogenase activity; acyl-CoA dehydrogenase activity accepting C7 building blocks and central precursors as substrates; glutaryl-CoA dehydrogenase activity; or pimeloyl-CoA synthetase activity.

In some embodiments, the recombinant host overexpresses one or more genes encoding a polypeptide having: acetyl-CoA synthetase activity; transketolase activity; puridine nucleotide transhydrogenase activity; formate dehydrogenase activity; glyceraldehyde-3P-dehydrogenase activity; malic enzyme activity; glucose-6-phosphate dehydrogenase activity; fructose 1,6 diphosphatase activity; L-alanine dehydrogenase activity; PEP carboxylase activity, pyruvate carboxylase activity; PEP carboxykinase activity; PEP synthase activity; L-glutamate dehydrogenase activity specific to the NADPH used to generate a co-factor imbalance; methanol dehydrogenase activity, formaldehyde dehydrogenase activity, lysine transporter activity; dicarboxylate transporter activity; S-adenosylmethionine synthetase activity; 3-phosphoglycerate dehydrogenase activity; 3-phosphoserine aminotransferase activity; phosphoserine phosphatase activity; or a multidrug transporter activity.

The present document further provides a recombinant host comprising at least one exogenous nucleic acid encoding having (i) β-ketoacyl-[acp] synthase activity or β-ketothiolase activity, (ii) 3-hydroxybutyryl-CoA dehydrogenase activity, and (iii) enoyl-CoA hydratase activity.

In some embodiments, the recombinant host further includes one or more exogenous polypeptides having homocitrate synthase, homocitrate dehydratase, homoaconitate hydratase, isohomocitrate dehydrogenase, 2-hydroxyglutarate dehydrogenase, glutaconate CoA-tramsferase, or 2-hydroxyglutaryl-CoA dehydratase activity.

In some embodiments, the recombinant host further includes one or more exogenous polypeptides having glutarate semialdehyde dehydrogenase, 4-hydroxy-2-oxoheptanedioate aldolase, 2-oxo-hept-3-ene-1,7-dioate hydratase, 2-en oate reductase, 2-hydroxyglutarate dehydrogenase, glutaconate CoA-transferase, or 2-hydroxyglutaryl-CoA dehydratase activity.

In some embodiments, the recombinant host further includes one or more exogenous polypeptides having thioesterase, aldehyde dehydrogenase, 7-oxoheptanoate dehydrogenase, 6-oxohexanoate dehydrogenase, glutaconate CoA-transferase, reversible succinyl-CoA ligase, acetylating aldehyde dehydrogenase, or carboxylate reductase activity, the host further producing pimelic acid or pimelate semialdehyde.

In some embodiments, the recombinant host further includes an exogenous polypeptide having ω-transaminase activity, the host further producing 7-aminoheptanoate.

In some embodiments, the recombinant host further includes one or more exogenous polypeptides having 4-hydroxybutyrate dehydrogenase, 5-hydroxypentanoate dehydrogenase, 6-hydroxyhexanoate dehydrogenase, or alcohol dehydrogenase activity, the host further producing 7-hydroxyheptanoic acid.

In some embodiments, the recombinant host further includes one or more exogenous polypeptides having ω-transaminase, deacetylase, N-acetyl transferase, or alcohol dehydrogenase activity, the host further producing heptamethylenediamine.

In some embodiments, the recombinant host further includes one or more exogenous polypeptides having (a) carboxylate reductase activity enhanced by phosphopantetheinyl transferase activity, or (b) alcohol dehydrogenase activity, the host further producing 1,7-heptanediol.

The invention is further described in the following examples, which do not limit the scope of the invention described in the claims.

EXAMPLES

Example 1

Enzyme Activity of Thioesterases Using Pimeloyl-CoA as a Substrate and Forming Pimelic Acid A sequence encoding an N-terminal His tag was added to the tesB gene from *Escherichia coli* that encodes a thioesterase (SEQ ID NO: 21, see FIG. 9K), such that an N-terminal HIS tagged thioesterase could be produced. The modified tesB gene was cloned into a pET15b expression vector under control of the T7 promoter. The expression vector was transformed into a BL21[DE3] *E. coli* host. The resulting recombinant *E. coli* strain was cultivated at 37° C. in a 500 mL shake flask culture containing 50 mL Luria Broth (LB) media and antibiotic selection pressure, with shaking at 230 rpm. The culture was induced overnight at 17° C. using 0.5 mM IPTG.

The pellet from the induced shake flask culture was harvested via centrifugation. The pellet was resuspended and lysed in Y-per™ solution (ThermoScientific, Rockford, Ill.). The cell debris was separated from the supernatant via centrifugation. The thioesterase was purified from the supernatant using Ni-affinity chromatography and the eluate was buffer exchanged and concentrated via ultrafiltration.

The enzyme activity assay was performed in triplicate in a buffer composed of 50 mM phosphate buffer (pH=7.4), 0.1 mM Ellman's reagent, and 667 µM of pimeloyl-CoA (as substrate). The enzyme activity assay reaction was initiated by adding 0.8 µM of the tesB gene product to the assay buffer containing the pimeloyl-CoA and incubating at 37° C. for 20 minutes. The release of Coenzyme A was monitored by absorbance at 412 nm. The absorbance associated with the substrate only control, which contained boiled enzyme, was subtracted from the active enzyme assay absorbance and compared to the empty vector control. The gene product of tesB accepted pimeloyl-CoA as substrate as confirmed via relative spectrophotometry (see, FIG. 10) and synthesized pimelate as a reaction product.

Example 2

Enzyme Activity of ω-Transaminase Using Pimelate Semialdehyde as Substrate and Forming 7-Aminoheptanoate A sequence encoding an N-terminal His-tag was added to the genes from *Chromobacterium violaceum*, *Pseudomonas syringae*, *Rhodobacter sphaeroides*, and *Vibrio fluvialis* encoding the ω-transaminases of SEQ ID NOs: 13, 15, 16, and 18, respectively (see, FIGS. 9I and 9J) such that N-terminal HIS tagged ω-transaminases could be produced. Each of the resulting modified genes was cloned into a pET21a expression vector under control of the T7 promoter and each expression vector was transformed into a BL21 [DE3] *E. coli* host. The resulting recombinant *E. coli* strains were cultivated at 37° C. in a 250 mL shake flask culture containing 50 mL LB media and antibiotic selection pressure, with shaking at 230 rpm. Each culture was induced overnight at 16° C. using 1 mM IPTG.

The pellet from each induced shake flask culture was harvested via centrifugation. Each pellet was resuspended and lysed via sonication. The cell debris was separated from the supernatant via centrifugation and the cell free extract was used immediately in enzyme activity assays.

Enzyme activity assays in the reverse direction (i.e., 7-aminoheptanoate to pimelate semialdehyde) were performed in a buffer composed of a final concentration of 50 mM HEPES buffer (pH=7.5), 10 mM 7-aminoheptanoate, 10 mM pyruvate and 100 µM pyridoxyl 5' phosphate. Each enzyme activity assay reaction was initiated by adding cell free extract of the ω-transaminase gene product or the empty vector control to the assay buffer containing the 7-aminoheptanoate and incubated at 25° C. for 4 hours, with shaking at 250 rpm. The formation of L-alanine from pyruvate was quantified via RP-HPLC.

Each enzyme only control without 7-aminoheptanoate demonstrated low base line conversion of pyruvate to L-alanine. See, FIG. 16. The gene product of SEQ ID NO: 13, SEQ ID NO: 15, SEQ ID NO: 16, and SEQ ID NO: 18 accepted 7-aminoheptanote as substrate as confirmed against the empty vector control. See, FIG. 17.

Enzyme activity in the forward direction (i.e., pimelate semialdehyde to 7-aminoheptanoate) was confirmed for the transaminases of SEQ ID NO: 15, SEQ ID NO: 16, and SEQ ID NO: 18. Enzyme activity assays were performed in a buffer composed of a final concentration of 50 mM HEPES buffer (pH=7.5), 10 mM pimelate semialdehyde, 10 mM L-alanine and 100 µM pyridoxyl 5' phosphate. Each enzyme activity assay reaction was initiated by adding a cell free extract of the ω-transaminase gene product or the empty vector control to the assay buffer containing the pimelate semialdehyde and incubated at 25° C. for 4 hours, with shaking at 250 rpm. The formation of pyruvate was quantified via RP-HPLC.

The gene product of SEQ ID NO: 15, SEQ ID NO: 16, and SEQ ID NO: 18 accepted pimelate semialdehyde as substrate as confirmed against the empty vector control. See, FIG. 18. The reversibility of the ω-transaminase activity was confirmed, demonstrating that the ω-transaminases of SEQ ID NO: 13, SEQ ID NO: 15, SEQ ID NO: 16, and SEQ ID NO: 18 accepted pimelate semialdehyde as substrate and synthesized 7-aminoheptanoate as a reaction product.

Example 3

Enzyme Activity of Carboxylate Reductase Using Pimelate as Substrate and Forming Pimelate Semialdehyde A sequence encoding a HIS-tag was added to the genes from *Segniliparus rugosus* and *Segniliparus rotundus* that encode the carboxylate reductases of SEQ ID NOs: 9 and 12, respectively (see FIGS. 9E and 9H), such that N-terminal HIS tagged carboxylate reductases could be produced. Each of the modified genes was cloned into a pET Duet expression vector along with a sfp gene encoding a HIS-tagged phosphopantetheine transferase from *Bacillus subtilis*, both under the T7 promoter. Each expression vector was transformed into a BL21 [DE3] *E. coli* host and the resulting recombinant *E. coli* strains were cultivated at 37° C. in a 250 mL shake flask culture containing 50 mL LB media and antibiotic selection pressure, with shaking at 230 rpm. Each culture was induced overnight at 37° C. using an auto-induction media.

The pellet from each induced shake flask culture was harvested via centrifugation. Each pellet was resuspended and lysed via sonication, and the cell debris was separated from the supernatant via centrifugation. The carboxylate reductases and phosphopantetheine transferases were purified from the supernatant using Ni-affinity chromatography, diluted 10-fold into 50 mM HEPES buffer (pH=7.5), and concentrated via ultrafiltration.

Enzyme activity assays (i.e., from pimelate to pimelate semialdehyde) were performed in triplicate in a buffer composed of a final concentration of 50 mM HEPES buffer (pH=7.5), 2 mM pimelate, 10 mM $MgCl_2$, 1 mM ATP and 1 mM NADPH. Each enzyme activity assay reaction was initiated by adding purified carboxylate reductase and phosphopantetheine transferase gene products or the empty vector control to the assay buffer containing the pimelate and then incubated at room temperature for 20 minutes. The consumption of NADPH was monitored by absorbance at 340 nm. Each enzyme only control without pimelate demonstrated low base line consumption of NADPH. See, FIG. 11.

The gene products of SEQ ID NO: 9 and SEQ ID NO: 12, enhanced by the gene product of sfp, accepted pimelate as substrate, as confirmed against the empty vector control (see FIG. 12), and synthesized pimelate semialdehyde.

Example 4

Enzyme Activity of Carboxylate Reductase Using 7-Hydroxyheptanoate as Substrate and Forming 7-Hydroxyheptanal

A sequence encoding a His-tag was added to the genes from *Mycobacterium marinum*, *Mycobacterium smegmatis*, *Segniliparus rugosus*, *Mycobacterium smegmatis*, *Mycobacterium massiliense*, and *Segniliparus rotundus* that encode the carboxylate reductases of SEQ ID NOs: 7 to 12 respectively (see, FIGS. 9C-9H) such that N-terminal HIS tagged carboxylate reductases could be produced. Each of the modified genes was cloned into a pET Duet expression vector alongside a sfp gene encoding a His-tagged phosphopantetheine transferase from *Bacillus subtilis*, both under control of the T7 promoter.

Each expression vector was transformed into a BL21 [DE3] *E. coli* host and the resulting recombinant *E. coli* strains were cultivated at 37° C. in a 250 mL shake flask culture containing 50 mL LB media and antibiotic selection pressure, with shaking at 230 rpm. Each culture was induced overnight at 37° C. using an auto-induction media.

The pellet from each induced shake flask culture was harvested via centrifugation. Each pellet was resuspended and lysed via sonication. The cell debris was separated from the supernatant via centrifugation. The carboxylate reductases and phosphopantetheine transferase were purified from the supernatant using Ni-affinity chromatography, diluted 10-fold into 50 mM HEPES buffer (pH=7.5) and concentrated via ultrafiltration.

Enzyme activity (i.e., 7-hydroxyheptanoate to 7-hydroxyheptanal) assays were performed in triplicate in a buffer composed of a final concentration of 50 mM HEPES buffer (pH=7.5), 2 mM 7-hydroxyheptanoate, 10 mM $MgCl_2$, 1 mM ATP, and 1 mM NADPH. Each enzyme activity assay reaction was initiated by adding purified carboxylate reductase and phosphopantetheine transferase or the empty vector control to the assay buffer containing the 7-hydroxyheptanoate and then incubated at room temperature for 20 min. The consumption of NADPH was monitored by absorbance at 340 nm. Each enzyme only control without 7-hydroxyheptanoate demonstrated low base line consumption of NADPH. See, FIG. 11.

The gene products of SEQ ID NOs: 7 to 12, enhanced by the gene product of sfp, accepted 7-hydroxyheptanoate as substrate as confirmed against the empty vector control (see, FIG. 13), and synthesized 7-hydroxyheptanal.

Example 5

Enzyme Activity of ω-Transaminase for 7-Aminoheptanol, Forming 7-Oxoheptanol

A nucleotide sequence encoding an N-terminal His-tag was added to the *Chromobacterium violaceum*, *Pseudomonas syringae* and *Rhodobacter sphaeroides* genes encoding the ω-transamtinases of SEQ ID NOs: 13, 15, and 16, respectively (see, FIGS. 9I and 9J) such that N-terminal HIS tagged ω-transaminases could be produced. The modified genes were cloned into a pET21a expression vector under the T7 promoter. Each expression vector was transformed into a BL21 [DE3] *E. coli* host. Each resulting recombinant *E. coli* strain were cultivated at 37° C. in a 250 mL shake flask culture containing 50 mL LB media and antibiotic selection pressure, with shaking at 230 rpm. Each culture was induced overnight at 16° C. using 1 mM IPTG.

The pellet from each induced shake flask culture was harvested via centrifugation. Each pellet was resuspended and lysed via sonication. The cell debris was separated from the supernatant via centrifugation and the cell free extract was used immediately in enzyme activity assays.

Enzyme activity assays in the reverse direction (i.e., 7-aminoheptanol to 7-oxoheptanol) were performed in a buffer composed of a final concentration of 50 mM HEPES buffer (pH=7.5), 10 mM 7-aminoheptanol, 10 mM pyruvate, and 100 μM pyridoxyl 5' phosphate. Each enzyme activity assay reaction was initiated by adding cell free extract of the ω-transaminase gene product or the empty vector control to the assay buffer containing the 7-aminoheptanol and then incubated at 25° C. for 4 hours, with shaking at 250 rpm. The formation of L-alanine was quantified via RP-HPLC.

Each enzyme only control without 7-aminoheptanol had low base line conversion of pyruvate to L-alanine. See, FIG. 16.

The gene products of SEQ ID NOs: 13, 15, and 16 accepted 7-aminoheptanol as substrate as confirmed against the empty vector control (see FIG. 21) and synthesized 7-oxoheptanol as reaction product. Given the reversibility of the ω-transaminase activity (see Example 2), it can be concluded that the gene products of SEQ ID NOs.: 13, 15, and 16 accept 7-oxoheptanol as substrate and form 7-aminoheptanol.

Example 6

Enzyme Activity of ω-Transaminase Using Heptamethylenediamine as Substrate and Forming 7-Aminoheptanal

A sequence encoding an N-terminal His-tag was added to the *Chromobacterium violaceum*, *Pseudomonas aeruginosa*, *Pseudomonas syringae*, *Rhodobacter sphaeroides*, *Escherichia coli*, and *Vibrio fluvialis* genes encoding the ω-transaminases of SEQ ID NOs: 13 to 18, respectively (see, FIGS. 9I and 9J) such that N-terminal HIS tagged ω-transaminases could be produced. The modified genes were cloned into a pET21a expression vector under the T7 promoter. Each expression vector was transformed into a BL21[DE3] *E. coli* host. Each resulting recombinant *E. coli* strain were cultivated at 37° C. in a 250 mL shake flask culture containing 50 mL LB media and antibiotic selection pressure, with shaking at 230 rpm. Each culture was induced overnight at 16° C. using 1 mM IPTG.

The pellet from each induced shake flask culture was harvested via centrifugation. Each pellet was resuspended and lysed via sonication. The cell debris was separated from the supernatant via centrifugation and the cell free extract was used immediately in enzyme activity assays.

Enzyme activity assays in the reverse direction (i.e., heptamethylenediamine to 7-aminoheptanal) were performed in a buffer composed of a final concentration of 50 mM HEPES buffer (pH=7.5), 10 mM heptamethylenediamine, 10 mM pyruvate, and 100 μM pyridoxyl 5' phosphate. Each enzyme activity assay reaction was initiated by adding cell free extract of the ω-transaminase gene product or the empty vector control to the assay buffer containing the heptamethylenediamine and then incubated at 25° C. for 4 hours, with shaking at 250 rpm. The formation of L-alanine was quantified via RP-HPLC.

Each enzyme only control without heptamethylenediamine had low base line conversion of pyruvate to L-alanine. See, FIG. 16.

The gene products of SEQ ID NOs: 13 to 18 accepted heptamethylenediamine as substrate as confirmed against the empty vector control (see, FIG. 19) and synthesized 7-aminoheptanal as reaction product. Given the reversibility of the ω-transaminase activity (see Example 2), it can be concluded that the gene products of SEQ ID NOs: 13 to 18 accept 7-aminoheptanal as substrate and form heptamethylenediamine.

Example 7

Enzyme Activity of Carboxylate Reductase for N7-Acetyl-7-Aminoheptanoate, Forming N7-Acetyl-7-Aminoheptanal The activity of each of the N-terminal His-tagged carboxylate reductases of SEQ ID NOs: 8, 11, and 12 (see Example 4, and FIGS. 9D, 9G, and 9H) for converting N7-acetyl-7-aminoheptanoate to N7-acetyl-7-aminoheptanal was assayed in triplicate in a buffer composed of a final concentration of 50 mM HEPES buffer (pH=7.5), 2 mM N7-acetyl-7-aminoheptanoate, 10 mM $MgCl_2$, 1 mM ATP, and 1 mM NADPH. The assays were initiated by adding purified carboxylate reductase and phosphopantetheine transferase or the empty vector control to the assay buffer containing the N7-acetyl-7-aminoheptanoate then incubated at room temperature for 20 minutes. The consumption of NADPH was monitored by absorbance at 340 nm. Each enzyme only control without N7-acetyl-7-aminoheptanoate demonstrated low base line consumption of NADPH. See, FIG. 11.

The gene products of SEQ ID NOs: 8, 11, and 12 enhanced by the gene product of sfp, accepted N7-acetyl-7-aminoheptanoate as substrate as confirmed against the empty vector control (see, FIG. 14), and synthesized N7-acetyl-7-aminoheptanal.

Example 8

Enzyme Activity of ω-Transaminase Using N7-Acetyl-1,7-Diaminoheptane, and Forming N7-Acetyl-7-Aminoheptanal The activity of the N-terminal His-tagged ω-transaminases of SEQ ID NOs: 13 to 18 (see, Example 6, and FIGS. 9I and 9J) for converting N7-acetyl-1,7-diaminoheptane to N7-acetyl-7-aminoheptanal was assayed using a buffer composed of a final concentration of 50 mM HEPES buffer (pH=7.5), 10 mM N7-acetyl-1,7-diaminoheptane, 10 mM pyruvate and 100 μM pyridoxyl 5' phosphate. Each enzyme activity assay reaction was initiated by adding a cell free extract of the ω-transaminase or the empty vector control to the assay buffer containing the N7-acetyl-1,7-diaminoheptane then incubated at 25° C. for 4 hours, with shaking at 250 rpm. The formation of L-alanine was quantified via RP-HPLC.

Each enzyme only control without N7-acetyl-1,7-diaminoheptane demonstrated low base line conversion of pyruvate to L-alanine. See, FIG. 16.

The gene product of SEQ ID NOs: 13 to 18 accepted N7-acetyl-1,7-diaminoheptane as substrate as confirmed against the empty vector control (see FIG. 20) and synthesized N7-acetyl-7-aminoheptanal as reaction product.

Given the reversibility of the ω-transaminase activity (see example 2), the gene products of SEQ ID NOs: 13 to 18 accept N7-acetyl-7-aminoheptanal as substrate forming N7-acetyl-1,7-diaminoheptane.

Example 9

Enzyme Activity of Carboxylate Reductase Using Pimelate Semialdehyde as Substrate and Forming Heptanedial The N-terminal His-tagged carboxylate reductase of SEQ ID NO: 12 (see, Example 4 and FIG. 9H) was assayed using pimelate semialdehyde as substrate. The enzyme activity assay was performed in triplicate in a buffer composed of a final concentration of 50 mM HEPES buffer (pH=7.5), 2 mM pimelate semialdehyde, 10 mM $MgCl_2$, 1 mM ATP and 1 mM NADPH. The enzyme activity assay reaction was initiated by adding purified carboxylate reductase and phosphopantetheine transferase or the empty vector control to the assay buffer containing the pimelate semialdehyde and then incubated at room temperature for 20 minutes. The consumption of NADPH was monitored by absorbance at 340 nm. The enzyme only control without pimelate semialdehyde demonstrated low base line consumption of NADPH. See, FIG. 11.

The gene product of SEQ ID NO: 12, enhanced by the gene product of sfp, accepted pimelate semialdehyde as substrate as confirmed against the empty vector control (see, FIG. 15) and synthesized heptanedial.

Example 10

Enzyme Activity of Pimeloyl-[Acp] Methyester Methylesterase Using Pimeloyl-CoA Methyl Ester as Substrate and Forming Pimeloyl-CoA A nucleotide sequence encoding a C-terminal His-tag was added to the gene from *Escherichia coli* encoding the pimeloyl-[acp] methylester methylesterase of SEQ ID NO: 6 (see, FIG. 9B) such that a C-terminal HIS tagged pimeloyl-[acp] methyl ester methylesterase could be produced. The resulting modified gene was cloned into a pET28b+ expression vector under control of the T7 promoter and the expression vector was transformed into a BL21 [DE3] *E. coli* host. The resulting recombinant *E. coli* strain was cultivated at 37° C. in a 500 mL shake flask culture containing 100 mL LB media and antibiotic selection pressure, with shaking at 230 rpm. Each culture was induced overnight at 18° C. using 0.3 mM IPTG.

The pellet from each induced shake flask culture was harvested via centrifugation. Each pellet was resuspended and lysed via sonication. The cell debris was separated from the supernatant via centrifugation. The pimeloyl-[acp] methyl ester methylesterase was purified from the supernatant using Ni-affinity chromatography, buffer exchanged and concentrated into 20 mM HEPES buffer (pH=7.5) via ultrafiltration and stored at 4° C.

Enzyme activity assays converting pimeloyl-CoA methyl ester to pimeloyl-CoA were performed in triplicate in a buffer composed of a final concentration of 25 mM Tris.HCl buffer (pH=7.0) and 5 [mM] pimeloyl-CoA methyl ester. The enzyme activity assay reaction was initiated by adding pimeloyl-[acp] methyl ester methylesterase to a final concentration of 10 [μM] to the assay buffer containing the pimeloyl-CoA methyl ester and incubated at 30° C. for 1 hour, with shaking at 250 rpm. The formation of pimeloyl-CoA was quantified via LC-MS.

The substrate only control without enzyme demonstrated no conversion of the substrate pimeloyl-CoA methyl ester to pimeloyl-CoA. See, FIG. 22. The pimeloyl-[acp]methyl ester methylesterase of SEQ ID NO: 6 accepted pimeloyl-CoA methyl ester as substrate and synthesized pimeloyl-CoA as reaction product as confirmed via LC-MS. See, FIG. 22.

Example 11

Enzyme Activity of 6Ketothiolases Using Glutaryl-CoA and Acetyl-CoA as Substrates and Forming 3-Ketopimeloyl-CoA A nucleotide sequence encoding a N-terminal His-tag was added to the gene from *Pseudomonas reinekei* MT1, *Pseudomonas putida*, *Burkholderia xenovorans*, *Arthrobacter* sp., *Burkholderia xenovorans*, *Geobacillus kaustophilus*, *Gordonia bronchialis*, *Citrobacter freundii*, *Burkholderia* sp., *Beijerinckia indica*, *Arthrobacter arilaitensis*, *Cupriavidus necator* and *Escherichia coli* encoding the β-ketothiolase of SEQ ID NOs: 28 to 40 (see, FIGS. 9M-9Q) such that a N-terminal HIS tagged β-ketothiolase could be produced. The resulting modified gene was cloned into a pET15b expression vector under control of the T7 promoter and the expression vector was transformed into a BL21 [DE3] *E. coli* host. The resulting recombinant *E. coli* strain was cultivated at 37° C. in a 1 L shake flask culture containing 350 mL LB media and ampicilin antibiotic selection pressure, with shaking at 230 rpm. Each culture was induced overnight at 25° C. using 1 mM IPTG.

The pellet from each induced shake flask culture was harvested via centrifugation. Each pellet was resuspended and lysed via sonication. The cell debris was separated from the supernatant via centrifugation. The β-ketothiolase was purified from the supernatant using Ni-affinity chromatography, buffer exchanged and concentrated into 50 mM potassium phosphate buffer (pH=6.8) via ultrafiltration.

Enzyme activity assays converting glutaryl-CoA and acetyl-CoA to 3-ketopimeloyl-CoA were performed in triplicate in a buffer composed of a final concentration of 50 mM potassium phosphate buffer (pH=6.8) and 1 mM glutaryl-CoA and 1 mM acetyl-CoA. The enzyme activity assay reaction was initiated by adding β-ketothiolase to a final concentration of 7 [µM] to the assay buffer containing the 1 mM glutaryl-CoA and 1 mM acetyl-CoA and incubated at 30° C. for three hours, with gentle shaking. The formation of 3-ketopimeloyl-CoA was quantified via LC-MS.

The substrate only control without enzyme demonstrated no conversion of the substrate pimeloyl-CoA methyl ester to pimeloyl-CoA. See, FIG. 23. The β-ketothiolase of SEQ ID NOs: 28 to 40 accepted glutaryl-CoA and acetyl-CoA as substrates and synthesized 3-ketopimeloyl-CoA as reaction product as confirmed via LC-MS against the empty vector control. See, FIG. 23.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of shielding a carbon chain aliphatic backbone, functionalized with terminal carboxyl groups, in a recombinant host using at least one exogenous polypeptide expressed by said host, said method comprising:
enzymatically converting a n-carboxy-2-enoic acid to a n-carboxy-2-enoate methyl ester in said host by contacting said n-carboxy-2-enoic acid with a polypeptide having fatty acid O-methyltransferase activity, wherein n+1 reflects the length of the carbon chain aliphatic backbone and the polypeptide having fatty acid O-methyltransferase activity has at least 85% sequence identity to any one of the amino acid sequences set forth in SEQ ID NOs: 1-3.

2. A method of producing 2(E)-heptenedioyl-CoA methyl ester in a recombinant host using at least one exogenous polypeptide expressed by said host, said method comprising:
enzymatically converting 2(E)-heptenedioate to 2(E)-heptenedioate methyl ester by contacting 2(E)-heptenedioate with a polypeptide having fatty acid O-methyltransferase activity, wherein said polypeptide having fatty acid O-methyltransferase activity has at least 85% sequence identity to any one of the amino acid sequences set forth in SEQ ID NOs: 1-3;
enzymatically converting 2(E)-heptenedioate methyl ester to 2(E)-heptenedioyl-CoA methyl ester by contacting 2(E)-heptenedioate methyl ester with a polypeptide having the activity of a CoA ligase, wherein said polvpeptide having the activity of a CoA ligase has at least 85% sequence identity to the amino acid sequence set forth in SEQ ID NO: 22 or SEQ ID NO: 23;
enzymatically converting 2(E)-heptenedioyl-CoA methyl ester to pimeloyl-CoA methyl ester by contacting 2(E)-heptenedioyl-CoA methyl ester with a polypeptide having the activity of a trans-2-enoyl-CoA reductase, wherein said polvpeptide having the activity of a trans-2-enoyl-CoA reductase has at least 85% sequence identity to the amino acid sequence of SEQ ID NO: 26 or SEQ ID NO: 27; and
enzymatically converting pimeloyl-CoA methyl ester to pimeloyl-CoA by contacting pimeloyl-CoA methyl ester with a polypeptide having the activity of a pimelyl-[acp]methyl ester esterase, wherein said polypeptide having the activity of a pimelyl-[acp]methyl ester esterase has at least 85% sequence identity to the amino acid sequence set forth in SEQ ID NO: 6.

3. The method of claim 2, further comprising enzymatically converting pimeloyl-CoA to a product selected from pimelic acid, pimelate semialdehyde, 7-aminoheptanoate, 7-hydroxyheptanoate, heptamethylenediamine, and 1,7-heptanediol, wherein pimeloyl-CoA is converted to said product using at least one exogenous polypeptide expressed by said host, wherein said exogenous polypeptide has thioesterase, reversible CoA-ligase, glutaconate CoA-transferase, ω-transaminase, 6-hydroxyhexanoate dehydrogenase, 5-hydroxypentanoate dehydrogenase, 4-hydroxybutyrate dehydrogenase, alcohol dehydrogenase, carboxylate reductase, or phosphopantetheine transferase enhancer activity, wherein:
said polypeptide having the activity of a thioesterase has at least 85% sequence similarity to the amino acid sequence set forth in any one of SEQ ID NOs: 4, 5, or 21;
said polypeptide having the activity of a reversible CoA-ligase is classified under EC 6.2.1.5;
said polypeptide having the activity of a glutaconate CoA-transferase has at least 85% sequence identity to the amino acid sequence set forth in SEQ ID NO: 24 and SEQ ID NO: 25;
said polypeptide having the activity of a ω-transaminase has at least 85% sequence identity to the amino acid sequence set forth in any one of SEQ ID NOs: 13-18;
said polypeptide having the activity of a 6-hydroxyhexanoate dehydrogenase has at least 85% sequence identity to the amino acid sequence of a gene product of chnD;
said polypeptide having the activity of a 5-hydroxypentanoate dehydrogenase has at least 85% sequence identity to the amino acid sequence of a gene product of cpnD;
said polypeptide having the activity of a 4-hydroxybutyrate dehydrogenase has at least 85% sequence identity to the amino acid sequence of a gene product of gbd;
said polypeptide having the activity of an alcohol dehydrogenase has at least 85% sequence identity to the amino acid seauence of a gene product of any one of hadH, ldhA, yghD, or YMR318C or the amino acid sequence of the protein having GenBank Accession No. CAA81612.1;
said polypeptide having the activity of a carboxylate reductase has at least 85% sequence identity to the amino acid sequence set forth in any one of SEQ ID NOs: 7-12; and
said polypeptide having the activity of a phosphopantetheine transferase enhancer has at least 85% sequence identity to the amino acid sequence set forth in SEQ ID NO: 19 or SEQ ID NO: 20 or at least 85% sequence identity to the amino acid sequence of the gene products of griC and griD.

4. The method of claim 3, wherein said product is pimelate semialdehyde and said method comprises:
contacting pimeloyl-CoA with a polypeptide having acetylating aldehyde dehydrogenase activity, wherein said polypeptide having acetylating aldehyde dehydrogenase activity has at least 85% seauence identity to the amino acid sequence of the gene product of pduB or pduP; or contacting pimeloyl-CoA with a polypeptide having thioesterase, reversible CoA-ligase, or glutaconate CoA-transferase activity to produce pimelic acid and contacting pimelic acid with a polypeptide having carboxylate reductase activity optionally in combination with a polypeptide having the activity of a phosphopantetheine transferase enhancer to produce pimelate semialdehyde, wherein said polypeptide having thioesterase activity has at least 85% sequence identity to the amino acid sequence set forth in any one of SEQ ID NOs: 4, 5, or 21;

said polypeptide having reversible CoA-ligase activity is classified under EC 6.2.1.5;

said polypeptide having glutaconate CoA-transferase activity has at least 85% sequence identity to SEQ ID NOs: 24 and 25;

said polypeptide having the activity of a carboxylate reductase has at least 85% seauence identity to the amino acid seauence set forth in any one of SEQ ID NOs: 7-12; and said polypeptide having the activity of a phosphopantetheine transferase enhancer has at least 85% sequence identity to the amino acid sequence set forth in SEQ ID NO: 19 or SEQ ID NO: 20 or at least 85% sequence identity to the amino acid sequence of the gene products of griC and griD.

5. The method of claim 4, said method further comprising enzymatically converting pimelate semialdehyde to 7-aminoheptanoate by contacting pimelate semialdehyde with a polypeptide having ω-transaminase activity, wherein said polypeptide having ω-transaminase activity has at least 85% sequence identity to the amino acid sequence set forth in any one of SEQ ID NOs: 13-18.

6. The method of claim 1, wherein one or more steps of said method are performed by fermentation.

7. The method of claim 1, wherein said recombinant host is subjected to a cultivation strategy under aerobic, anaerobic, micro-aerobic, or mixed oxygen/denitrification cultivation conditions.

8. The method of claim 1, wherein said recombinant host is cultured under conditions of phosphate, oxygen, and/or nitrogen limitation.

9. The method of claim 1, wherein said recombinant host is retained using a ceramic membrane to maintain a high cell density during fermentation.

10. The method of claim 6, wherein the principal carbon source fed to the fermentation derives from biological or non-biological feedstocks, wherein the biological feedstock is, or derives from, monosaccharides, disaccharides, lignocellulose, hemicellulose, cellulose, lignin, levulinic acid, formic acid, triglycerides, glycerol, fatty acids, agricultural waste, condensed distillers' solubles, or municipal waste; and wherein the non-biological feedstock is, or derives from, natural gas, syngas, $CO_2/H_2$, methanol, ethanol, benzoate, non-volatile residue (NVR) caustic wash waste stream from cyclohexane oxidation processes, or terephthalic acid/isophthalic acid mixture waste streams.

11. The method of claim 6, wherein said recombinant host comprises one or more polypeptides having attenuated polyhydroxyalkanoate synthase, acetyl-CoA thioesterase, acetyl-CoA specific β-ketothiolase, phosphotransacetylase forming acetate, acetate kinase, lactate dehydrogenase, menaquinol-fumarate oxidoreductase, 2-oxoacid decarboxylase producing isobutanol, alcohol dehydrogenase forming ethanol, triose phosphate isomerase, pyruvate decarboxylase, glucose-6-phosphate isomerase, transhydrogenase dissipating the NADPH imbalance, glutamate dehydrogenase dissipating the NADPH imbalance, NADH/NADPH-utilizing glutamate dehydrogenase, pimeloyl-CoA dehydrogenase, acyl-CoA dehydrogenase accepting C7 building blocks and central precursors as substrates, glutaryl-CoA dehydrogenase, or pimeloyl-CoA synthetase activity, and optionally wherein the recombinant host overexpresses one or more genes encoding a polypeptide having acetyl-CoA synthetase, 6-phosphogluconate dehydrogenase, transketolase, puridine nucleotide transhydrogenase, formate dehydrogenase, glyceraldehyde-3P-dehydrogenase, malic enzyme, glucose-6-phosphate dehydrogenase, fructose 1,6 diphosphatase, L-alanine dehydrogenase, PEP carboxylase, pyruvate carboxylase, PEP carboxykinase, PEP synthase, L-glutamate dehydrogenase specific to the NADPH used to generate a co-factor imbalance, methanol dehydrogenase, formaldehyde dehydrogenase, lysine transporter, dicarboxylate transporter, S-adenosylmethionine synthetase, 3-phosphoglycerate dehydrogenase, 3 phosphoserine aminotransferase, phosphoserine phosphatase, or a multidrug transporter activity.

12. The method of claim 1, wherein the host is:
a prokaryote selected from the genus *Escherichia, Clostridia, Corynebacteria, Cupriavidus, Pseudomonas, Delftia, Bacilluss, Lactobacillus, Lactococcus,* or *Rhodococcus*; or
a eukaryote selected from the genus *Aspergillus, Saccharomyces, Pichia, Yarrowia, Issatchenkia, Debaryomyces, Arxula,* or *Kluyveromyces.*

13. The method of claim 1, wherein the n-carboxy-2-enoic acid is 2(E) heptenedioic acid and the n-carboxy-2-enoate methyl ester is 2(E)-heptenedioate methyl ester.

14. The method of claim 2, wherein 2(E)-heptenedioate is enzymatically produced from 2(E)-heptenedioyl-CoA by contacting 2(E)-heptenedioyl-CoA with a polypeptide having thioesterase or glutaconate CoA-transferase activity, wherein said polypeptide having thioesterase activity has at least 85% sequence identity to the amino acid sequence set forth in any one of SEQ ID NOs: 4, 5, or 21 and said polypeptide having CoA-transferase activity has at least 85% sequence identity to the amino acid sequence set forth in SEQ ID NO: 24 or SEQ ID NO: 25.

15. The method of claim 3, wherein said product is pimelic acid and said method comprises contacting pimeloyl-CoA with a polypeptide having thioesterase, reversible CoA-ligase, or glutaconate CoA-transferase activity, wherein said polypeptide having thioesterase activity has at least 85% sequence identity to the amino acid sequence set forth in any one of SEQ ID NOs: 4, 5, or 21;

said polypeptide having reversible CoA-ligase activity is classified under EC 6.2.1.5; and said polypeptide having glutaconate CoA-transferase activity has at least 85% sequence identity to SEQ ID NOs: 24 and 25.

16. The method of claim 4, said method further comprising enzymatically converting pimelate semialdehyde to pimelic acid by contacting pimelate semialdehyde with a polypeptide having the activity of a 7-oxoheptanoate dehydrogenase, 6-oxohexanoate dehydrogenase, or 5-oxopentanoate dehydrogenase, wherein said polypeptide having the activity of a 7-oxoheptanoate dehydrogenase has at least 85% sequence identity to the amino acid sequence of the gene product of thnG;

said polypeptide having the activity of a 6-oxohexanoate dehydrogenase has at least 85% sequence identity to the amino acid sequence of the gene product of chnE; and said polypeptide having the activity of a 5-oxopentanoate dehydrogenase has at least 85% sequence identity to the amino acid sequence of the gene product of cpnE.

17. The method of claim 4, said method further comprising enzymatically converting pimelate semialdehyde to heptamethylenediamine by contacting pimelate semialdehyde with a polypeptide having the activity of a carboxylate reductase optionally in combination with a polypeptide having the activity of a phosphopantetheine transferase enhancer to produce heptanedial, contacting heptanedial with a polypeptide having the activity of a ω-transaminase to produce 7-aminoheptanal, and contacting 7-aminoheptanal with a polypeptide having the activity of a ω-transaminase to produce heptamethylenediamine, wherein said polypeptide having the activity of a carboxylate reductase has at least 85% sequence identity to the amino acid sequence set forth in SEQ ID NOs: 7-12;

said polypeptide having the activity of a phosphopantetheine transferase enhancer has at least 85% sequence identity to the amino acid sequence set forth in SEQ ID NO: 19 or SEQ ID NO: 20 or at least 85% sequence identity to the amino acid sequence of the gene products of griC and griD; and said polypeptide having the activity of a ω-transaminase has at least 85% sequence identity to the amino acid sequence set forth in any one of SEQ ID NOs: 13-18.

18. The method of claim 5, further comprising enzymatically converting 7-aminoheptanoate to heptamethylenediamine by:

contacting 7-aminoheptanoate with a polypeptide having the activity of a carboxylate reductase optionally in combination with a polypeptide having the activity of a phosphopantetheine transferase enhancer to produce 7-aminoheptanal and contacting 7-aminoheptanal with a polypeptide having the activity of a ω-transaminase to produce heptamethylenediamine, wherein said polypeptide having the activity of a carboxylate reductase has at least 85% sequence identity to the amino acid sequence set forth in SEQ ID NOs: 7-12;

said polypeptide having the activity of a phosphopantetheine transferase enhancer has at least 85% sequence identity to the amino acid sequence set forth in SEQ ID NO: 19 or SEQ ID NO: 20 or at least 85% sequence identity to the amino acid sequence of the gene products of griC and griD; and said polypeptide having the activity of a ω-transaminase has at least 85% sequence identity to the amino acid sequence set forth in any one of SEQ ID NOs: 13-18;

or contacting 7-aminoheptanoate with a polypeptide having the activity of a N-acetyltransferase to produce N7-acetyl-7-aminoheptanoate, contacting N7-acetyl-7-aminoheptanoate with a polypeptide having the activity of a carboxylate reductase optionally in combination with a polypeptide having the activity of a phosphopantetheine transferase enhancer to produce N7-acetyl-7-aminoheptanal, contacting N7-acetyl-7-aminoheptanal with a polypeptide having the activity of a ω-transaminase to produce N7-acetyl-1,7-diaminoheptane, and contacting N7-acetyl-1,7-diaminoheptane with a polypeptide having the activity of an acetylputrescine deacetylase to produce heptamethylenediamine, wherein said polypeptide having the activity of a N-acetyltransferase is classified under EC 2.3.1.32;

said polypeptide having the activity of a carboxylate reductase has at least 85% sequence identity to the amino acid sequence set forth in SEQ ID NOs: 7-12;

said polypeptide having the activity of a phosphopantetheine transferase enhancer has at least 85% sequence identity to the amino acid sequence set forth in SEQ ID NO: 19 or SEQ ID NO: 20 or at least 85% sequence identity to the amino acid sequence of the gene products of griC and griD;

said polypeptide having the activity of a ω-transaminase has at least 85% sequence identity to the amino acid sequence set forth in any one of SEQ ID NOs: 13-18; and said polypeptide having the activity of an acetylputrescine deacetylase is classified under EC 3.5.1.62.

19. The method of claim 4, said method further comprising enzymatically converting pimelate semialdehyde to 7-hydroxyheptanoate by contacting 7-hydroxyheptanoate with a polypeptide having 6-hydroxyhexanoate dehydrogenase, 5-hydroxypentanoate dehydrogenase, 4-hydroxybutyrate dehydrogenase, or alcohol dehydrogenase activity, wherein said polypeptide having the activity of a 6-hydroxyhexanoate dehydrogenase has at least 85% sequence identity to the amino acid sequence of a gene product of chnD;

said polypeptide having the activity of a 5-hydroxypentanoate dehydrogenase has at least 85% sequence identity to the amino acid sequence of a gene product of cpnD;

said polypeptide having the activity of a 4-hydroxybutyrate dehydrogenase has at least 85% sequence identity to the amino acid sequence of a gene product of a gbd; and said polypeptide having the activity of an alcohol dehydrogenase has at least 85% sequence identity to the amino acid sequence of a gene product of hgdH, IdhA, yqhD, or YMR318C or the amino acid sequence of the protein having GenBank Accession No. CAA81612.1.

20. The method of claim 19, said method further comprising enzymatically converting 7-hydroxyheptanoate to 1,7-heptanediol by contacting 7-hydroxyheptanoate with a polypeptide having the activity of a carboxylate reductase optionally in combination with a polypeptide having the activity of a phosphopantetheine transferase enhancer to produce 7-hydroxyheptanal and contacting 7-hydroxyheptanal with a polypeptide having the activity of an alcohol dehydrogenase to produce 1,7-heptanediol, wherein said polypeptide having the activity of a carboxylate reductase has at least 85% sequence identity to the amino acid sequence set forth in SEQ ID NOs: 7-12;

said polypeptide having the activity of a phosphopantetheine transferase enhancer has at least 85% sequence identity to the amino acid sequence set forth in SEQ ID NO: 19 or SEQ ID NO: 20 or at least 85% sequence identity to the amino acid sequence of the gene products of griC and griD; and said polypeptide having the activity of an alcohol dehydrogenase has at least 85% sequence identity to the amino acid sequence of a gene product of hgdH, IdhA, yqhD, or YMR318C or the amino acid sequence of the protein having GenBank Accession No. CAA81612.1.

21. The method of claim 19, said method further comprising enzymatically converting 7-hydroxyheptanoate to heptamethylenediamine by contacting 7-hydroxyheptanoate with a polypeptide having the activity of a carboxylate reductase optionally in combination with a polypeptide having the activity of a phosphopantetheine transferase enhancer to produce 7-hydroxyheptanal, contacting 7-hydroxyheptanal with a polypeptide having the activity of a ω-transaminase to produce 7-aminoheptanol, contacting 7-aminoheptanol with a polypeptide having the activity of an alcohol dehydrogenase to produce 7-aminoheptanal, and contacting 7-aminoheptanal with a polypeptide having the activity of a ω-transaminase to produce heptamethylenediamine, wherein said polypeptide having the activity of a carboxylate reductase has at least 85% sequence identity to the amino acid sequence set forth in SEQ ID NOs: 7-12;

said polypeptide having the activity of a phosphopantetheine transferase enhancer has at least 85% sequence identity to the amino acid sequence set forth in SEQ ID NO: 19 or SEQ ID NO: 20 or at least 85% sequence identity to the amino acid sequence of the gene products of griC and griD;

said polypeptide having the activity of a ω-transaminase has at least 85% sequence identity to the amino acid sequence set forth in any one of SEQ ID NOs: 13-18; and said polypeptide having the activity of an alcohol dehydrogenase has at least 85% sequence identity to the amino acid sequence of a gene product of hgdH, IdhA, yqhD, or YMR318C or the amino acid sequence of the protein having GenBank Accession No. CAA81612.1.

22. A method of shielding a carbon chain aliphatic backbone, functionalized with terminal carboxyl groups, in a recombinant host using at least one exogenous polypeptide expressed by said host, said method comprising:

enzymatically converting a n-carboxy-2-enoic acid to a n-carboxy-2-enoate methyl ester in said host by contacting said n-carboxy-2-enoic acid with a polypeptide having at least 85% sequence identity to any one of the amino acid sequences set forth in SEQ ID NOs: 1-3, wherein n+1 reflects the length of the carbon chain aliphatic backbone.

23. The method of claim 22, wherein the n-carboxy-2-enoic acid is 2(E) heptenedioic acid and the n-carboxy-2-enoate methyl ester is 2(E)-heptenedioate methyl ester.

24. A method of producing 2(E)-heptenedioyl-CoA methyl ester in a recombinant host using at least one exogenous polypeptide expressed by said host, said method comprising:

enzymatically converting 2(E)-heptenedioate to 2(E)-heptenedioate methyl ester by contacting 2(E)-heptenedioate with a polypeptide having at least 85% sequence identity to any one of the amino acid sequences set forth in SEQ ID NOs: 1-3;

enzymatically converting 2(E)-heptenedioate methyl ester to 2(E)-heptenedioyl-CoA methyl ester by contacting 2(E)-heptenedioate methyl ester with a polypeptide having at least 85% sequence identity to the amino acid sequence set forth in SEQ ID NO: 22 or SEQ ID NO: 23;

enzymatically converting 2(E)-heptenedioyl-CoA methyl ester to pimeloyl-CoA methyl ester by contacting 2(E)-heptenedioyl-CoA methyl ester with a polypeptide having at least 85% sequence identity to the amino acid sequence of SEQ ID NO: 26 or SEQ ID NO: 27; and enzymatically converting pimeloyl-CoA methyl ester to pimeloyl-CoA by contacting pimeloyl-CoA methyl ester with a polypeptide having at least 85% sequence identity to the amino acid sequence set forth in SEQ ID NO: 6.

25. The method of claim 24, wherein 2(E)-heptenedioate is enzymatically produced from 2(E)-heptenedioyl-CoA by contacting 2(E)-heptenedioyl-CoA with a polypeptide having at least 85% sequence identity to the amino acid sequence set forth in any one of SEQ ID NOs: 4, 5, 21, 24, or 25.

26. The method of claim 24, wherein said method further comprises:

contacting pimeloyl-CoA with a polypeptide having at least 85% sequence identity to the amino acid sequence of the gene product of pduB or pduP to produce pimelate semialdehyde; or contacting pimeloyl-CoA with a polypeptide having at least 85% sequence identity to the amino acid sequence set forth in any one of SEQ ID NOs: 4, 5, 21, 24, or 25 to produce pimelic acid and contacting pimelic acid with a polypeptide having at least 85% sequence identity to the amino acid sequence set forth in any one of SEQ ID NOs: 7-12 optionally in combination with a polypeptide having at least 85% sequence identity to the amino acid sequence set forth in SEQ ID NO: 19 or SEQ ID NO: 20 or at least 85% sequence identity to the amino acid sequence of the gene products of griC and griD to produce pimelate semialdehyde.

27. The method of claim 26, wherein said method further comprises enzymatically converting pimelate semialdehyde to 7-aminoheptanoate by contacting pimelate semialdehyde with a polypeptide having at least 85% sequence identity to the amino acid sequence set forth in any one of SEQ ID NOs: 13-18.

28. The method of claim 26, wherein said method further comprises enzymatically converting pimelate semialdehyde to heptamethylenediamine by contacting pimelate semialdehyde with a polypeptide having at least 85% sequence identity to the amino acid sequence set forth in SEQ ID NOs: 7-12 optionally in combination with a polypeptide having at least 85% sequence identity to the amino acid sequence set forth in SEQ ID NO: 19 or SEQ ID NO: 20 or at least 85% sequence identity to the amino acid sequence of the gene products of griC and griD to produce heptanedial, contacting heptanedial with a polypeptide having at least 85% sequence identity to the amino acid sequence set forth in any one of SEQ ID NOs: 13-18 to produce 7-aminoheptanal, and contacting 7-aminoheptanal with a polypeptide having at least 85% sequence identity to the amino acid sequence set forth in any one of SEQ ID NOs: 13-18 to produce heptamethylenediamine.

29. The method of claim 26, wherein said method further comprises enzymatically converting pimelate semialdehyde to 7-hydroxyheptanoate by contacting 7-hydroxyheptanoate with a polypeptide having at least 85% sequence identity to the amino acid sequence of any one of a gene product of chnD, gbd, hgdH, IdhA, yqhD, or YMR318C or the amino acid sequence of the protein having GenBank Accession No. CAA81612.1.

30. The method of claim 29, wherein said method further comprises enzymatically converting 7-hydroxyheptanoate to 1,7-heptanediol by contacting 7-hydroxyheptanoate with a polypeptide having at least 85% sequence identity to the amino acid sequence set forth in SEQ ID NOs: 7-12 optionally in combination with a polypeptide having at least 85% sequence identity to the amino acid sequence set forth in SEQ ID NO: 19 or SEQ ID NO: 20 or at least 85% sequence identity to the amino acid sequence of the gene products of gnrC and griD to produce 7-hydroxyheptanal and contacting 7-hydroxyheptanal with a polypeptide having at least 85% sequence identity to the amino acid sequence of a gene product of hgdH, IdhA, yqhD, or YMR318C or the amino acid sequence of the protein having GenBank Accession No. CAA81612.1 produce 1,7-heptanediol.

* * * * *

UNITED STATES PATENT AND TRADEMARK OFFICE
CERTIFICATE OF CORRECTION

PATENT NO. : 9,896,702 B2
APPLICATION NO. : 14/740554
DATED : February 20, 2018
INVENTOR(S) : Alex Van Eck Conradie et al.

Page 1 of 1

It is certified that error appears in the above-identified patent and that said Letters Patent is hereby corrected as shown below:

In the Claims

Claim 2, Column 157, Line 43, "polvpeptide" should read as --polypeptide--.

Claim 2, Column 157, Line 51, "polvpeptide" should read as --polypeptide--.

Claim 3, Column 158, Line 50, "hadH," should read as --hgdH,--.

Signed and Sealed this
Seventeenth Day of April, 2018

Andrei Iancu
*Director of the United States Patent and Trademark Office*